United States Patent [19]
Nakamura et al.

[11] Patent Number: 5,874,255
[45] Date of Patent: Feb. 23, 1999

[54] DNA ENCODING HUMANIZED ANTIBODIES SPECIFIC FOR THE GANGLIOSIDE $GM_2$

[75] Inventors: Kazuyasu Nakamura; Masamichi Koike, both of Tokyo, Japan; Kenya Shitara, San Diego, Calif.; Nobuo Hanai, Kanagawa, Japan; Yoshihisa Kuwana, Tokyo, Japan; Mamoru Hasegawa, Kanagawa, Japan

[73] Assignee: Kyowa Hakko Kogyo Co., Ltd., Tokyo, Japan

[21] Appl. No.: 438,562

[22] Filed: May 10, 1995

Related U.S. Application Data

[62] Division of Ser. No. 116,778, Sep. 7, 1993.

[30] Foreign Application Priority Data

Sep. 7, 1992 [JP] Japan ............................. HEI-4238452

[51] Int. Cl.$^6$ ............................. C12P 21/04; C12P 21/08; C12N 15/00; C07H 21/04
[52] U.S. Cl. .................. 435/69.6; 435/70.21; 435/172.2; 435/320.1; 435/328; 435/330; 435/332; 435/344.1; 435/346; 530/387.3; 530/387.5; 530/387.7; 530/388.1; 530/388.2; 530/867; 536/23.53; 935/15
[58] Field of Search ............................. 424/137.1, 133.1; 435/69.6, 70.21, 240.27, 172.2, 320.1, 328, 330, 332, 344.1, 346; 935/15; 530/387.3, 387.5, 867, 387.7, 388.1, 388.2; 536/23.53

[56] References Cited

FOREIGN PATENT DOCUMENTS 0 508 472 A2  10/1992  European Pat. Off. .

OTHER PUBLICATIONS

Livingston, "Approaches to Augmenting the Immunogenicity of Melanoma Gangliosides: From Whole Melanoma Cells to Ganglioside–KLH Conjugate Vaccines", Immunological Reviews 145:147–166 (1995).

Natoli et al, Caner Research, vol. 46:4116–4120, Aug. 1986.
Miyake et al., Cancer Research, vol. 48: 6154–6160, Nov. 1, 1988.
Fredman et al, Journal of Biological Chemistry, vol. 21: 12122–12125, Jul. 25, 1989.
Riechmann et al, Nature, vol. 332: 323–327, Mar. 24, 1988.
Morrison et al, PNAS vol. 81: 6851–6855, Nov. 1984.
Hodgson, Bio/Technology vol. 8:1245–1247, Dec. 8, 1990.
Morrison et al. Advances in Immunology 44, Dixon et al. Eds. Academic Press 198 pp. 65–92. Schlom et al. "Molecular Foundations of Oncology", Broder Ed., Williams & Wilkins, 1991 pp. 95–134.
Hakomori et al. in Monoclonal Antibodies and Functional Cell Lines Kennett et al., eds. 1985 pp. 67–100.
Kannagi et al., Handbook of Expt'l Immunology 4:1986, 117.1–117.21 Irie et al. Lancet, Apr. 8, 1989 786–7.

*Primary Examiner*—Anthony C. Caputa
*Assistant Examiner*—Mark Navarro
*Attorney, Agent, or Firm*—Nixon & Vanderhye

[57] ABSTRACT

Chimeric human antibody expression vectors are constructed by inserting the antibody heavy chain variable region-encoding cDNA and antibody light chain variable region-encoding cDNA isolated from hybridomas producing a mouse or rat monoclonal antibody reacting with the ganglioside $GM_2$ respectively into an expression vector for use in animal cells which contains the human antibody heavy chain constant region- or human antibody light chain constant region-encoding cDNA. The expression vectors are introduced into animal cells and the transformant thus obtained is cultured for the production of a chimeric human antibody reacting with the ganglioside $GM_2$.

In contrast to mouse monoclonal antibodies, the chimeric human antibodies of the invention will not cause anti-mouse immunoglobulin antibody production in the patient's body but shows a prolonged blood half-life, with a reduced frequency of adverse effects, so that it can be expected to be superior to mouse monoclonal antibodies in the efficacy in the treatment of human cancer, for instance.

6 Claims, 61 Drawing Sheets

FIG. 1
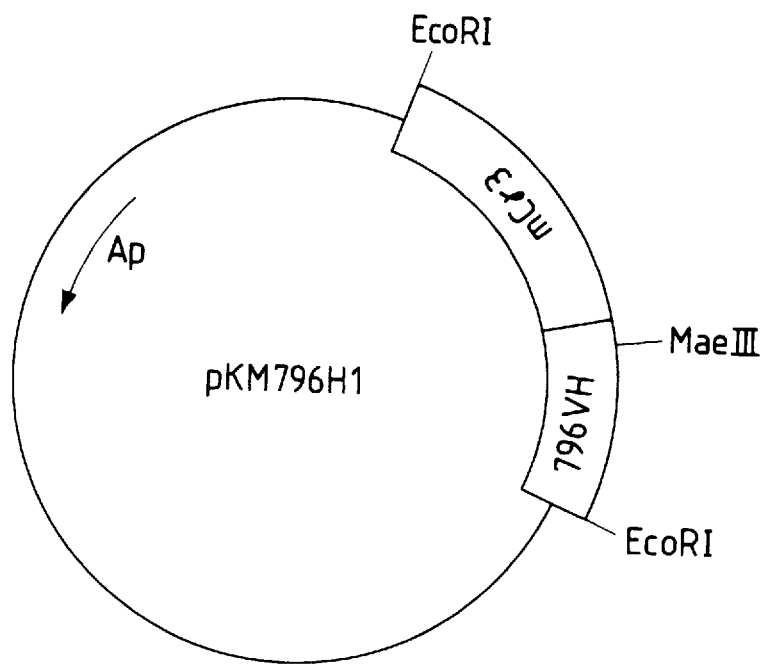
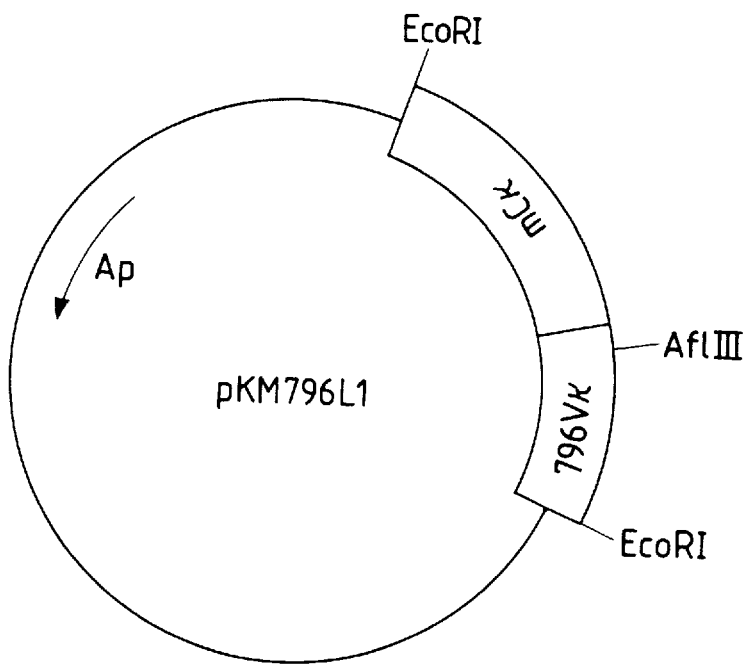

FIG. 2
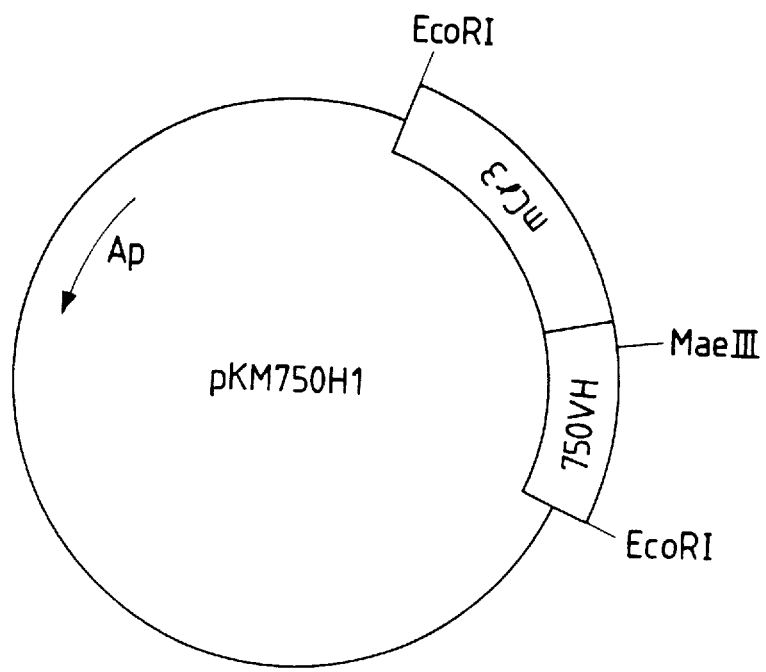
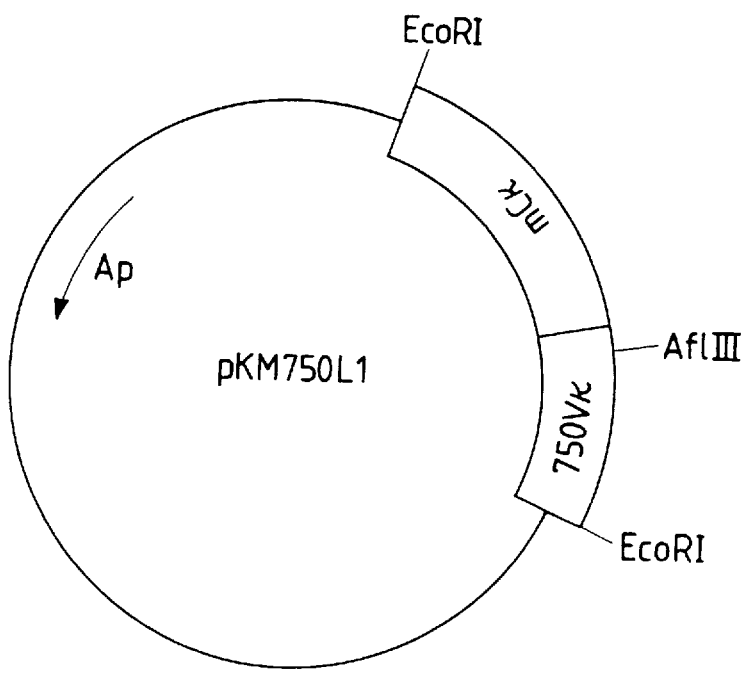

FIG. 3
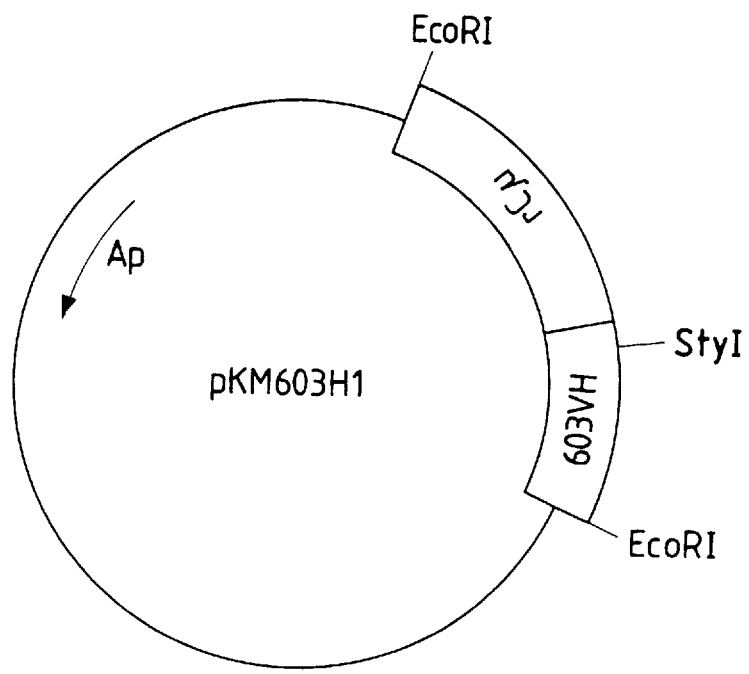
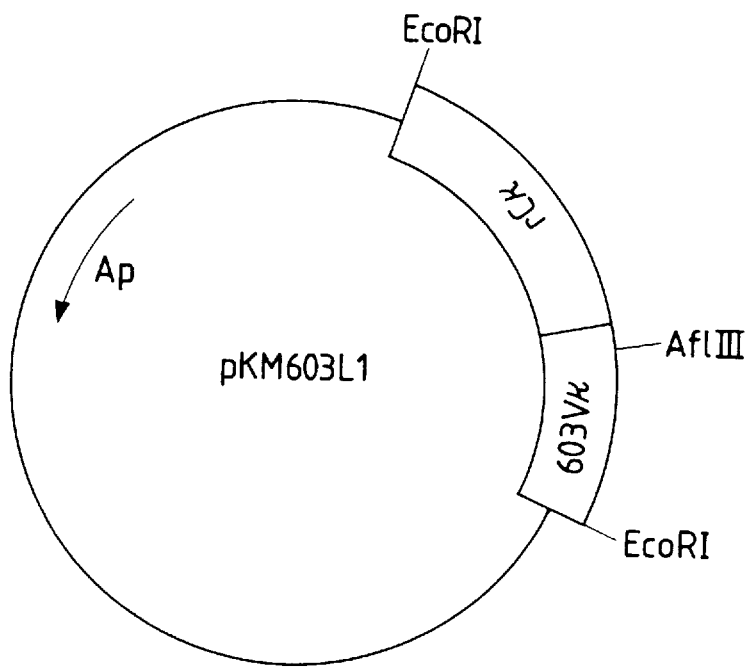

FIG. 12
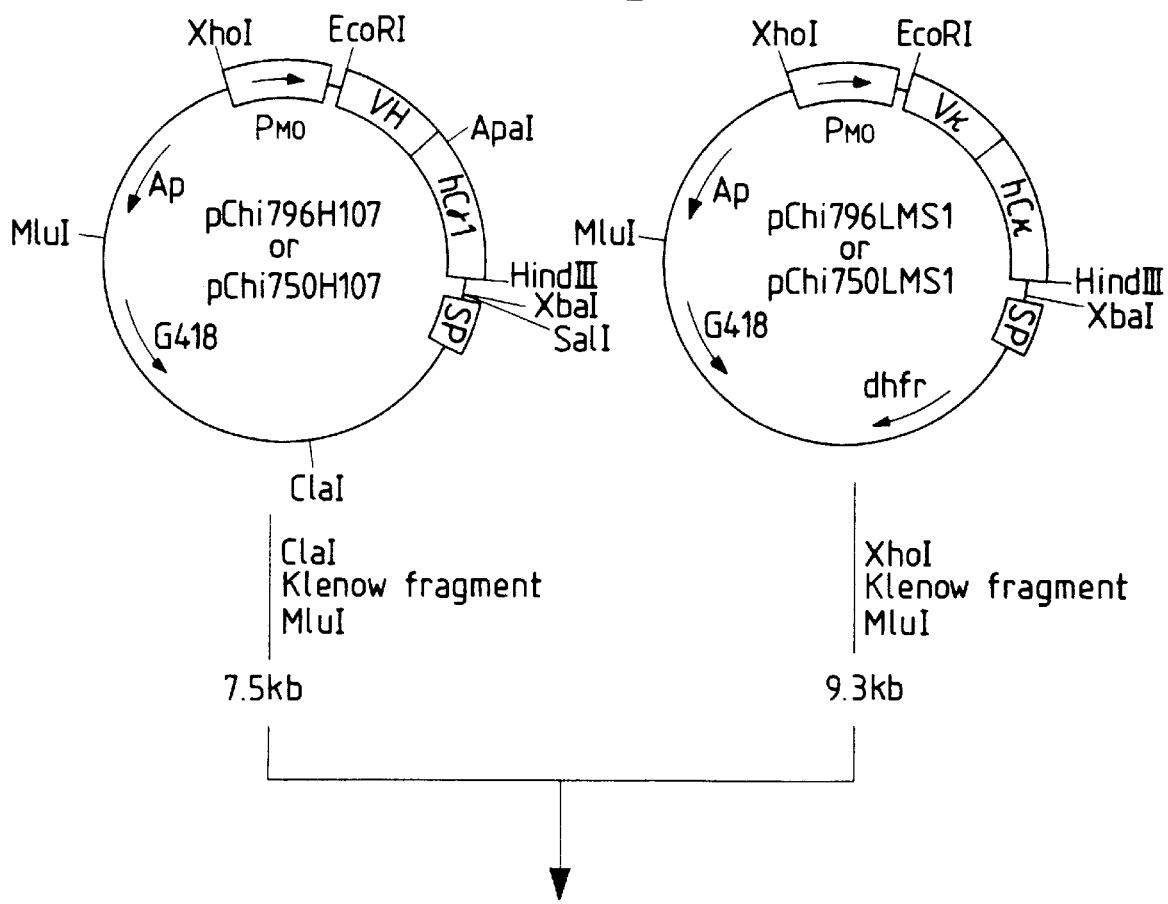
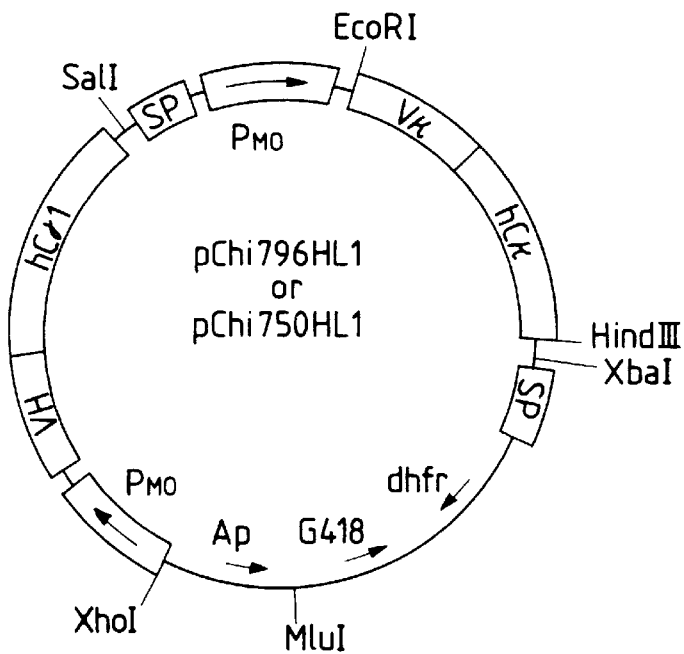

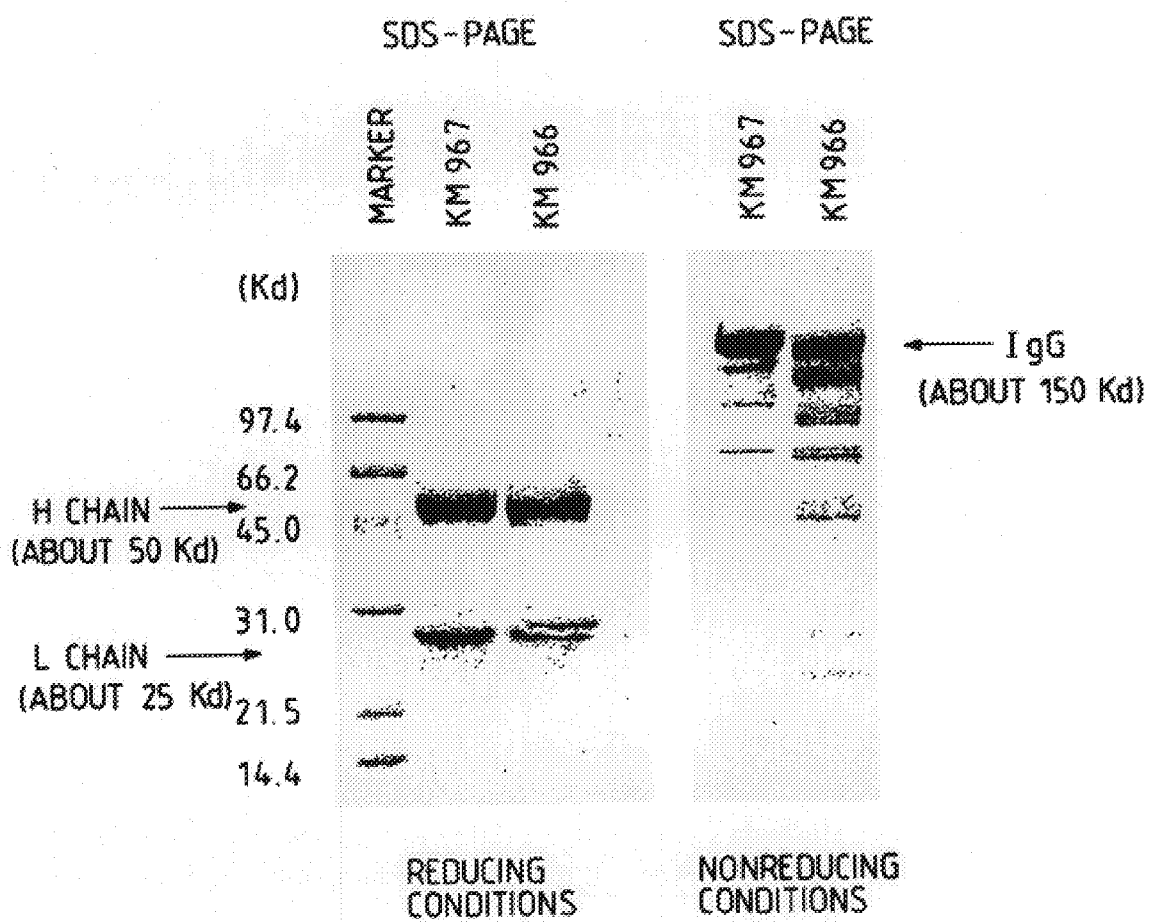

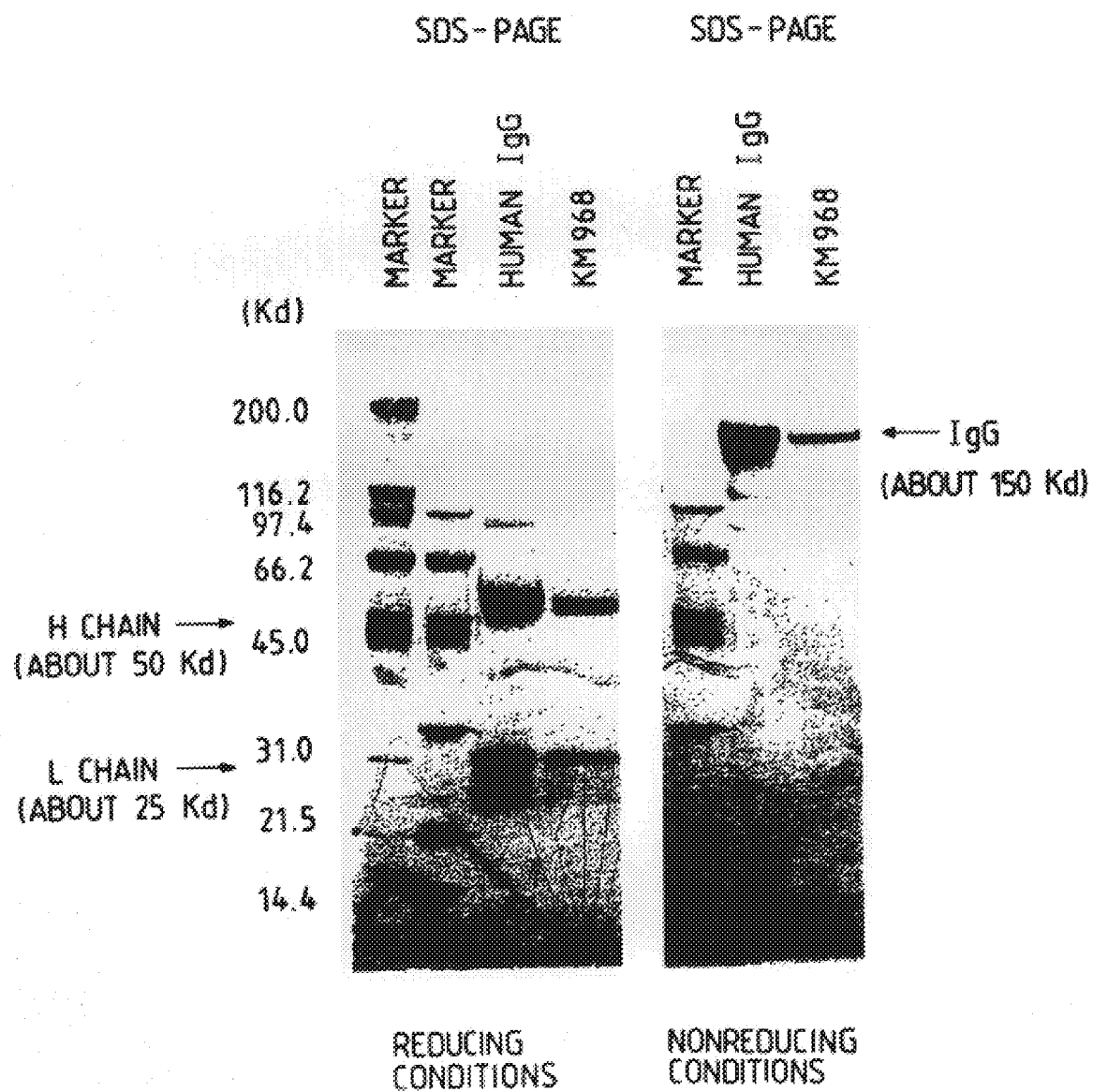

FIG. 32
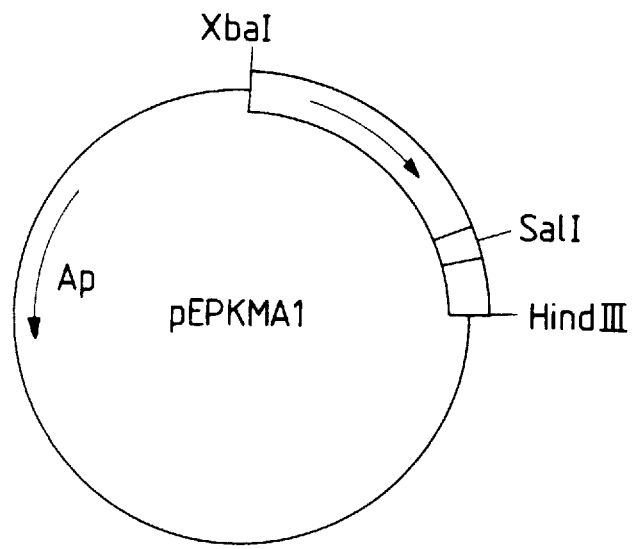
Xbal
Klenow fragment
Xhol linker pCCTCGAGG
            GGAGCTCCp
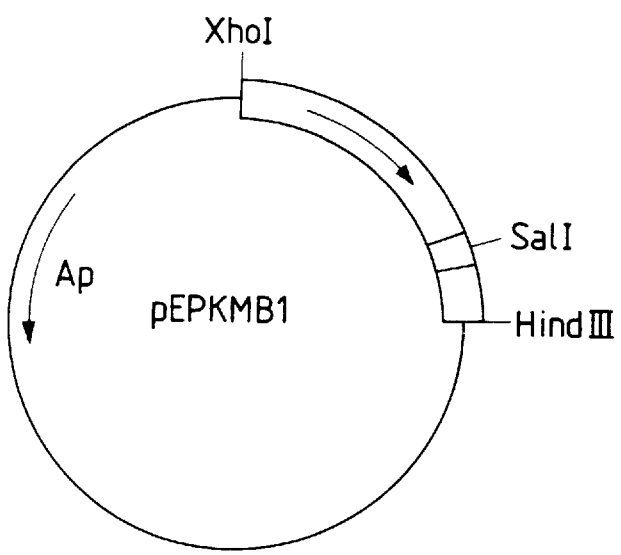

FIG. 34
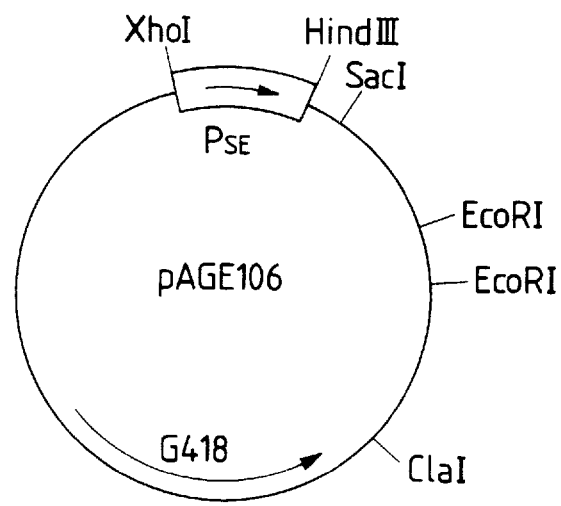
↓ EcoRI
SacI
Klenow fragment
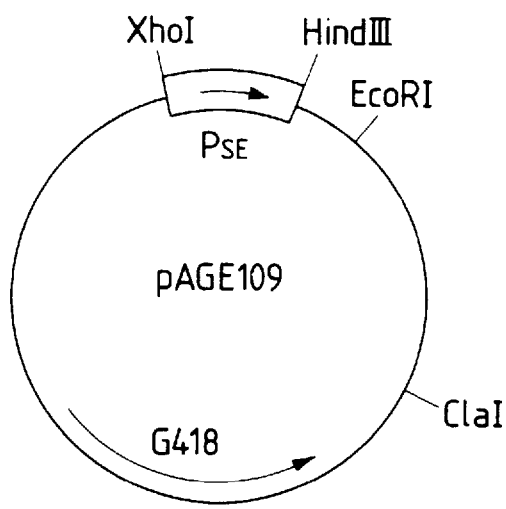

FIG. 38
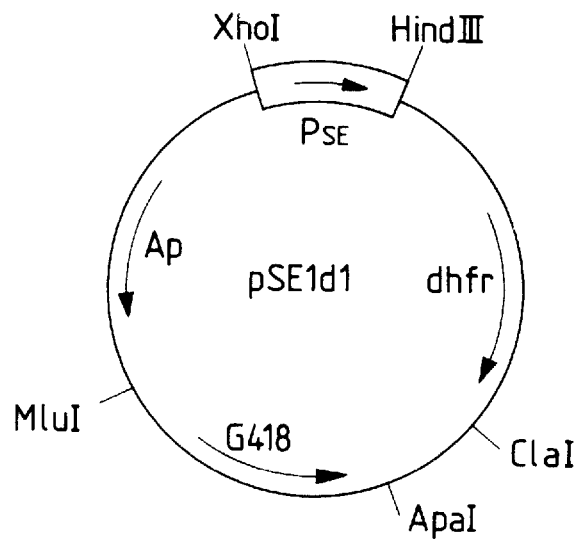
HindIII
Klenow fragment
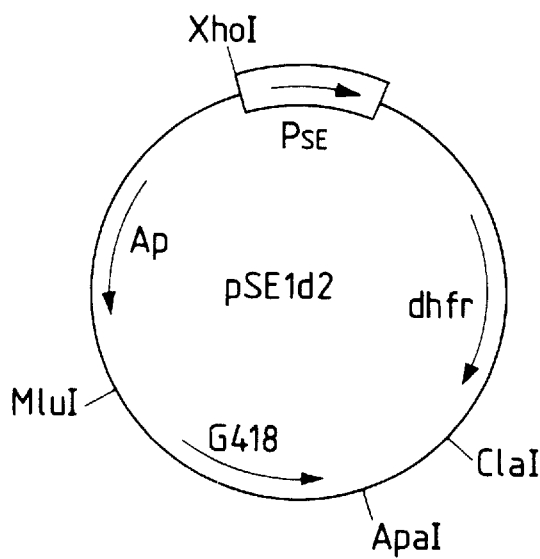

FIG. 40
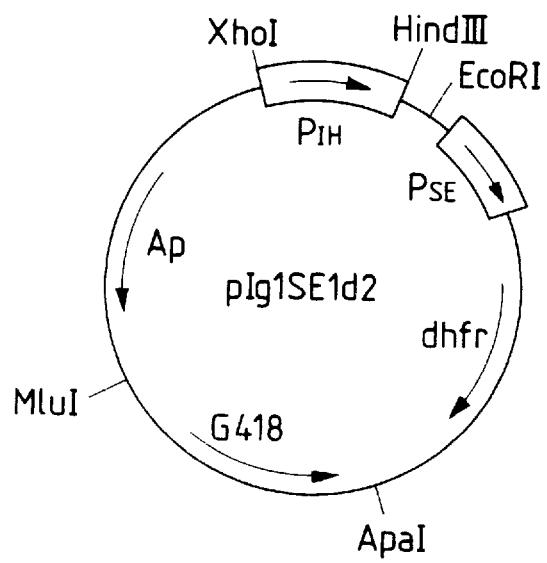
ApaI
Klenow fragment
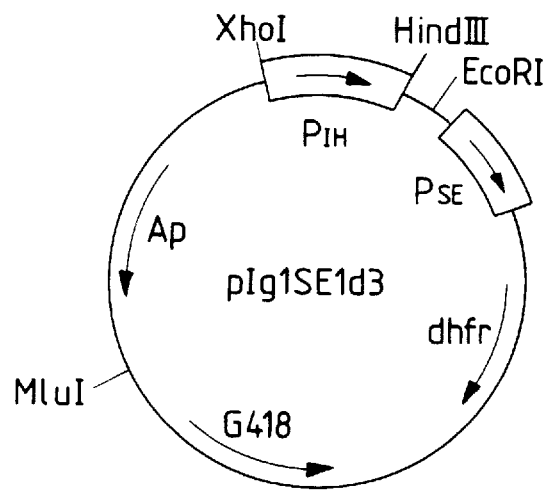

FIG. 42
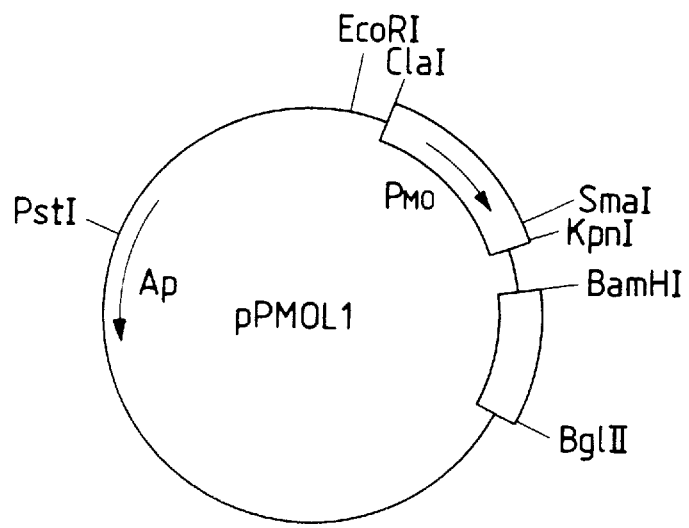
ClaI
Klenow fragment
XhoI linker pCCTCGAGG
            GGAGCTCCp
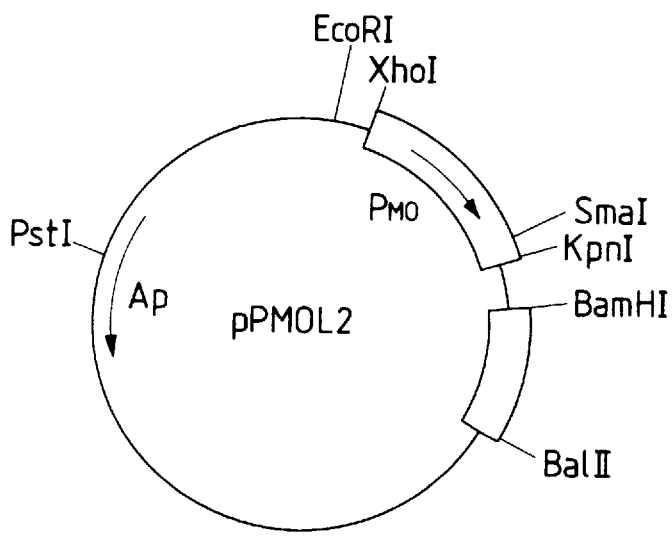

FIG. 43
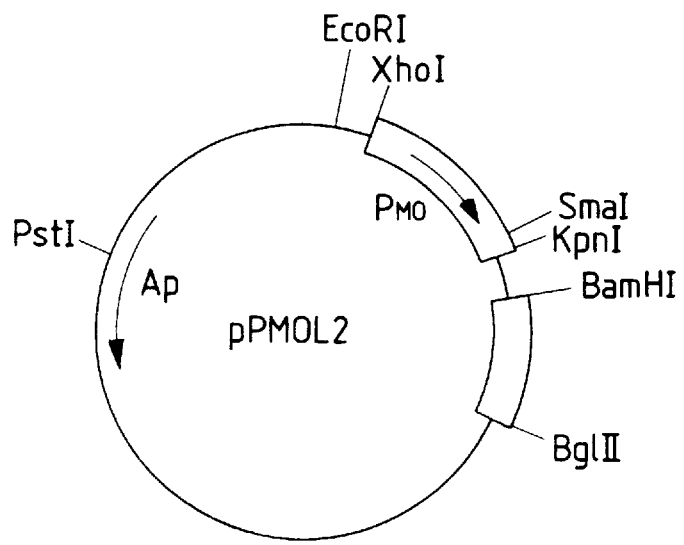
SmaI
EcoRI linker pGGAATTCC
              CCTTAAGGp
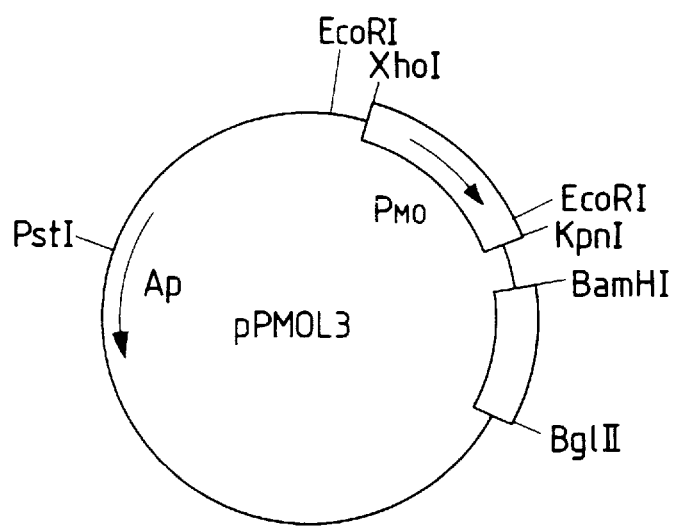

FIG. 45
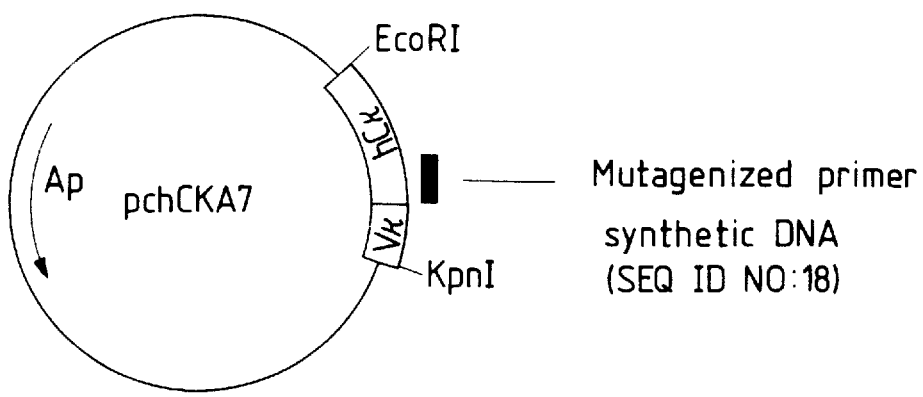
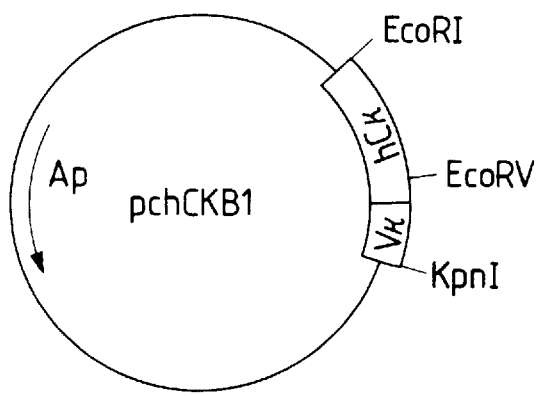

FIG. 46
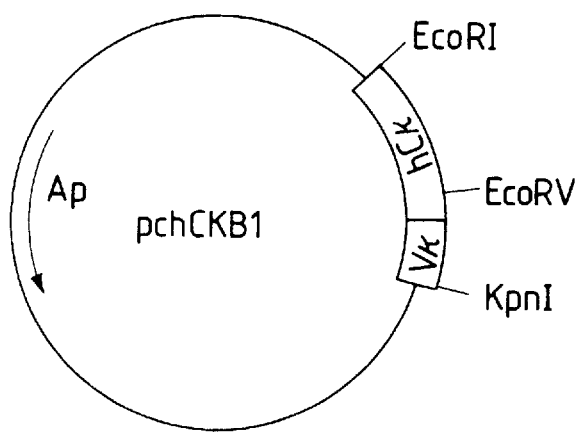
EcoRI
Klenow fragment
HindIII linker pCAAGCTTG
              GTTCGAACp
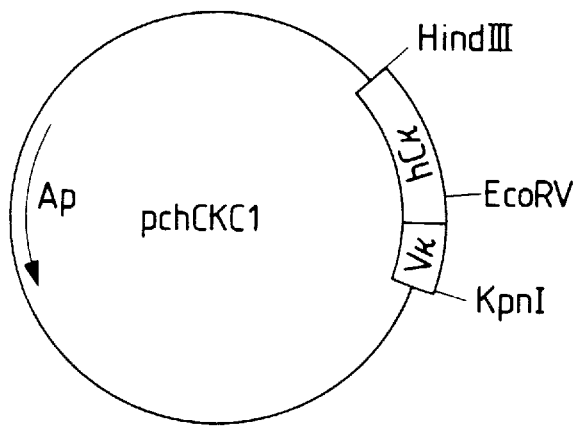

FIG. 57
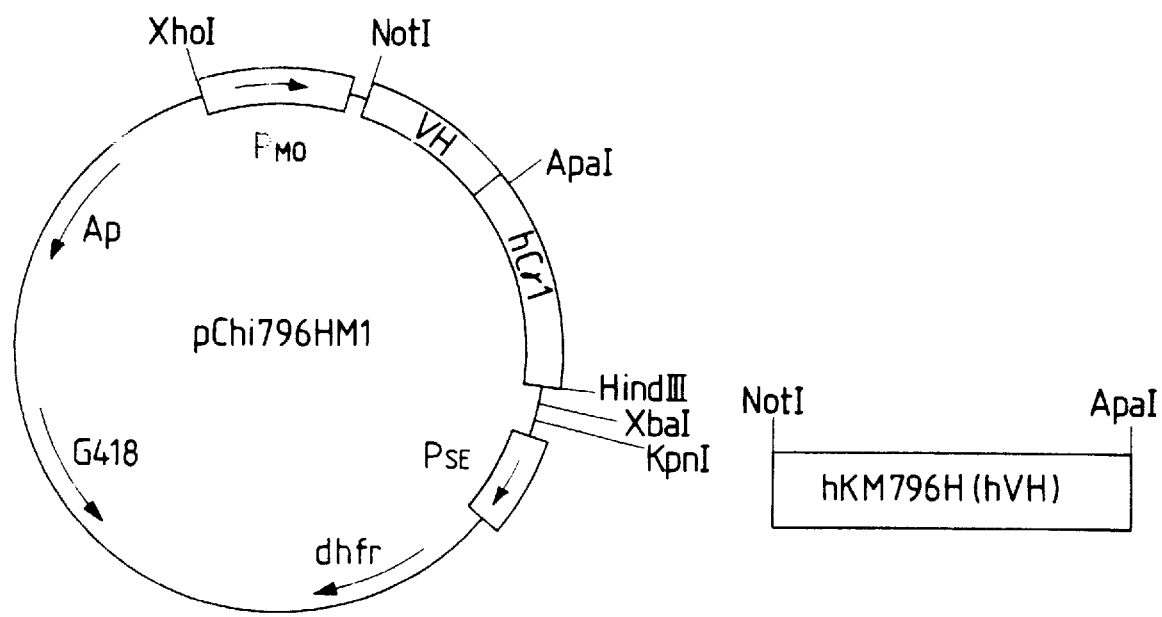
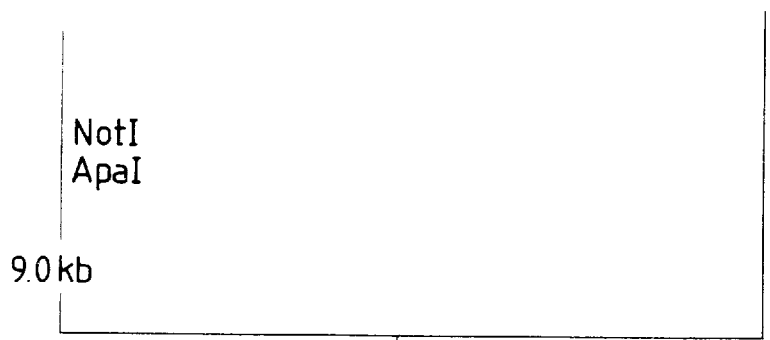
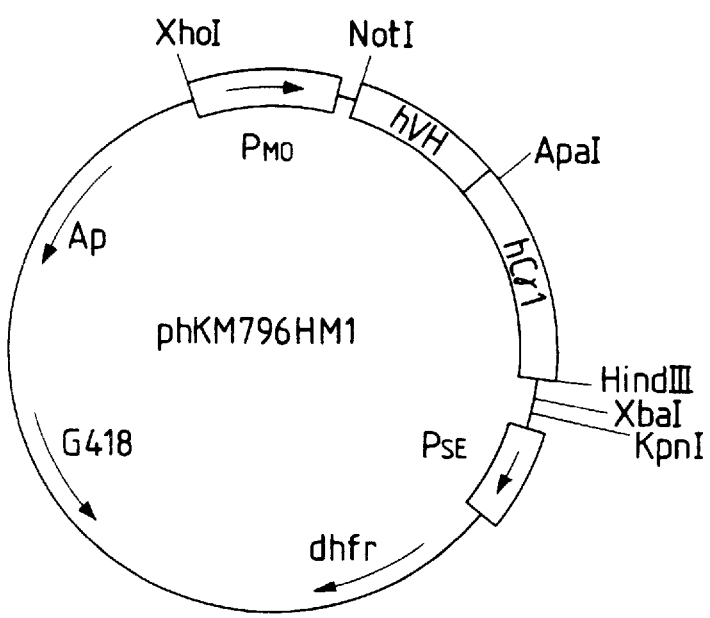

FIG. 59
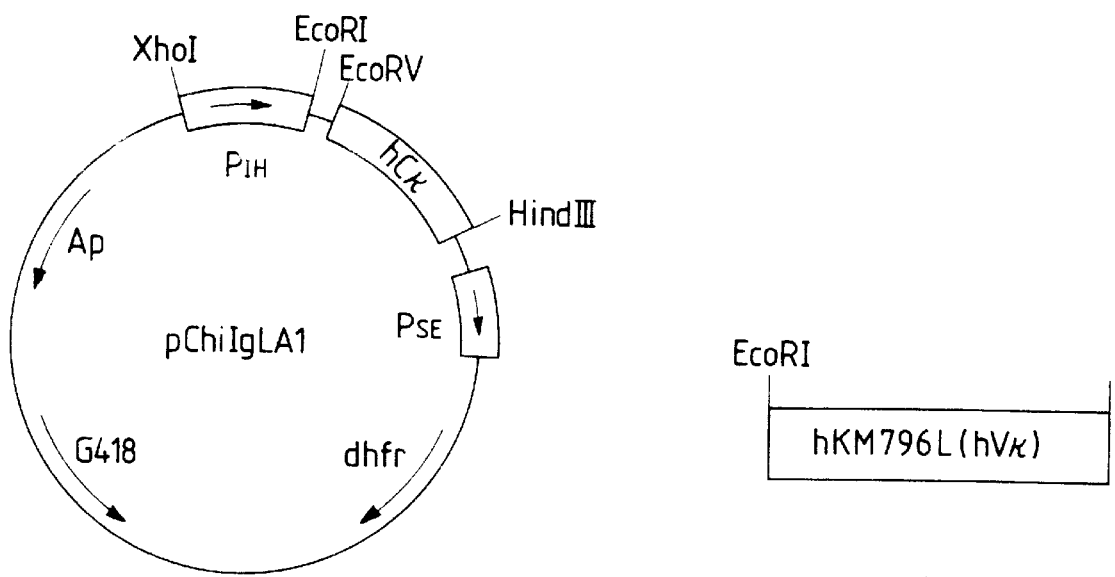
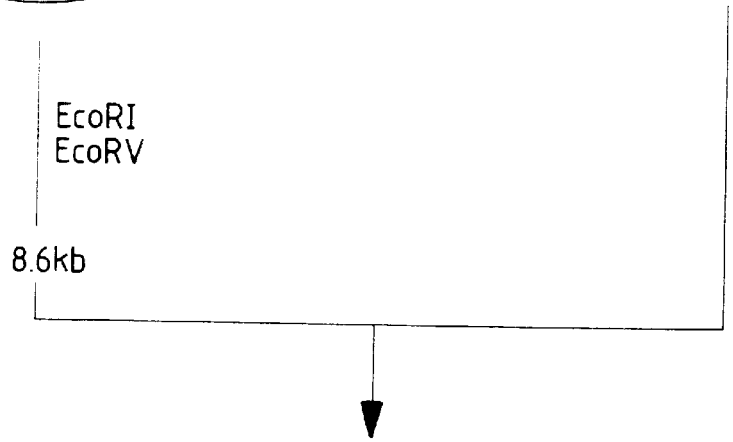
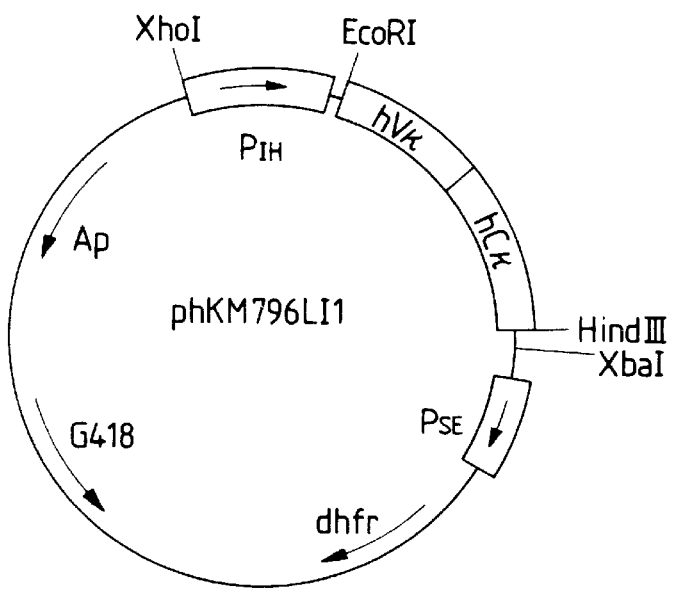

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 139 amino acids
        ( B ) TYPE: amino acid
        ( D ) TOPOLOGY: linear ( i i ) MOLECULE TYPE: protein ( i x ) FEATURE:
        ( A ) NAME/KEY: sig_peptide
        ( B ) LOCATION: -19..-1
        ( C ) IDENTIFICATION METHOD: BY SIMILARITY
            WITH KNOWN SEQUENCE OR TO AN
            ESTABLISHED CONSENSUS ( i x ) FEATURE:
        ( A ) NAME/KEY: domain
        ( B ) LOCATION: 31..35
        ( C ) IDENTIFICATION METHOD: BY SIMILARITY
            WITH KNOWN SEQUENCE OR TO AN ESTABLISHED CONSENSUS
( D ) OTHER INFORMATION: /product="HYPERVARIABLE REGION 1"

( i x ) FEATURE:
    ( A ) NAME/KEY: domain
    ( B ) LOCATION: 50..66
    ( C ) IDENTIFICATION METHOD: BY SIMILARITY
        WITH KNOWN SEQUENCE OR TO AN ESTABLISHED
        CONSENSUS
    ( D ) OTHER INFORMATION: /product="HYPERVARIABLE REGION 2"

( i x ) FEATURE:
    ( A ) NAME/KEY: domain
    ( B ) LOCATION: 99..109
    ( C ) IDENTIFICATION METHOD: BY SIMILARITY
        WITH KNOWN SEQUENCE OR TO AN ESTABLISHED
        CONSENSUS
    ( D ) OTHER INFORMATION: /product="HYPERVARIABLE REGION 3"

( x i ) SEQUENCE DESCRIPTION: SEQ ID NO:1:

```
Met Gly Trp Ser Trp Ile Phe Leu Phe Leu Leu Ser Gly Thr Ala Gly
 1               5                  10                  15
Val Leu Ser Glu Val Gln Leu Gln Gln Ser Gly Pro Glu Leu Val Lys
                20                  25                  30
Pro Gly Ala Ser Val Lys Ile Ser Cys Lys Ala Ser Gly Tyr Thr Phe
            35                  40                  45
Thr Asp Tyr Asn Met Asp Trp Val Lys Gln Ser His Gly Lys Ser Leu
        50                  55                  60
Glu Trp Ile Gly Tyr Ile Tyr Pro Asn Asn Gly Gly Thr Gly Tyr Asn
 65                 70                  75                  80
Gln Lys Phe Lys Ser Lys Ala Thr Leu Thr Val Asp Lys Ser Ser Ser
                85                  90                  95
Thr Ala Tyr Met Glu Leu His Ser Leu Thr Ser Glu Asp Ser Ala Val
            100                 105                 110
Tyr Tyr Cys Ala Thr Tyr Gly His Tyr Tyr Gly Tyr Met Phe Ala Tyr
        115                 120                 125
Trp Gly Gln Gly Thr Leu Val Thr Val Ser Ala
        130                 135
```

( 2 ) INFORMATION FOR SEQ ID NO:2:

( i ) SEQUENCE CHARACTERISTICS:
        ( A ) LENGTH: 129 amino acids
        ( B ) TYPE: amino acid
        ( D ) TOPOLOGY: linear ( i i ) MOLECULE TYPE: protein ( i x ) FEATURE:
        ( A ) NAME/KEY: sig_peptide
        ( B ) LOCATION: -22..-1
        ( C ) IDENTIFICATION METHOD: BY SIMILARITY
            WITH KNOWN SEQUENCE TO TO AN ESTABLISHED
            CONSENSUS ( i x ) FEATURE:
        ( A ) NAME/KEY: domain
        ( B ) LOCATION: 24..33
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 1"

( i x ) FEATURE:
        ( A ) NAME/KEY: domain
        ( B ) LOCATION: 49..55
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 2"

( i x ) FEATURE:
        ( A ) NAME/KEY: domain
        ( B ) LOCATION: 88..96
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 3"

( x i ) SEQUENCE DESCRIPTION: SEQ ID NO:2:

```
Met  His  Phe  Gln  Val  Gln  Ile  Phe  Ser  Phe  Leu  Leu  Ile  Ser  Ala  Ser
 1                  5                        10                      15

Val  Ile  Met  Ser  Arg  Gly  Gln  Ile  Val  Leu  Thr  Gln  Ser  Pro  Ala  Ile
              20                       25                      30

Met  Ser  Ala  Ser  Pro  Gly  Glu  Lys  Val  Thr  Ile  Thr  Cys  Ser  Ala  Ser
          35                       40                      45

Ser  Ser  Val  Ser  Tyr  Met  His  Trp  Phe  Gln  Gln  Lys  Pro  Gly  Thr  Ser
     50                       55                      60

Pro  Lys  Leu  Trp  Ile  Tyr  Ser  Thr  Ser  Asn  Leu  Ala  Ser  Gly  Val  Pro
65                       70                      75                        80

Ala  Arg  Phe  Ser  Gly  Ser  Gly  Ser  Gly  Thr  Ser  Tyr  Ser  Leu  Thr  Ile
                    85                       90                      95

Ser  Arg  Met  Glu  Ala  Glu  Asp  Ala  Ala  Thr  Tyr  Tyr  Cys  Gln  Gln  Arg
               100                      105                     110

Ser  Ser  Tyr  Pro  Tyr  Thr  Phe  Gly  Gly  Gly  Thr  Lys  Leu  Glu  Ile  Lys
              115                      120                     125

Arg
```

( 2 ) INFORMATION FOR SEQ ID NO:3:

( i ) SEQUENCE CHARACTERISTICS:
        ( A ) LENGTH: 137 amino acids
        ( B ) TYPE: amino acids
        ( D ) TOPOLOGY: linear ( i i ) MOLECULE TYPE: protein ( i x ) FEATURE:
        ( A ) NAME/KEY: sig_peptide
        ( B ) LOCATION: -19..-1
        ( C ) IDENTIFICATION METHOD: BY SIMILARITY
            WITH KNOWN SEQUENCE OR TO AN ESTABLISHED
            CONSENSUS ( i x ) FEATURE:
        ( A ) NAME/KEY: domain
        ( B ) LOCATION: 31..35
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 1"

( i x ) FEATURE:
        ( A ) NAME/KEY: domain
        ( B ) LOCATION: 55..66
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 2"

( i x ) FEATURE:
        ( A ) NAME/KEY: domain
        ( B ) LOCATION: 99..107
        ( C ) IDENTIFICATION METHOD: BY SIMILARITY
            WITH KNOWN SEQUENCE OR TO AN ESTABLISEHD
            CONSENSUS
        ( D ) OTHER INFORMATION: /product="HYPERVARIABLE REGION 3"

( x i ) SEQUENCE DESCRIPTION: SEQ ID NO:3:

| Met | Gly | Trp | Ser | Trp | Ile | Phe | Leu | Phe | Leu | Leu | Ser | Gly | Thr | Ala | Gly |
|---|---|---|---|---|---|---|---|---|---|---|---|---|---|---|---|
| 1 | | | | 5 | | | | | 10 | | | | | 15 | |

| Val | Leu | Ser | Glu | Val | Gln | Leu | Gln | Gln | Ser | Gly | Pro | Glu | Leu | Val | Lys |
|---|---|---|---|---|---|---|---|---|---|---|---|---|---|---|---|
| | | | 20 | | | | | 25 | | | | | 30 | | |

| Pro | Gly | Ala | Ser | Val | Lys | Ile | Ser | Cys | Lys | Ala | Ser | Gly | Tyr | Thr | Phe |
|---|---|---|---|---|---|---|---|---|---|---|---|---|---|---|---|
| | | 35 | | | | | 40 | | | | | 45 | | | |

| Thr | Asp | Tyr | Asn | Met | Asp | Trp | Val | Lys | Gln | Ser | His | Gly | Lys | Ser | Leu |
|---|---|---|---|---|---|---|---|---|---|---|---|---|---|---|---|
| | 50 | | | | | 55 | | | | | 60 | | | | |

| Glu | Trp | Ile | Gly | Tyr | Ile | Tyr | Pro | Asn | Asn | Gly | Gly | Thr | Gly | Tyr | Asn |
|---|---|---|---|---|---|---|---|---|---|---|---|---|---|---|---|
| 65 | | | | | 70 | | | | | 75 | | | | | 80 |

| Gln | Lys | Phe | Lys | Ser | Lys | Ala | Thr | Leu | Thr | Val | Asp | Lys | Ser | Ser | Ser |
|---|---|---|---|---|---|---|---|---|---|---|---|---|---|---|---|
| | | | | 85 | | | | | 90 | | | | | 95 | |

| Thr | Ala | Tyr | Met | Glu | Leu | His | Ser | Leu | Thr | Ser | Glu | Asp | Ser | Ala | Val |
|---|---|---|---|---|---|---|---|---|---|---|---|---|---|---|---|
| | | | 100 | | | | | 105 | | | | | 110 | | |

| Tyr | Tyr | Cys | Ala | Arg | Ala | Gly | Arg | Tyr | Tyr | Tyr | Ala | Trp | Asp | Trp | Gly |
|---|---|---|---|---|---|---|---|---|---|---|---|---|---|---|---|
| | | 115 | | | | | 120 | | | | | 125 | | | |

| Gln | Gly | Thr | Leu | Val | Thr | Val | Ser | Ala |
|---|---|---|---|---|---|---|---|---|
| | 130 | | | | | 135 | | |

(2) INFORMATION FOR SEQ ID NO:4:

(i) SEQUENCE CHARACTERISTICS:
        (A) LENGTH: 405 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: sig_peptide
        (B) LOCATION: 10..66
        (C) IDENTIFICATION METHOD: BY SIMILARITY
            WITH KNOWN SEQUENCE OR TO AN ESTABLISHED
            CONSENSUS (ix) FEATURE:
        (A) NAME/KEY: domain
        (B) LOCATION: 157..171
        (C) IDENTIFICATION METHOD: BY SIMILARITY
            WITH KNOWN SEQUENCE OR TO AN ESTABLISHED
            CONSENSUS
        (D) OTHER INFORMATION: /product="HYPERVARIABLE REGION 1"

(ix) FEATURE:
        (A) NAME/KEY: domain
        (B) LOCATION: 214..261
        (C) IDENTIFICATION METHOD: BY SIMILARITY
            WITH KNOWN SEQUENCE OR TO AN ESTABLISHED
            CONSENSUS
        (D) OTHER INFORMATION: /product="HYPERVARIABLE REGION 2"

(ix) FEATURE:
        (A) NAME/KEY: domain
        (B) LOCATION: 358..369
        (C) IDENTIFICATION METHOD: BY SIMILARITY
            WITH KNOWN SEQUENCE OR TO AN ESTABLISHED
            CONSENSUS
        (D) OTHER INFORMATION: /product="HYPERVARIABLE REGION 3"

(xi) SEQUENCE DESCRIPTION: SEQ ID NO:4:

```
CATCACAGC ATG GCT GTC CTG GTG CTG TTG CTC TGC CTG GTG ACA TTT            48
          Met Ala Val Leu Val Leu Leu Leu Cys Leu Val Thr Phe
              -15                                  -10

CCA AGC TGT GTC CTG TCC CAA GTG CAG CTG AAG GAG TCA GGA CCT GGT          96
Pro Ser Cys Val Leu Ser Gln Val Gln Leu Lys Glu Ser Gly Pro Gly
    -5                    1               5                   10

CTG GTG CAG CCC TCA CAG ACC CTG TCC CTC ACC TGC ACT GTC TCT GGG         144
```

| | | | | | | | | | | | | | | | |
|---|---|---|---|---|---|---|---|---|---|---|---|---|---|---|---|
| Leu | Val | Gln | Pro | Ser | Gln | Thr | Leu | Ser | Leu | Thr | Cys | Thr | Val | Ser | Gly |
| | | | | 15 | | | | | 20 | | | | | 25 | |

| TTC | TCA | TTA | ACC | AGC | TAT | ACT | GTA | AGC | TGG | GTT | CGC | CAG | CCT | CCA | GGA | 192 |
|---|---|---|---|---|---|---|---|---|---|---|---|---|---|---|---|---|
| Phe | Ser | Leu | Thr | Ser | Tyr | Thr | Val | Ser | Trp | Val | Arg | Gln | Pro | Pro | Gly | |
| | | | 30 | | | | | 35 | | | | | 40 | | | |

| AAG | GGT | CTG | GAG | TGG | ATT | GCA | GCA | ATA | TCA | AGT | GGT | GGA | AGC | ACA | TAT | 240 |
|---|---|---|---|---|---|---|---|---|---|---|---|---|---|---|---|---|
| Lys | Gly | Leu | Glu | Trp | Ile | Ala | Ala | Ile | Ser | Ser | Gly | Gly | Ser | Thr | Tyr | |
| | | | 45 | | | | | 50 | | | | | 55 | | | |

| TAT | AAT | TCA | GCT | CTC | AAA | TCA | CGA | CTG | AGC | ATC | AGC | AGG | GAC | ACC | TCC | 288 |
|---|---|---|---|---|---|---|---|---|---|---|---|---|---|---|---|---|
| Tyr | Asn | Ser | Ala | Leu | Lys | Ser | Arg | Leu | Ser | Ile | Ser | Arg | Asp | Thr | Ser | |
| | 60 | | | | | 85 | | | | | 70 | | | | | |

| AAG | AGC | CAA | GTT | TTC | TTA | AAA | ATG | AAC | AGT | CTG | CAA | ACT | GAA | GAC | ACA | 336 |
|---|---|---|---|---|---|---|---|---|---|---|---|---|---|---|---|---|
| Lys | Ser | Gln | Val | Phe | Leu | Lys | Met | Asn | Ser | Leu | Gln | Thr | Glu | Asp | Thr | |
| 75 | | | | | 80 | | | | | 85 | | | | | 90 | |

| GCC | ATG | TAC | TTC | TGT | GCC | CCT | TCT | GAG | GGG | GCC | TGG | GGC | CAA | GGA | GTC | 384 |
|---|---|---|---|---|---|---|---|---|---|---|---|---|---|---|---|---|
| Ala | Met | Tyr | Phe | Cys | Ala | Pro | Ser | Glu | Gly | Ala | Trp | Gly | Gln | Gly | Val | |
| | | | | 95 | | | | | 100 | | | | | 105 | | |

| ATG | GTC | ACA | GTC | TCC | TCA | GAG | | | | | | | | | | 405 |
|---|---|---|---|---|---|---|---|---|---|---|---|---|---|---|---|---|
| Met | Val | Thr | Val | Ser | Ser | Glu | | | | | | | | | | |
| | | | 110 | | | | | | | | | | | | | |

( 2 ) INFORMATION FOR SEQ ID NO:5:

( i ) SEQUENCE CHARACTERISTICS:
        ( A ) LENGTH: 402 base pairs
        ( B ) TYPE: nucleic acid
        ( C ) STRANDEDNESS: double
        ( D ) TOPOLOGY: linear ( i i ) MOLECULE TYPE: cDNA to mRNA ( i x ) FEATURE:
        ( A ) NAME/KEY: sig_peptide
        ( B ) LOCATION: 19..78
        ( C ) IDENTIFICATION METHOD: BY SIMILARITY
            WITH KNOWN SEQUENCE OR TO AN ESTABLISHED
            CONSENSUS ( i x ) FEATURE:
        ( A ) NAME/KEY: domain
        ( B ) LOCATION: 148..180
        ( C ) IDENTIFICATION METHOD: BY SIMILARITY
            WITH KNOWN SEQUENCE OR TO AN ESTABILSHED
            CONSENSUS
        ( D ) OTHER INFORMATION: /product="HYPERVARIABLE REGION 1"

( i x ) FEATURE:
        ( A ) NAME/KEY: domain
        ( B ) LOCATION: 226..246
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 2"

( i x ) FEATURE:
        ( A ) NAME/KEY: domain
        ( B ) LOCATION: 343..369
        ( C ) IDENTIFICATION METHOD: BY SIMILARITY
            WITH KNOWN SEQUENCE OR TO AN ESTABLISHED
            CONSENSUS
        ( D ) OTHER INFORMATION: /product="HYPERVARIABLE REGION 3"

( x i ) SEQUENCE DESCRIPTION: SEQ ID NO:5:

| ACAGGACACA | GGTCAGTC | ATG | ATG | GCT | CCA | GTC | CAG | CTC | TTA | GGG | CTG | CTG | 51 |
|---|---|---|---|---|---|---|---|---|---|---|---|---|---|
| | | Met | Met | Ala | Pro | Val | Gln | Leu | Leu | Gly | Leu | Leu | |
| | | -20 | | | | -15 | | | | | | -10 | |

| CTG | ATT | TGG | CTC | CCA | GCC | ATG | AGA | TGT | GAC | ATC | CAG | ATG | ACC | CAG | TCT | 99 |
|---|---|---|---|---|---|---|---|---|---|---|---|---|---|---|---|---|
| Leu | Ile | Trp | Leu | Pro | Ala | Met | Arg | Cys | Asp | Ile | Gln | Met | Thr | Gln | Ser | |
| | | | | -5 | | | | | 1 | | | | | 5 | | |

| CCT | TCA | TTC | CTG | TCT | GCA | TCT | GTG | GGA | GAC | AGA | GTC | ACT | ATC | AAC | TGC | 147 |

```
Pro  Ser  Phe  Leu  Ser  Ala  Ser  Val  Gly  Asp  Arg  Val  Thr  Ile  Asn  Cys
          10                  15                       20

AAA  GCA  AGT  CAG  AAT  ATT  AAC  AAG  TAC  TTA  AAC  TGG  TAT  CAG  CAA  AAG      195
Lys  Ala  Ser  Gln  Asn  Ile  Asn  Lys  Tyr  Leu  Asn  Trp  Tyr  Gln  Gln  Lys
     25                  30                       35

CTT  GGA  GAA  GCT  CCC  AAA  CGC  CTG  ATA  TAT  AAT  ACA  AAC  AAT  TTG  CAA      243
Leu  Gly  Glu  Ala  Pro  Lys  Arg  Leu  Ile  Tyr  Asn  Thr  Asn  Asn  Leu  Gln
40                       45                  50                            55

ACG  GGC  ATT  CCA  TCA  AGG  TTC  AGT  GGC  AGT  GGA  TCT  GGT  ACA  GAT  TAC      291
Thr  Gly  Ile  Pro  Ser  Arg  Phe  Ser  Gly  Ser  Gly  Ser  Gly  Thr  Asp  Tyr
               60                       65                       70

ACA  CTC  ACC  ATC  AGC  AGC  CTG  CAG  CCT  GAA  GAT  TTT  GCC  ACA  TAT  TTC      339
Thr  Leu  Thr  Ile  Ser  Ser  Leu  Gln  Pro  Glu  Asp  Phe  Ala  Thr  Tyr  Phe
               75                       80                  85

TGC  TTG  CAG  CAT  AAT  AGT  TTT  CCG  AAC  ACG  TTT  GGA  GCT  GGG  ACC  AAG      387
Cys  Leu  Gln  His  Asn  Ser  Phe  Pro  Asn  Thr  Phe  Gly  Ala  Gly  Thr  Lys
          90                       95                  100

CTG  GAG  CTG  AAA  CGG                                                              402
Leu  Glu  Leu  Lys  Arg
105
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Asp  Tyr  Asn  Met  Asp
1                    5
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Tyr  Ile  Tyr  Pro  Asn  Asn  Gly  Gly  Thr  Gly  Tyr  Asn  Gln  Lys  Phe  Lys
1                   5                        10                       15
Ser
```

( 2 ) INFORMATION FOR SEQ ID NO:8:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Tyr  Gly  His  Tyr  Tyr  Gly  Tyr  Met  Phe  Ala  Tyr
1                   5                        10
```

( 2 ) INFORMATION FOR SEQ ID NO:9:

( i ) SEQUENCE CHARACTERISTICS:
        ( A ) LENGTH: 10 amino acids
        ( B ) TYPE: amino acid ( D ) TOPOLOGY: linear ( i i ) MOLECULE TYPE: peptide ( x i ) SEQUENCE DESCRIPTION: SEQ ID NO:9:

Ser  Ala  Ser  Ser  Ser  Val  Ser  Tyr  Met  His
 1                    5                         10

( 2 ) INFORMATION FOR SEQ ID NO:10:

( i ) SEQUENCE CHARACTERISTICS:
( A ) LENGTH: 7 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Ser  Thr  Ser  Asn  Leu  Ala  Ser
 1                    5

( 2 ) INFORMATION FOR SEQ ID NO:11:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Gln  Gln  Arg  Ser  Ser  Tyr  Pro  Tyr  Thr
 1                    5

( 2 ) INFORMATION FOR SEQ ID NO:12:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:12:

Val  Thr  Val  Ser  Ala  Ala  Ser  Thr  Lys  Gly
 1                    5                         10

( 2 ) INFORMATION FOR SEQ ID NO:13:

( i ) SEQUENCE CHARACTERISTICS:
( A ) LENGTH: 51 base pairs
( B ) TYPE: nucleic acid
( C ) STRANDEDNESS: double
( D ) TOPOLOGY: linear ( i i ) MOLECULE TYPE: other nucleic acid, synthetic DNA ( x i ) SEQUENCE DESCRIPTION: SEQ ID NO:13:

```
C  ACG  TTC  GGA  GGG  GGG  ACC  AAG  CTG  GAA  ATA  AAA  CGA  ACT  GTG  GCT      46
   Thr  Phe  Gly  Gly  Gly  Thr  Lys  Leu  Glu  Ile  Lys  Arg  Thr  Val  Ala
    1              5                        10                       15

GCA  CC                                                                            51
Ala
```

( 2 ) INFORMATION FOR SEQ ID NO:14:

( i ) SEQUENCE CHARACTERISTICS:
( A ) LENGTH: 43 base pairs
( B ) TYPE: nucleic acid

```
            ( C ) STRANDEDNESS: double
            ( D ) TOPOLOGY: linear ( i i ) MOLECULE TYPE: other nucleic acid, synthetic DNA ( x i ) SEQUENCE DESCRIPTION: SEQ ID NO:14:
```

```
CAA  GGA  GTC  ATG  GTC  ACA  GTC  TCG  AGC  GCC  TCC  ACC  AAG  GGC          42
Gln  Gly  Val  Met  Val  Thr  Val  Ser  Ser  Ala  Ser  Thr  Lys  Gly
 1              5                        10

C                                                                              43
```

( 2 ) INFORMATION FOR SEQ ID NO:15:

```
        ( i ) SEQUENCE CHARACTERISTICS:
                ( A ) LENGTH: 51 base pairs
                ( B ) TYPE: nucleic acid
                ( C ) STRANDEDNESS: double
                ( D ) TOPOLOGY: linear ( i i ) MOLECULE TYPE: other nucleic acid, synthetic DNA ( x i ) SEQUENCE DESCRIPTION: SEQ ID NO:15:
```

```
C  ACG  TTT  GGA  GCT  GGT  ACC  AAG  CTT  GAG  CTC  AAA  CGA  ACT  GTG  GCT   46
   Thr  Phe  Gly  Ala  Gly  Thr  Lys  Leu  Glu  Leu  Lys  Arg  Thr  Val  Ala
    1              5                        10                       15

GCA  CC                                                                        51
Ala
```

( 2 ) INFORMATION FOR SEQ ID NO:16:

```
        ( i ) SEQUENCE CHARACTERISTICS:
                ( A ) LENGTH: 812 base pairs
                ( B ) TYPE: nucleic acid
                ( C ) STRANDEDNESS: double
                ( D ) TOPOLOGY: linear ( i i ) MOLECULE TYPE: DNA (genomic)

( v i ) ORIGINAL SOURCE:
                ( B ) STRAIN: HYBRIDOMA KM50

( i x ) FEATURE:
                ( A ) NAME/KEY: TATA_signal
                ( B ) LOCATION: 261..267

( x i ) SEQUENCE DESCRIPTION: SEQ ID NO:16:
```

```
AAAGTCAGAC  AACTTTGTAG  AGTAGGTTCT  ATCAATCCTA  CTGCAATCCA  ACATCACTGA          60

GGACAAATGT  TTATACTGAG  GAACCTGGTC  TTGTGTGATA  CGTACTTTCT  GTGGGAAGCA         120

GATACGCACT  CTCATGTGGC  TCCTGAATTT  CCCATCACAG  AATGATACAT  CTTGAGTCCT         180

AAAATTTAAG  TACACCATCA  GTGTCAGCAC  CTGGTGAGGA  AATGCAAATC  TCTCCTGGAT         240

CCACCCAACC  TTGGGTTGAA  AAGCCAAAGC  TGGGCCTGGG  TACTCACTGG  TGTGCAGCC          299

ATG  GAC  AGG  CTT  ACT  TCC  TCA  TTC  CTA  CTG  CTG  ATG  GTC  CCT  GCA      344
Met  Asp  Arg  Leu  Thr  Ser  Ser  Phe  Leu  Leu  Leu  Met  Val  Pro  Ala
         -15                      -10                       -5

TGTGAGTACC  AAAGCTTCCT  AAGTGATGAA  CTGTTCTATC  CTCACCTGTT  CAAACCTGAC         404

CTCCTCCCCT  TTGATTTCTC  CACAG AT GTC CTG TCT CAG GTT ACT CTG AAA               455
                              Tyr Val Leu Ser Gln Val Thr Leu Lys
                                                  1                5

GAA  TCT  GGC  CCT  GGG  ATA  TTG  CAG  CCC  TCC  CAG  ACC  CTC  AGT  CTG  ACT 503
Glu  Ser  Gly  Pro  Gly  Ile  Leu  Gln  Pro  Ser  Gln  Thr  Leu  Ser  Leu  Thr
                         10                       15                        20

TGC  TCT  TTC  TCT  GGG  TTT  TCA  CTG  AGC  ACT  TAT  GGT  ATG  TGT  GTG  GGC 551
Cys  Ser  Phe  Ser  Gly  Phe  Ser  Leu  Ser  Thr  Tyr  Gly  Met  Cys  Val  Gly
                 25                       30                       35
```

```
TGG  ATT  CGT  CAG  TCT  TCA  GGG  AAG  GGT  CTG  GAG  TGG  CTG  GCA  AAC  GTT            599
Trp  Ile  Arg  Gln  Ser  Ser  Gly  Lys  Gly  Leu  Glu  Trp  Leu  Ala  Asn  Val
          40                      45                     50

TGG  TGG  AGT  GAT  GCT  AAG  TAC  TAC  AAT  CCA  TCT  CTG  AAA  AAC  CGG  CTC            647
Trp  Trp  Ser  Asp  Ala  Lys  Tyr  Tyr  Asn  Pro  Ser  Leu  Lys  Asn  Arg  Leu
     55                       60                       65

ACA  ATC  TCC  AAG  GAC  ACC  TCC  AAC  AAC  CAA  GCA  TTC  CTC  AAG  ATC  ACC            695
Thr  Ile  Ser  Lys  Asp  Thr  Ser  Asn  Asn  Gln  Ala  Phe  Leu  Lys  Ile  Thr
70                            75                       80                      85

AAT  ATG  GAC  ACT  GCA  GAT  ACT  GCC  ATA  TAC  TAC  TGT  GCT  GGG  AGA  GGG            743
Asn  Met  Asp  Thr  Ala  Asp  Thr  Ala  Ile  Tyr  Tyr  Cys  Ala  Gly  Arg  Gly
                         90                      95                     100

GCT  ACG  GAG  GGT  ATA  GTG  AGC  TTT  GAT  TAC  TGG  GGC  CAC  GGA  GTC  ATG            791
Ala  Thr  Glu  Gly  Ile  Val  Ser  Phe  Asp  Tyr  Trp  Gly  His  Gly  Val  Met
               105                      110                     115

GTC  ACA  GTC  TCC  TCA  GGTAAG                                                            812
Val  Thr  Val  Ser  Ser
          120
```

( 2 ) INFORMATION FOR SEQ ID NO:17:

( i ) SEQUENCE CHARACTERISTICS:
        ( A ) LENGTH: 46 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:17:

```
AGCTGAATTC  GGGCCCGATA  TCAAGCTTGT  CGACTCTAGA  GGTACC                                     46
```

( 2 ) INFORMATION FOR SEQ ID NO:18:

( i ) SEQUENCE CHARACTERISTICS:
        ( A ) LENGTH: 29 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:18:

```
GATGAAGACA  GATATCGCAG  CCACAGTTC                                                          29
```

( 2 ) INFORMATION FOR SEQ ID NO:19:

( i ) SEQUENCE CHARACTERISTICS:
        ( A ) LENGTH: 408 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( B ) STRAIN: HYBRIDOMA KM-641

( i x ) FEATURE:
        ( A ) NAME/KEY: sig_peptide
        ( B ) LOCATION: 25..84
        ( C ) IDENTIFICATION METHOD: BY SIMILARITY
            WITH KNOWN SEQUENCE OR TO AN ESTABLISHED
            CONSENSUS ( x i ) SEQUENCE DESCRIPTION: SEQ ID NO:19:

```
AATTCGGCAC  GAGTCAGCCT  GGAC  ATG  ATG  TCC  TCT  GCT  CAG  TTC  CTT  GGT                  51
                              Met  Met  Ser  Ser  Ala  Gln  Phe  Leu  Gly
```

|  |  |  |  |  |  |  |  |  |  |  |  |  |  |  |  |
|---|---|---|---|---|---|---|---|---|---|---|---|---|---|---|---|
|  |  |  |  |  |  |  | -20 |  |  |  |  | -15 |  |  |  |
| CTC | CTG | TTG | CTC | TGT | TTT | CAA | GGT | ACC | AGA | TGT | GAT | ATC | CAG | ATG | ACA |
| Leu | Leu | Leu | Leu | Cys | Phe | Gln | Gly | Thr | Arg | Cys | Asp | Ile | Gln | Met | Thr |
|  | -10 |  |  |  |  | -5 |  |  |  |  | 1 |  |  |  | 5 |

99

| CAG | ACT | GCA | TCC | TCC | CTG | CCT | GCC | TCT | CTG | GGA | GAC | AGA | GTC | ACC | ATC |
|---|---|---|---|---|---|---|---|---|---|---|---|---|---|---|---|
| Gln | Thr | Ala | Ser | Ser | Leu | Pro | Ala | Ser | Leu | Gly | Asp | Arg | Val | Thr | Ile |
|  |  |  |  | 10 |  |  |  |  | 15 |  |  |  |  | 20 |  |

147

| AGT | TGC | AGT | GCA | AGT | CAG | GAC | ATT | AGT | AAT | TAT | TTA | AAC | TGG | TAT | CAA |
|---|---|---|---|---|---|---|---|---|---|---|---|---|---|---|---|
| Ser | Cys | Ser | Ala | Ser | Gln | Asp | Ile | Ser | Asn | Tyr | Leu | Asn | Trp | Tyr | Gln |
|  |  |  | 25 |  |  |  |  | 30 |  |  |  |  | 35 |  |  |

195

| CAG | AAA | CCA | GAT | GGA | ACT | GTT | AAA | CTC | CTG | ATC | TTT | TAC | TCA | TCA | AAT |
|---|---|---|---|---|---|---|---|---|---|---|---|---|---|---|---|
| Gln | Lys | Pro | Asp | Gly | Thr | Val | Lys | Leu | Leu | Ile | Phe | Tyr | Ser | Ser | Asn |
|  |  | 40 |  |  |  |  | 45 |  |  |  |  | 50 |  |  |  |

243

| TTA | CAC | TCG | GGA | GTC | CCA | TCA | AGG | TTC | AGT | GGC | GGT | GGG | TCC | GGG | ACA |
|---|---|---|---|---|---|---|---|---|---|---|---|---|---|---|---|
| Leu | His | Ser | Gly | Val | Pro | Ser | Arg | Phe | Ser | Gly | Gly | Gly | Ser | Gly | Thr |
|  | 55 |  |  |  |  | 60 |  |  |  |  | 65 |  |  |  |  |

291

| GAT | TAT | TCT | CTC | ACC | ATC | AGC | AAC | CTG | GAG | CCT | GAA | GAT | ATT | GCC | ACT |
|---|---|---|---|---|---|---|---|---|---|---|---|---|---|---|---|
| Asp | Tyr | Ser | Leu | Thr | Ile | Ser | Asn | Leu | Glu | Pro | Glu | Asp | Ile | Ala | Thr |
| 70 |  |  |  |  | 75 |  |  |  |  | 80 |  |  |  |  | 85 |

339

| TAC | TTT | TGT | CAT | CAG | TAT | AGT | AAG | CTT | CCG | TGG | ACG | TCC | GGT | GGA | GGC |
|---|---|---|---|---|---|---|---|---|---|---|---|---|---|---|---|
| Tyr | Phe | Cys | His | Gln | Tyr | Ser | Lys | Leu | Pro | Trp | Thr | Ser | Gly | Gly | Gly |
|  |  |  |  | 90 |  |  |  |  | 95 |  |  |  |  | 100 |  |

387

| ACC | AAG | CTG | GAA | ATC | AAA | CGG |
|---|---|---|---|---|---|---|
| Thr | Lys | Leu | Glu | Ile | Lys | Arg |
|  |  |  |  | 105 |  |  |

408

( 2 ) INFORMATION FOR SEQ ID NO:20:

( i ) SEQUENCE CHARACTERISTICS:
        ( A ) LENGTH: 403 base pairs
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( B ) STRAIN: HYBRIDOMA KM-641

( i x ) FEATURE:
        ( A ) NAME/KEY: sig_peptide
        ( B ) LOCATION: 14..43
        ( C ) IDENTIFICATION METHOD: BY SIMILARITY
            WITH KNOWN SEQUENCE OR TO AN ESTABLISHED
            CONSENSUS ( x i ) SEQUENCE DESCRIPTION: SEQ ID NO:20:

| AATTCGGCAC | GAG | CTT | GTC | CTT | GTT | TTC | AAA | GGT | GTT | CAG | TGT | GAA | GTG |
|---|---|---|---|---|---|---|---|---|---|---|---|---|---|
|  | Leu | Val | Leu | Val | Phe | Lys | Gly | Val | Gln | Cys | Glu | Val |  |
|  |  | -10 |  |  |  | -5 |  |  |  |  | 1 |  |  |

49

| ACG | CTG | GTG | GAG | TCT | GGG | GGA | GAC | TTT | GTG | AAA | CCT | GGA | GGG | TCC | CTG |
|---|---|---|---|---|---|---|---|---|---|---|---|---|---|---|---|
| Thr | Leu | Val | Glu | Ser | Gly | Gly | Asp | Phe | Val | Lys | Pro | Gly | Gly | Ser | Leu |
|  |  | 5 |  |  |  |  | 10 |  |  |  |  | 15 |  |  |  |

97

| AAA | GTC | TCC | TGT | GCA | GCC | TCT | GGA | TTC | GCT | TTC | AGT | CAT | TAT | GCC | ATG |
|---|---|---|---|---|---|---|---|---|---|---|---|---|---|---|---|
| Lys | Val | Ser | Cys | Ala | Ala | Ser | Gly | Phe | Ala | Phe | Ser | His | Tyr | Ala | Met |
|  | 20 |  |  |  |  | 25 |  |  |  |  | 30 |  |  |  |  |

145

| TCT | TGG | GTT | CGC | CAG | ACT | CCG | GCG | AAG | AGG | CTG | GAA | TGG | GTC | GCA | TAT |
|---|---|---|---|---|---|---|---|---|---|---|---|---|---|---|---|
| Ser | Trp | Val | Arg | Gln | Thr | Pro | Ala | Lys | Arg | Leu | Glu | Trp | Val | Ala | Tyr |
| 35 |  |  |  |  | 40 |  |  |  |  | 45 |  |  |  |  | 50 |

193

| ATT | AGT | AGT | GGT | GGT | AGT | GGC | ACC | TAC | TAT | TCA | GAC | AGT | GTA | AAG | GGC |
|---|---|---|---|---|---|---|---|---|---|---|---|---|---|---|---|
| Ile | Ser | Ser | Gly | Gly | Ser | Gly | Thr | Tyr | Tyr | Ser | Asp | Ser | Val | Lys | Gly |
|  |  |  |  | 55 |  |  |  |  | 60 |  |  |  |  | 65 |  |

241

| CGA | TTC | ACC | ATT | TCC | AGA | GAC | AAT | GCC | AAG | AAC | ACC | CTG | TAC | CTG | CAA |
|---|---|---|---|---|---|---|---|---|---|---|---|---|---|---|---|
| Arg | Phe | Thr | Ile | Ser | Arg | Asp | Asn | Ala | Lys | Asn | Thr | Leu | Tyr | Leu | Gln |
|  |  |  | 70 |  |  |  |  | 75 |  |  |  |  | 80 |  |  |

289

```
ATG  CGC  AGT  CTG  AGG  TCT  GAG  GAC  TCG  GCC  ATG  TAT  TTC  TGT  ACA  AGA        337
Met  Arg  Ser  Leu  Arg  Ser  Glu  Asp  Ser  Ala  Met  Tyr  Phe  Cys  Thr  Arg
          85                            90                       95

GTT  AAA  CTG  GGA  ACC  TAC  TAC  TTT  GAC  TCC  TGG  GGC  CAA  GGC  ACC  ACT        385
Val  Lys  Leu  Gly  Thr  Tyr  Tyr  Phe  Asp  Ser  Trp  Gly  Gln  Gly  Thr  Thr
          100                           105                      110

CTC  ACT  GTC  TCC  TCA  GCT                                                           403
Leu  Thr  Val  Ser  Ser  Ala
115                      120
```

( 2 ) INFORMATION FOR SEQ ID NO:21:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:21:

```
AATTCACC  ATG  GAG  TTT  GGG  CTC  AGC  TGG  CTT  TTT                                   35
          Met  Glu  Phe  Gly  Leu  Ser  Trp  Leu  Phe
          1                   5
```

( 2 ) INFORMATION FOR SEQ ID NO:22:

( i ) SEQUENCE CHARACTERISTICS:
        ( A ) LENGTH: 43 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:22:

```
CAA  GGT  ACC  ACG  TTA  ACT  GTC  TCC  TCA  GCC  TCC  ACC  AAG  GGC                   42
Gln  Gly  Thr  Thr  Leu  Thr  Val  Ser  Ser  Ala  Ser  Thr  Lys  Gly
1                   5                        10

C                                                                                       43
```

( 2 ) INFORMATION FOR SEQ ID NO:23:

( i ) SEQUENCE CHARACTERISTICS:
        ( A ) LENGTH: 80 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:23:

```
GGCCGCACCA  TGGGATGGAG  CTGGATCTTT  CTCTTCCTCC  TGTCAGGAAC  TGCTGGTGTC        60

CTCTCTCAGG  TCCAACTGCA                                                         80
```

( 2 ) INFORMATION FOR SEQ ID NO:24:

( i ) SEQUENCE CHARACTERISTICS:
        ( A ) LENGTH: 59 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:24:

```
GGAGAGCGGT  CCAGGTCTTG  TGAGGCCTAG  CCAGACCCTG  AGCCTGACCT  GCACCGTGT         59
```

( 2 ) INFORMATION FOR SEQ ID NO:25:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:25:

CCGGATTCAC CTTCAGCGAC TACAACATGG ACTGGGTGAG ACAGCCACCT GGACGAGGTC    60

( 2 ) INFORMATION FOR SEQ ID NO:26:

( i ) SEQUENCE CHARACTERISTICS:
        ( A ) LENGTH: 81 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:26:

TCGAGTGGAT TGGATATATT TATCCTAACA ATGGTGGTAC TGGCTACAAC CAGAAGTTCA    60

AGAGCAGAGT GACAATGCTG G    81

( 2 ) INFORMATION FOR SEQ ID NO:27:

( i ) SEQUENCE CHARACTERISTICS:
        ( A ) LENGTH: 61 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:27:

TCGACACCAG CAAGAACCAG TTCAGCCTGA GACTCAGCAG CGTGACAGCC GCCGACACCG    60

C    61

( 2 ) INFORMATION FOR SEQ ID NO:28:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:28:

GGTCTATTAT TGTGCGCGCT ACGGTCATTA CTACGGCTAC ATGTTTGCTT ACTGGGGTCA    60

AGGTAC    66

( 2 ) INFORMATION FOR SEQ ID NO:29:

( i ) SEQUENCE CHARACTERISTICS:
        ( A ) LENGTH: 35 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:29:

CACCGTCACA GTCTCCTCAG CCTCCACCAA GGGCC   35

( 2 ) INFORMATION FOR SEQ ID NO:30:

( i ) SEQUENCE CHARACTERISTICS:
    ( A ) LENGTH: 77 base pairs
    ( B ) TYPE: nucleic acid
    ( C ) STRANDEDNESS: double
    ( D ) TOPOLOGY: linear ( i i ) MOLECULE TYPE: other nucleic acid, synthetic DNA ( x i ) SEQUENCE DESCRIPTION: SEQ ID NO:30:

AATTCACCAT GCATTTTCAA GTGCAGATTT TCAGCTTCCT GCTAATCAGT GCCTCAGTCA   60

TAATGTCCAG AGGAGAT   77

( 2 ) INFORMATION FOR SEQ ID NO:31:

( i ) SEQUENCE CHARACTERISTICS:
    ( A ) LENGTH: 62 base pairs
    ( B ) TYPE: nucleic acid
    ( C ) STRANDEDNESS: double
    ( D ) TOPOLOGY: linear ( i i ) MOLECULE TYPE: other nucleic acid, synthetic DNA ( x i ) SEQUENCE DESCRIPTION: SEQ ID NO:31:

ATCCAGCTGA CCCAGAGCCC AAGCAGCCTG AGCGCTAGCG TGGGTGACAG AGTGACCATG   60

AC   62

( 2 ) INFORMATION FOR SEQ ID NO:32:

( i ) SEQUENCE CHARACTERISTICS:
    ( A ) LENGTH: 65 base pairs
    ( B ) TYPE: nucleic acid
    ( C ) STRANDEDNESS: double
    ( D ) TOPOLOGY: linear ( i i ) MOLECULE TYPE: other nucleic acid, synthetic DNA ( x i ) SEQUENCE DESCRIPTION: SEQ ID NO:32:

GTGCAGTGCC AGCTCAAGTG TAAGTTACAT GCACTGGTAT CAGCAGAAGC CAGGTAAGGC   60

TCCAA   65

( 2 ) INFORMATION FOR SEQ ID NO:33:

( i ) SEQUENCE CHARACTERISTICS:
    ( A ) LENGTH: 45 base pairs
    ( B ) TYPE: nucleic acid
    ( C ) STRANDEDNESS: double
    ( D ) TOPOLOGY: linear ( i i ) MOLECULE TYPE: other nucleic acid, synthetic DNA ( x i ) SEQUENCE DESCRIPTION: SEQ ID NO:33:

AGCTTCTGAT CTACAGCACA TCCAACCTGG CTTCTGGTGT GCCAT   45

( 2 ) INFORMATION FOR SEQ ID NO:34:

( i ) SEQUENCE CHARACTERISTICS:
    ( A ) LENGTH: 76 base pairs
    ( B ) TYPE: nucleic acid
    ( C ) STRANDEDNESS: double
    ( D ) TOPOLOGY: linear ( i i ) MOLECULE TYPE: other nucleic acid, synthetic DNA ( x i ) SEQUENCE DESCRIPTION: SEQ ID NO:34:

```
CTAGATTCAG CGGTAGCGGT AGCGGTACAG ACTTCACCTT CACCATCAGC AGCCTCCAGC      60

CAGAGGACAT CGCTAC                                                       76
```

( 2 ) INFORMATION FOR SEQ ID NO:35:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: other nucleic acid, synthetic DNA ( x i ) SEQUENCE DESCRIPTION: SEQ ID NO:35:

```
GTACTACTGC CAGCAAAGGA GTAGTTACCC GTACACGTTC GGCGGGGGGA CCAAGGTGGA      60

AATCAAACGT ACGGTGGCTG CACC                                              84
```

( 2 ) INFORMATION FOR SEQ ID NO:36:

( i ) SEQUENCE CHARACTERISTICS:
        ( A ) LENGTH: 144 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Met Gly Trp Ser Trp Ile Phe Leu Phe Leu Leu Ser Gly Thr Ala Gly
 1               5                  10                  15

Val Leu Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Thr Phe
            35                  40                  45

Ser Asp Tyr Asn Met Asp Trp Val Arg Gln Pro Pro Gly Arg Gly Leu
        50                  55                  60

Glu Trp Ile Gly Tyr Ile Tyr Pro Asn Asn Gly Gly Thr Gly Tyr Asn
65                  70                  75                  80

Gln Lys Phe Lys Ser Arg Val Thr Met Leu Val Asp Thr Ser Lys Asn
                85                  90                  95

Gln Phe Ser Leu Arg Leu Ser Ser Val Thr Ala Ala Asp Thr Ala Val
            100                 105                 110

Tyr Tyr Cys Ala Arg Tyr Gly His Tyr Tyr Gly Tyr Met Phe Ala Tyr
            115                 120                 125

Trp Gly Gln Gly Thr Thr Val Thr Val Ser Ser Ala Ser Thr Lys Gly
            130                 135                 140
```

( 2 ) INFORMATION FOR SEQ ID NO:37:

( i ) SEQUENCE CHARACTERISTICS:
        ( A ) LENGTH: 133 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Met His Phe Gln Val Gln Ile Phe Ser Phe Leu Leu Ile Ser Ala Ser
 1               5                  10                  15

Val Ile Met Ser Arg Gly Asp Ile Gln Leu Thr Gln Ser Pro Ser Ser
            20                  25                  30

Leu Ser Ala Ser Val Gly Asp Arg Val Thr Ile Thr Cys Ser Ala Ser
```

|   |   |   |   |   | 35 |   |   |   |   | 40 |   |   |   |   | 45 |   |
|---|---|---|---|---|---|---|---|---|---|---|---|---|---|---|---|---|
| Ser | Ser | Val | Ser | Tyr | Met | His | Trp | Tyr | Gln | Gln | Lys | Pro | Gly | Lys | Ala |   |
|   | 50 |   |   |   |   | 55 |   |   |   |   | 60 |   |   |   |   |   |
| Pro | Lys | Leu | Leu | Ile | Tyr | Ser | Thr | Ser | Asn | Leu | Ala | Ser | Gly | Val | Pro |   |
| 65 |   |   |   |   | 70 |   |   |   |   | 75 |   |   |   |   | 80 |   |
| Ser | Arg | Phe | Ser | Gly | Ser | Gly | Ser | Gly | Thr | Asp | Phe | Thr | Phe | Thr | Ile |   |
|   |   |   |   | 85 |   |   |   |   | 90 |   |   |   |   | 95 |   |   |
| Ser | Ser | Leu | Gln | Pro | Glu | Asp | Ile | Ala | Thr | Tyr | Tyr | Cys | Gln | Gln | Arg |   |
|   |   |   | 100 |   |   |   |   | 105 |   |   |   |   | 110 |   |   |   |
| Ser | Ser | Tyr | Pro | Tyr | Thr | Phe | Gly | Gly | Gly | Thr | Lys | Val | Glu | Ile | Lys |   |
|   |   | 115 |   |   |   |   | 120 |   |   |   |   | 125 |   |   |   |   |
| Arg | Thr | Val | Ala | Ala |   |   |   |   |   |   |   |   |   |   |   |   |
|   | 130 |   |   |   |   |   |   |   |   |   |   |   |   |   |   |   |

( 2 ) INFORMATION FOR SEQ ID NO:38:

( i ) SEQUENCE CHARACTERISTICS:
        ( A ) LENGTH: 449 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:38:

| CTCCACAGTC | CCTGAAGACA | CTGACTCTAA | CCATGGGATG | GAGCTGGATC | TTTCTCTTCC | 60 |
| TCCTGTCAGG | AACTGCAGGT | GTCCTCTCTG | AGGTCCAGCT | GCAGCAGTCT | GGACCTGAGC | 120 |
| TGGTGAAGCC | TGGGGCTTCA | GTGAAGATAT | CCTGCAAGGC | TTCTGGATAC | ACATTCACTG | 180 |
| ACTACAACAT | GGACTGGGTG | AAGCAGAGCC | ATGGAAAGAG | CCTTGAGTGG | ATTGGATATA | 240 |
| TTTATCCTAA | CAATGGTGGT | ACTGGCTACA | ACCAGAAGTT | CAAGAGCAAG | GCCACATTGA | 300 |
| CTGTAGACAA | GTCCTCCAGC | ACAGCCTACA | TGGAGCTCCA | CAGCCTGACA | TCTGAGGACT | 360 |
| CTGCAGTCTA | TTACTGTGCA | ACCTACGGTC | ATTACTACGG | CTACATGTTT | GCTTACTGGG | 420 |
| GCCAAGGGAC | TCTGGTCACT | GTCTCTGCA |   |   |   | 449 |

( 2 ) INFORMATION FOR SEQ ID NO:39:

( i ) SEQUENCE CHARACTERISTICS:
        ( A ) LENGTH: 393 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:39:

| GACAAAATGC | ATTTTCAAGT | GCAGATTTTC | AGCTTCCTGC | TAATCAGTGC | CTCAGTCATA | 60 |
| ATGTCCAGAG | GACAAATTGT | TCTCACCCAG | TCTCCAGCAA | TCATGTCTGC | ATCTCCAGGG | 120 |
| GAGAAGGTCA | CCATAACCTG | CAGTGCCAGC | TCAAGTGTAA | GTTACATGCA | CTGGTTCCAG | 180 |
| CAGAAGCCAG | GCACTTCTCC | CAAACTCTGG | ATTTATAGCA | CATCCAACCT | GGCTTCTGGA | 240 |
| GTCCCTGCTC | GCTTCAGTGG | CAGTGGATCT | GGGACCTCTT | ACTCTCTCAC | AATCAGCCGA | 300 |
| ATGGAGGCTG | AAGATGCTGC | CACTTATTAC | TGCCAGCAAA | GGAGTAGTTA | CCCGTACACG | 360 |
| TTCGGAGGGG | GGACCAAGCT | GGAAATAAAA | CGG |   |   | 393 |

( 2 ) INFORMATION FOR SEQ ID NO:40:

( i ) SEQUENCE CHARACTERISTICS:

( A ) LENGTH: 443 base pairs
( B ) TYPE: nucleic acid
( C ) STRANDEDNESS: both
( D ) TOPOLOGY: linear ( i i ) MOLECULE TYPE: other nucleic acid ( x i ) SEQUENCE DESCRIPTION: SEQ ID NO:40:

| | | | | | |
|---|---|---|---|---|---|
| CTCCACAGTC | CCTGAAGACA | CTGACTCTAA | CCATGGGATG | GAGCTGGATC | TTTCTCTTCC | 60 |
| TCCTGTCAGG | AACTGCAGGT | GTCCTCTCTG | AGGTCCAGCT | GCAGCAGTCT | GGACCTGAGC | 120 |
| TGGTGAAGCC | TGGGGCTTCA | GTGAAGATAT | CCTGCAAGGC | TTCTGGATAC | ACATTCACTG | 180 |
| ACTACAACAT | GGACTGGGTG | AAGCAGAGCC | ATGGAAAGAG | CCTTGAGTGG | ATTGGATATA | 240 |
| TTTATCCTAA | CAATGGTGGT | ACTGGCTACA | ACCAGAAGTT | CAAGAGCAAG | GCCACATTGA | 300 |
| CTGTAGACAA | GTCCTCCAGC | ACAGCCTACA | TGGAGCTCCA | CAGCCTGACA | TCTGAGGACT | 360 |
| CTGCAGTCTA | TTACTGTGCA | AGAGCGGGGA | GGTATTACTA | CGCCTGGGAC | TGGGGCCAAG | 420 |
| GGACTCTGGT | CACTGTCTCT | GCA | | | | 443 |

( 2 ) INFORMATION FOR SEQ ID NO:41:

( i ) SEQUENCE CHARACTERISTICS:
( A ) LENGTH: 15 base pairs
( B ) TYPE: nucleic acid
( C ) STRANDEDNESS: both
( D ) TOPOLOGY: linear ( i i ) MOLECULE TYPE: other nucleic acid ( x i ) SEQUENCE DESCRIPTION: SEQ ID NO:41:

GACTACAACA TGGAC                                                          15

( 2 ) INFORMATION FOR SEQ ID NO:42:

( i ) SEQUENCE CHARACTERISTICS:
( A ) LENGTH: 51 base pairs
( B ) TYPE: nucleic acid
( C ) STRANDEDNESS: both
( D ) TOPOLOGY: linear ( i i ) MOLECULE TYPE: other nucleic acid ( x i ) SEQUENCE DESCRIPTION: SEQ ID NO:42:

TATATTTATC CTAACAATGG TGGTACTGGC TACAACCAGA AGTTCAAGAG C                  51

( 2 ) INFORMATION FOR SEQ ID NO:43:

( i ) SEQUENCE CHARACTERISTICS:
( A ) LENGTH: 33 base pairs
( B ) TYPE: nucleic acid
( C ) STRANDEDNESS: both
( D ) TOPOLOGY: linear ( i i ) MOLECULE TYPE: other nucleic acid ( x i ) SEQUENCE DESCRIPTION: SEQ ID NO:43:

TACGGTCATT ACTACGGCTA CATGTTTGCT TAC                                     33

( 2 ) INFORMATION FOR SEQ ID NO:44:

( i ) SEQUENCE CHARACTERISTICS:
( A ) LENGTH: 30 base pairs
( B ) TYPE: nucleic acid
( C ) STRANDEDNESS: both
( D ) TOPOLOGY: linear ( i i ) MOLECULE TYPE: other nucleic acid ( x i ) SEQUENCE DESCRIPTION: SEQ ID NO:44:

AGTGCCAGCT CAAGTGTAAG TTACATGCAC 30

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:45:

AGCACATCCA ACCTGGCTTC T 21

( 2 ) INFORMATION FOR SEQ ID NO:46:

( i ) SEQUENCE CHARACTERISTICS:
        ( A ) LENGTH: 27 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:46:

CAGCAAAGGA GTAGTTACCC GTACACG 27

( 2 ) INFORMATION FOR SEQ ID NO:47:

( i ) SEQUENCE CHARACTERISTICS:
        ( A ) LENGTH: 442 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:47:

GGCCGCACCA TGGGATGGAG CTGGATCTTT CTCTTCCTCC TGTCAGGAAC TGCTGGTGTC 60

CTCTCTCAGG TCCAACTGCA GGAGAGCGGT CCAGGTCTTG TGAGGCCTAG CCAGACCCTG 120

AGCCTGACCT GCACCGTGTC CGGATTCACC TTCAGCGACT ACAACATGGA CTGGGTGAGA 180

CAGCCACCTG GACGAGGTCT CGAGTGGATT GGATATATTT ATCCTAACAA TGGTGGTACT 240

GGCTACAACC AGAAGTTCAA GAGCAGAGTG ACAATGCTGG TCGACACCAG CAAGAACCAG 300

TTCAGCCTGA GACTCAGCAG CGTGACAGCC GCCGACACCG CGGTCTATTA TTGTGCGCGC 360

TACGGTCATT ACTACGGCTA CATGTTTGCT TACTGGGGTC AAGGTACCAC CGTCACAGTC 420

TCCTCAGCCT CCACCAAGGG CC 442

( 2 ) INFORMATION FOR SEQ ID NO:48:

( i ) SEQUENCE CHARACTERISTICS:
        ( A ) LENGTH: 409 base pairs
        ( B ) TYPE: nucleic acid
        ( C ) STRANDEDNESS: both
        ( D ) TOPOLOGY: linear ( i i ) MOLECULE TYPE: other nucleic acid ( x i ) SEQUENCE DESCRIPTION: SEQ ID NO:48:

AATTCACCAT GCATTTTCAA GTGCAGATTT TCAGCTTCCT GCTAATCAGT GCCTCAGTCA 60

TAATGTCCAG AGGAGATATC CAGCTGACCC AGAGCCCAAG CAGCCTGAGC GCTAGCGTGG 120

```
GTGACAGAGT  GACCATCACG  TGCAGTGCCA  GCTCAAGTGT  AAGTTACATG  CACTGGTATC        180

AGCAGAAGCC  AGGTAAGGCT  CCAAAGCTTC  TGATCTACAG  CACATCCAAC  CTGGCTTCTG        240

GTGTGCCATC  TAGATTCAGC  GGTAGCGGTA  GCGGTACAGA  CTTCACCTTC  ACCATCAGCA        300

GCCTCCAGCC  AGAGGACATC  GCTACGTACT  ACTGCCAGCA  AAGGAGTAGT  TACCCGTACA        360

CGTTCGGCGG  GGGGACCAAG  GTGGAAATCA  AACGTACGGT  GGCTGCACC                    409
```

( 2 ) INFORMATION FOR SEQ ID NO:49:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

```
AAACGAACTG  TGGCTGCACC  ATCTGTC                                               27
```

DNA ENCODING HUMANIZED ANTIBODIES SPECIFIC FOR THE GANGLIOSIDE $GM_2$

This is a divisional of application Ser. No. 08/116,778, filed Sep. 7, 1993.

FIELD OF THE INVENTION

The present invention relates to humanized antibodies reacting with the ganglioside $GM_2$. The humanized antibodies do not cause production of anti-mouse immunoglobulins in the patient's body as compared with mouse monoclonal antibodies, hence the incidence of adverse effects possibly caused by them is much lower, their blood half-lives are longer and, further, their anti-tumor effector effect is greater. Therefore, the humanized antibodies are expected to produce improved therapeutic effects as compared with mouse monoclonal antibodies.

BACKGROUND OF THE INVENTION

When administered to humans, mouse antibodies are generally recognized as foreign matters, inducing production of anti-mouse immunoglobulin antibodies in the human body. It is known that the former antibodies react with the latter antibodies to produce adverse effects [J. Clin. Oncol., 2, 881 (1984); Blood, 65, 1349 (1985); J. Natl. Cancer Inst., 80, 932 (1988); Proc. Natl. Acad. Sci. U.S.A., 82, 1242 (1985)] and that the mouse antibodies undergo rapid clearance [J.Nucl. Med., 26, 1011 (1985); Blood, 65, 1349 (1985); J. Natl. Cancer Inst., 80, 937 (1988)], thus showing only a reduced efficacy [J. Immunol., 135, 1530(1985); Cancer Res., 46, 6489 (1986)]. Attempts have been made to solve these problems by deriving, from mouse monoclonal antibodies, chimeric human antibodies or CDR (complementarity determining region)-transplanted antibodies (reshaped antibodies) using gene engineering technique. In a human chimeric antibody, .the variable regions thereof are of mouse origin and the constant regions thereof are of human origin [Proc. Natl. Acad. Sci. U.S.A., 81, 6851 (1984)] and it is reported that when administered to humans, said antibody causes litte human anti-mouse immunoglobulin antibody production, its blood half-life being 6-fold longer [Proc. Natl. Acad. Sci. U.S.A., 86, 4220 (1989)]. The CDR-transplanted antibodies are antibodies resulting from replacement of the CDRs in a human antibody alone with the CDRs from an animal other than the human [Nature, 321, 522 (1986)] and, in an experiment with monkeys, such antibodies showed reduced immunogenicity and 4- to 5-fold higher serum half-lives as compared with mouse antibodies [J. Immunol., 147, 1352 (1991)].

As regards the cytocidal activity of antibodies, it is reported that the Fc region of a human antibody is more potent in activating human complement and human effector cells than the Fc region of a mouse antibody. Thus, for instance, a chimeric antibody derived from a mouse monoclonal antibody to the ganglioside $GD_2$ and containing a human antibody Fc region enhances the human effector cell-mediated antitumor effect [J. Immunol., 144, 1382 (1990)]. Similar results are reported for CDR-transplanted antibodies [Nature, 332, 323 (1988)]. Such results indicate that, for clinical use, humanized monoclonal antibodies are preferred to mouse monoclonal antibodies.

The antibody classes include IgA, IgM, IgG, IgD and IgE and, in mice, the class IgG includes four subclasses, namely $IgG_1$, $IgG_2a$, $IgG_2b$ and $IgG_3$ (in humans, $IgG_1$, $IgG_2$, $IgG_3$ and $IgG_4$). When antigens are administered to animals, the antibodies produced mostly belong to the classes IgM or IgG. IgG molecules have a molecular weight of about 160,000 daltons and a dimeric structure and are relatively easy to handle. IgM molecules are large with a molecular weight of about 900,000 daltons and occur in the form of a complicated pentameric structure coupled with the joining (J) chain, hence they have the following drawbacks: they are difficult to purify; they tend to agglutinate, hence are difficult to store; they are readily inactivated by partial decomposition in the presence of a protease, hence it is difficult to prepare Fab fragments; and they lose their binding activity in many instances upon chemical modification, for example chemical binding of an anticancer agent or a toxin [J. W. Goding: Monoclonal Antibodies: Principles and Practice, Academic Press, 1986]. As to which are superior in therapeutic effect against cancer, IgG class monoclonal antibodies or IgM class monoclonal antibodies, reference may be made to a detailed study made by Bernstein et al. using an IgG class monoclonal antibody and an IgM class monoclonal antibody to the lymphocyte Thy-1 antigen [Monoclonal Antibodies, edited by R. H. Kennet, T. J. Mckearn and K. B. Bechtol, Plenum Press, 1980, p. 275]. According to the reference, an IgG class monoclonal antibody and an IgM class monoclonal antibody comparable in terms of reactivity to Thy-1 antigen-positive lymphocytes, were compared in terms of antitumor effect. While the IgM monoclonal antibody was superior in in vitro complement-dependent antitumor effect, the IgG class monoclonal antibody showed a significant antitumor effect in in vivo antitumor effect in cancer-bearing mice, with no antitumor effect being observed with the IgM class monoclonal antibody. It was further revealed that, as compared with the IgG class monoclonal antibody, the IgM class monoclonal antibody showed a very short half-life in the blood after administration, in an isotope-labeled form, to mice. These results indicate that the monoclonal antibodies to be used clinically in humans should preferably be of the IgG class.

Gangliosides, a class of glycolipids, are constiuents of animal cell membranes. These molecules are composed of a carbohydrate chain, which constitutes a hydrophilic side chain, and sphingosine and a fatty acid, which constitute hydrophobic side chains. It is known that the ganglioside species expressed and the amount thereof differ between cell species, organ species, and animal species, among others. Furthermore, it has been reported that the ganglioside expressed changed quantitatively and qualitatively during the process of cancer development [Cancer Res., 45, 2405 (1985)]. For example, expression of the gangliosides $GD_2$, $GD_3$ and $GM_2$ has been reported in neuroblastoma, lung small cell carcinoma, and melanoma, which are highly malignant neural ectodermal tumors [J. Exp. Med., 155, 1133 (1982); J. Biol. Chem., 257, 12752 (1982); Cancer Res., 47, 225 (1987); ibid., 47, 1098 (1987); ibid., 45, 2642 (1985); Proc. Natl. Acad. Sci. U.S.A., 80, 5392 (1983)].

$GM_2$, one of the gangliosides that are sialic acid residue containing glycolipids, occurs only in trace amounts in normal cells but is found in increased amounts in cancer cells in lung small cell carcinoma, melanoma, neuroblastoma, etc. Monoclonal antibodies to $GM_2$ are considered to be useful in the treatment of such cancers [Lancet, 48, 6154 (1988)]. However, those monoclonal antibodies to $GM_2$ that have so far been reported are of the human IgM class or of the rat IgM, mouse IgM or mouse IgG class [Cancer Res., 46, 4116 (1986); Proc. Natl. Acad. Sci. U.S.A., 79, 7629 (1982); Cancer Res., 48, 6154 (1988); J. Biol. Chem., 264, 12122 (1989)].

Anti-ganglioside $GM_2$ monoclonal antibodies, if produced in the form of humanized antibodies, for example chimeric human antibodies or CDR-transplanted antibodies, which are not expected to induce anti-mouse immunoglobulin antibody production in the patient's body, produce reduced adverse effects and show a prolonged blood half-life and an enhanced antitumor effector effect. These antibodies are thus expected to be superior in therapeutic effect to the corresponding mouse monoclonal antibodies.

SUMMARY OF THE INVENTION

It is an object of the present invention to provide humanized antibodies to the ganglioside $GM_2$ (hereinafter, "humanized anti-$GM_2$ antibodies") which are useful in the treatment of cancers of neural ectodermal origin, among others.

The present inventors prepared the antibody heavy chain (hereinafter, "H chain") variable region (hereinafter "$V_H$") cDNA and light chain (hereinafter, "L chain") variable region (hereinafter, "$V_L$") cDNAs from mRNAs isolated from the hybridomas KM750 and KM796, described in EP-A-0 508 472.

These hybridomas produce $IgG_3$ class mouse monoclonal antibodies to the ganglioside $GM_2$. $V_H$ and $V_L$ cDNAs were also prepared from mRNAs isolated from the hybridoma KM603, which produces an IgM class rat monoclonal antibody to the ganglioside $GM_2$. Chimeric human antibody expression vectors were constructed by inserting the cDNA into an expression vector containing human antibody H chain constant region (hereinafter, "$C_H$") or human antibody L chain constant region (hereinafter, "$C_L$") encoding sequences. Such vectors were then introduced into animal cells to effect the production of anti-ganglioside $GM_2$ chimeric human antibodies. Among the chimeric antibodies produced, the anti-ganglioside $GM_2$ chimeric human antibody, KM966, was found to react with the ganglioside $GM_2$ and show cytocidal activity. The H chain variable region of KM966 contains an amino acid sequence segment as defined by SEQ ID NO:1 and includes the 1st to 120th amino acids of that sequence and the L chain variable region of KM966 contains an amino acid sequence segment as defined by SEQ ID NO:2 and includes the 1st to 107th amino acids of said sequence. The present invention is based, at least in part, on these findings.

The present invention thus relates to a humanized antibody reacting with the ganglioside $GM_2$.

BRIEF DESCRIPTION OF THE DRAWINGS

FIG. 1 illustrates plasmids, pKM796H1 and pKM796L1.

FIG. 2 illustrates plasmids, pKM750H1 and pKM750L1.

FIG. 3 illustrates plasmids, pKM603H1 and pKM603L1.

FIG. 12 shows a construction scheme for plasmids, pChi796HL1 and pChi750HL1.

FIGS. 18A and 18B show the electrophoretic patterns in SDS-PAGE (using 4–15% gradient gels) of purified chimeric human anti-$GM_2$ antibodies, KM966 and KM967. The patterns obtained under reducing conditions are shown on the left side and those obtained under nonreducing conditions on the right side. From the left, the lanes include low molecular weight markers, KM967 and KM966 (reducing conditions), and KM967 and KM966 (nonreducing conditions).

FIGS. 19A and 19B show the electrophoretic patterns in SDS-PAGE (using 4–15% gradient gels) of a purified chimeric human anti-$GM_2$ antibody, KM968. The pattern obtained under reducing conditions is shown on the left side and that obtained under nonreducing conditions on the right side. From the left, the lanes include high molecular weight markers, low molecular weight markers, a standard human IgG, KM968 (reducing conditions), the same low molecular weight markers, the standard human IgG, and KM968 (nonreducing conditions).

FIG. 32 shows a construction scheme for a plasmid, pEPKMB1.

FIG. 34 shows a construction scheme for a plasmid, pAGE109.

FIG. 38 shows a construction scheme for a plasmid, pSE1D2.

FIG. 40 shows a construction scheme for a plasmid, pIG1SE1d3.

FIG. 42 shows a construction scheme for a plasmid, pPMOL2.

FIG. 43 shows a construction scheme for a plasmid, pPMOL3.

FIG. 45 shows a construction scheme for a plasmid, pchCKB1.

FIG. 46 shows a construction scheme for a plasmid, pckCKC1.

FIG. 57 shows a construction scheme for a plasmid, phKM796HM1.

FIG. 59 shows a construction scheme for a plasmid, phKM796LI1.

DETAILED DESCRIPTION OF THE INVENTION

Figure 4:
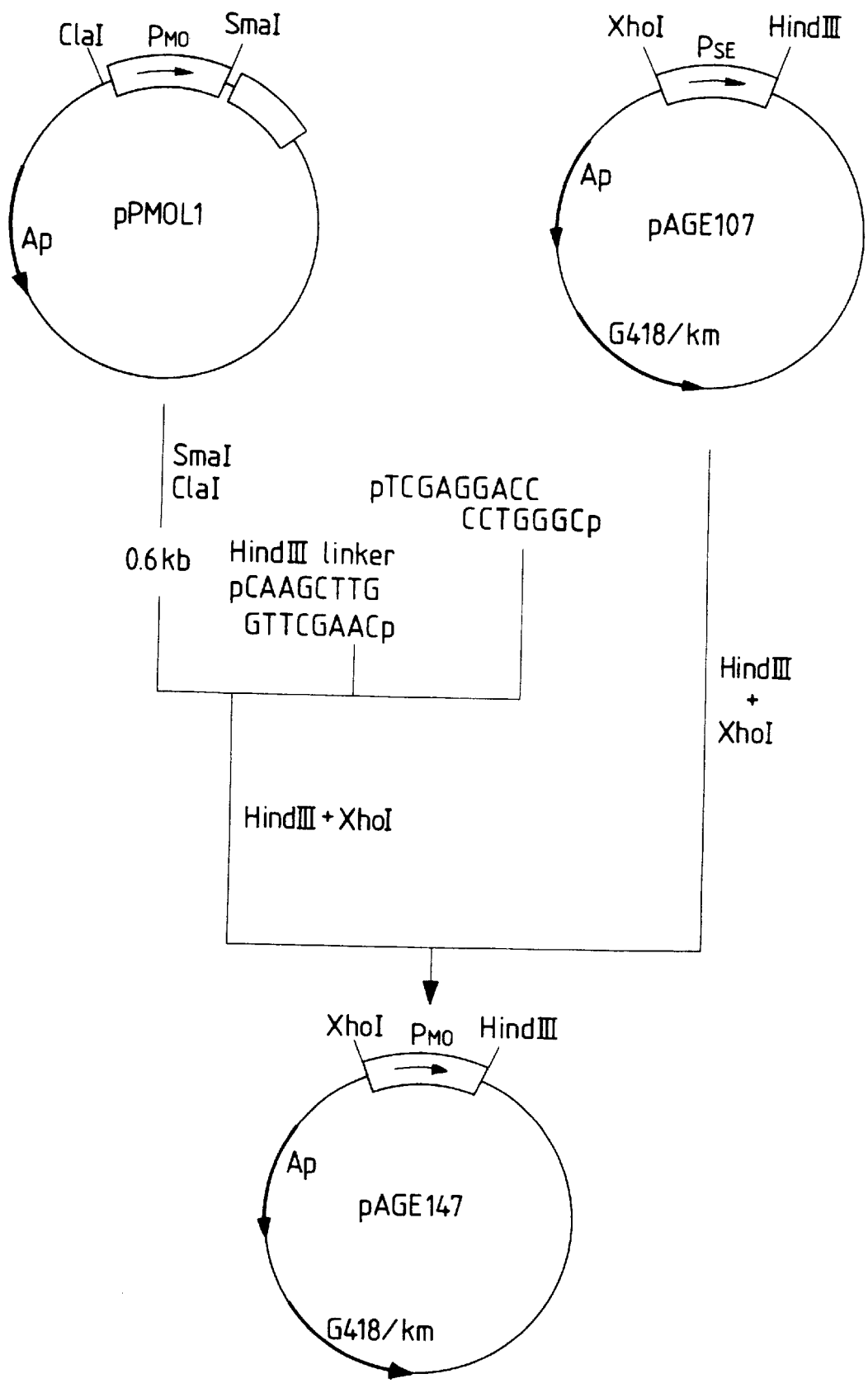
FIG. 4 shows a construction scheme for a plasmid, pAGE147.

The present invention relates to humanized antibodies specific for the ganglioside $GM_2$. The antibodies can be of any of the immunoglobulin (Ig) classes, it is preferable, however, that the antibodies be of the IgG type. The term "humanized antibody", as used herein, includes within its meaning, chimeric human antibodies and CDR-transplanted antibodies. Chimeric human antibodies of the invention include the $V_H$ and $V_L$ of an antibody of an animal other than a human and the $C_H$ and $C_L$ Of a human antibody. The CDR-transplanted antibodies of the invention result from the replacement of CDRs of the $V_H$ and $V_L$ Of a human antibody with those of the $V_H$ and $V_L$, respectively, of an antibody of an animal other than a human.

An example of a chimeric human antibody of the invention is an antibody the $V_H$ of which contains an amino acid sequence segment as defined by SEQ ID NO:1, including the 1st to 120th amino acids of that sequence, and the $V_L$ of which contains an amino acid sequence segment as defined by SEQ ID NO:2, including the 1st to 107th amino acids of that sequence.

An example of a CDR-transplanted antibody of the invention is an antibody the $V_H$ CDRs of which have the amino acid sequences defined by SEQ ID NO:6, SEQ ID NO:7 and SEQ ID NO:8 and the $V_L$ CDRs of which have the amino acid sequences defined by SEQ ID NO:9, SEQ ID NO:10 and SEQ ID NO:11.

The chimeric human antibodies of the invention can be produced in the following manner:

(1) Preparation of cDNAs coding for the $V_H$ and $V_L$ of an antibody of nonhuman animal cDNAs coding for the $V_H$ and $V_L$ of an antibody of a nonhuman animal, for example a mouse anti-$GM_2$ monoclonal antibody, can be prepared as follows.

mRNAs can be extracted from hybridomas producing the mouse anti-$GM_2$ monoclonal antibody, for example hybridomas producing the mouse anti-$GM_2$ monoclonal antibody KM796, and cDNAs reverse transcribed therefrom. Using the cDNAs, a library can be constructed using phage or plasmid vectors. The recombinant phage or recombinant plasmid containing the cDNA coding f or the $V_H$, and the recombinant phage or recombinant plasmid containing the cDNA coding for the $V_L$ can be isolated from the library using a constant region portion or a variable region portion of an antibody of a nonhuman animal, for example a mouse antibody, as a probe. The base sequences of the $V_H$-encoding cDNA and $V_L$-encoding cDNA in the recombinant phage or recombinant plasmid can then be determined. Examples of the nonhuman animals include mice, rats, hamsters and monkeys.

(2) Construction of a vector for chimeric human antibody expression

Expression of chimeric human antibody H chain and L chains can be effected using expression vectors suitable for use in animal cells, inserted into which are the cDNAs coding for the human $C_H$ and $C_L$. Any expression vector suitable for use in animal cells can be used, provided that it allows integration and expression of the human antibody constant region-encoding cDNAs. Examples include pAGE107 [Cytotechnology, 3, 133 (1990)], pAGE103 [J. Biochem., 101, 1307 (1987)], pHSG274 [Gene, 27, 223 (1984)], PKCR [Proc. Natl. Acad. Sci. U.S.A., 78, 1527 (1981)) and pSG1βd2–4 [Cytotechnology, 4, 173 (1990)], among others. Examples of promoters and enhancers suitable for use in such expression vectors include the SV40 early promoter and enhancer [J. Biochem., 101, 1307 (1987) ], the Moloney mouse leukemia virus LTR (long terminal repeat) promoter and enhancer [Biochem. Biophys. Res. Conuaun., 149, 960 (1987)] and the immunoglobulin H chain promoter [Cell, 41, 479 (1985)] and enhancer [Cell, 33, 717 (1983)]. The promoters and enhancers are located in the expression vector in operable linkage with the coding sequences.

(3) Construction of a chimeric human antibody expression vector

The vector for chimeric human antibody H chain and L chain expression, as obtained in (2), is provided with a cloning site upstream of the human constant region, for insertion of a cDNA coding for the variable region of an antibody of a nonhuman animal. Insertion, at this cloning site, of the cDNA coding for the variable region of a nonhuman animal antibody, using a synthetic DNA comprising a 5' terminal base sequence of the human antibody constant region and a 3' terminal base sequence of the variable region of the nonhuman animal antibody and having restriction enzyme sites on both ends, gives a chimeric human antibody expression vector with the cDNA coding for the human antibody constant region and the cDNA coding for the variable region of the nonhuman animal antibody joinedly inserted therein via the synthetic DNA for producing appropriate restriction enzyme sites. The synthetic DNA can be synthesized using a DNA synthesizer based on the 5' terminal base sequence of the human antibody constant region and the base sequence of said 3' terminal base sequence of the nonhuman animal antibody variable region.

(4) Construction of a chimeric human antibody H chain expression vector

A vector for chimeric human antibody H chain expression is constructed, for example, by excising that portion of the human antibody $C_H$-encoding cDNA which covers from the ApaI site near the 5' terminus to the 3' terminus and inserting that portion into an expression vector suitable for use in animal cells. This vector for chimeric human antibody H chain expression is provided with a cloning site for insertion of a cDNA coding for a nonhuman animal $V_H$. cDNA coding for the nonhuman animal $V_H$, excised using an appropriate restriction enzyme, is inserted into the vector at the cloning site using a synthetic DNA comprising that portion of the human antibody $C_H$ gene which covers from the 5' terminus to the ApaI site and the base sequence of a 3' terminal portion of the nonhuman animal antibody $V_H$ gene and having restriction enzyme sites on both ends, to give a chimeric human antibody H chain expression vector which allows no change in the amino acid sequence of $V_H$ upon expression thereof and has appropriate restriction enzyme sites.

(5) Construction of a chimeric human antibody L chain expression vector

A vector for chimeric human antibody L chain expression is constructed, for example by introducing an EcoRV site into the human antibody $C_L$-encoding cDNA in the vicinity of the 5' terminus by mutagenesis, excising that portion which covers from the EcoRV site to the 3' terminus and inserting that portion into a plasmid, such as the plasmid pIg1SE1d4. This vector for chimeric human antibody L chain expression is provided with a cloning site for insertion of the cDNA coding for nonhuman animal $V_L$. The nonhuman animal antibody $V_L$-encoding cDNA, excised with an appropriate restriction enzyme, is inserted into the vector at the cloning site using a synthetic DNA comprising that portion of the human antibody $C_1$ gene which covers from the 5' terminus to the EcoRV site and the base sequence of a 3' terminal portion of the nonhuman animal antibody $V_L$ gene and having restriction enzyme sites on both ends, to give a chimeric human antibody L chain expression vector which allows no change in the amino acid sequence of $V_L$ upon expression thereof.

(6) Introduction of the chimeric human antibody expression vectors into host cells Introduction of the chimeric human antibody H chain expression vector and chimeric human antibody L chain expression vector into host cells gives a transformant producing the chimeric human antibody. In introducing the vectors into host cells, a splicing signal may be introduced into the chimeric human antibody H chain and L chain expression vectors for mRNA stabilization [Cell, 17, 737 (1979)].

The chimeric human antibody H chain and L chain vectors can be introduced into host cells, for example, simultaneously by electroporation [JP-A-2-257891 (the term "JP-A" used herein means an unexamined published Japanese patent application.); Cytotechnology, 3, 133 (1990)]. In addition, an expression vector containing genes coding for both the chimeric human antibody H chain and L chain [tandem expression vector] can be introduced into host cells [BIO/TECHNOLOGY, 9, 64 (1991)]. The use of a tandem expression vector is preferred since a higher level of chimeric human antibody expression can be attained thereby, with approximately equal H chain and L chain expression levels.

An example of a method of producing the CDR-transplanted antibodies of the invention is described as follows.

First, a CDR-transplanted antibody expression vector can be constructed by the method of Winter et al. [Nature, 332, 323 (1988)] as follows.

Three synthetic DNAs are constructed designed so as to comprise the cDNAs coding for three CDR peptides of the $V_H$ of a nonhuman animal antibody, for example, peptides having the amino acid sequences defined by SEQ ID NO:6, SEQ ID NO:7 and SEQ ID NO:8, with DNAs coding for amino acid sequences comprising of several amino acids from both ends of the corresponding CDRs of the $V_H$ of a human antibody being located at the respective both ends of the cDNAs, DNA synthesis is carried out with a plasmid containing the human antibody $V_H$ gene as a template. An example of the human antibody $V_H$ gene-containing plasmid is the M13 plasmid containing a human antibody NEW gene-derived sequence [J. Biol. Chem., 253, 585 (1978); Nature, 332, 323 (1988)].

The DNA obtained is inserted into the vector for chimeric human antibody H chain expression in the same manner as in the construction of the chimeric human antibody expression vector mentioned above to give a CDR-transplanted antibody H chain expression vector.

Similarly, using, as primers, three synthetic DNAs designed to comprise the cDNAs coding for three CDR peptides of the $V_L$ Of a nonhuman animal antibody, for example, the peptides having the amino acid sequences defined by SEQ ID NO:9, SEQ ID NO:10 and SEQ ID NO:11, with DNAs coding for amino acid sequences comprising several amino acids from both ends of the corresponding CDRs of the human antibody $V_L$ being located at the respective both ends of said cDNAs, DNA synthesis is carried out with a human antibody $V_L$ gene-containing plasmid as a template. An example of the human antibody $V_L$ gene-containing plasmid is the M13 plasmid containing a human myeloma protein (Bence-Jones protein) REI gene-derived sequence [Eur. J. Biachem., 45, 513 (1974); Nature, 332, 323 (1988)].

By inserting the DNA obtained into a vector for chimeric human L chain expression in the same manner as described in respect of the construction of the chimeric human antibody expression vector, a CDR-transplanted antibody L chain expression vector can be constructed.

It is also possible to construct the CDR-transplanted antibody H chain and L chain expression vectors by synthesizing DNAs coding for the peptides having amino acid sequences resulting from replacement of the three CDRs each of the H chain and L chain of a human antibody with the corresponding CDRs of the H chain and L chain of a nonhuman animal antibody and then inserting the DNAs into a vector for chimeric human antibody H chain or L chain expression in the same manner as described in respect of the construction of the chimeric human antibody expression vector mentioned above.

The CDR-transplanted antibody expression vector can be introduced into host cells in the same manner as the chimeric human antibody expression vector to give a transformant producing the CDR-transplanted antibody.

The host cells suited for the introduction thereinto of the chimeric human antibody or CDR-transplanted antibody expression vector may be any host cells provided that the chimeric human antibody or CDR-transplanted antibody can be expressed therein. Examples include mouse SP2/0-Ag14 cells (ATCC CRL1581; hereinafter, "SP2/0 cells"), mouse P3X63-Ag8.653 cells (ATCC CRL1580), CHO cells deficient in the dihydrofolate reductase gene (hereinafter, "dhfr") [Urlaub et al.: Proc. Natl. Acad. Sci. U.S.A., 77, 4216 (1980)] and rat YB2/3HL.P2G11.16Ag.20 cells (ATCC CRL1662; hereinafter, "YB2/0 cells"), with YB2/0 cells being preferred.

The transformants producing the chimeric human antibody or CDR-transplanted antibody are selected by the method disclosed in JP-A-2-257891 using PRMI1640 medium containing G418 and fetal calf serum. A particular example of the chimeric human antibody-producing transformant is the transformant KM966 producing a chimeric human antibody that reacts with the ganglioside $GM_2$.— KM966 has been deposited, under the terms of the Budapest Treaty, with the Fermentation Research Institute, Agency of Industrial Science and Technology, of 1-3, Higashi 1-chome, Tsukuba-shi, Ibaraki 305 JAPAN, as of Jul. 15, 1992 under the deposit number FERM BP-3931.

When the transformant obtained is cultivated in a medium, the chimeric human antibody or CDR-transplanted antibody can be produced and accumulated in the culture fluid. The activity of the chimeric human antibody or CDR-transplanted antibody in the medium can be determined by an enzyme-linked immunosorbent assay (ELISA; E. Harlow et al. (ed.): Antibodies—A Laboratory Manual, Cold Spring Harbor Laboratory, 1988). The antibody productivity of the transformant can be increased by utilizing a dhfr amplification system as disclosed in JP-A-2-257891.

The chimeric human antibody and CDR-transplanted antibody can be purified from the culture supernatants obtained as mentioned above using a protein A column (E. Harlow et al. (ed.): Antibodies—A Laboratory Manual, Cold Spring Harbor Laboratory, 1988). As noted above, the chimeric human antibody KM966, which reacts with the ganglioside $GM_2$, is a specific example of the thus-obtained chimeric human antibodies and CDR-transplanted antibodies.

The reactivity of the chimeric human antibody or CDR-transplanted antibody of the invention can be checked by ELISA. The molecuar weight of the purified antibody H chain or L chain or whole antibody molecule can be determined by polyacrylamide gel electrophoresis (SDS-PAGE) or western blotting (E. Harlow et al. (ed.): Antibodies—A Laboratory Manual, Cold Spring Harbor Laboratory, 1988).

The binding activity of the chimeric human antibody or CDR-transplanted antibody that reacts with the ganglioside $GM_2$ of cultured cancer cells can be measured, for example, by the fluorescent antibody technique or by ELISA. The complement dependent cytotoxic activity (CDC activity) and antibody dependent cell mediated cytotoxic activity (ADCC activity) of the chimeric human antibody or CDR-transplanted antibody are measured by the methods described in the monograph "Men-ekigaku Jikken Nyumon (A Manual of Experiments in Immunology)" (Matsuhashi et al., published by Gakkai Shuppan Center, 1981).

The humanized antibodies of the invention specifically bind to human cancer cells and exhibit CDC activity and ADCC activity against human cancer cells and therefore are useful in the treatment of human cancers, among others.

The humanized antibodies according to the present invention can be used alone as an anticancer agent. They may be formulated into an anticancer composition together with at least one pharmaceutically acceptable carrier. For instance, the humanized antibodies are dissolved in physiological saline, an aqueous solution of glucose, lactose or mannitol and the like. The powder of the humanized antibodies for injection can be prepared by lyophilizing the humanized antibodies in accordance with the conventional method and mixing the lyophilized products with sodium chloride. The anticancer composition may further contain additives conventionally used well known in the art of medical preparation, for example, pharmaceutically acceptable salts.

The humanized antibodies according to the present invention can be administered in the form of the above-described anticancer composition to mammals including human in a dose of 0.2 to 20 mg/kg/day. The dose may vary depending on the age, condition, etc. of patients. The administration of the anticancer composition can be effected by intravenous injection once a day (single administration or consecutive administration) or intermittently one to three times a week or once every two to three weeks.

The anticancer composition is expected to be useful for treating cancer such as melanoma, neuroblastoma and glioma.

The following Examples and Reference Examples are further illustrative of the present invention, but are not to be construed to limit the scope of the present invention.

EXAMPLE 1

Production of chimeric human anti-$GM_2$ antibodies

1. Isolation of mRNAs from hybridoma cells producing the mouse anti-$GM_2$ monoclonal antibody KM-796 or KM-750 and from hybridoma cells producing the rat anti-$GM_2$ monoclonal antibody KM-603

Using mRNA extraction kit Fast Track (product number K1593-02) manufactured by Invitorogen and following the description of the manual attached to the kit, mRNAs were isolated from $1 \times 10^8$ cells each of the mouse anti-$GM_2$ monoclonal antibody KM-796-producing hybridoma cell line (FERM BP-3340), the mouse anti-$GM_2$ monoclonal antibody KM-750-producing hybridoma cell line (FERM BP-3339) and the rat anti-$GM_2$ monoclonal antibody KM-603-producing hybridoma cell line (FERM BP-2636).

2. Construction of monoclonal antibody KM-796 and KM-750 H chain and L chain cDNA libraries Using cDNA Synthesis Kit (product number 27-9260-01) manufactured by Pharmacia and following the manual attached to the kit, cDNA having the EcoRI adapter on both ends was synthesized from 5 µg each of the KM-796- and KM-750-derived mRNAs obtained as described in Paragraph 1 above. About 6 µg of each cDNA product obtained was dissolved in 10 µl of sterilized water and fractionated by agarose gel electrophoresis, and a cDNA fragment (about 1.8 kb) corresponding to the IgG antibody H chain and a cDNA fragment (about 1.0 kb) corresponding to the L chain were recovered (about 0.1 µg each). Then, 0.1 µg of each cDNA fragment of about 1.8 kb and 0.1 µg of each cDNA fragment of about 1.0 kb were respectively dissolved in 11.5 µl of T4 ligase buffer, together with 1 µg of the Lambda-ZAPII vector (cleaved with EcoRI and then treated with calf intestine alkaline phosphatase; product of Stratagene). After addition of 175 units of T4 DNA ligase, each solution was incubated at 12° C. for 24 hours and then at room temperature for 2 hours. A 4-µl portion of each reaction mixture was subjected to packaging into the lambda phage in the conventional manner [Maniatis et al. (ed.): Molecular Cloning, 2.95 Cold pring Harbor Laboratory, 1989] using Giga Pak Gold (Stratagene), followed by transfection, in the conventional manner [Maniatis et al. (ed.): Molecular Cloning, 2.95–107, Cold Spring Harbor Laboratory, 1989] of the *Escherichia coli* strain XL1-Blue [Biotechniques, 5, 376 (1987)] attached to Giga Pak Gold, to give about 4,000 phage clones each as a KM-796 or KM-750 H chain or L chain cDNA library. Then the phage clones of each library were fixed on a nitrocellulose filter in the conventional manner [Maniatis et al. (ed.): Molecular Cloning, 2.112, Cold Spring Harbor Laboratory, 1989].

3. Construction of KM-603 H chain and L chain cDNA libraries

Using 5 µg of the KM-603 mRNA obtained as mentioned above in Paragraph 1 and cDNA Synthesis Kit (product number 27-9260-01) manufactured by Pharmacia, cDNA having the EcoRI adapter on both ends was synthesized. About 6 µg of the cDNA produced was dissolved in 10 µl of sterilized water and fractionated by agarose gel electrophoresis. A cDNA fragment (about 2.2 kb) corresponding to the IgG antibody H chain and a cDNA fragment (about 1.0 kb) corresponding to the L chain were recovered (about 0.1 µg each). Then 0.1 µg of the cDNA fragment of about 2.2 kb and 0.1 µg of the cDNA fragment of about 1.0 kb were respectively dissolved in 11.5 µl of T4 ligase buffer, together with 1 µg of the Lambda ZAPII vector (cleaved with EcoRI and then treated with calf intestine alkaline phosphatase; product of Stratagene) and, after addition of 175 units of T4 DNA ligase, the resultant solution was incubated at 12° C. for 24 hours and then at room temperature for 2 hours. A 4µl portion of each reaction mixture was subjected to packaging into the lambda phage in the conventional manner [Maniatis et al. (ed.): Molecular Cloning, 2.95, Cold Spring Harbor Laboratory, 1989] using Giag Pak Gold (Stratagene), followed by transfection, in the conventional manner (Maniatis et al. (ed.): Molecular Cloning, 2.95–107, Cold Spring Harbor Laboratory, 1989], of the *Escherichia coli* strain XL-Blue attached to Giga Pak Gold, whereby about 10,000 phage clones were obtained each as a KM-603 H chain or L chain cDNA library. Then, the phage clones of each library were fixed on a nitrocellulose filter in the conventional manner [Maniatis et al. (ed.): Molecular Cloning, 2.112, Cold Spring Harbor Laboratory, 1989].

4. Cloning of the KM-796 and KM-750 H chain and L chain cDNAs

From among the KM-796 and KM-750 H chain cDNA libraries and L chain cDNA libraries constructed as described above in Paragraph 2, phage clones firmly bound at 65° C. to a probe prepared by labeling a mouse immunoglobulin constant region cDNA [for the H chain, the BamHI-XhoI fragment of the mouse Cγ3 cDNA (Wels et al: EMBO J., 3, 2041–2046, 1984); for the L chain, the HpaI-XhoI fragment of the mouse Cκ cDNA (Hieter et at.: Cell, 22, 197–207, 1980)] with $^{32}P$ were recovered in the conventional manner [Maniatis et al.: Molecular Cloning, 2.108, Cold Spring Harbor Laboratory, 1989]. Then, using a ZAP-cDNA Synthesis Kit (cDNA synthesis kit; product number sc200400) manufactured by Stratagene, phage clones were converted into pBluescript plasmids, and a KM-796 H chain cDNA-containing recombinant plasmid (pKM796H1) and a KM-796 L chain cDNA-containing recombinant plasmid (pKM796L1) (FIG. 1) as well as a KM-750 H chain cDNA-containing recombinant plasmid (pKM750H1) and a KM-750 L chain cDNA-containing recombinant plasmid (pKM750L1) (FIG. 2) were obtained. Cleavage of pKM796H1, pKM750H1, pKM796L1 and pKM750L1 with EcoRI revealed that a cDNA fragment of about 1.8 kb had been inserted into pKM796H1 and pKM750H1 and a cDNA fragment of about 0.9 kb into pKM796L1 and pKM750L1.

5. Cloning of KM-603 H chain and L chain cDNAs

Phage clones firmly bound at 65° C. to a probe prepared by labeling a mouse immunoglobulin constant region chromosomal gene [mouse Cµ gene-containing SmaI-KpnI fragment of about 11.5 kb (Kataoka et al.: Proc. Natl. Acad. Sci. U.S.A., 77, 919–923, 1980) and mouse Cκ gene-containing HindIII-BamaHI fragment of about 3 kb (Sakano et al.: Nature, 280, 288, 1979)] with $^{32}P$ were isolated from the KM-603 H chain cDNA library and L chain cDNA library constructed as mentioned above in Paragraph 3 in the conventional manner [Maniatis et al. (ed.): Molecular Cloning, 2.108, Cold Spring Harbor Laboratory, 1989]. Then, using ZAP-cDNA Synthesis kit (product number sc200400) manufactured by Stratagene, the phage clones were converted to pBluescript plasmids and a KM-603 H chain cDNA-containing recombinant plasmid, pKM603H1, and a KM-603 L chain cDNA-containing recombinant plasmid, pKM603L1, were obtained (FIG. 3). Cleavage of pKM603H1 and pKM603L1 revealed that pKM603H1 contained a cDNA fragment of about 2.0 kb as inserted therein and pKM603L1 a cDNA fragment of about 0.9 kb as inserted therein.

6. Base sequences of the variable regions in the H chain cDNA and L chain cDNA

The base sequences of the variable regions in the H chain cDNA and L chain cDNA obtained as mentioned above in Paragraphs 4 and 5 were determined by the dideoxy method [Maniatis et al. (ed.): Molecular Cloning, 13.42, Cold Spring Harbor Laboratory, 1989] using Sequenase version 2.0 DNA Sequencing Kit manufactured by United States Biochemical Corporation. All the cDNA had a methionine codon, presumably the initiation codon ATG, at the 5' terminus and were leader sequence-containing full-length cDNAs. Based on the base sequences of the respective cDNAs, the amino acid sequences of the H chain and L chain of KM-796, KM-750 and KM-603 were deduced. The amino acid sequence of the KM-796 H chain is shown in SEQ ID NO:1, that of the L chain of KM-796 and KM-750 in SEQ ID NO:2, that of the KM-750 H chain in SEQ ID NO:3, that of the KM-603 H chain in SEQ ID NO:4 and that of the KM-603 L chain in SEQ ID NO:5.

7. Construction of KM-796- and KM-750-derived chimeric human antibody H chain and L chain expression vectors (1) Construction of a vector, pAGE147, carrying the Moloney mouse leukemia virus terminal repeat promoter/enhancer The plasmid pPMOL1 (2 μg), described in JP-A-1-63394, was dissolved in 30 μl of 10 mM Tris-hydrochloride buffer (pH 7.5) containing 6 mM magnesium chloride and 6 mM 2-mercaptoethanol, 20 units of SmaI was added, and digestion was carried out at 30° C. for 3 hours. Then, sodium chloride was added to a concentration of 50 mM, 20 units of ClaI was added, and digestion was conducted at 37° C. for 2 hours. The reaction mixture was subjected to agarose gel electrophoresis, and a DNA fragment (about 0.6 kb) containing the Moloney mouse leukemia virus terminal repeat promoter/enhancer was recovered.

Then, the following two synthetic DNAs were synthesized using an automatic DNA synthesizer (model 380A manufactured by Applied Biosystems Co., Ltd.).

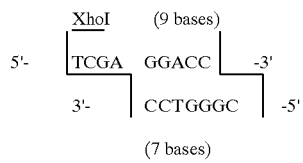

The thus-obtained synthetic DNAs (25 picomoles each) were dissolved in 10 μl of 50 mM Tris-hydrochloride buffer (pH 7.6) containing 10 mM magnesium chloride, 5 mM DTT (dithiothreitol), 0.1 mM EDTA and 0.5 mM adenosine triphosphate (hereinafter, "ATP"), 5 units of T4 DNA kinase was added, and 5'-phosphorylation was carried out at 37° C. for 30 minutes.

The plasmid pPMOL1-derived ClaI-SmaII fragment (0.6 kb, 0.05 μg) and two 5'-phosphorylated synthetic DNAs (1 picomole each), obtained as described above, and a HindIII linker (5'-pCAAGCTTG-3'; Takara Shuzo) (1 picomole) were dissolved in 30 μl of 66 mM Tris-hydrochloride buffer (pH 7.5) containing 6.6 mM magnesium chloride, 10 mM DTT and 0.1 mM ATP, 200 units of T4 DNA ligase (Takara Shuzo; hereinafter the same shall apply) were added, and ligation was carried out at 12° C. for 16 hours. The resultant DNA fragment was recovered by ethanol precipitation and dissolved in 20 μl of 10 mM Tris-hydrochloride buffer (pH 7.5) containing 6 mM magnesium chloride, 100 mM sodium chloride and 6 mM 2-mercaptoethanol, 10 units of HindIII and 10 units of XhoI were added, and digestion was carried out at 37° C. for 2 hours. The reaction was terminated by phenol-chloroform extraction, and the DNA fragment was recovered by ethanol precipitation.

Separately, 1 μg of the plasmid pAGE107 [Cytotechnology, 3, 133 (1990)] was dissolved in 30 μl of 10 mM Tris-hydrochloride buffer (pH 7.5) containing 6 mM magnesium chloride, 100 mM sodium chloride and 6 mM 2-mercaptoethanol, 10 units of HindIII and 10 units of XhoI were added, and digestion was carried out at 37° C. for 2 hours. The reaction mixture was subjected to agarose gel electrophoresis, and a DNA fragment (about 6.0 kb) containing the G418 resistance gene and ampicillin (hereinafter, "Ap") resistance gene was recovered.

The plasmid pAGE107-derived HindIII-XhoI fragment (6.0 kb, 0.3 μg) and plasmid pPMOL1-derived HindIII-XhoI fragment (0.63 kb, 0.01 μg) obtained as mentioned above were dissolved in 20 μl of 66 mM Tris-hydrochloride buffer (pH 7.5) containing 6.6 mM magnesium chloride, 10 mM DTT and 0.1 mM ATP, 200 units of T4 DNA ligase were added, and ligation was carried out at 12° C. for 16 hours. The thus-obtained recombinant plasmid DNA was used to transform Escherichia coli HB101, and the plasmid pAGE147 shown in FIG. 4 was obtained.

(2) Construction of a vector, pAGE148, carrying the β-globulin 3' splicing signal (SP)

For introducing the β-globulin 3' splicing signal into the chimeric human antibody expression vector at a site downstream from the antibody constant region gene, a vector (pAGE148), was constructed as follows, which contained the β-globulin 3' splicing signal and the same genes as those in the chimeric human antibody expression vector (except for the human antibody constant region gene).

Two μg of pSE1UK1SEd1-3, described in JP-A-2-257851, were added to 30 μl of 10 mM Tris-hydrochloride buffer (pH 7.5) containing 10 mM magnesium chloride, 50 mM sodium chloride and 1 mM DTT. After addition of 10 units of HindIII, digestion was carried out at 37° C. for 4 hours. The reaction mixture was subjected to phenol-chloroform extraction and then to ethanol precipitation. The precipitate was dissolved in 20 μl of DNA polymerase I buffer, 5 units of Escherichia coli-derived DNA polymerase I Klenow fragment were added, and the 5' cohesive ends produced by HindIII digestion were rendered blunt by incubation at 22° C. for 30 minutes. The reaction mixture was subjected to phenol-chloroform extraction and then to ethanol precipitation, 30 μl of 10 mM Tris-hydrochloride buffer (pH 7.5) containing 10 mM magnesium chloride and 1 mM DTT and 10 units of KpnI were added, and digestion was effected at 37° C. for 4 hours. The reaction mixture was subjected to phenol-chloroform extraction and then to ethanol precipitation, 30 μl of 50 mM Tris-hydrochloride buffer (pH 7.5) containing 10 mM magnesium chloride, 100 mM sodium chloride and 1 mM DTT and 10 units of XhoI were added, and digestion was carried out at 37° C. for 4 hours. The reaction mixture was fractionated by agarose gel electrophoresis and two DNA fragments, about 6.67 kb and about 1.98 kb in size, were recovered (about 0.2 μg each).

Then, 2 μg of pAGE147 obtained in (1) was added to 30 μl of 10 mM Tris-hydrochloride buffer (pH 7.5) containing 10 mM magnesium chloride and 1 mM DTT, 10 units of LpnI was added, and digestion was effected at 37° C. for 4 hours. The reaction mixture was subjected to phenol-chloroform extraction and then to ethanol precipitation, 30 μl of 50 mM Tris-hydrochloride buffer (pH 7.5) containing 10 mM magnesium chloride, 100 mM sodium chloride and 1 mM DTT and 10 units of XhoI were added, and digestion was carried out at 37° C. for 4 hours. The reaction mixture was fractionated by agarose gel electrophoresis and about 0.2 μg of a DNA fragment of about 0.66 kb was recovered.

Figure 5:
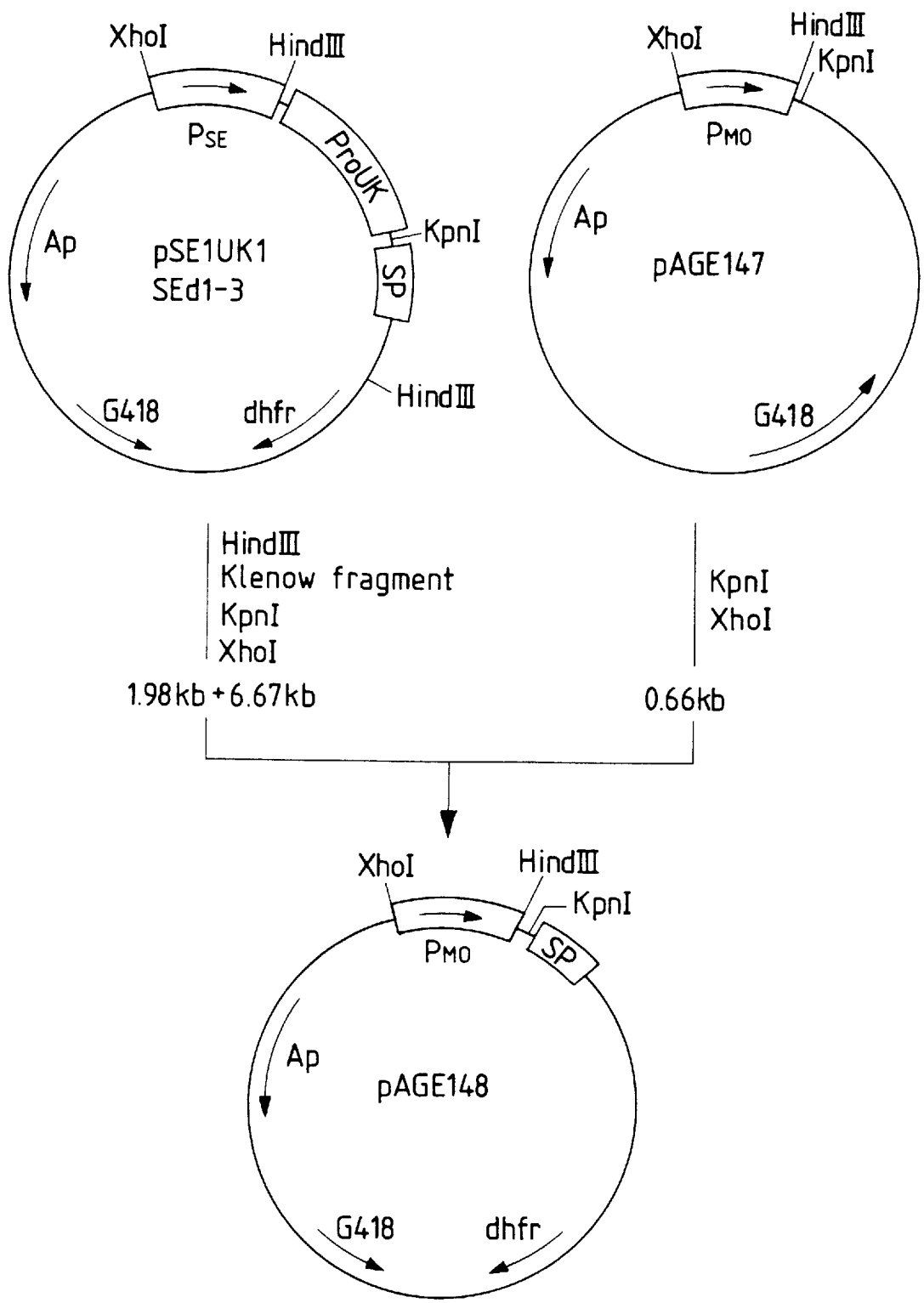
FIG. 5 shows a construction scheme for a plasmid, pAGE148.

Then, 0.1 μg of the XhoI-HindIII fragment (about 6.67 kb) of pSE1UK1SEd1–3, as obtained above, 0.1 μg of the KpnI-HindIII fragment (about 1.98 kb), obtained above, and 0.1 μg of the XhoI-KpnI fragment (about 0.66 kb) of pAGE147, as obtained above, were dissolved in a total of 20 μl of T4 ligase buffer. Three hundred fifty units of T4 ligase were added to the solution, and ligation was carried out at 4° C. for 24 hours. The thus-obtained-recombinant plasmid DNA was used to transform *Escherichia coli* HB101, and the plasmid pAGE148 shown in FIG. 5 was obtained.

Figure 6:
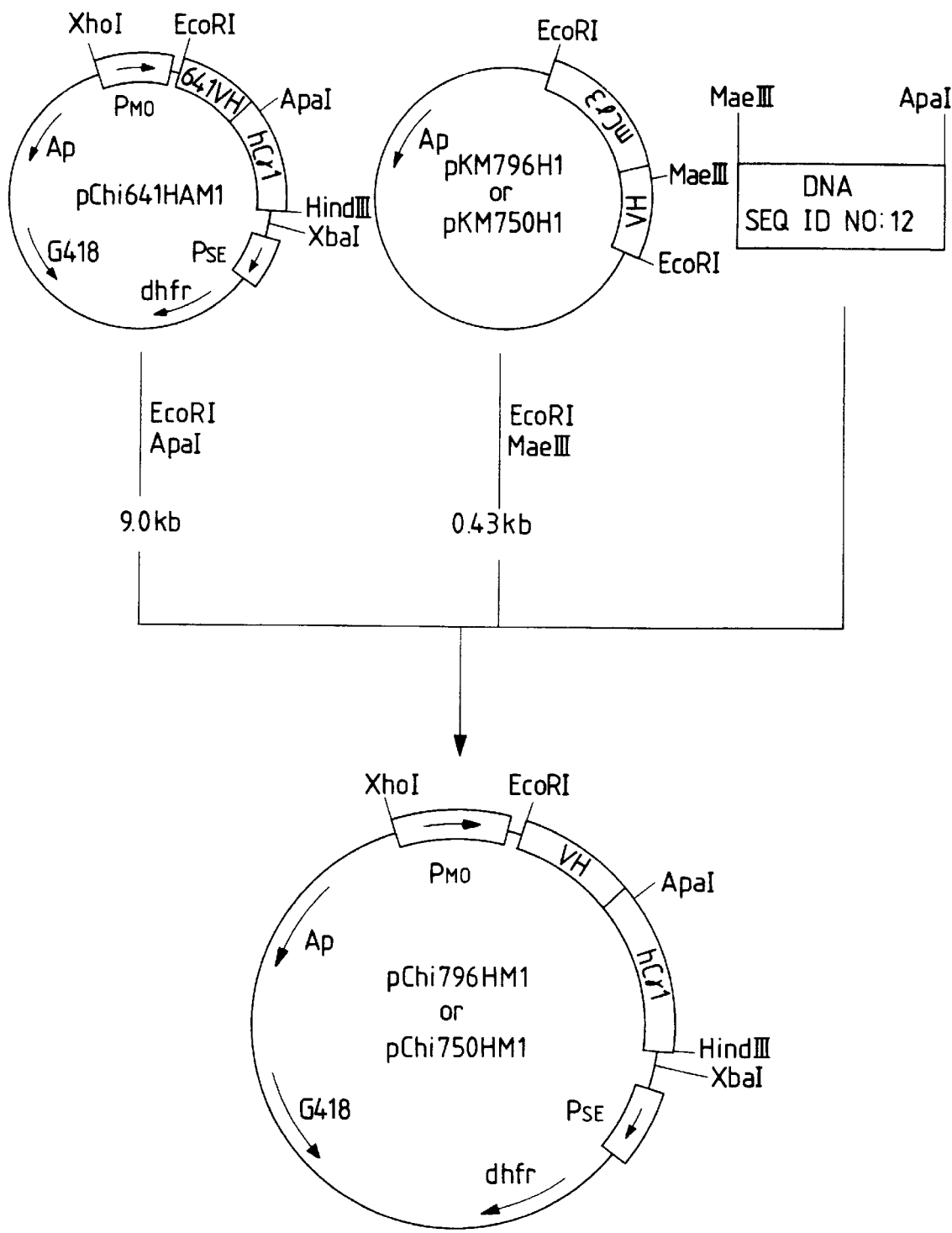
FIG. 6 shows a construction scheme for plasmids, pChi796HM1 and pChi750HM1.

(3) Construction of KM-796- and KM-750-derived chimeric human antibody H chain expression vectors First, the cDNA coding for the antibody variable region in the plasmid pKM796H1 or pKM750H1 was excised by cleavage at the 5'-terminal EcoRI site and the MaeIII site near the 3' end of said cDNA and joined, together with a synthetic DNA having the base sequence shown in SEQ ID NO:12, to the chimeric human antibody H chain expression vector pChi641HAM1, as follows (FIG. 6).

Three μg of pKM796H1 or pKM750H1, obtained in Paragraph 4, were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of MaeIII were added, and digestion was effected at 37° C. for 4 hours. The reaction mixture was fractionated by agarose gel electrophoresis and about 0.3 μg of a DNA fragment of about 0.43 kb was recovered. Then, 3 μg of pChi641HAM1, obtained in Reference Example 2, was added to 30 μl of 10 mM Tris-hydrochloride buffer (pH 7.5) containing 10 mM magnesium chloride and 1 mM DTT, 10 units of EcoRI and 10 units of ApaI were also added, and digestion was carried out at 37° C. for 4 hours. The reaction mixture was fractionated by agarose gel electrophoresis and about 1.0 μg of a DNA fragment of about 9.0 kb was recovered. Then, 0.1 μg of the EcoRI-MaeIII fragment (about 0.43 kb) of pKM796H1 or pKM750H1, as obtained above, 0.1 μg of the EcoRI-ApaI fragment (about 9.0 kb) of pChi641HAM1, as obtained above, and 0.3 μg of a synthetic DNA having the base sequence shown in SEQ ID NO:12 were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HE101. In this way, the plasmids pChi796HM1 and pChi750HM1, shown in FIG. 6, were obtained.

Figure 7:
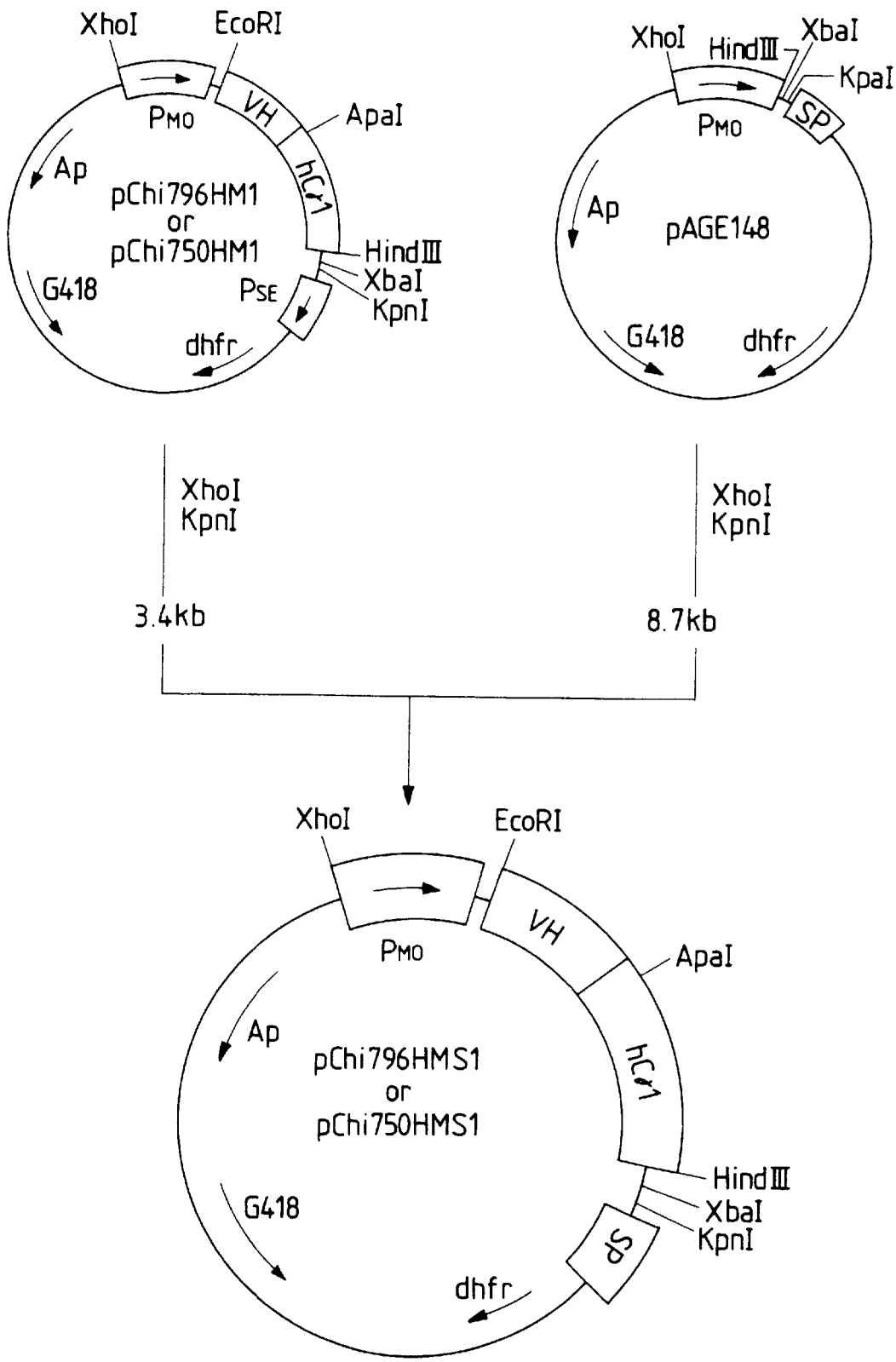
FIG. 7 shows a construction scheme for plasmids, pChi796HMS1 and pChi750HMS1.

Then, the β-globulin 3' splicing signal was introduced into the plasmids pChi796HM1 and pChi750HM1 by the method described below to construct KM796- and KM-750-derived chimeric human antibody H chain expression vectors (FIG. 7).

Three μg of pChi796HM1 or pChi750HM1 were added to 30 μl of 33 mM Tris-acetate buffer (pH 7.9) containing 10 mM magnesium acetate, 66 mM potassium acetate, 0.5 mM DTT and 0.01% bovine serum albumin (hereinafter, "BSA"). Ten units of XhoI and 10 units of KpnI were also added, and digestion was carried out at 37° C. for 4hours. The reaction mixture was fractionated by agarose gel electrophoresis and about 0.3 μg of a DNA fragment of about 3.4 kb was recovered. Then, 3 μg of pAGE148 obtained in (2) was added to 30 μl of 33 mM Tris-acetate buffer (pH 7.9) containing 10 mM magnesium acetate, 66 mM potassium acetate, 0.5 mM DTT and 0.01% BSA; 10 units of XhoI and 10 units of KpnI were further added, and digestion was effected at 37° C. for 4 hours. The reaction mixture was fractionated by agarose gel electrophoresis and about 0.3 μg of a DNA fragment of about 8.7 kb was recovered. Then, 0.1 μg of the XhoI-KpnI fragment of pChi796HM1 or pKM750HM1 and 0.1 μg of the XhoI-KpnI fragment of pAGE148 were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HB101. The plasmids pChi796HMS1 and pChi750HMS1 shown in FIG. 7 were thus obtained.

Figure 8:
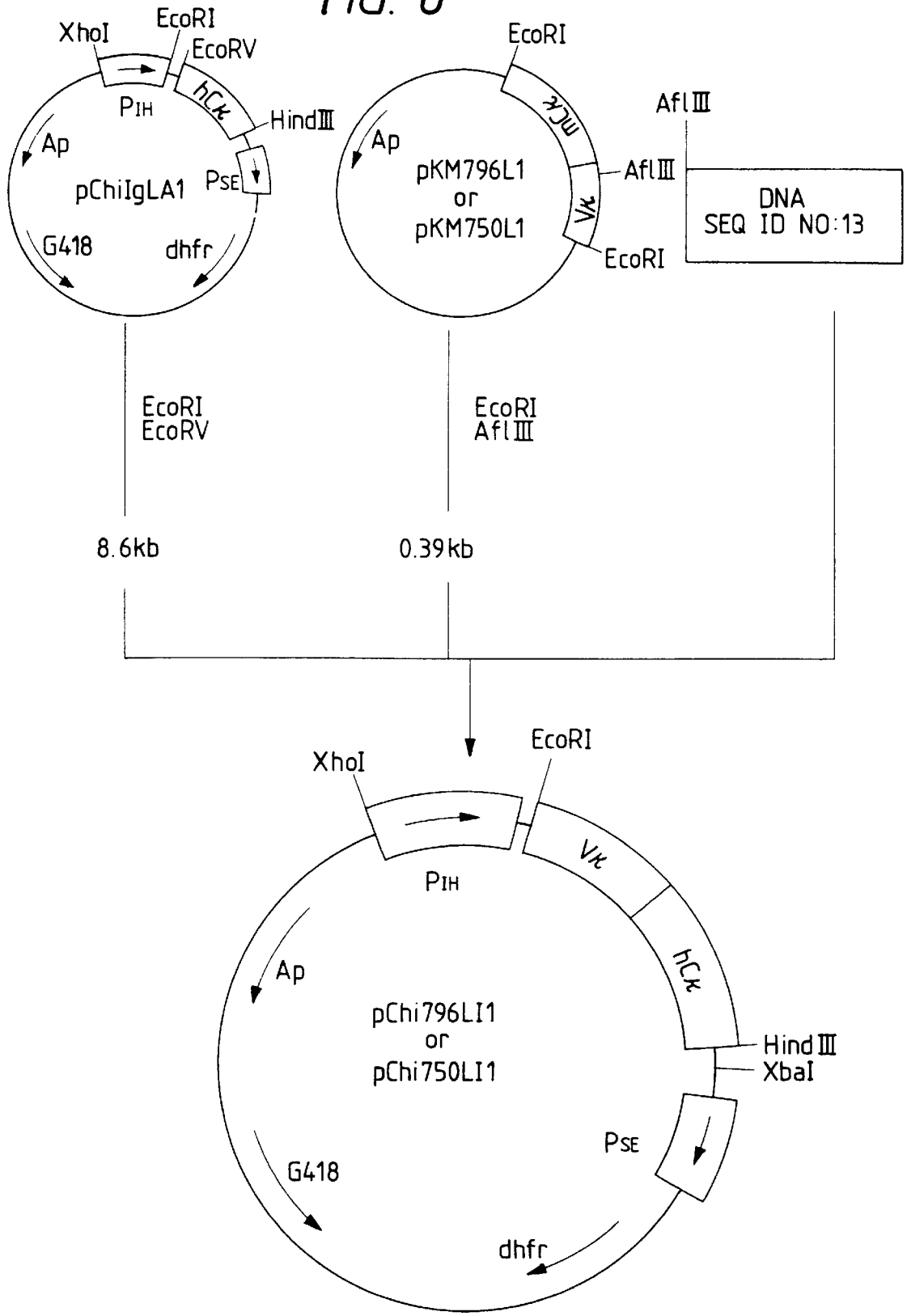
FIG. 8 shows a construction scheme for plasmids, pChi796LI1 and pChi750LI1.

(4) Construction of KM-796- and KM-750-derived chimeric human antibody L chain expression vectors First, the cDNA coding for the antibody variable region in the plasmid pKM796L1 or pKM750L1 was excised by cleavage at the 5'-terminal EcoRI site and the AflIII site near the 3' end of said cDNA and joined, together with a synthetic DNA having the base sequence shown in SEQ ID NO:13, to the chimeric human antibody L chain expression vector pChiIgLA1, as follows (FIG. 8).

Three μg of pKM796L1 or pKM750L1 were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of AflIII were added, and digestion was effected at 37° C. for 4 hours. The reaction mixture was fractionated by agarose gel electrophoresis and about 0.3 μg of a DNA fragment of about 0.39 kb was recovered. Then, 3 μg of pChiIgLA1 obtained in Reference Example 1 was added to 30 μl of 50 mM Tris-hydrochloride buffer (pH 7.5) containing 10 mM magnesium chloride, 100 mM sodium chloride and 1 mM DTT, 10 units of EcoRI and 10 units of EcoRV were further added, and digestion was carried out at 37° C. for 4 hours. The reaction mixture was fractionated by agarose gel electrophoresis and about 1 μg of a DNA fragment of about 8.6 kb was recovered.

Then, 0.1 μg of the EcoRI-AflIII fragment of pKM796L1 or pKM750L1, as obtained above, 0.1 μg of the EcoRI-EcoRV fragment of pChiIgLA1, as obtained above, and 0.3 μg of a synthetic DNA, having the base sequence shown in SEQ ID NO:13, were dissolved in a total of 20 μl of T4 ligase buffer; 350 units of T4 ligase was further added to the solution, and ligation was carried out at 4° C. for 24 hours. The thus-obtained recombinant plasmid DNA was used to transform *Escherichia coli* HB101. In this way, the plasmids pChi796LI1 and pChi750LI1 shown in FIG. 8 were obtained.

Figure 9:
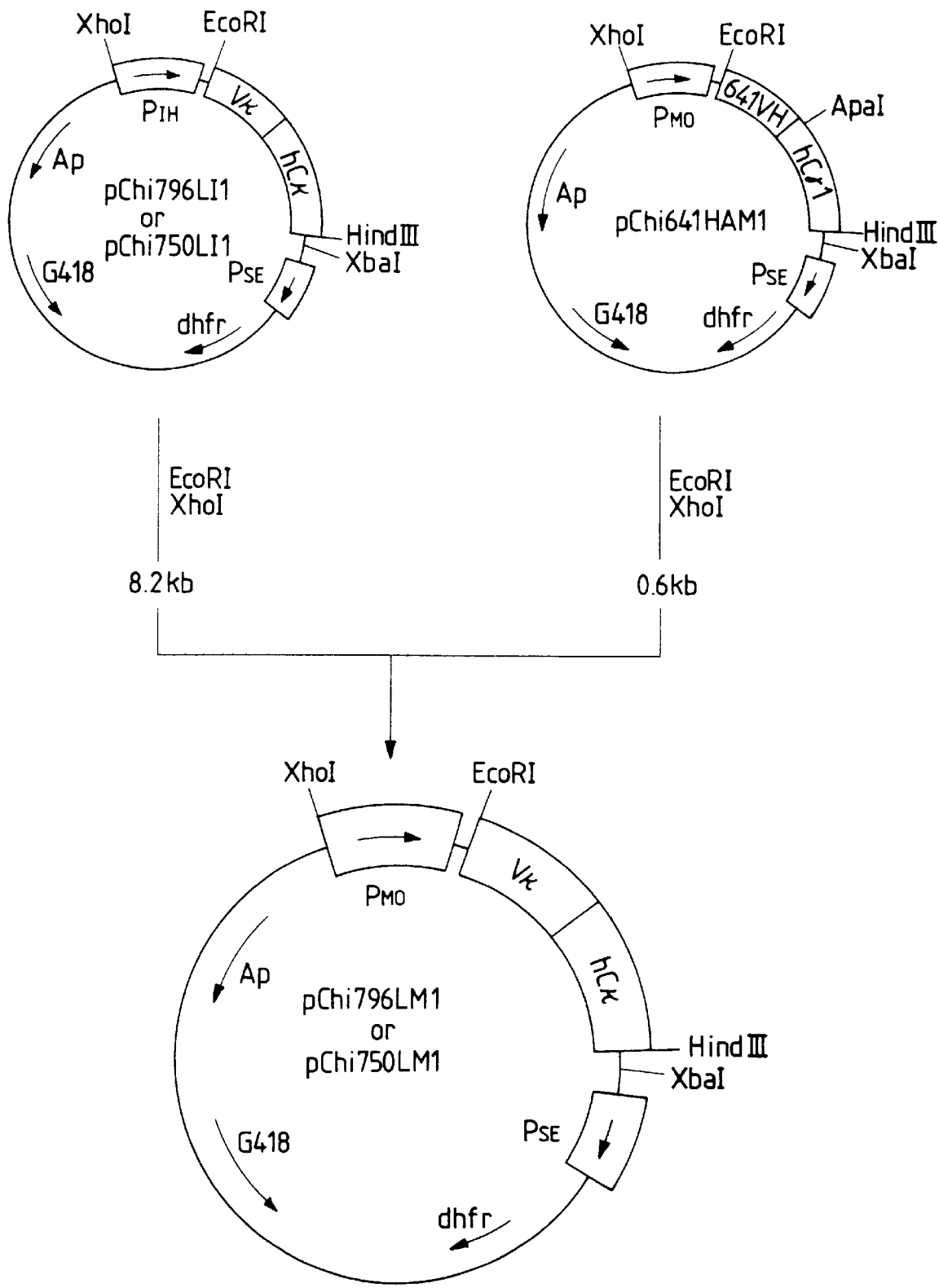
FIG. 9 shows a construction scheme for plasmids, pChi796LM1 and pChi750LM1.

Then, the Moloney mouse leukemia virus terminal repeat promoter/enhancer was introduced into the plasmids pChi796LI1 and pChi750LI1 in the following manner (FIG. 9).

Three μg of pChi796LI1 and pChi750LI1 were added to 30 μl of 50 mM Tris-hydrochloride buffer (pH 7.5) containing 10 mM magnesium chloride, 100 mM sodium chloride and 1 mM DTT. Further, 10 units of EcoRI and 10 units of XhoI were added, and digestion was effected at 37° C. f or 4 hours. The reaction mixture was fractionated by agarose gel electrophoresis and about 0.3 μg of a DNA fragment of about 8.2 kb was recovered Then, 3 μg of the chimeric human antibody H chain expression vector pChi641HAM1 obtained in Reference Example 2 was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was carried out at 37° C. for 4 hours. The reaction mixture was fractionated by agarose gel electrophoresis and about 0.3 μg of a DNA fragment of about 0.6 kb was recovered.

Then, 0.1 μg of the EcoRI-XhoI fragment of pChi796LI1 or pKM750LI1 as obtained above and 0.1 μg of the EcoRI-XhoI fragment of pChi641HAM1 as obtained above were dissolved in a total of 20 μl of T4 ligase buffer, 350 units of T4 ligase was further added to the solution, and ligation was carried out at 4° C. for 24 hours. The thus-obtained recombinant plasmid DNA was used to transform *Escherichia coli* HB101. In this way, the plasmids pChi796LM1 and pChi750LM1 shown in FIG. 9 were obtained.

Figure 10:
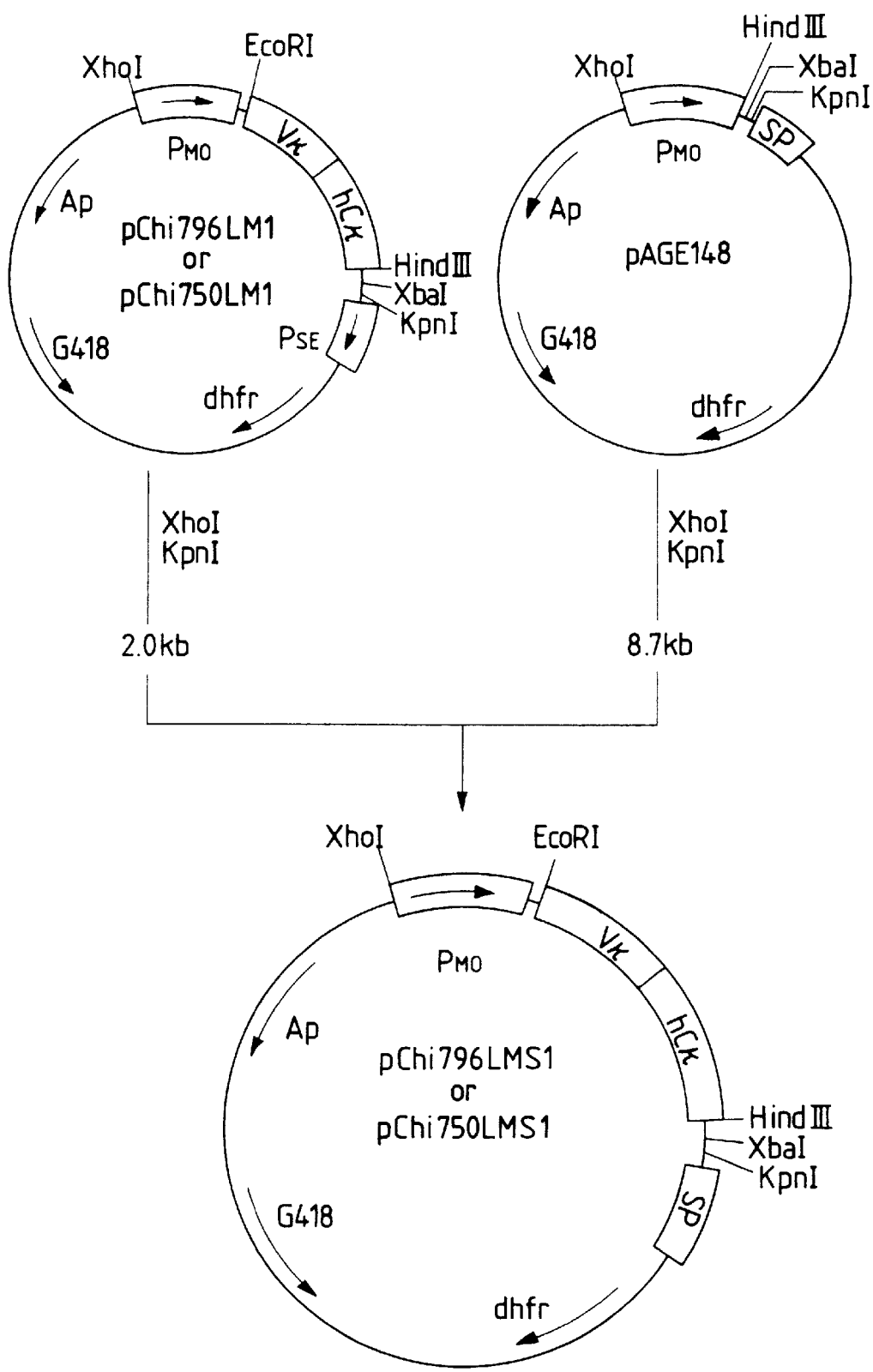
FIG. 10 shows a construction scheme for plasmids, pChi796LMS1 and pChi750LMS1.

Then, the β-globulin 3' splicing signal was introduced into the plasmids pChi796LM1 and pChi750LM1 in the manner mentioned below to construct KM-796- and KM-750-derived chimeric human antibody L chain expression vectors (FIG. 10).

Three μg of pChi796LM1 or pChi750LM1 were added to 30 μl of 33 mM Tris-acetate buffer (pH 7.9) containing 10 mM magnesium acetate, 66 mM potassium acetate, 0.5 mM DTT and 0.01% BSA. Further, 10 units of XhoI and 10 units of KpnI were added, and digestion was carried out at 37° C. for 4 hours. The reaction mixture was fractionated by agarose gel electrophoresis and about 0.3 μg of a DNA fragment of about 2.0 kb was recovered. Then, 3 μg of pAGE148 obtained in (2) was added to 30 μl of 33 mM Tris-acetate buffer (pH 7.9) containing 10 mM magnesium acetate, 66 mM potassium acetate, 0.5 mM DTT and 0.01% BSA; 10 units of XhoI and 10 units of KpnI were further added, and digestion was carried out at 37° C. for 4 hours. The reaction mixture was fractionated by agarose gel electrophoresis and about 0.3 μg of a DNA fragment of about 8.7 kb was recovered. Then 0.1 μg of the XhoI-KpnI fragment of pChi796LM1 or pKM750LM1 as obtained above and 0.1 μg of the XhoI-KpnI fragment of pAGE148 were dissolved in a total of 20 μl of T4 ligase buffer, 350 units of T4 ligase was further added, and ligation was carried out at 4° C. for 24 hours. The thus-obtained recombinant plasmid DNA was used to transform *Escherichia coli* HB101. In this way, the plasmids pChi796LMS1 and pChi750LMS1 shown in FIG. 10 were obtained.

Figure 11:
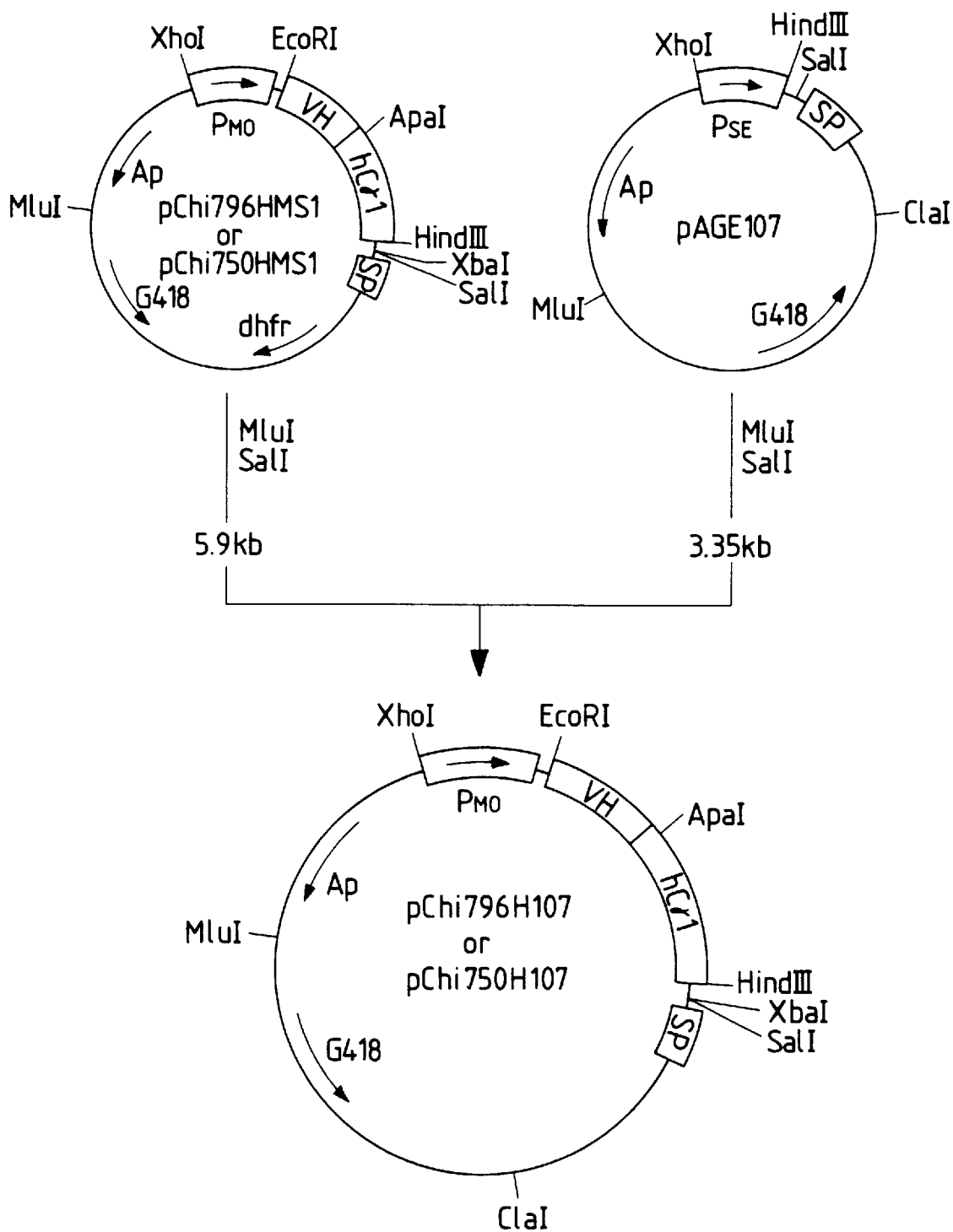
FIG. 11 shows a construction scheme for plasmids, pChi796H107 and pChi750H107.

8. Construction of KM-796- and KM-750-derived chimeric human antibody H chain and L chain tandem expression vectors Tandem expression vectors containing the chimeric human antibody H chain-encoding cDNA and L chain-encoding cDNA on one and the same vector were constructed (FIG. 11 and FIG. 12).

Three μg of pChi796HMS1 or pChi750HMS1, obtained in Paragraph 7, were added to 30 μl of 10 mM Tris-hydrochloride buffer (pH 7.5) containing 10 mM magnesium chloride, 50 mM sodium chloride and 1 mM DTT. Further, 10 units of MluI and 10 units of SalI were added, and digestion was carried out at 37° C. for 4 hours. The reaction mixture was fractionated by agarose gel electrophoresis. In each case, about 0.3 μg of a DNA fragment of about 5.9 kb was recovered. Then, 2 μg of pAGE107 described in EP-A-0 405 285 was dissolved in 30 μl of 10 mM Tris-hydrochloride buffer (pH 7.5) containing 10 mM magnesium chloride, 50 mM sodium chloride and 1 mM DTT; 10 units of MluI and 10 units of SalI were further added, and digestion was carried out at 37° C. for 4 hours. The reaction mixture was fractionated by agarose gel electrophoresis and about 0.2 μg of a DNA fragment of about 3.55 kb was recovered. Then, 0.1 μg of the MluI-SalI fragment of pChi796HMS1 or pChi750HMS1 and 0.1 μg of the MluI-SalI fragment of pAGE107 were dissolved in a total of 20 μl of T4 ligase buffer, 350 units of T4 ligase was added, and ligation was carried out at 4° C. for 24 hours. The thus-obtained recombinant plasmid DNA was used to transform *Escherichia coli* HB101 to give the plasmid pChi796H107 or pChi750H107 shown in FIG. 11.

Then, 3 μg of pChi796H107 or pChi750H107 was added to 30 μl of 10 mM Tris-hydrochloride buffer (pH 7.5) containing 10 mM magnesium chloride, 50 mM sodium chloride and 1 mM DTT, 10 units of ClaI was further added, and digestion was carried out at 37° C. for 4 hours. The reaction mixture was subjected to phenol-chloroform extraction and then to ethanol precipitation. The precipitate was dissolved in 20 μl of DNA polymerase I buffer, 5 units of *Escherichia coli*-derived DNA polymerase I Klenow fragment was added, and the mixture was incubated at 22° C. for 30 minutes for rendering the cohesive ends formed upon ClaI digestion blunt-ended. The reaction mixture was further subjected to phenol-chloroform extraction and then to ethanol precipitation. To the precipitate were added 30 μl of 10 mM Tris-hydrochloride buffer (pH 7.5) containing 10 mM magnesium chloride, 50 mM sodium chloride and 1 mM DTT, and 10 units of MluI. Digestion was carried out at 37° C. for 4 hours and the reaction mixture was fractionated by agarose gel electrophoresis. In each case, about 0.3 μg of a DNA fragment of about 7.5 kb was recovered. Then, 3 μg of pChi796LMS1 or pChi750LMS1 was added to 30 μl of 20 mM Tris-hydrochloride buffer (pH 8.5) containing 10 mM magnesium chloride, 100 mM potassium chloride and 1 mM DTT, 10 units of XhoI was further added, and digestion was carried out at 37 ° C. for 4 hours. The reaction mixture was subjected to phenol-chloroform extraction and then to ethanol precipitation. The precipitate was dissolved in 20 μl of DNA polymerase I buffer, 5 units of *Escherichia coli*-derived DNA polymerase I Klenow fragment was added, and the mixture was incubated at 22° C. for 30 minutes for rendering the cohesive ends formed upon XhoI digestion blunt-ended. The reaction mixture was further subjected to phenol-chloroform extraction and then to ethanol precipitation. To the precipitate was added 30 μl of 10 mM Tris-hydrochloride buffer (pH 7.5) containing 10 mM magnesium chloride, 50 mM sodium chloride and 1 mM DTT as well as 10 units of MluI. Digestion was carried out at 37° C. for 4 hours and the reaction mixture was fractionated by agarose gel electrophoresis. In each case, about 0.3 μg of a DNA fragment of about 9.3 kb was recovered. Then, 0.1 μg of the MluI-ClaI fragment of pChi796H107 or pChi750H107, as obtained above, and 0.1 μg of the MluI-XhoI fragment of pChi796LMS1 or pChi750LMS1, as obtained above, were dissolved in a total of 20 μl of T4 ligase buffer; 350 units of T4 ligase was further added, and ligation was carried out at 4° C. for 24 hours. The thus-obtained recombinant plasmid DNA was used to transform *Escherichia coli* HB101, and the plasmid pChi796HL1 or pChi750HL1 shown in FIG. 12 was obtained.

Figure 13:
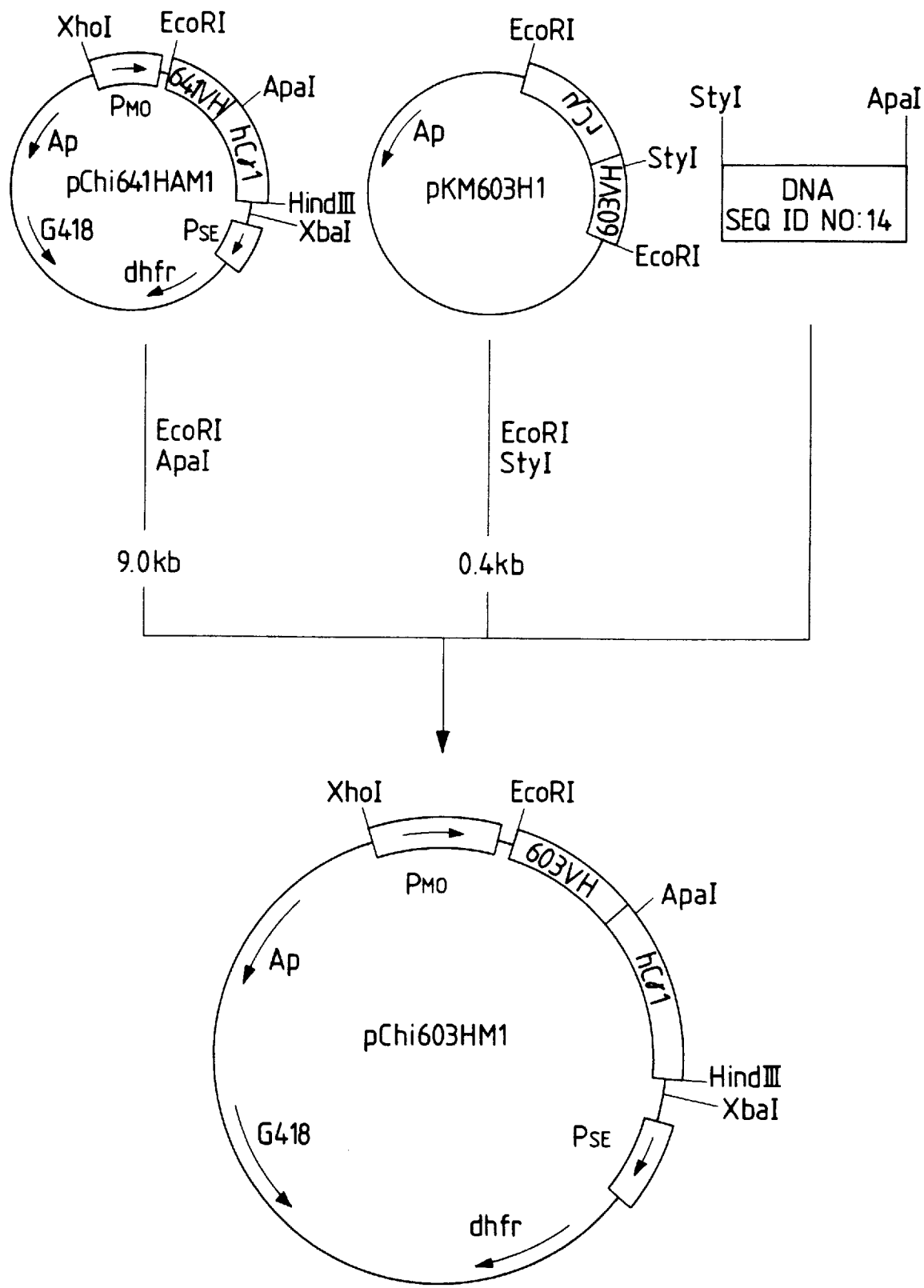
FIG. 13 shows a construction scheme for a plasmid, pChi603HM1.

9. Construction of a KM-603-derived chimeric human antibody H chain expression vector First, the antibody variable region-encoding cDNA of the plasmid pKM603H1 was excised by cleavage at the 5'-terminal EcoRI site and the StyI site near the 3' end of said cDNA and joined to the chimeric human antibody H chain expression vector pChi641HAM1 together with a synthetic DNA having the base sequence shown in SEQ ID NO:14 in the following manner (FIG. 13).

Three μg of pKM603H1 obtained in Paragraph 5 were added to 30 μl of 50 mM Tris-hydrochloride buffer (pH 7.5) containing 10 mM magnesium chloride, 100 mM sodium chloride and 1 mM DTT, followed by further addition of 10 units of EcoRI and 10 units of StyI. Digestion was carried out at 37° C. for 4 hours. The reaction mixture was fractionated by agarose gel electrophoresis and about 0.3 μg of a 0.4-kb DNA fragment was recovered. Then, 3 μg of pChi641HAM1, obtained in Reference Example 2, was added to 30 μl of 10 mM Tris-hydrochloride (pH 7.5) containing 10 mM magnesium chloride and 1 mM DTT, 10 units of EcoRI and 10 units of ApaI were further added, and digestion was effected at 37° C. for 4 hours. The reaction mixture was fractionated by agarose gel electrophoresis and about 1.0 μg of a DNA fragment of about 9.0 kb was recovered. Then, 0.1 μg of the EcoRI-StyI fragment (about 0.4 kb) of pKM603H1, as obtained above, and 0.1 μg of the EcoRI-ApaI fragment (about 9.0 kb) of pChi641HAM1, as obtained above, were dissolved, together with 0.3 μg of a synthetic DNA having the base sequence shown in SEQ ID NO:14, in a total of 20 μl of T4 ligase buffer; 350 units of T4 ligase was added to the solution, and ligation was effected at 4° C. for 24 hours. The thus-obtained recombinant plasmid DNA was used to transform *Escherichia coli* HB101 and the plasmid pChi603HM1 shown in FIG. 13 was obtained.

Figure 14:
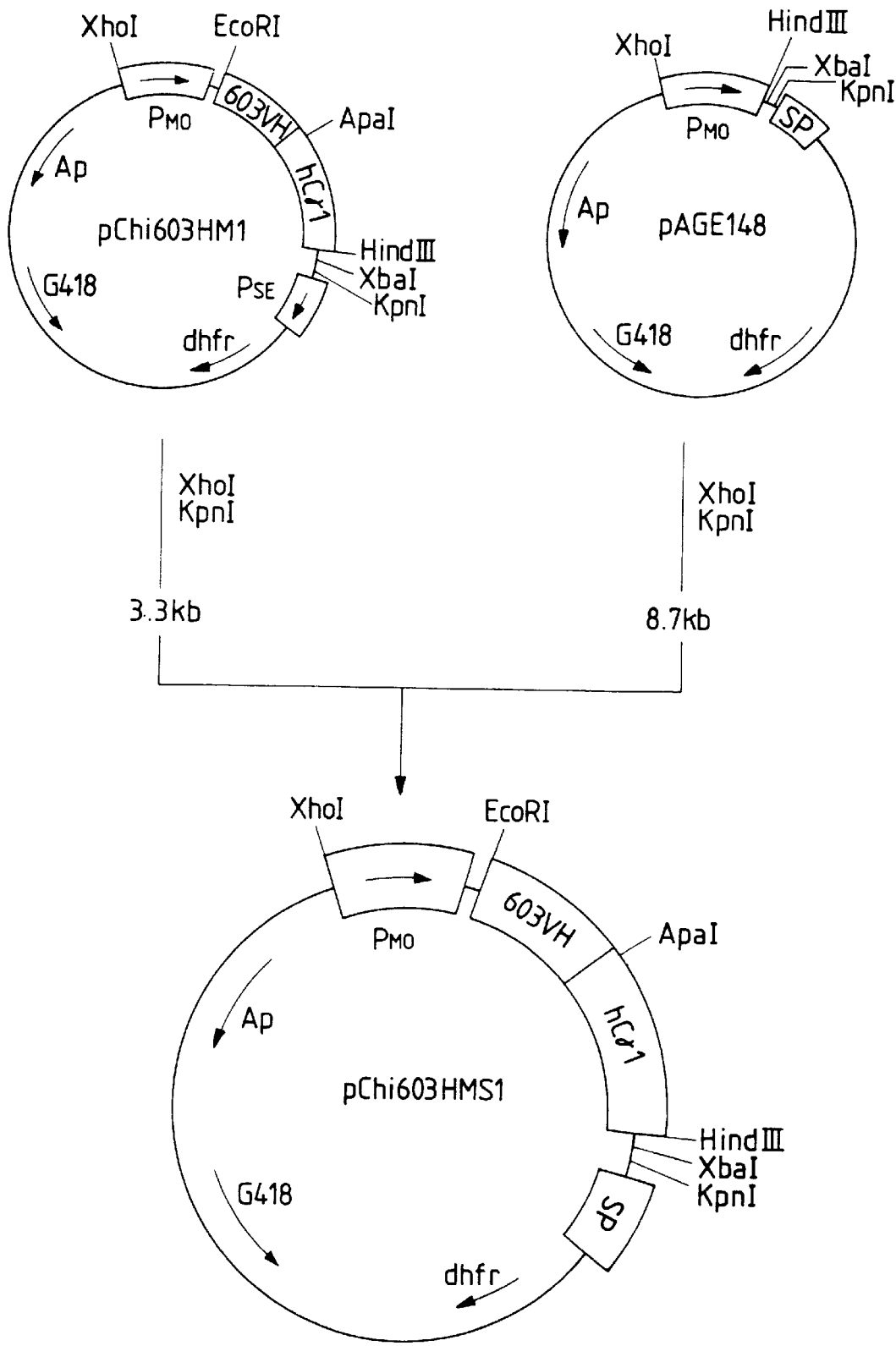
FIG. 14 shows a construction scheme for a plasmid, pChi603HMS1.

Then, a KM-603-derived chimeric human antibody H chain expression vector was constructed by introducing the β-globulin 3' splicing signal into the plasmid pChi603HM1 in the following manner (FIG. 14).

Three μg of pChi603HM1 obtained above were added to 30 μl of 33 mM Tris-acetate buffer (pH 7.9) containing 10 mM magnesium acetate, 66 mM potassium acetate, 0.5 mM DTT and 0.01% BSA. Further, 10 units of XhoI and 10 units of KpnI were added, and digestion was carried out at 37° C. for 4 hours. The reaction mixture was fractionated by agarose gel electrophoresis and about 0.3 μg of a DNA fragment of about 3.3 kb was recovered.

Then, 3 μg of pAGE148 obtained in Paragraph 7 (2) was added to 30 μl of 33 mM Tris-acetate buffer (pH 7.9) containing 10 mM magnesium acetate, 66 mM sodium acetate, 0.5 mM DTT and 0.01% BSA; 10 units of XhoI and 10 units of KpnI were further added, and digestion was carried out at 37° C. for 4 hours. The reaction mixture was fractionated by agarose gel electrophoresis and about 0.3 μg of a DNA fragment of about 8.7 kb was recovered. Then, 0.1 μg of the XhoI-KpnI fragment of pChi603HM1, as obtained above, and 0.1 μg of the XhoI-KpnI fragment of pAGE148, as obtained above, were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pChi603HMS1 shown in FIG. 14 was obtained.

Figure 15:
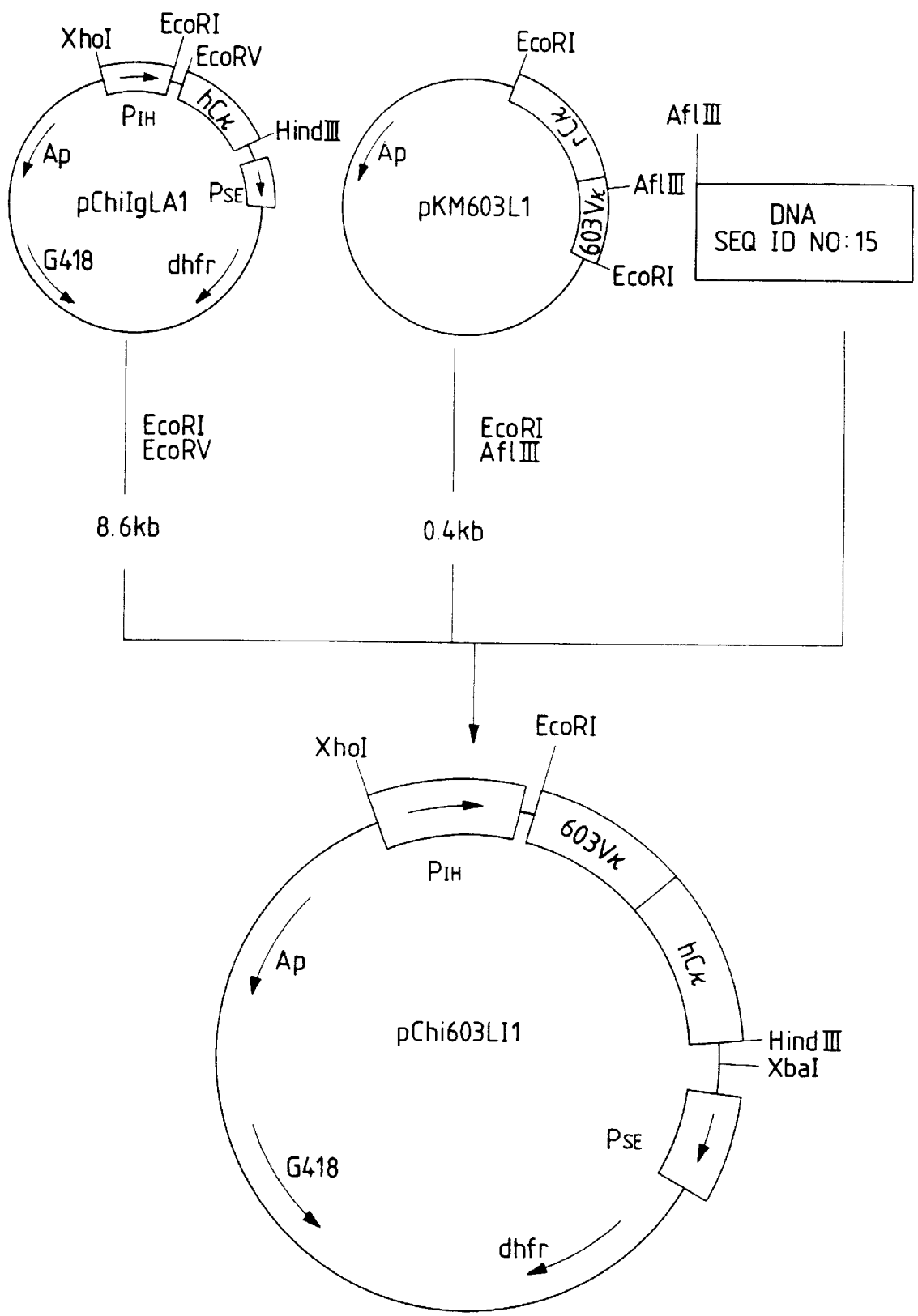
FIG. 15 shows a construction scheme for a plasmid, pChi603LI1.

10. Construction of a KM-603-derived chimeric human antibody L chain expression vector First, the antibody variable region cDNA in the plasmid pKM603L1 was excised by cleavage at the 5' terminal EcoRI site and the AflIII site near the 3' end and joined to the chimeric human antibody L chain expression vector pChiIgLA1 together with a synthetic DNA having the base sequence defined by SEQ ID NO:15 (FIG. 15).

Thus, 3 μg of pKM603L1 obtained in Paragraph 5 was added to 30 μl of 50 mM Tris-hydrochloride buffer (pH 7.5) containing 10 mM magnesium chloride, 100 mM sodium chloride and 1 mM DTT, 10 units of EcoRI and 10 units of AflIII were further added, and digestion was carried out at 37° C. for 4 hours. The reaction mixture was fractionated by agarose gel electrophoresis and about 0.3 μg of a DNA fragment of about 0.4 kb was recovered. Then, 3 μg of pChiIgLA1 obtained in Reference Example 1 was added to 30 μl of 50 mM Tris-hydrochloride buffer (pH 7.5) containing 10 mM magnesium chloride, 100 mM sodium chloride and 1 mM DTT, 10 units of EcoRI and 10 units of EcoRV were further added, and digestion was carried out at 37° C. for 4 hours. The reaction mixture was fractionated by agarose gel electrophoresis and about 1 μg of a DNA fragment of about 8.6 kb was recovered. Then, 0.1 μg of the EcoRI-AflIII fragment of pKM603L1, as obtained above, 0.1 μg of the EcoRI-EcoRV fragment of pChiIgLA1, as obtained above, and 0.3 μg of a synthetic DNA, having the base sequence defined by SEQ ID NO:15, were dissolved in a total of 20 μl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pChi603LI1 shown in FIG. 15 was obtained.

Figure 16:
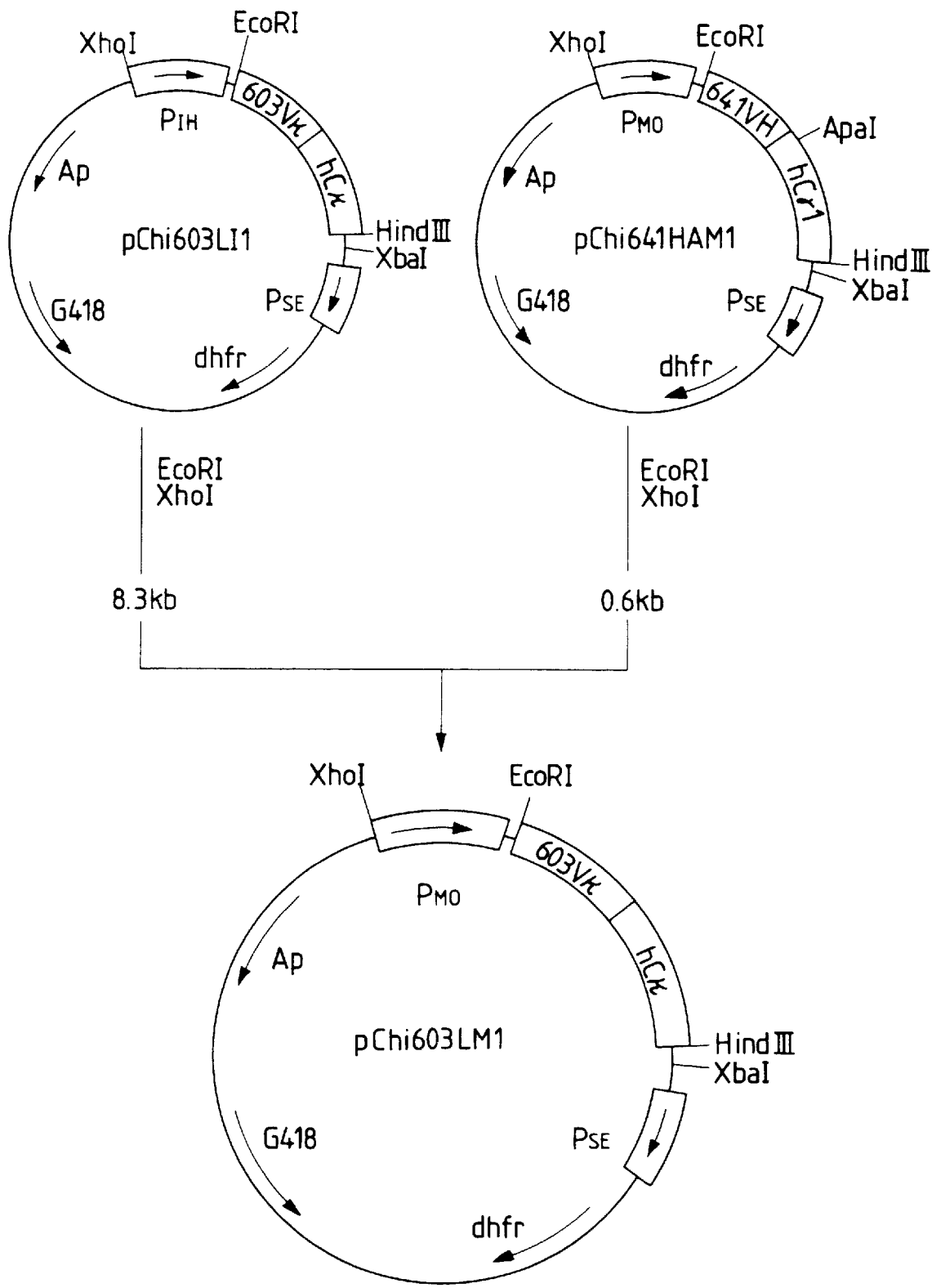
FIG. 16 shows a construction scheme for a plasmid, pChi603LM1.

Then, the Moloney mouse leukemia virus terminal repeat promoter/enhancer was introduced into the plasmid pChi603LI1 in the following manner (FIG. 16).

Thus, 3 μg of pChi603LI1 obtained above was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was carried out at 37° C. for 4 hours. The reaction mixture was fractionated by agarose gel electrophoresis and about 0.3 μg of a DNA fragment of about 8.3 kb was recovered. Then, 3 μg of pChi641HAM1 obtained in Reference Example 2 was added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were further added, and digestion was effected at 37° C. for 4 hours. The reaction mixture was fractionated by agarose gel electrophoresis and about 0.3 μg of a DNA fragment of about 0.6 kb was recovered. Then, 0.1 μg of the EcoRI-XhoI fragment of pChi603LI1 as obtained above and 0.1 μg of the EcoRI-XhoI fragment of pChi641HAM1 as obtained above were dissolved in a total of 20 μl of T4 ligase buffer; 350 units of T4 ligase was added to the solution, and ligation was effected at 4° C. for 24 hours. The thus-obtained recombinant plasmid DNA was used to transform *Eschrichia coli* HB101 to give the plasmid pChi603LM1 shown in FIG. 16.

Figure 17:
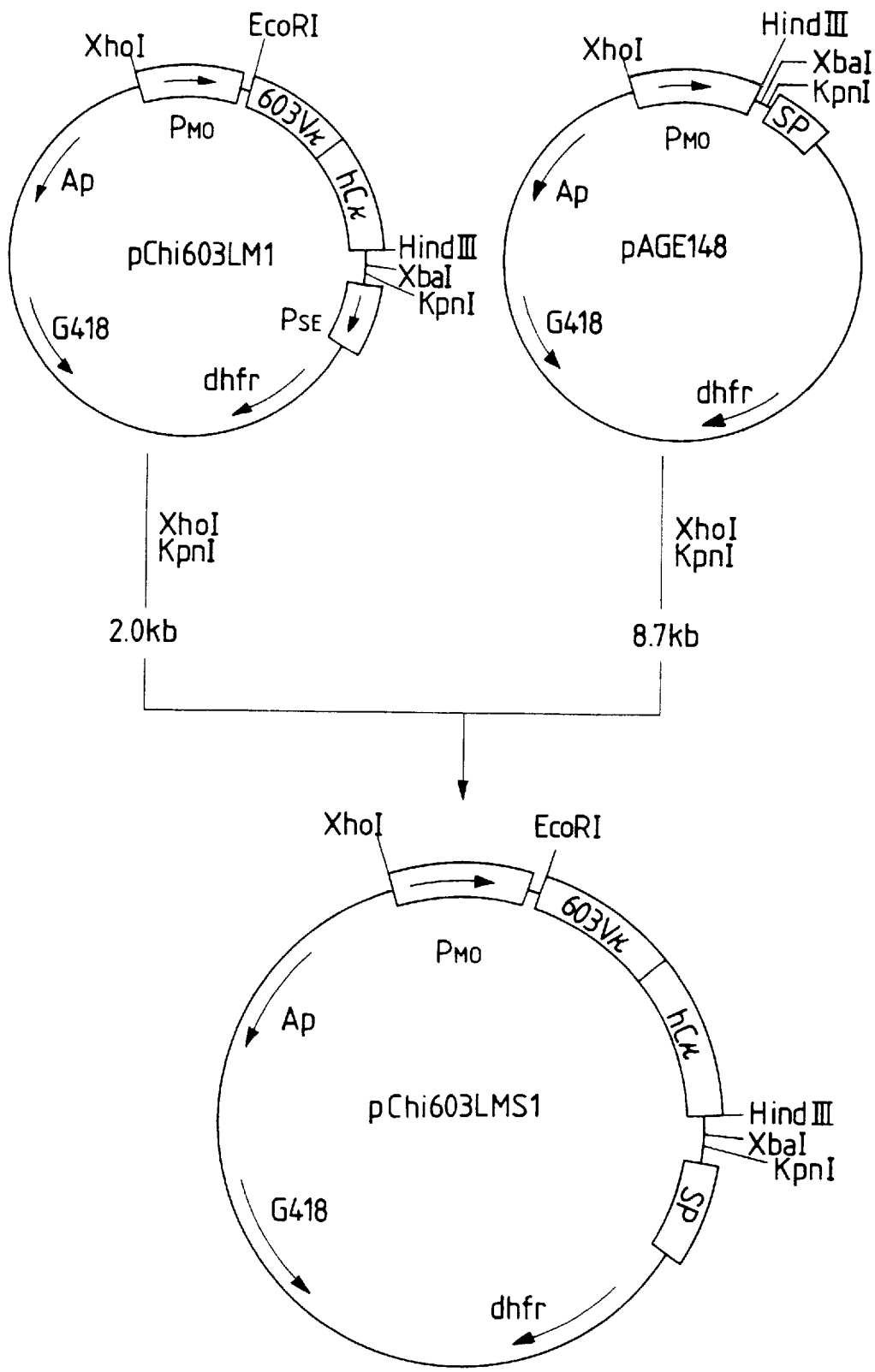
FIG. 17 shows a construction scheme for a plasmid, pChi603LMS1.
Figure 20A:
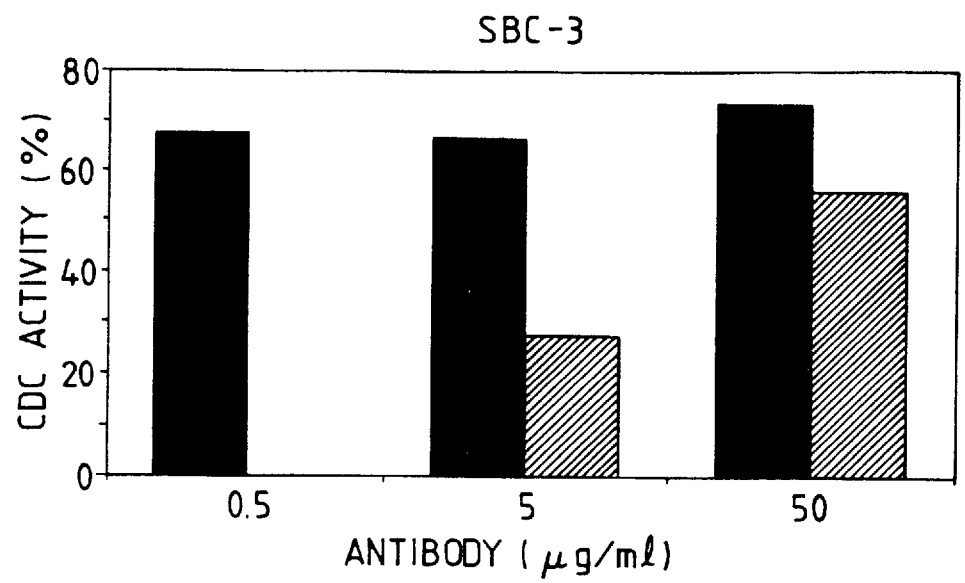
FIGS. 20A and 20B graphically show the CDC (complement dependent cytotoxicity) activities of KM966 against the human lung small cell carcinoma cell lines SBC-3 and LU-135. The ordinate indicates the cytotoxic activity and the abscissa the concentration of the antibody added. The solid bars indicate the CDC activities of KM-696 and the shaded bars the CDC activities of KM966.
Figure 20B:
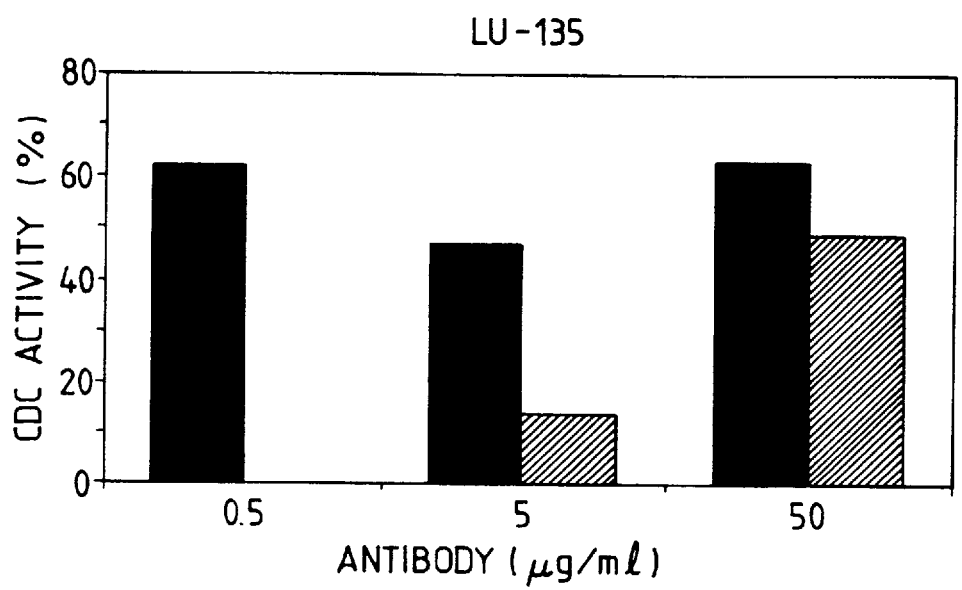
Figure 21A:
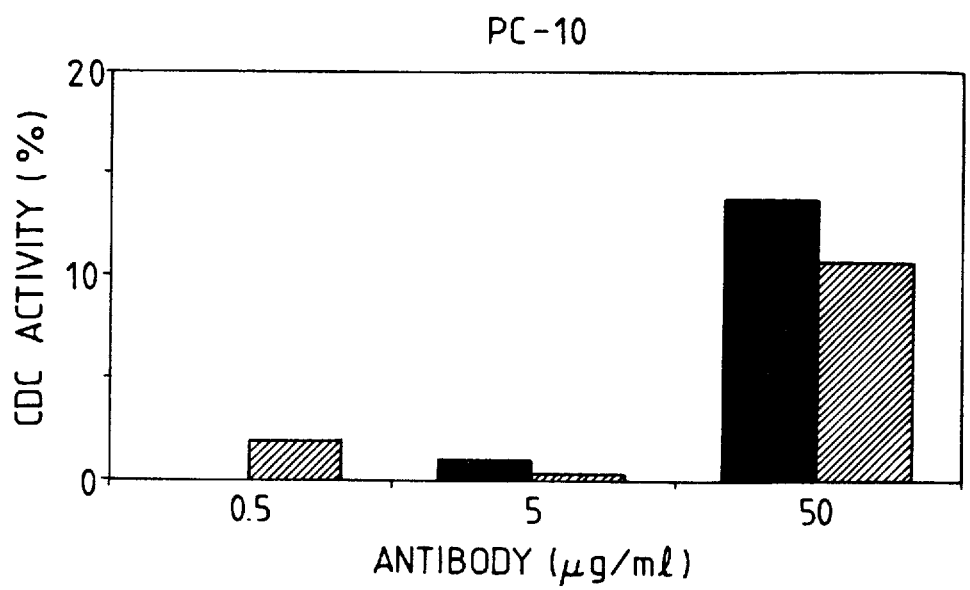
FIGS. 21A and 21B graphically show the CDC activities of KM966 against the human lung squamous cell carcinoma cell line PC-10 and human lung adenocarcinoma cell line RERF-LC-MS. The ordinate indicates the cytotoxicity and the abscissa the concentration of the antibody added. The solid bars indicate the CDC activities of KM-696 and the shaded bars the CDC activities of KM966.
Figure 21B:
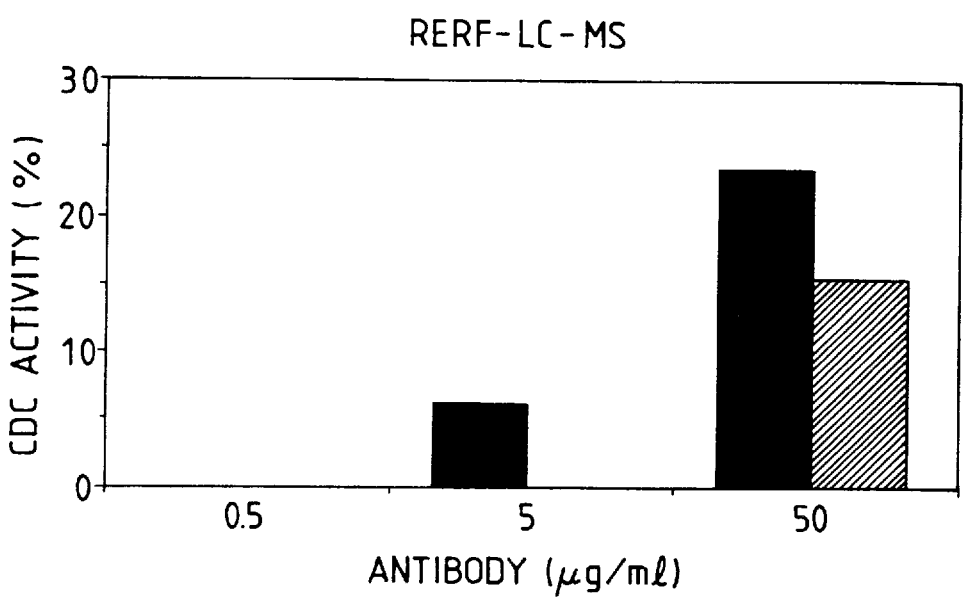
Figure 22A:
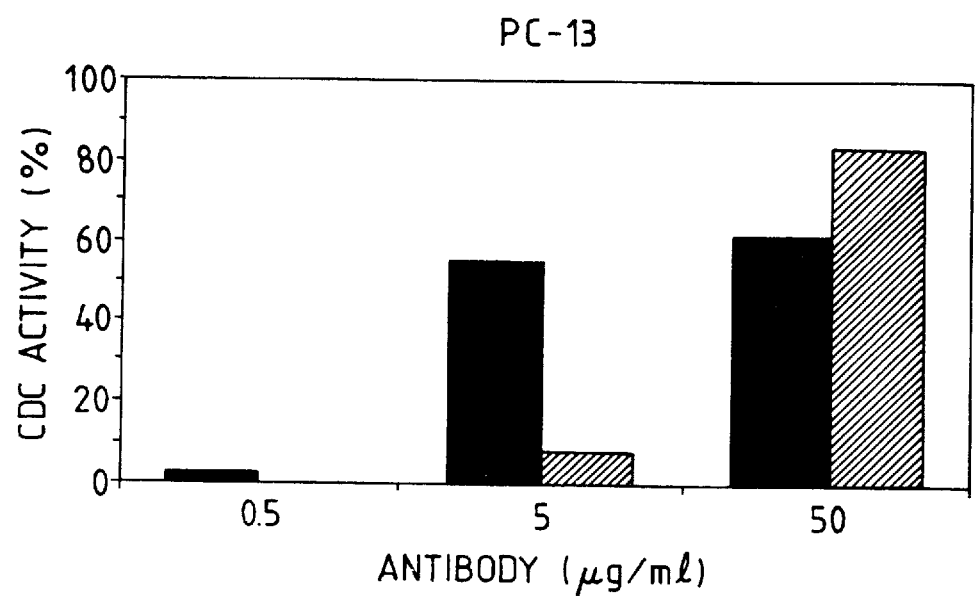
FIGS. 22A and 22B graphically show the CDC activities of KM966 against the human lung large cell carcinoma cell line PC-13 and human neuroblastoma cell line NAGAI. The ordinate indicates the cytotoxic activity and the abscissa the concentration of the antibody added. The solid bars indicate the CDC activities of KM-696 and the shaded bars the CDC activities of KM966.
Figure 22B:
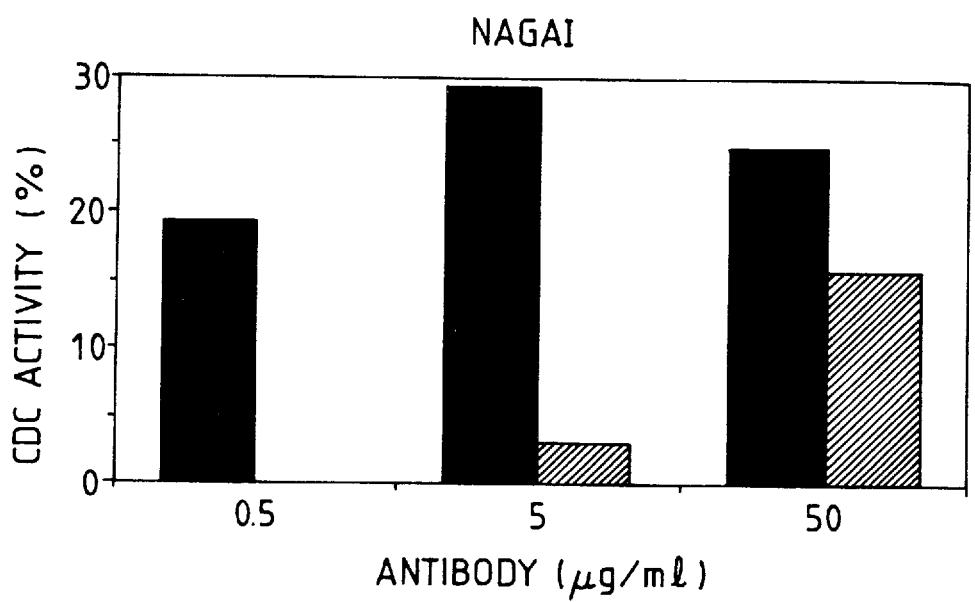
Figure 23A:
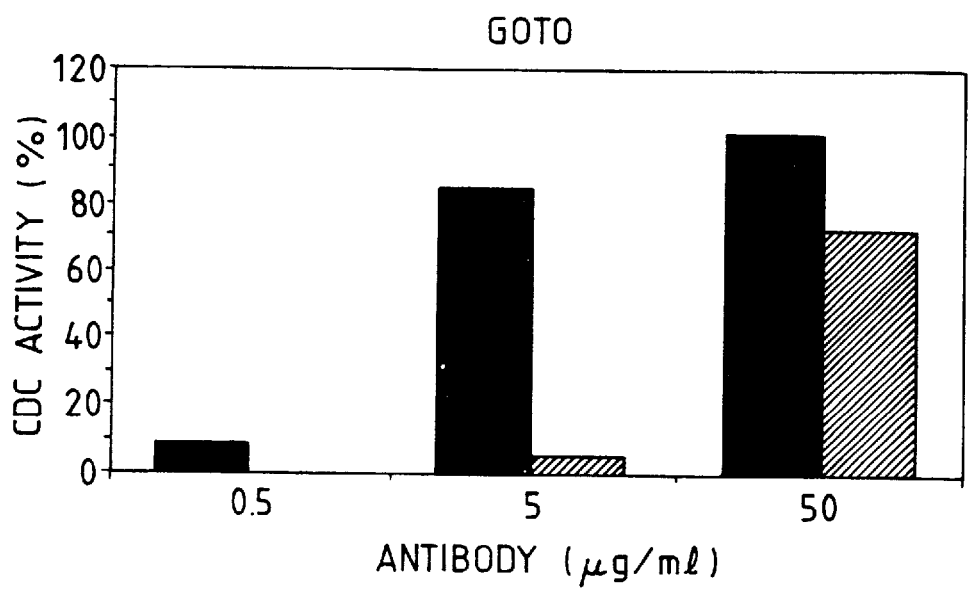
FIGS. 23A and 23B graphically shows the CDC activities of KM966 against the human neuroblastoma cell line GOTO and human brain tumor cell line A172. The ordinate indicates the cytotoxic activity and the abscissa the concentration of the antibody added. The solid bars indicate the CDC activities of KM696 and the shaded bars the CDC activities of KM966.
Figure 23B:
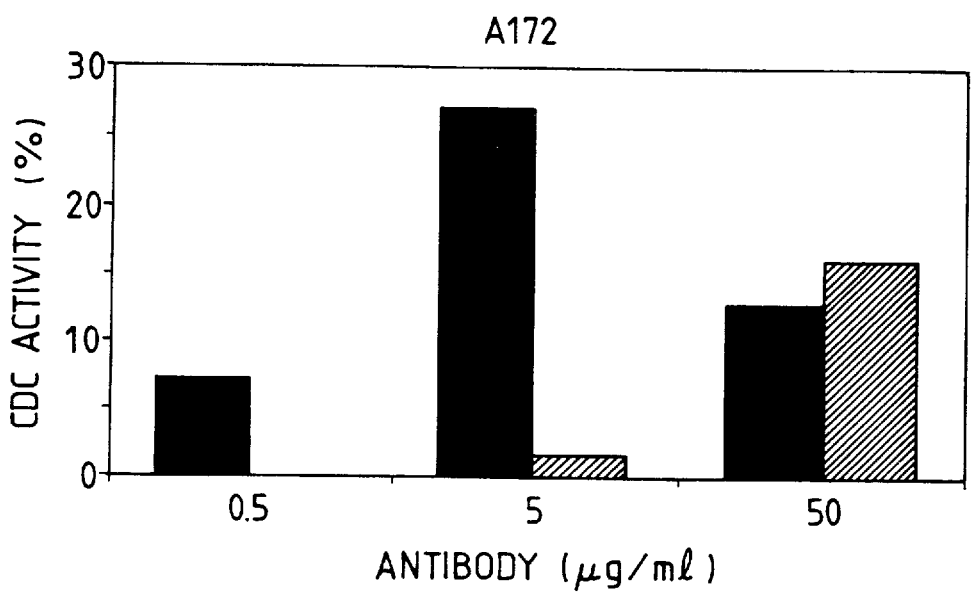
Figure 24A:
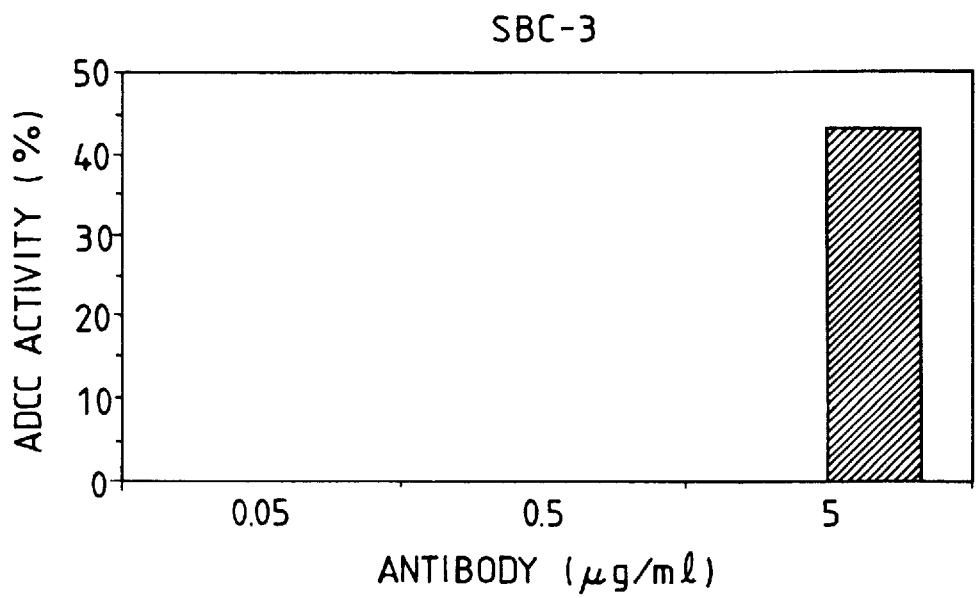
FIGS. 24A and 24B graphically show the ADCC (antibody dependent cell mediated cytotoxicity) activities of KM966 against the human lung small cell carcinoma cell lines SBC-3 and LU-135. The ordinate indicates the cytotoxic activity and the abscissa the concentration of the antibody added. The solid bars indicate the ADCC activities of KM-696 and the shaded bars the ADCC activities of KM966.
Figure 24B:
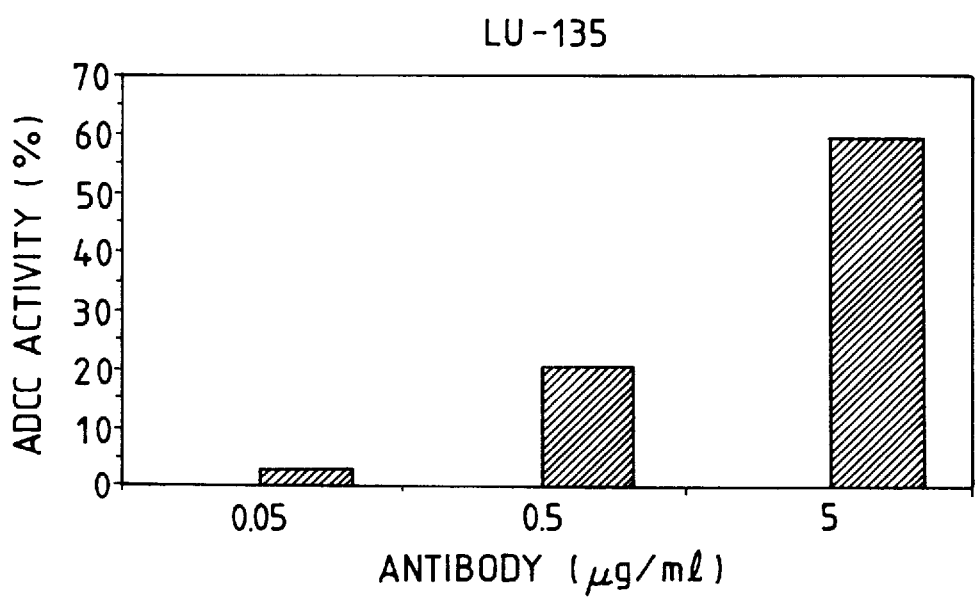
Figure 25A:
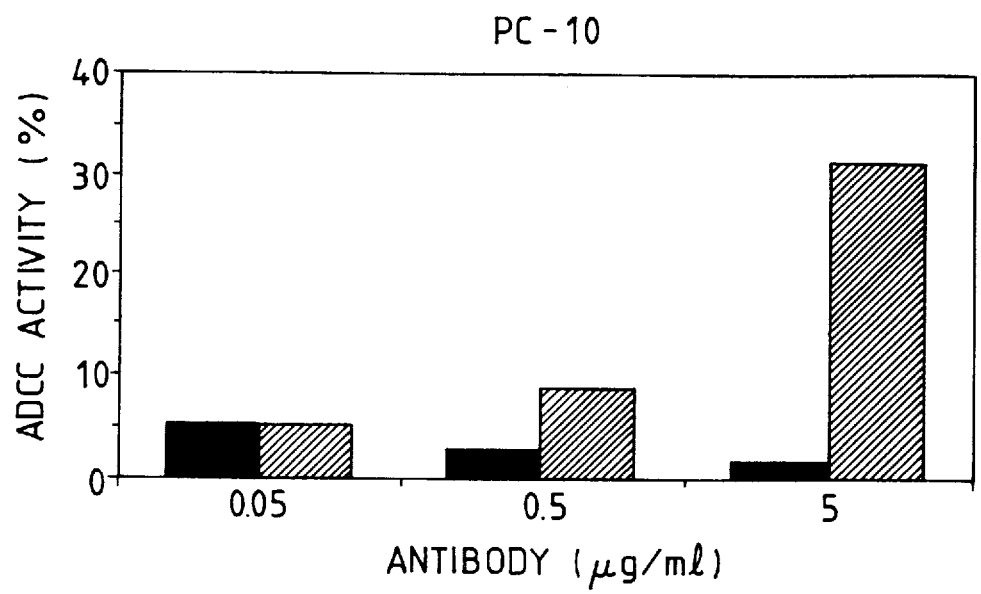
FIGS. 25A and 25B graphically show the ADCC activities of KM966 against the human lung squamous carcinoma cell line PC-10 and human lung adenocarcinoma cell line RERF-LC-MS. The ordinate indicates the cytotoxic activity and the abscissa the concentration of the antibody added. The solid bars indicate the ADCC activities of KM-696 and the shaded bars the ADCC activities of KM966.
Figure 25B:
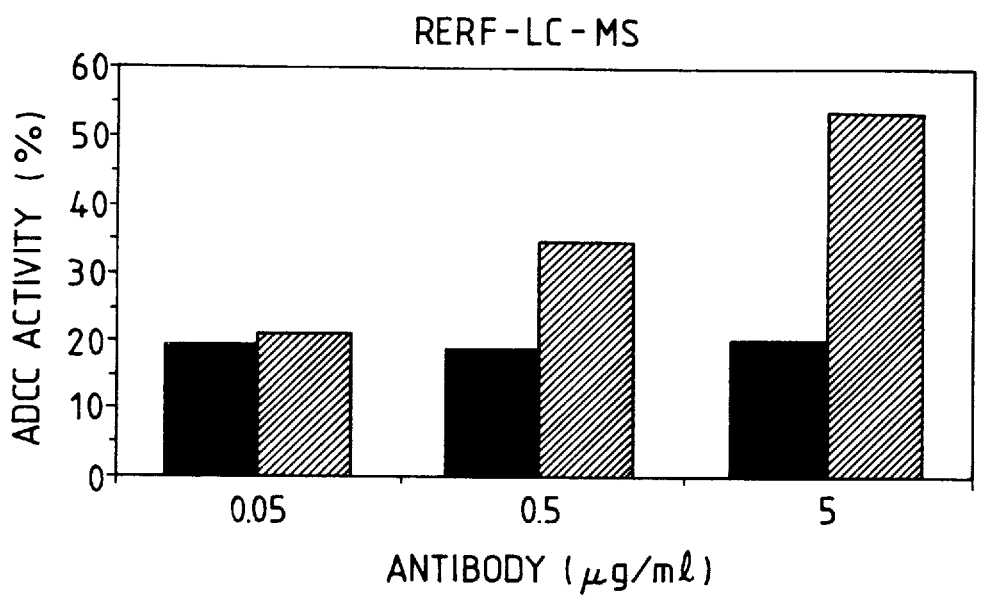
Figure 26A:
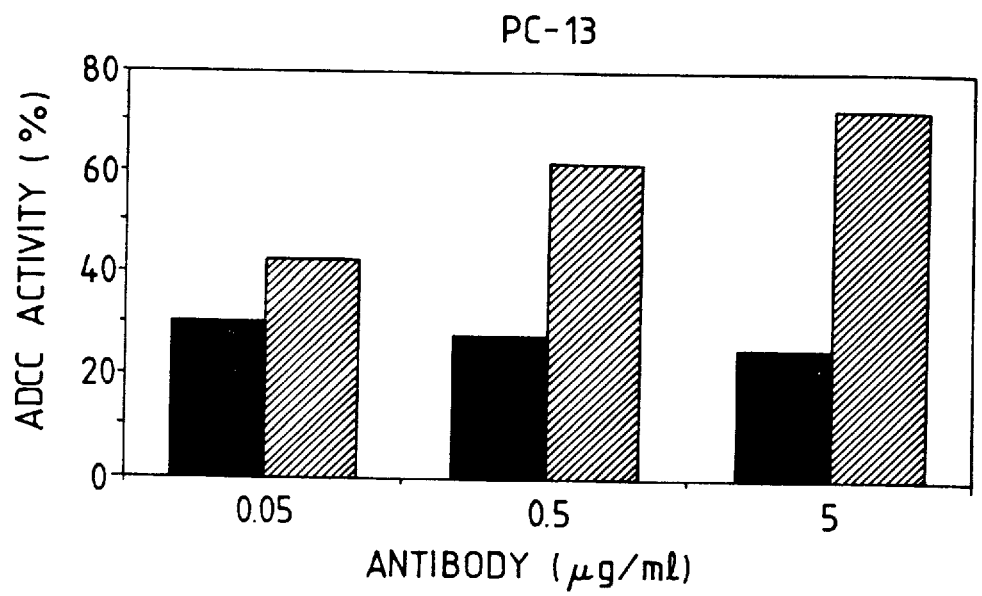
FIGS. 26A and 26B graphically show the ADCC activities of KM966 against the human lung large cell carcinoma cell line PC-13 and human neuroblastoma cell line NAGAI. The ordinate indicates the cytotoxicity and the abscissa the concentration of the antibody added. The solid bars indicate the ADCC activities of KM-696 and the shaded bars the ADCC activities of KM966.
Figure 26B:
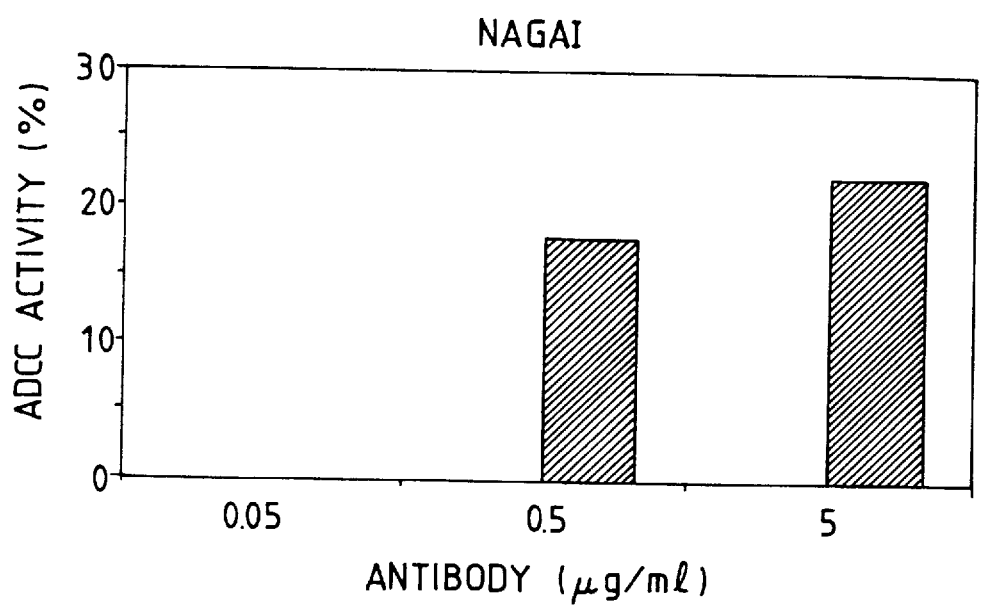
Figure 27A:
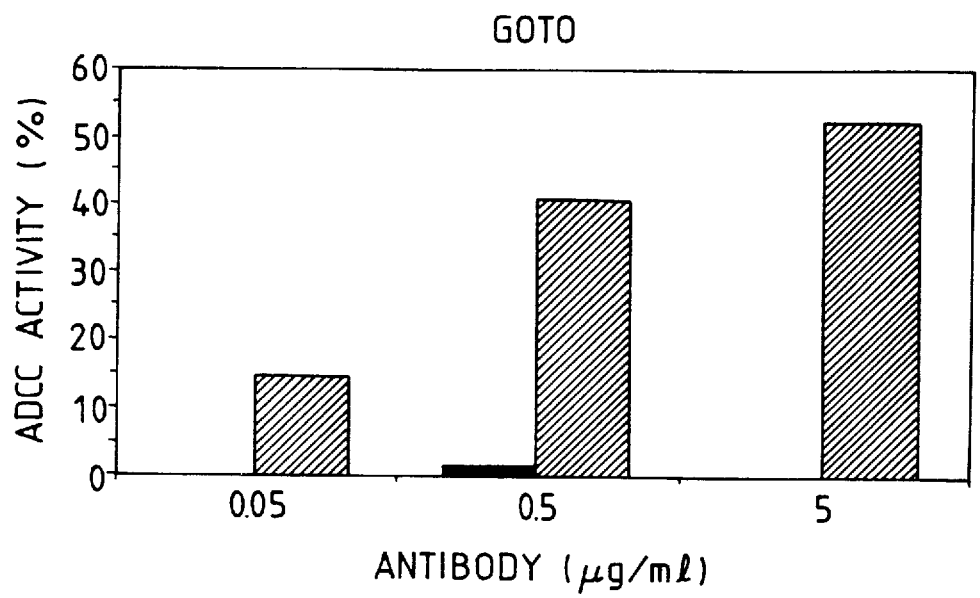
FIGS. 27A and 27B graphically show the ADCC activities of KM966 against the human neuroblastoma cell line GOTO and human brain tumor cell line A172. The ordinate indicates the cytotoxicity and the abscissa the concentration of the antibody added. The solid bars indicate the ADCC activities of KM-696 and the shaded bars the ADCC activities of KM966.
Figure 27B:
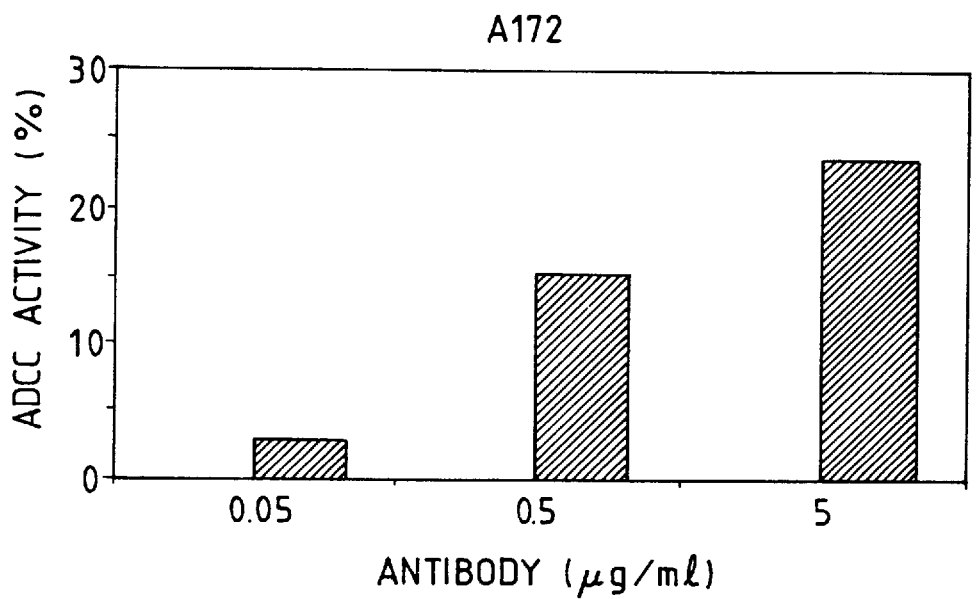

A KM-603-derived chimeric human antibody L chain expression vector was then constructed by introducing the β-globulin 3' splicing signal into the plasmid pChi603LM1, as follows (FIG. 17).

Thus, 3 μg of pChi603LM1 obtained above was added to 30 μl of 33 mM Tris-acetate buffer (pH 7.9) containing 10 mM magnesium acetate, 66 mM potassium acetate, 0.5 mM DTT and 0.01% BSA, 10 units of XhoI and 10 units of KpnI were further added, and digestion was effected at 37° C. for 4 hours. The reaction mixture was fractionated by agarose gel electrophoresis and about 0.3 μg of a DNA fragment of about 2.0 kb was recovered. Then, 3 μg of pAGE148 obtained in Paragraph 7 (2) was added to 30 μl of 33 mM Tris-acetate buffer (pH 7.9) containing 10 mM magnesium acetate, 66 mM potassium acetate, 0.5 mM DTT and 0.01% BSA, 10 units of XhoI and 10 units of KpnI were further added, and digestion was effected at 37° C. for 4 hours. The reaction mixture was fractionated by agarose gel electrophoresis and about 0.3 μg of a DNA fragment of about 8.7 kb was recovered. Then, 0.1 μg of the XhoI-KpnI fragment of pChi603LM1 as obtained above and 0.1 μg of the XhoI-KpnI fragment of pAGE148, as obtained above, were dissolved in a total of 20 μl of T4 ligase. buffer; 350 units of T4 ligase was added to the solution, and ligation was carried out at 4° C. for 24 hours. The thus-obtained recombinant plasmid DNA was used to transform *Escherichia coli* HB101 to give the plasmid pChi603LMS1 shown in FIG. 17.

11. Expression of the KM-796- and KM-750-derived chimeric human anti-$GM_2$ antibody in YB2/0 cells The plasmids were introduced into YB2/0 cells by the electroporation method of Miyaji et al. [Cytotechnbology, 3, 133–140 (1990)].

After introduction of 4 μg of pChi750HL1 or pChi796HL1 obtained in Paragraph 8 into $4\times10^6$ YB2/0 (ATCC CRL1581) cells, the cells were suspended in 40 ml of RPMI-1640-FCS(10) [RPMI1640 medium (Nissui Pharmaceutical) containing 10% of FCS, 1/40 volume of 7.5% $NaHCO_3$, 3% of 200 mM L-glutamine solution (Gibco) and 0.5% of penicillin-streptomycin solution (Gibco; containing 5,000 units/ml penicillin and 5,000 μg/ml streptomycin)], and the suspension was distributed in 200-μl portions into wells of 96-well microtiter plates. After 24 hours of incubation at 37° C. in a $CO_2$ incubator, G418 (Gibco) was added to a concentration of 0.5 mg/ml and then incubation was continued for 1 to 2 weeks. Transformant colonies appeared, the culture fluid was recovered from each well in which the cells had grown to confluence and an enzyme-linked immunosorbent assay (ELISA) was conducted for anti-$GM_2$ chimeric human antibody activity measurement.

Enzyme-Linked Immunosorbent Assay (ELISA)

In a solution of 5 ng of phosphatidylcholine (Sigma) and 2.5 ng of cholesterol (Sigma) in 2 ml of ethanol was dissolved 2 ng of $GM_2$ (N-acetyl-$GM_2$; Boehringer Mannheim) or some other ganglioside. The solution or dilutions thereof were respectively distributed in 20-μl portions into wells of 96-well microliter plates (Greiner) and, after air drying, blocking was effected with PBS containing 1% BSA. Each culture supernatant for each transformant, each purified mouse monoclonal antibody solution and each purified chimeric human antibody solution were distributed in 50- to 100-μl portions into the wells and the reaction was allowed to proceed at room temperature for 1 to 2 hours. The wells were then washed with PBS, and 50 to 100 μl of peroxidase-labeled antibody were added thereto followed by reaction at room temperature for 1 to 2 hours. The wells were washed with PBS and an ABTS substrate solution [prepared by dissolving 550 mg of 2,2'-azinobis(3-ethylbenzothiazoline-6-sulfonic acid) diammonium salt in 0.1M citrate buffer (pH 4.2) and adding, just prior to use, hydrogen peroxide to a concentration of 1 μl/ml] was added in 50- to 100-μl portions to each well for color development, followed by $OD_{415}$ measurement.

The clone showing the highest activity in ELISA among the clones obtained gave a chimeric human anti-$GM_2$ antibody content of about 1.0 μg/ml of culture fluid.

Cells of the clone showing the above-mentioned chimeric human anti-$GM_2$ antibody activity were suspended in RPMI1640-FCS(10) medium containing 0.5 mg/ml G418 and 50 nM methotrexate (hereinafter, "MTX") to a concentration of 1 to $2\times10^5$ cells/ml, and the suspension was distributed in 2-ml portions into wells of 24-well plates. Incubation was performed at 37° C. in a $CO_2$ incubator for 1 to 2 weeks to induce 50 nM MTX-resistant clones. At the time of confluence, the chimeric human anti-$GM_2$ antibody activity in each culture fluid was determined by ELISA. The 50 nM MTX-resistant clone showing the highest activity among the clones obtained showed a chimeric human anti-$GM_2$ antibody content of about 5.0 μg/ml.

Cells of the above 50 nM MTX-resistant clone were suspended in RPMI1640-FCS(10) medium containing 0.5 mg/ml G418 and 200 nM MTX to a concentration of 1 to $2\times10^5$ cells/ml, and the suspension was distributed in 2-ml portions into wells of 24-well plates. Incubation was carried out at 37° C. in a $CO_2$ incubator for 1 to 2 weeks to induce 200 nM MTX-resistant clones. At the time of confluence, each culture fluid was assayed for chimeric human anti-$GM_2$ antibody activity by ELISA. The 200 nM MTX-resistant clone showing the highest activity among the clones obtained had a chimeric human anti-$GM_2$ antibody content of about 10 μg/ml. The 200 nM MTX-resistant clones obtained from pChi750HL1 and pChi796HL1 were named transformants "KM966" (KM-796-derived chimeric human antibody KM966-producing strain) and "KM967" (KM-750-derived chimeric human antibody KM967-producing strain), respectively.

The following SDS-polyacrylamide gel electrophoresis (SDS-PAGE) confirmed that the above transformants KM966 and KM967 express the respective chimeric human anti-$GM_2$ antibodies.

The transformants KM966 and KM967 were each suspended in GIT medium (Nippon Pharmaceutical) containing 0.5 mg/ml G418 and 200 nM MTX to a concentration of 1 to $2\times10^5$ cells/ml. Each suspension was distributed in 100-ml portions into 175 $cm^2$ flasks (Greiner). Cultivation was performed at 37° C. in a $CO_2$ incubator for 5 to 7 days. At the time of confluence, the culture fluid was recovered. Treatment of about 1 liter of the culture fluid with Affi-Gel Protein A MAPS-II kit (Bio-Rad) gave about 5 mg of a purified chimeric human anti-$GM_2$ antibody for each transformant. About 2 μg of the purified chimeric human anti-$GM_2$ antibody KM966 or KM967 was electrophoresed by the conventional method [Laemmli: Nature, 227, 680 (1970)] for molecular weight checking. The results are shown in FIG. 18. As shown in FIG. 18, both KM966 and KM967 gave an antibody H chain molecular weight of about 50 kilodaltons and an antibody L chain molecular weight of about 25 kilodaltons under reducing conditions, indicating the correctness in molecular weight of the H chain and L chain expressed. For each of KM966 and KM967, the molecular weight of the chimeric human antibody under nonreducing conditions was about 150 kilodaltons, indicating that the antibody expressed was composed of two H chains and two L chains and was correct in size.

12. Expression of KM-603-derived chimeric human anti-$GM_2$ antibodies in SP2/0 cells A 2-μg portion of the plasmid pChi603HMS1 or pChi603LMS1 obtained in Paragraph 9 was introduced into $4\times10^6$ cells of YB2/0 (ATCC CRL1581) by electroporation in the same manner in Paragraph 11. The cells were suspended in 40 ml of RPMI1640-FCS(10) and the suspension was distributed in 200-μl portions into wells of 96-well microliter plates. After 24 hours of incubation in a $CO_2$ incubator at 37° C., G418 (Gibco) was added to a concentration of 0.5 mg/ml and incubation was continued for 1 to 2 weeks. Transformant colonies appeared. The culture fluid was recovered from confluent wells and the chimeric human anti-$GM_2$ antibody activity was measured by ELISA as described above. The clone showing the highest chimeric human anti-$GM_2$ antibody activity among the clones obtained gave a chimeric human anti-$GM_2$ antibody content of about 0.1 μg/ml of culture fluid.

Cells of the clone showing the above-mentioned chimeric human anti-$GM_2$ antibody activity were suspended in RPMI1640-FCS(10) medium containing 0.5 mg/ml G418 and 50 nM MTX to a concentration of 1 to 2×10$^5$ cells/ml and the suspension was distributed in 2-ml portions into wells of 24-well plates. Clones resistant to 50 nM MTX were induced by incubating in a $CO_2$ incubator at 37° C. for 2 to 3 weeks. When confluence was attained, the culture fluids were subjected to ELISA for chimeric human anti-$GM_2$ antibody activity measurement. Among the 50 nM MTX-resistant clones obtained, the clone showing the highest activity gave a chimeric human anti-$GM_2$ antibody content of about 0.3 μg/ml of culture fluid.

Cells of the above 50 nM MTX-resistant clone were suspended in RPMI1640-FCS(10) medium containing 0.5 mg/ml G418 and 200 nM MTX to a concentration of 1 to 2×10$^5$ cells/ml and the suspensions as distributed in 2-ml portions into well of 24-well plates. Clones resistant to 200 nM MTX were induced by following incubation in a $CO_2$ incubator at 37° C. for 2 to 3 weeks. When confluence was attained, the human anti-$GM_2$ antibody activity in the culture fluid was measured by ELISA. Among the 200 nM MTX-resistant clones obtained, the clone showing the highest activity gave a chimeric human anti-$GM_2$ antibody content of about 0.5 μg/ml of culture fluid.

Cells of the above 200 nM MTX-resistant clone were suspended in RPMI1640-FCS(10) medium containing 0.5 mg/ml G418 and 500 nM MTX to a concentration of 1 to 2×10$^5$ cells/ml and the suspension was distributed in 2-ml portions into well of 24-well plates. Clones resistant to 500 nM MTX were induced following incubation in a $CO_2$ incubator at 37° C. for 1 to 2 weeks. When confluence was attained, the chimeric human anti-$GM_2$ antibody activity in the culture fluid was determined by ELISA. Among the 500 nM MTX-resistant clones obtained, the one showing the highest activity gave a chimeric human anti-$GM_2$ antibody content of about 1.0 μg/ml of culture fluid. This 500 nM MTX-resistant clone was named "transformant KM968".

The following SDS-PAGE confirmed the expression of a chimeric human anti-$GM_2$ antibody in the above transformant KM968.

Cells of the transformant KM968 were suspended in GIT medium (Nippon Pharmaceutical) containing 0.5 mg/ml G418 and 500 nM XTX to a concentration of 1 to 2×10$^5$ cells/ml and the suspension was distributed in 100-ml portions into 175 cm$^2$ flasks (Greiner). Cultivation was conducted in a $CO_2$ incubator at 37° C. for 5 to 7 days and, when confluence was attained, the culture fluid was recovered. Treatment of about 3.0 liters of the culture fluid with Affi-Gel Protein A MAPS-II kit (Bio-Rad) gave about 1 mg of a purified chimeric human anti-$GM_2$ antibody. About 2 μg of this purified chimeric human anti-$GM_2$ antibody KM968 was electrophoresed by the conventional method [Laemmli: Nature, 227, 680 (1970)] for molecular weight checking. The results are shown in FIG. 19. Under reducing conditions, the molecular weight of the antibody H chain was about 50 kilodaltons and the molecular weight of the antibody L chain was about 25 kilodaltons, thus confirming the expression of the H chain and L chain having the correct molecular weight. Under nonreducing conditions, the molecular weight of the chimeric human antibody was about 150 kilodaltons, confirming that the antibody expressed was composed of two H chains and two L chains and was correct in size.

13. Reaction specificity of the chimeric human anti-$GM_2$ antibodies

The reactivities of the chimeric anti-$GM_2$ antibodies with ganglioside $GM_1$, N-acetyl-$GM_2$ (Boehringer Mannheim), N-glycolyl-$GM_2$, N-acetyl-$GM_3$, N-glycolyl-$GM_3$, $GD_{1a}$, $GD_{1b}$ (Iatron), $GD_2$, $GD_3$ (Iatron) and $GQ_{1b}$ (Iatron) were examined by the technique of ELISA. The results are shown below in Table 1. $GM_1$ and $GD_{1a}$ were purified from the bovine brain, N-glycolyl-$GM_2$ and N-glycolyl-$GM_3$ from the mouse liver, N-acetyl-$GM_3$ from canine erythrocytes, and $GD_2$ from the cultured cell line IMR32 (ATCC CCL127), by a known method [J. Biol. Chem., 263, 10915 (1988)].

As shown in Table 1, it was confirmed that the chimeric human anti-$GM_2$ antibodies KM966 and KM967 specifically react with $GM_2$. The reactivity of KM966 was greater than that of KM967, however. On the contrary, KM968 (KM-603-derived chimeric human antibody) did not show any reactivity for $GM_2$.

TABLE 1

| Ganglioside | Binding activity of antibody ($OD_{415}$) | |
|---|---|---|
| | KM966 (5 μg/ml) | KM967 (5 μg/ml) |
| $GM_1$ | 0.105 | 0.000 |
| N-Acetyl-$GM_2$ | 0.870 | 0.423 |
| N-Glycolyl-$GM_2$ | 0.774 | 0.065 |
| N-Acetyl-$GM_3$ | 0.002 | 0.000 |
| N-Glycolyl-$GM_3$ | 0.122 | 0.001 |
| $GD_{1a}$ | 0.004 | 0.000 |
| $GD_{1b}$ | 0.002 | 0.000 |
| $GD_2$ | 0.095 | 0.001 |
| $GD_3$ | 0.004 | 0.000 |
| $GQ_{1b}$ | 0.005 | 0.000 |

14. Reactivities of the chimeric human anti-$GM_2$ antibodies KM966 and KM967 with cancer cells (fluorescent antibody technique)

Suspended in PBS were 1×10$^6$ cells of cultured human lung small cell carcinoma cell line QC90 [Cancer Res., 49, 2683 (1989)], NCI-H69 (ATCC HTB119), NCI-H128 (ATCC HTB120), SBC-1 (JCRB 0816), SBC-2 (JCRB 0817), SBC-3 (JCRB 0818), SBC-5 (JCRB 0819), RERF-LC-MA (JCRB 0812), Lu-134-A-H (JCRB 0235), Lu-139 (RCB 469), Lu-130 (RCB 465), Lu-135 (RCB 468), Lu-134-B (RCB 467), Lu-140 (RCB 470), PC-6 [Naito et al.: Gann to Kagaku Ryoho (Cancer and Chemotherapy), 5 (suppl.), 89 (1978)], cultured human lung squamous carcinoma cell line PC-1 [Naito et al.: Gann to Kagaku Ryoho, 5 (suppl.), 89 (1978)], PC-10 [Naito et al.: Gann to Kagaku Ryoho, 5 (suppl.), 89 (1978)], Colo16 [Moor et al.: Cancer Res., 35, 2684 (1975)], Calu-1 (ATCC HTB54), SK-LC-4 [Proc. Natl. Acad. Sci. U.S.A., 85, 4441 (1988)], cultured human lung adenocarcinoma cell line PC-7 [Hayata et al.: Hito Gansaibo no Baiyo (Human Cancer Cell Culture), 131 (1975)], PC-9 [Kinjo et al.: Brit. J. Cancer, 39, 15 (1979)], PC-12 (ATCC CRL1721), RERF-LC-MS (JCRB 0081), HLC-1 (RCB 083), cultured human lung large cell carcinoma cell line PC-13 [Ohya et al.: Tanpakushitsu, Kakusan, Koso (Protein, Nucleic Acid, Enzyme), 23, 697 (1978)], Lu65 (JCRB 0079), CALU-6 (ATCC HTB56), SK-LC-6 [Proc. Natl. Acad. Sci. U.S.A.,.85, 4441 (1988)], cultured human neuroblastoma cell line YT-nu [Ishikawa et al.: Acta Path. Jap., 27, 697 (1977)], NAGAI [Ishikawa et al.: Acta Path. Jap., 29, 289 (1979)], NB-1 [Ishikawa et al.: Acta Path. Jap., 27, 697 (1977)], IMR32 (ATCC CCL127), GOTO (JCRB 0612), NB-9 (RCB 477), SK-N-MC (ATCC HTB10), cultured human brain tumor (glioma) cell line P122 [EMBO J., 6, 2939 (1987)], A172 (ATCC CRL1620), T98G (ATCC CRL1690), U-118MG (ATCC HTB15), cultured human leukemia cell line HSB-2 (ATCC CCL120.1), ATN-1, U-937 (ATCC CRL1593), HPB-ALL [Ohya et al.: Tanpakushitsu, Kakusan, Koso, 23, 697 (1978)], CCRF-SB (ATCC CCL120), KOPN-K [Hanei et al.: Haigan (Lung Cancer), 25, 524 (1985)], TYH [Haranaka et al.: Int. J. Cancer, 36, 313 (1985)], MOLT-3 (ATCC CRL1552), CCRF-CEM (ATCC CCL119), TALL-1 (JCRB 0086), NALL-1 [Ohya et al.: Tanpakushitsu, Kakusan, Koso, 23, 697 (1978), CCRF-SB (JCRB 0032), THP-1 (ATCC TIB202), HEL92-1-7 (ATCC TIB180), cultured human maligant melanoma cell line C24.32 ( EP-A-0 493 686, KHm-3/P [J. Natl. Cancer Inst., 59, 775 (1977)] or G361 (ATCC CRL1424). The suspension was placed in a microtube (Tref) and centrifuged (3,000 rpm, 2 minutes) to wash the cells, 50 μl of KM966 or KM967 (50 μg/ml) was added, the mixture was stirred, and the reaction was allowed to proceed at 4° C. for 1 hour. Then, the cells were washed three times by centrifugation with PBS, 20 μl of fluorescein isocyanate-labeled protein A (30-fold dilution; Boehringer Mannheim Yamanouchi) was added and, after stirring, the reaction was allowed to proceed at 4° C. for 1 hour. Then, the cells were washed three times by centrifugation with PBS, then suspended in PBS and subjected to analysis using flow cytometer EPICS Elite (Coulter). In a control run, the same procedure as described above was followed without adding the chimeric human antibody. The results thus obtained are shown in Table 2. The chimeric human antibody KM966 reacted with 9 (NCI-H128, SBC-1, SBC-3, SBC-5, Lu-139, Lu-130, Lu-135, Lu-134-B and Lu-140) of the 14 lung small cell carcinoma cell lines, 2 (PC-10 and Calu-1) of the 5 lung squamous carcinoma cell lines, 2 (PC-9 and RERF-LC-MS) of the 5 lung adenocarcinoma cell-lines, 2 (PC-13 and SK-LC-6) of the 4 lung large cell carcinoma cell lines, 7 (YT-nu, NAGAI, NB-1, IMR32, GOTO, NB-9 and SK-N-MC) of the 7 neuroblastoma cell lines and 4 (P122, A172, T98G and U-118MG) of the 4 brain tumor (glioma) cell lines. On the other hand, the chimeric human antibody KM967 did not react with any of the cultured cell lines. The above results indicate that the chimeric human antibody KM966 is useful in the diagnosis and treatment of brain tumors, peripheral nervous system tumors and lung cancer, among others.

TABLE 2

| Cell line | KM966 (%) (50 μg/ml) | | KM967 (%) (50 μg/ml) | |
| --- | --- | --- | --- | --- |
| Lung small cell carcinoma | 9/14 | (64) | 0/14 | (0) |
| Lung squamous cell carcinoma | 2/5 | (40) | 0/5 | (0) |
| Lung adenocarcinoma | 2/5 | (40) | 0/5 | (0) |
| Lung large cell carcinoma | 2/4 | (50) | 0/4 | (0) |
| Neuroblastoma | 7/7 | (100) | 0/7 | (0) |
| Brain tumor (glioma) | 4/4 | (100) | 0/4 | (0) |
| Leukemia | 0/14 | (0) | 0/14 | (0) |
| Malignant melanoma | 0/3 | (0) | 0/3 | (0) |

15. In vitro antitumor activity of the chimeric human anti-$GM_2$ antibody KM966: complement dependent cytotoxicity (CDC)

(1) Preparation of target cells

The target cells SBC-3, Lu-135, PC-10, RERF-LC-MS, PC-13, NAGAI, GOTO or A172, cultured in RPMI1640 medium supplemented with 10% FCS, were adjusted to a cell concentration of $5\times10^6$ cells/ml, $Na_2{}^{51}CrO_4$ was added to a concentration of 100 μCi/$5\times10^6$ cells, then the reaction was allowed to proceed at 37° C. for 1 hours, and the cells were washed three times with the medium. The cells were then allowed to stand in the medium at 4° C. for 30 minutes for spontaneous dissociation and then, after centrifugation, the medium was added to adjust the cell concentration to $1\times10^6$ cells/ml.

(2) Preparation of the complement

Sera from three healthy subjects were combined and used as a complement source.

(3) CDC activity measurement

The chimeric human anti-$GM_2$ antibody KM966 or mouse anti-$GM_2$ antibody KM696 (FERM BP-3337) was added to wells of 96-well U-bottom plates within the final concentration range of 0.5 to 50 μg/ml and then $5\times10^4$ cells/well of the target cells prepared in (1) were added. The reaction was allowed to proceed at room temperature for 30 minutes. After centrifugation, the supernatants were discarded, 150 μl of the human serum obtained in (2) was added to each well (final concentration 15% v/v), and the reaction was allowed to proceed at 37° C. for 1 hour. After centrifugation, the amount of $^{51}Cr$ in each supernatant was determined using a gamma counter. The amount of spontaneously dissociated $^{51}Cr$ was determined by adding to the target cells the medium alone in lieu of the antibody and complement solutions and measuring the amount of $^{51}Cr$ in the supernatant in the same manner as mentioned above. The total amount of dissociated $^{51}Cr$ was determined by adding to the target cells 5N sodium hydroxide in lieu of the antibody and complement solutions and measuring the amount of $^{51}Cr$ in the supernatant in the same manner as mentioned above. The CDC activity was calculated as follows:

$$CDC\ activity\ (\%) = \frac{\text{Amount of }^{51}Cr\text{ in sample supernatant} - \text{Amount of }^{51}Cr\text{ spontaneously dissociated}}{\text{Total amount of }^{51}Cr\text{ dissociated} - \text{Amount of }^{51}Cr\text{ spontaneously dissociated}} \times 100$$

The results thus obtained are shown in FIGS. 20 to 23. It was shown that the chimeric human antibody KM966 show CDC activity against all the cells tested.

16. In vitro antitumor activity of the chimeric human anti-$GM_2$ antibody KM966: antibody dependent cell mediated cytotoxicity (ADCC)

(1) Preparation of target cells

The target cells SBC-3, Lu-135, PC-10, RERF-LC-MS, PC-13, NAGAI, GOTO or A172, cultured in RPMI1640 medium supplemented with 10% FCS, were adjusted to a cell concentration of $1\times10^6$ cells/ml, $Na_2{}^{51}CrO4$ was added to a concentration of 50 μCi/$1\times10^6$ cells, then the reaction was allowed to proceed at 37° C. for 1 hour, and the cells were washed three times with the medium. The cells were then allowed to stand in the medium at 4° C. for 30 minutes for spontaneous dissociation and then, after centrifugation, the medium was added to adjust the cell concentration to $2\times10^5$ cells/ml.

(2) Preparation of effector cells

Human venous blood (25 ml) was collected, 0.5 ml of heparin sodium (Takeda Chemical Industries; 1,000 units/ml) was added, and the mixture was gently stirred. This mixture was centrifuged (1,500 to 1,800 g, 30 minutes) using Polymorphprep (Nycomed Pharma AS), the lymphocyte layer was separated and washed three times by centrifugation with RPMI-1640 medium (15,00 to 1,800 g, 15 minutes), and the cells were suspended in RPMI1640 medium supplemented with 10% FCS ($5\times10^6$ cells/ml) for use as effector cells.

(3) ADCC activity measurement

The chimeric human anti-$GM_2$ antibody KM966 or mouse anti-$GM_2$ antibody KM696 were added to wells of 96-well U-bottom plates within the final concentration range of 0.05 to 5 μg/ml and then 50 μl ($1\times10^4$ cells/well) of the target cell suspension prepared in (1) and 100 μl (5×10⁵ cells/well) of the effector cell suspension prepared in (2) were added to each well (the ratio between the effector cells and target cells being 50:1). The reaction was allowed to proceed at 37° C. for 4 hours and, after centrifugation, the amount of $^{51}$Cr in each supernatant was measured using a gamma counter. The amount of spontaneously dissociated $^{51}$Cr was determined by adding to the target cells the medium alone in lieu of the antibody and effector cells and measuring the amount of $^{51}$Cr in the supernatant in the same manner as mentioned above. The total amount of dissociated $^{51}$Cr was determined by adding to the target cells 5N sodium hydroxide in lieu of the antibody and effector cells and measuring the amount of $^{51}$Cr in the supernatant in the same manner as mentioned above. The ADCC activity was calculated as follows:

ADCC activity (%) =

$$\frac{\text{Amount of }^{51}\text{Cr in sample supernatant} - \text{Amount of }^{51}\text{Cr spontaneously dissociated}}{\text{Total amount of }^{51}\text{Cr dissociated} - \text{Amount of }^{51}\text{Cr spontaneously dissociated}} \times 100$$

The results thus obtained are shown in FIGS. 24 to 27. The chimeric antibody KM966 showed ADCC activity against all the cells whereas the mouse anti=GM₂ antibody KM696 showed no or low ADCC activity. The above results indicate that the chimeric human antibody KM966 is more effective in the treatment of human cancer than the mouse antibody KM-696.

REFERENCE EXAMPLE 1

Construction of the vector pChiIgLA1 for chimeric human antibody L chain expression 1. Isolation of the KM50 cell-derived immunoglobulin H chain promoter and enhancer genes (1) Preparation of chromosomal DNAs from KM50 cells, P3U1 cells and rat kidney Chromosal DNAs were prepared by the conventional method [Maniatis et al. (ed.): Molecular Cloning, 1989, p. 9.16], as follows.

KM50 cells (1.2×10⁸ cells) P3U1 cells (ATCC CRL1597) (2×10⁸ cells) and a rat kidney sample (frozen at 80° C. and then smashed to a sufficient extent using a wooden hammer) (1.6 g) were suspended in 2 ml of 10 mM Tris-hydrochloride buffer (pH 7.5) containing 150 mM sodium chloride and 10 mm ethylenediaminetetraacetic acid disodium salt (hereinafter, "EDTA"), 0.8 mg of proteinase K (Sigma) and 10 mg of sodium lauryl sulfate (hereinafter, "SDS"), were added to each suspension, and the suspension was incubated at 37° C. for 10 hours. Then, each mixture was extracted once with an equal volume of phenol, twice with an equal volume of chloroform and then once with an equal volume of ether, and dialyzed for 10 hours against 10 mM Tris-hydrochloride buffer (pH 7.5) containing 1 mM EDTA. The DNA solution was recovered from the dialysis tube and ribonuclease A (Sigma) was added to the solution to a final concentration of 20 μg/ml. Each resultant solution was incubated at 37° C. for 6 hours for sufficient decomposition of RNA, 15 mg of SDS and 1 mg of proteinase K were then added and the mixture was incubated at 37° C. for 10 hours. The mixture was then extracted twice with an equal volume of phenol, twice with an equal volume of chloroform and twice with an equal volume of ether and then dialyzed for 10 hours against 10 mM Tris-hydrochloride buffer (pH 7.5) containing 1 mM EDTA. The DNA solution was recovered from the dialysis tube for use as a chromosomal DNA sample. DNA concentration measurement in terms of the absorbance at 260 nm revealed that the yield of chromosomal DNA from 1.2×10⁸ KM50 cells was 1.6 mg, that from 2×10⁸ P3U1 cells 1.5 mg, and that from 1.6 g of rat liver 1.9 mg.

(2) Identification of the active-form immunoglobulin H chain gene in KM50 cells by Southern blotting The KM50 cell, p3U1 cell and rat kidney chromosomal DNAs obtained in (1) (3 μg each) were dissolved in 25 μl of 10 mM Tris-hydrochloride buffer (pH 7.5) containing 6 mM magnesium chloride and 100 mM sodium chloride, 15 units of XbaI (Takara Shuzo; hereinafter the restriction enzymes used were products of Takara Shuzo) was added and incubation was carried out at 37° C. for 2 hours for effecting cleavage at the XbaI sites. Each reaction mixture was subjected to agarose gel electrophoresis, then DNA transfer onto a nitrocellulose filter was effected by the method of Southern et al. [J. Mol. Biol., 98, 503 (1975)] and hybridization was carried out by the conventional method [Kameyama et al.: FEBS Letters, 244, 301–306 (1989)] using the mouse JH probe described in the last-cited reference. The KM50 cell DNA alone gave a band at a site corresponding to about 9.3 kb. Therefore, the immunoglobulin XbaI fragment DNA was considered to code for the active-form immunoglobulin H chain gene in KM50 cells.

(3) Construction of a KM50 cell genomic DNA library

A 60-μg portion of the KM50 cell-derived chromosomal DNA obtained in (1) was dissolved in 250 μl of 10 mM Tris-hydrochloride buffer (pH 7.5) containing 6 mM magnesium chloride and 100 mM sodium chloride, 150 units of XbaI was added, and incubation was conducted at 37° C. for 2 hours for causing cleavage at the XbaI sites. The reaction mixture was fractionated by agarose gel electrophoresis and a KM50 cell-derived 9.3 kb DNA fraction sample (about 2 μg) was recovered using, for example, the DEAE paper method (Maniatis et al. (ed.): Molecular Cloning, 1989, p. 6.24]. Separately, 3 μg of Lambda ZAP (Stratagene), for use as the vector, was dissolved in 200 μl of 10 mM Tris-hydrochloride buffer (pH 7.5) containing 6 mM magnesium chloride and 100 mM sodium chloride, 50 units of XbaI was added, and the mixture was incubated at 37° C. for 2 hours to effect cleavage at the XbaI sites. The reaction mixture was subjected to phenol-chloroform extraction and then to ethanol precipitation, whereby about 3 μg of DNA was recovered. This DNA was dissolved in 100 μl of 100 mM Tris-hydrochloride buffer (pH 7.5), 1 unit of alkaline phosphatase (Takara Shuzo) was added, dephosphorylation was effected at the restriction enzyme cleavage ends of the vector DNA. The reaction mixture was subjected to phenol-chloroform extraction and then to ethanol precipitation, whereby 2 μg of DNA was recovered. This DNA was dissolved in 10 μl of 10 mM. Tris-hydrochloride buffer (pH 7.5) containing 1 mM EDTA for use as a vector sample. Two tenths μg of the vector DNA sample and 0.2 μg of the KM50 cell-derived 9.3 kb DNA sample were dissolved in 5 μl of T4 ligase buffer, 175 units of T4 ligase (Takara Shuzo) was added, and the mixture was incubated at 4° C. for 3 days. A 2-μl portion of this mixture was packaged into the lambda phage by the conventional method [Maniatis et al. (ed.): Molecular Cloning, 1989, p. 2.95] using Giga Pak Gold (Stratagene), and the packaging mixture was used to transfect *Escherichia coli* BB4 to give 200,000 phage clones. Among them, 100,000 clones were fixed on a nitrocellulose filter by the conventional method [Maniatis et al. (ed.): Molecular Cloning, 1989, p. 2.112].

(4) Selection of a recombinant DNA containing the gene for the H chain variable region of an immunoglobulin occurring as an active form in KM50 cells (anti-human serum albumin)

From among the phage library composed of 100,000 clones, as constructed in (3), two clones firmly associable at 65° C. with the $^{32}$P-labeled mouse JH probe [labeled by the method of Kameyama et al. [FEBS Letters, 44, 301–306 (1989)]] were isolated. The phage DNA was recovered from them by the conventional method [Maniatis et al. (ed.): Molecular Cloning, 1989, p. 2.118–2.169], whereupon the 9.3 kb XbaI fragment of the KM50 cell-derived chromosomal DNA was found to have been inserted therein.

(5) Base sequence of the gene for the H chain variable region of the immunoglobulin occurring as an active form in KM50 cells (anti-human serum albumin)

Figure 28:
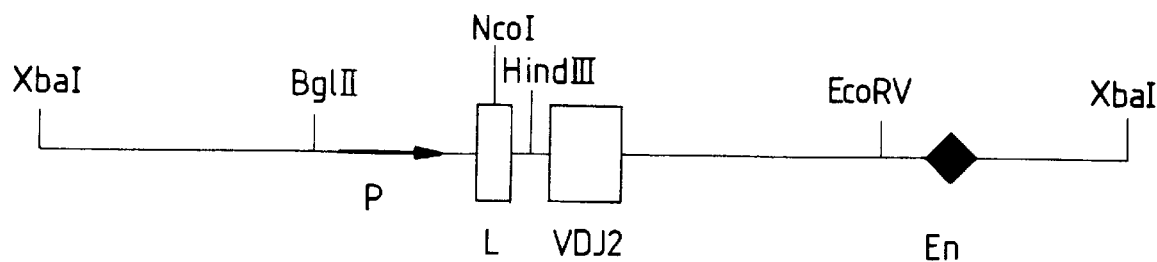
FIG. 28 shows a restriction enzyme cleavage map of a 9.3 kb XbaI fragment of the KM50 cell chromosomal DNA.

For the two clones obtained in (4), restriction enzyme cleavage maps were prepared by conducting digestion using various restriction enzymes, whereby it was revealed that the same DNA fragment (9.3 kb) had been inserted therein (FIG. 28). Therefore, those portions of this 9.3 kb DNA fragment which were supposed to be coding for the rat immunoglobulin H chain promoter region and variable region were sequenced by the method of Sanger [Sanger et al.: Proc. Natl. Acad. Sci. U.S.A., 74, 5463 (1977); AMERSHAM M13 cloning and sequencing handbook]. In SEQ ID NO:16, the portion containing the octamer sequence such as ATG-CAAAT and the TATA box sequence such as TTGAAAA is considered to be the immunoglobulin promoter region.

2. Construction of heterologous protein expression vectors using the promoter and enhancer for the H chain variable region gene for an immunoglobulin occurring as an active form in KM50 cells (anti-human serum albumin)

(1) Construction of pKMB11

Figure 29:
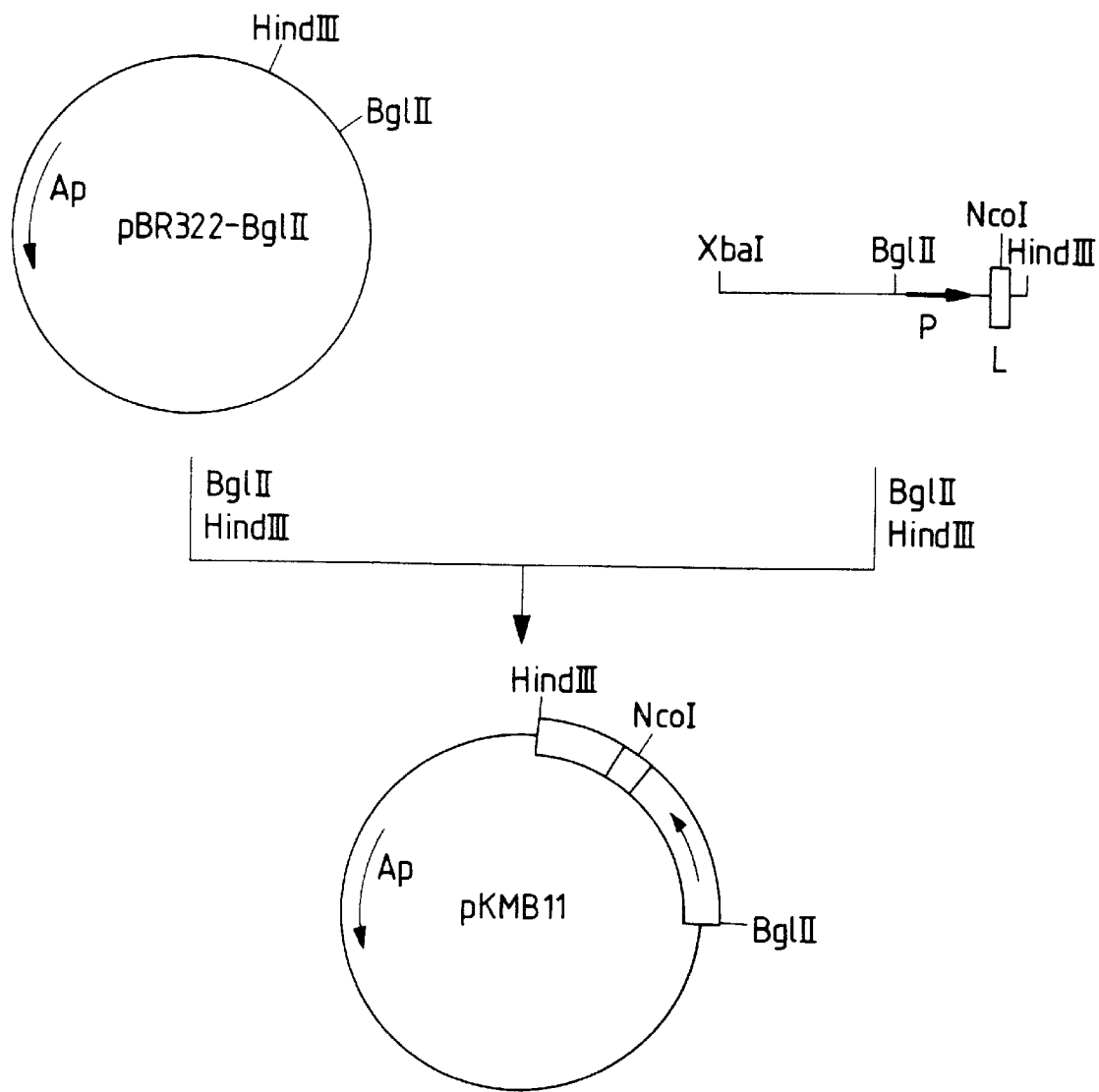
FIG. 29 shows a construction scheme for a plasmid, pKMB11.

A 1-μg portion of the 9.3 kb immunoglobulin H chain variable region gene fragment obtained in Paragraph 1 (5) was dissolved in 30 μl of 10 mM Tris-hydrochloride buffer (pH 7.5) containing 6 mM magnesium chloride and 100 mM sodium chloride, 10 units each of BglII and HindIII were added, and the mixture was incubated at 37° C. for 2 hours for causing cleavage at the BglII and HindIII sites. The reaction mixture was subjected to agarose gel electrophoresis and 0.01 μg of a DNA fragment containing the 0.8 kb immunoglobulin promoter was recovered. Then, 1 μg of the plasmid pBR322-BglII [Kuwana et al.: FEBS Letters, 219, 360 (1987)] was dissolved in 30 μl of 10 mM Tris-hydrochloride buffer (pH 7.5) containing 6 mM magnesium chloride and 100 mM sodium chloride, 10 units of BglII and 10 units of HindIII were added, and the mixture was incubated at 37° C. for 2 hours to effect cleavage at the BglII and HindIII sites. The reaction mixture was subjected to agarose gel electrophoresis and a DNA fragment of about 4.2 kb in size was recovered. The thus-obtained pBR322-BglII-derived DNA fragment ( about 4.2 kb, 0.1 μg) and immunoglobulin promoter-containing DNA fragment (0.01 μg) were dissolved in 20 μl of T4 ligase buffer, 175 units of T4 DNA ligase (Takara Shuzo) was added, and the mixture was incubated at 4° C. for 1 day. The reaction mixture was used to transform *Escherichia coli* HB101 [J. Mol. Biol., 41, 459 (1969)] by the method of Scott et al. [Masaru Shigesada: Saibo Kokagu (Cell Engineering), 2, 616 (1983)] to give an Ap-resistant colony. The recombinant plasmid DNA was recovered from this colony. Plasmid pKMB11, shown in FIG. 29, was thus obtained.

(2) Construction of pKMD6

Figure 30:
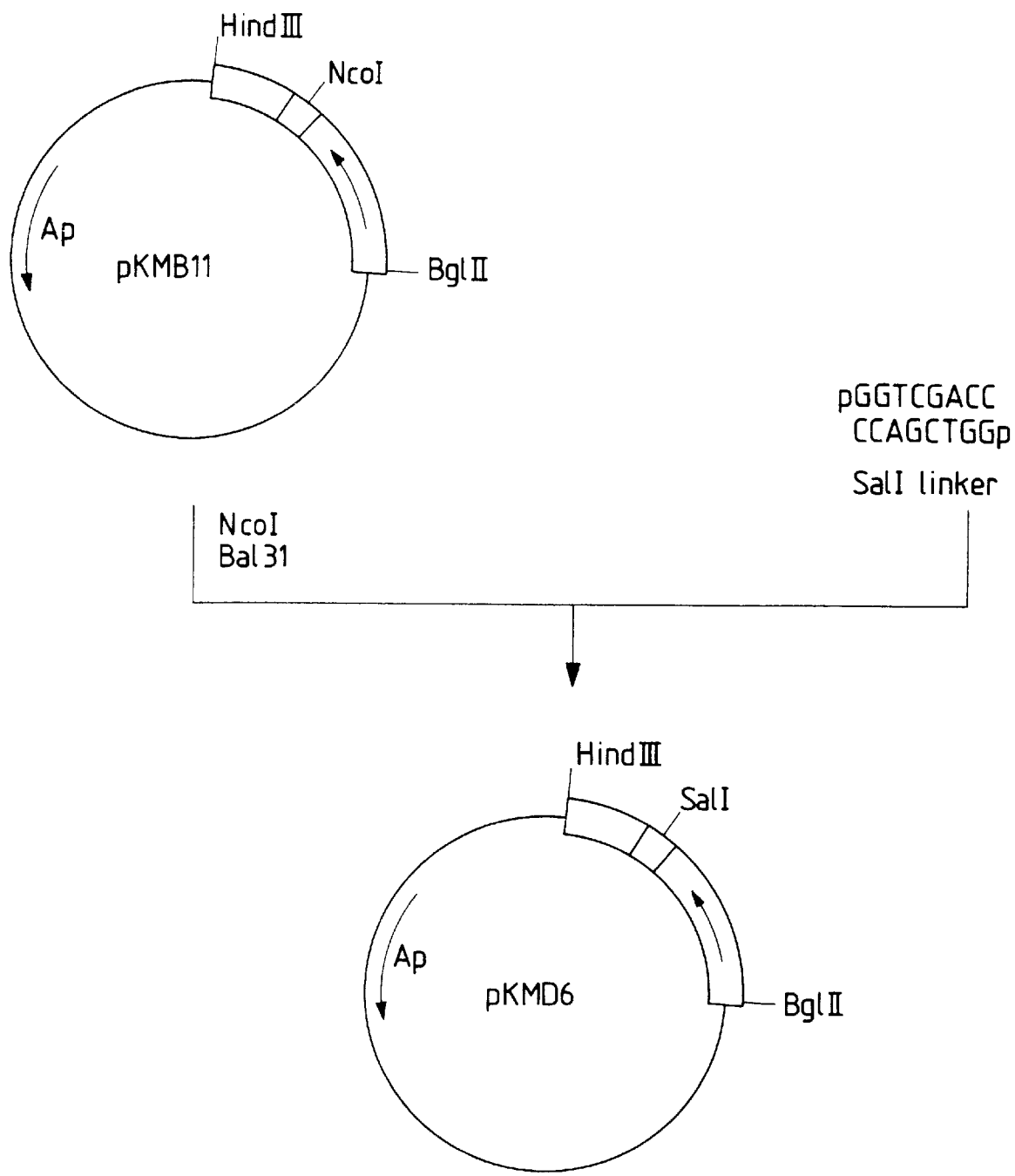
FIG. 30 shows a construction scheme for a plasmid, pKMD6.

For providing an appropriate restriction enzyme site downstream from the immunoglobulin promoter, the plasmid pKMB11 constructed in (1) was digested at the NcoI site using the nuclease BAL31. Thus, 10 μg of the plasmid pKMB11 was dissolved in 100 μl of 10 mM Tris-hydrochloride buffer (pH 7.5) containing 6 mM magnesium chloride and 50 mM potassium chloride, 30 units of NcoI was added, and the mixture was incubated at 37° C. for 2 hours to effect cleavage at the NcoI site. The reaction mixture was subjected to phenol-chloroform extraction and then to ethanol precipitation, the whole amount of the DNA fragment was dissolved in 100 μl of BAL31 buffer [20 mM Tris-hydrochloride buffer (pH 8.0) containing 600 mM sodium chloride, 12 mM calcium chloride, 12 mM magnesium chloride and 1 mM EDTA], 0.25 unit of BAL31 [Bethesda Research Laboratories (BRL)]] was added, and digestion was carried out at 37° C. for 5 seconds. The reaction was terminated by extraction with phenol and subjected to chloroform extraction and then to ethanol precipitation, and 1 μg of DNA was recovered. A 0.1-μg portion of this DNA and 0.01 μg of a synthetic DNA linker (SalI) were dissolved in 20 μl of T4 ligase buffer, 175 units of T4 DNA ligase was added, and the mixture was incubated at 4° C. for 1 day. The reaction mixture was used to transform *Escherichia coli* HB101 by the method of Scott et al. An Ap-resistant colony was obtained and the recombinant plasmid DNA was recovered from this colony to give the plasmid pKMD6 shown in FIG. 30. For this plasmid, the portion of BAL31 digestion was sequenced by the method of Sanger, whereupon deletion was found to the third base (303rd base in SEQ ID NO:16) toward the upstream of the initiation codon ATG for immunoglobulin.

(3) Construction of pEPKMA1, pEPKMB1 and pAGE501

The original immunoglobulin promoter and enhancer are positionally separated. Therefore, it was necessary to construct a vector containing the promoter and enhancer connected to each other for use of said vector as a heterologous protein expression vector. Accordingly, the following procedure was followed.

Figure 31:
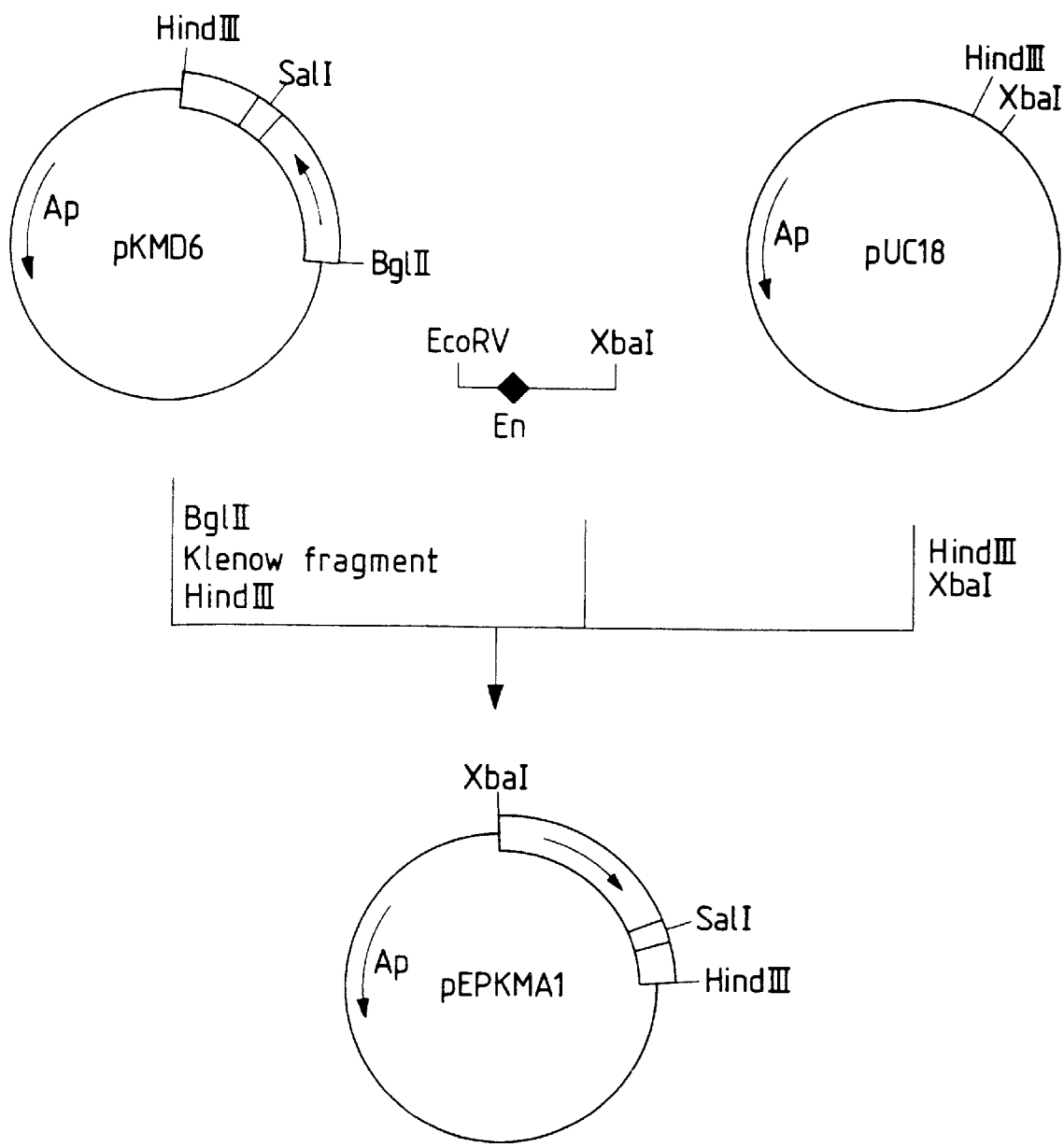
FIG. 31 shows a construction scheme for a plasmid, pEPKMA1.

Thus, 1 μg of the 9.3 kb immunoglobulin H chain variable region gene obtained in Paragraph 1 (5) was dissolved in 30 μl of 10 mM Tris-hydrochloride buffer (pH 7.5) containing 6 mM magnesium chloride and 100 mM sodium chloride, 10 units of EcoRV and 10 units of XbaI were added, and the mixture was incubated at 37° C. for 2 hours for causing cleavage at the EcoRV and XbaI sites. The reaction mixture was subjected to agarose gel electrophoresis and 0.1 μg of a DNA fragment (about 1 kb) containing the immunoglobulin enhancer region was recovered. Separately, 1 μg of the plasmid pKMD6 obtained in (2) was dissolved in 100 μl of 10 mM Tris-hydrochloride buffer (pH 7.5) containing 6 mM magnesium chloride and 100 mM sodium chloride, 10 units of BglII was added, and the mixture was incubated at 37° C. for 2 hours to effect cleavage at the BglII site. After phenol-chloroform extraction, the DNA was precipitated with ethanol and dissolved in a total of 40 μl of DNA polymerase I buffer, 6 units of *Escherichia coli*-derived DNA polymerase I Klenow fragment was added, and the reaction was allowed to proceed at 16° C. for 90 minutes for rendering the 5' protruding ends formed upon BglII digestion blunt-ended. The reaction was terminated by extraction with phenol, the mixture was extracted with chloroform and then subjected to ethanol precipitation, the DNA obtained was dissolved in 30 μl of 10 mM Tris-hydrochloride buffer (pH 7.5) containing 6 mM magnesium chloride and 50 mM sodium chloride, 10 units of HindIII was added, and the mixture was incubated at 37° C. for 2 hours to effect cleavage at the HindIII site. The reaction mixture was subjected to agarose gel electrophoresis and 0.1 μg of a DNA fragment (about 0.8 kb) containing the immunoglobulin promoter region was recovered. Then, 0.2 μg of the plasmid pUC18 [Messing: Methods in enzymology 101, 20 (1983)] was dissolved in 30 μl of 10 mM Tris-hydrochloride buffer (pH 7.5) containing 6 mM magnesium chloride and 100 mM sodium chloride, 10 units of HindIII and 10 units of XbaI were added, and the mixture was incubated at 37° C. for 2 hours for causing cleavage at the HindIII and XbaI sites. The reaction mixture was subjected agarose gel electrophoresis and 0.1 μg of a DNA fragment of about 2.7 kb in size was recovered. The thus-obtained pPKMD6-derived 0.8 kb DNA fragment (0.1 μg), immunoglobulin enhancer region-containing DNA fragment (0.02 μg) and pUC18 (0.1 μg) were dissolved in 20; of T4 ligase buffer, 175 units of T4 DNA ligase was added, and the mixture was incubated at 4° C. for 1 day. The reaction mixture was used to transform *Escherichia coli* HB101 to give an Ap-resistant colony. The recombinant plasmid DNA was recovered from this colony to give pEPKMA1 shown in FIG. 31.

Then, 1 μg of the plasmid pEPKMA1 was dissolved in 100 μl of 10 mM Tris-hydrochloride buffer (pH 7.5) containing 6 mM magnesium chloride and 100 mM sodium chloride, 10 units of XbaI was added, and the mixture was incubated at 37° C. for 2 hours for causing cleavage at the XbaI site. After phenol-chloroform extraction, the resultant DNA fragment was precipitated with ethanol and dissolved in a total of 40 μl of DNA polymerase I buffer, 6 units of *Escherichia coli*-derived DNA polymerase I Klenow fragment was added, and the reaction was allowed to proceed at 16° C. for 90 minutes for rendering the cohesive ends formed upon XbaI digestion blunt-ended. The reaction was terminated by extraction with phenol and, after chloroform extraction, the DNA fragment was recovered by ethanol precipitation. This DNA fragment and a synthetic DNA linker XhoI (Takara Shuzo) (0.01 μg) were dissolved in 20 μl of T4 ligase buffer, 175 units of T4 DNA ligase was added, and the mixture was incubated at 4° C. for 1 day. The reaction mixture was used to transform *Escherichia coli* HB101 to give an Ap-resistant colony. The recombinant plasmid DNA was recovered from this colony to give pEPKME1 shown in FIG. 32.

Then, the SV40 early gene promoter and enhancer regions (hereinafter abbreviated as $P_{SE}$) of the heterologous gene expression vector pAGE107 for use in animals [Miyaji et al.: Cytotechnology, 3, 133–140 (1990)] were replaced with the KM50-derived immunoglobulin H chain promoter and enhancer (hereinafter abbreviated as $P_{IH}$) of pEPKMB1 in the following manner.

Figure 33:
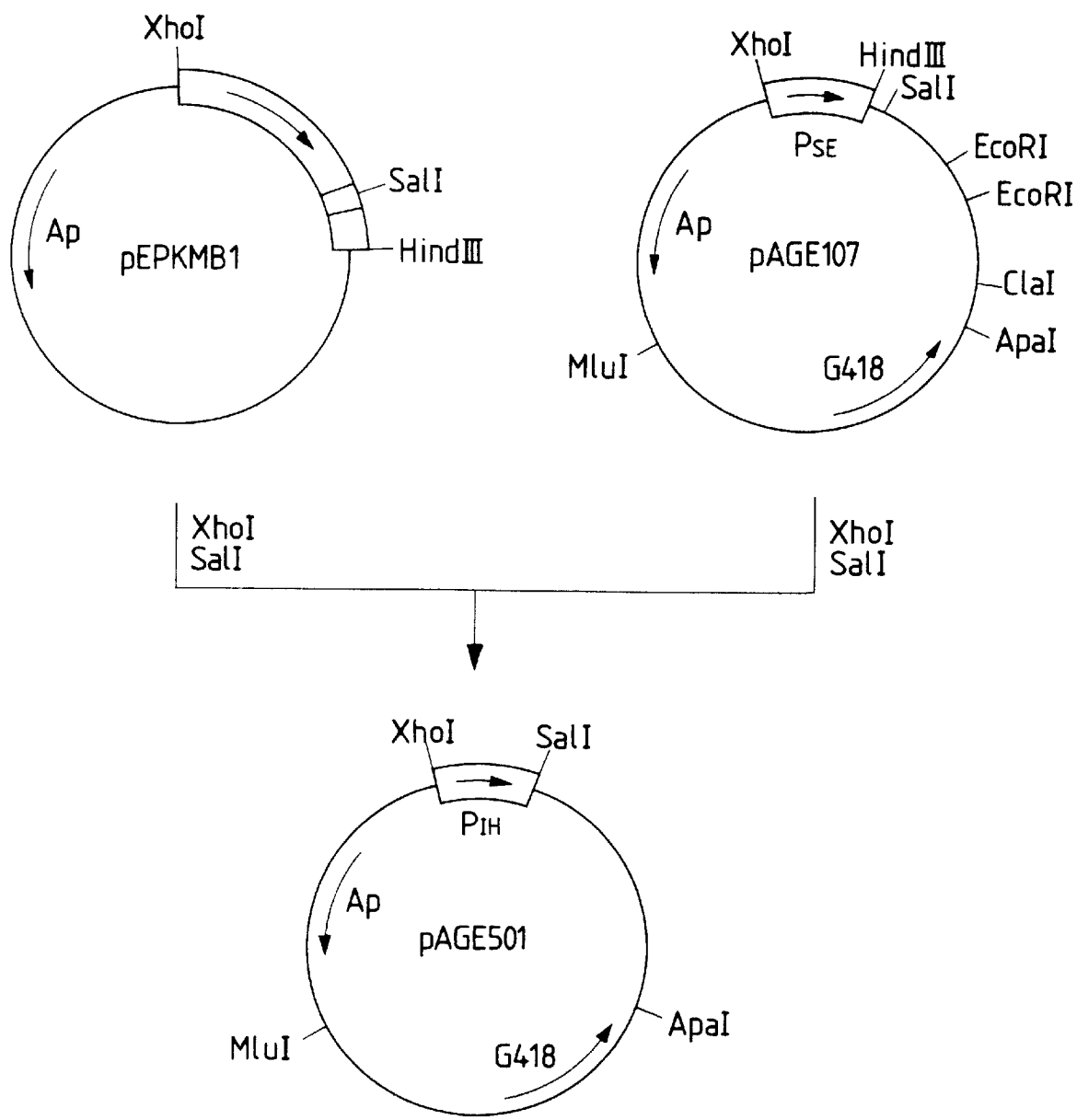
FIG. 33 shows a construction scheme for a plasmid, pAGE501.

One μg of the plasmid pAGE107 was dissolved in 30 μl of 10 mM Tris-hydrochloride buffer (pH 7.5) containing 6 mM magnesium chloride and 150 mM sodium chloride, 10 units of SalI and 10 units of XhoI were added, and the mixture was incubated at 37° C. for 2 hours to effect cleavage at the SalI and XhoI sites. The reaction mixture was subjected to agarose gel electrophoresis and 0.5 μg of a DNA fragment (about 5.95 kb) containing the G418 resistance gene, among others, was recovered. Then, 1 μg of the plasmid pEPKMB1 was dissolved in 30 μl of 10 mM Tris-hydrochloride buffer (pH 7.5) containing 6 mM magnesium chloride and 150 mM sodium chloride, 10 units of SalI and 10 units of XhoI were added, and the mixture was incubated at 37° C. for 2 hours to effect cleavage at the SalI and XhoI sites. The reaction mixture was subjected to agarose gel electrophoresis and 0.1 μg of a DNA fragment (about 1.7 kb) containing the immunoglobulin promoter and enhancer regions was recovered. The thus-obtained pAGE107-derived 5.95 kb DNA fragment (0.1 μg) and immunoglobulin promoter and enhancer region-containing DNA fragment (0.02 μg) were dissolved in 20 μl of T4 ligase buffer, 175 units of T4 DNA ligase was added, and the mixture was incubated at 4° C. for 1 day. The reaction mixture was used to transform *Escherichia coli* HB101. An Ap-resistant colony was isolated and the recombinant plasmid DNA was recovered therefrom to give pAGE501 shown in FIG. 33.

(4) Construction of pAGE109

A plasmid, pAGE109, derived from pAGE106 by deletion of one of the two EcoRI sites in pAGE106 was constructed as follows.

Thus, 2 μg of the heterologous gene expression vector pAGE106 for use in animal cells as described in EP-A-0 405 285 was added to 100 μl of 10 mM Tris-hydrochloride buffer (pH 7.5) containing 6 mM magnesium chloride and 50 mM sodium chloride; 10 units each of EcoRI and SacI were further added, and digestion was conducted at 37° C. for 4 hours. The reaction mixture was fractionated by agarose gel electrophoresis and about 1.5 μg of a DNA fragment (4.3 kb) resulting from cleavage of pAGE106 with EcoRI and SacI and containing the SV40 early gene promoter and G418 resistance gene was recovered. Then, this DNA fragment was dissolved in a total of 40 μl of DNA polymerase I buffer, 5 units of *Escherichia coli*-derived DNA polymerase I large fragment was added, and the reaction was conducted at 16° C. for 2 hours for rendering the 3' protruding ends formed upon SalI digestion and the 5' protruding ends formed upon EcoRI digestion blunt-ended. The reaction mixture was subjected to phenol-chloroform extraction and then to ethanol precipitation, the precipitate was dissolved in 20 μl of T4 ligase buffer; 350 units of T4 DNA ligase was further added to the mixed solution, and ligation was carried out at 4° C. for 4 hours. The thus-obtained recombinant plasmid DNA was used to transform *Escherichia coli* HB101 to give the plasmid pAGE109 shown in FIG. 34.

(5) Construction of pAGE502

For replacing the SV40 promoter and enhancer of pAGE107 with the immunoglobulin H chain promoter and enhancer, a plasmid named pAGE502 was constructed as follows.

Two μg of pAGE107 described in EP-A-0 405 285 was added to 100 μl of 10 mM Tris-hydrochloride buffer (pH 7.5) containing 6 mM magnesium chloride and 50 mM sodium chloride, 10 units of HindIII was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon HindIII digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of XhoI was further added, and digestion was effected at 37° C. for 4 hours. The reaction mixture was fractionated by agarose gel electrophoresis and about 1.5 μg of a DNA fragment (about 5.95 kb), resulting from cleavage of pAGE107 with XhoI and HindIII and containing the G418 resistance gene and Ap resistance, was recovered.

Two μg of pAGE501 obtained in (3) was added to 100 μl of 10 mM Tris-hydrochloride buffer (pH 7.5) containing 6 mM magnesium chloride and 175 mM sodium chloride, 10 units of SalI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*- derived DNA polymerase I Klenow fragment was added, and the reaction was conducted at 16° C. for 2 hours for rendering the 5' protruding ends formed upon SalI digestion blunt-ended. The reaction mixture was subjected to phenol-chloroform extraction and then to ethanol precipitation, the precipitate was added to 30 μl of 10 mM Tris-hydrochloride buffer (ph 7.5) containing 6 mM magnesium chloride and 100 mM sodium chloride, 10 units of XhoI was further added, and digestion was effected at 37° C. for 4 hours. The reaction mixture was fractionated by agarose gel electrophoresis and about 0.2 μg of a DNA fragment (1.8 kb) resulting from cleavage of pAGE501 with XhoI and SalI and containing the KM50 cell immunoglobulin H chain promoter and enhancer was recovered.

Figure 35:
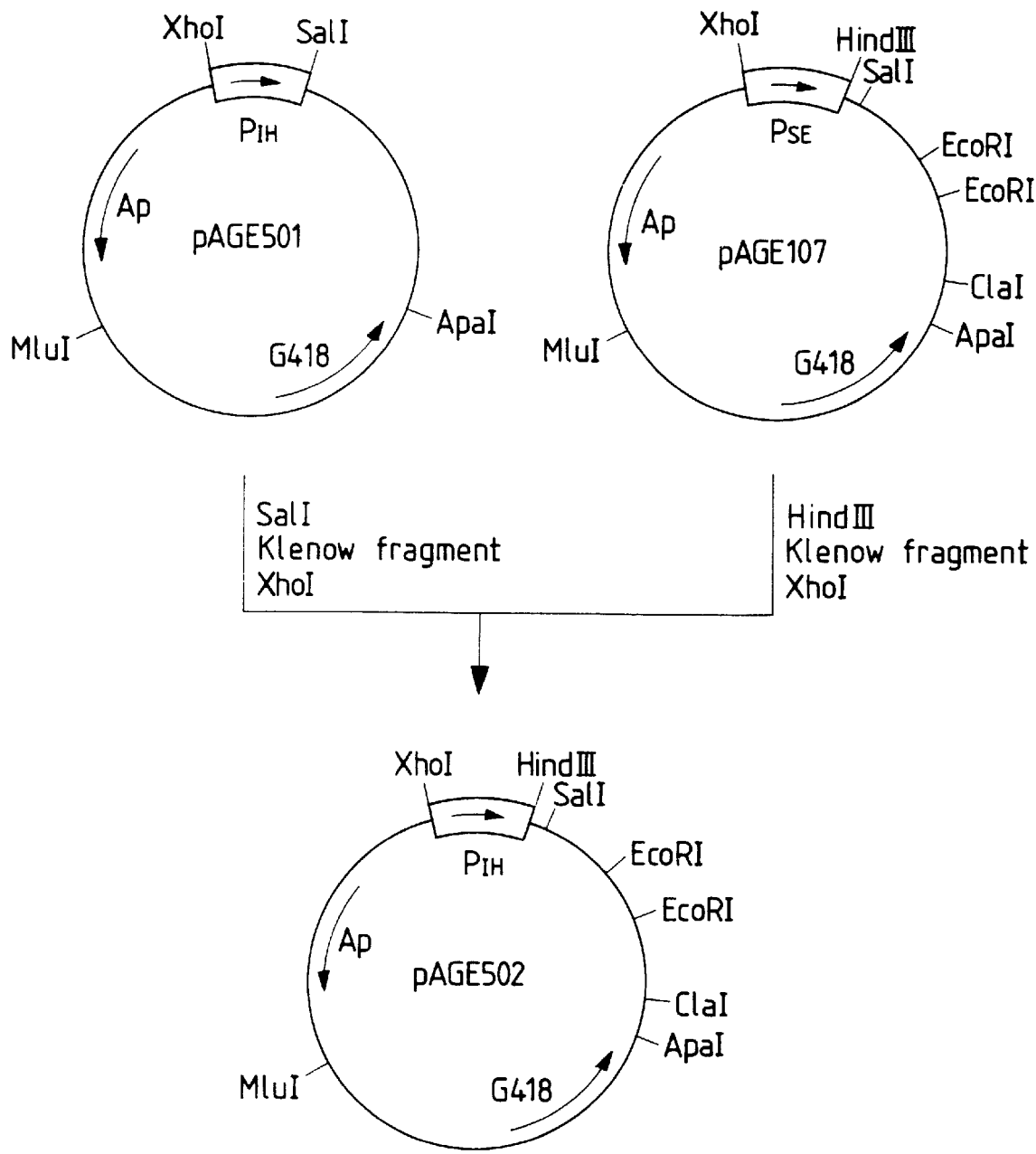
FIG. 35 shows a construction scheme for a plasmid, pAGE502.

Then, 0.1 μg of the HindIII-XhoI fragment (about 5.95 kb) of pAGE107 as obtained above and 0.1 μg of the SalI-XhoI fragment (about 1.8 kb) of pAGE501 were dissolved in a total of 20 μl of T4 ligase buffer; 350 units of T4 DNA ligase was added to the solution, and the mixture was incubated at 4° C. for 1 day. The thus-obtained recombinant plasmid DNA was used to transform *Escherichia coli* HB101 to give the plasmid pAGE502 shown in FIG. 35.

(6) Construction of pAGE503

A plasmid named pAGE503 derived from pAGE502 by deletion of one of the two EcoRI sites was constructed as follows.

Two μg of pAGE109 obtained in (4) was added to 30 μl of 10 mM Tris-hydrochloride buffer (pH 7.5) containing 6 mM magnesium chloride and 50 mM sodium chloride; 10 units of HindIII and 10 units of ClaI were further added, and digestion was carried out at 37° C. for 4 hours. The reaction mixture was fractionated by agarose gel electrophoresis and about 0.2 μg of a DNA fragment (about 1 kb) resulting from cleavage of pAGE109 with ClaI and HindIII and containing the poly-A signal gene for the beta globulin and SV40 early genes was recovered.

Figure 36:
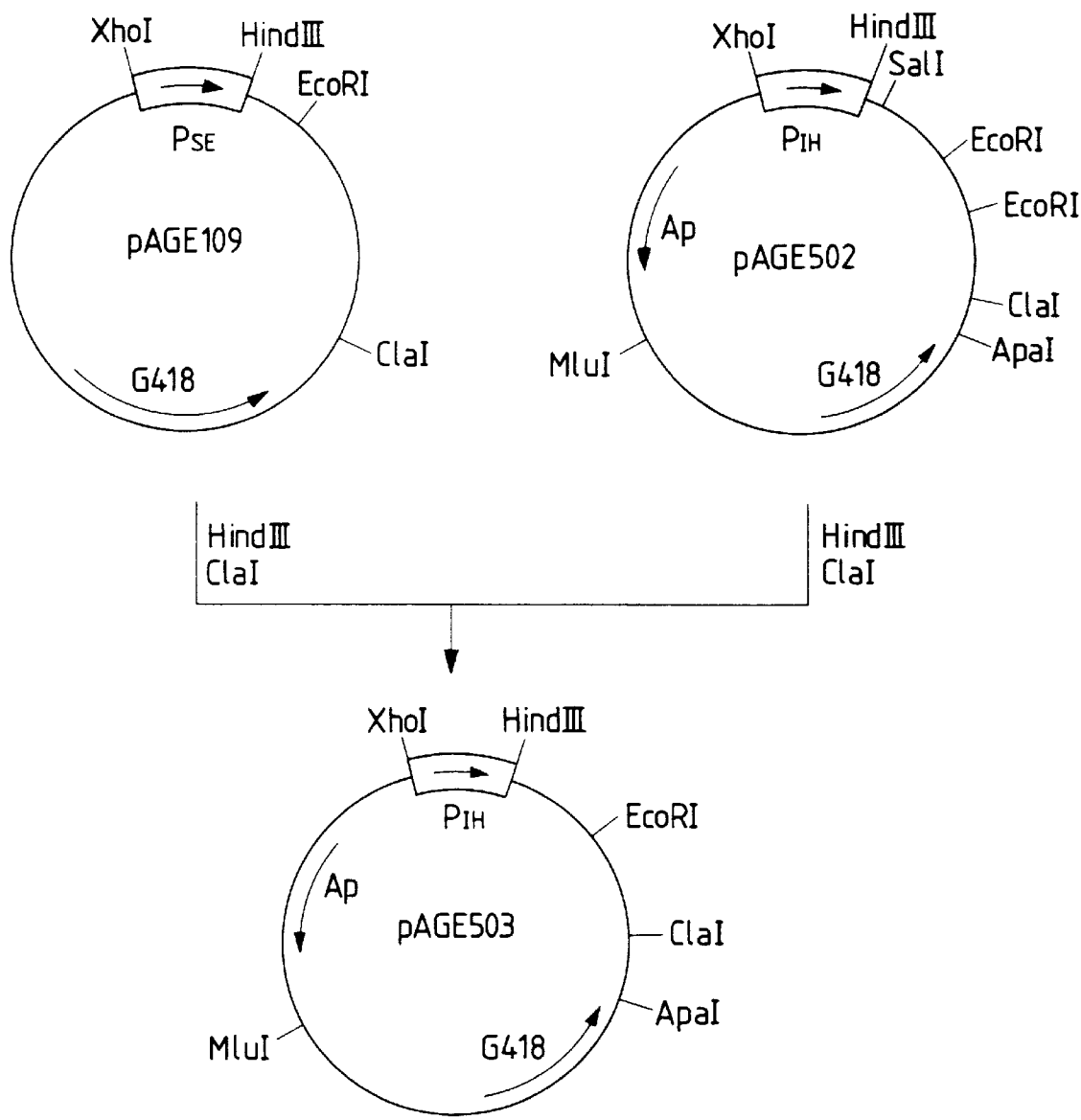
FIG. 36 shows a construction scheme for a plasmid, pAGE503.

Then, 2 μg of pAGE502 obtained in (5) was added to 30 μl of 10 mM Tris-hydrochloride buffer (pH 7.5) containing 6 mm magnesium chloride and 50 mM sodium chloride, 10 units of HindIII and 10 units of ClaI were further added, and digestion was conducted at 37° C. for 4 hours. The reaction mixture was fractionated by agarose gel electrophoresis and about 1 μg of a DNA fragment (about 6.1 kb) resulting from cleavage of pAGE502 with HindIII and ClaI and containing the KM50 cell immunoglobulin H chain promoter and enhancer genes, the Ap resistance gene and the G418 resistance gene was recovered by the DEAE paper method. Then, 0.1 μg of the HindIII-ClaI fragment (about 1 kb) of pAGE109 as obtained above and 0.1 μg of the HindIII-ClaI fragment (about 6.1 kb) of pAGE502 as obtained above were dissolved in a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pAGE503 shown in FIG. 36 was obtained.

(7) Construction of pSE1d1

A plasmid named pSE1d1 was constructed by introducing the dhfr gene into pAGE107, as follows.

Two μg of pAGE107 described in EP-A-0 405 285 was added to 100 μl of 100 mM Tris-hydrochloride buffer (pH 7.5) containing 6 mM magnesium chloride and,50 mM sodium chloride, 10 units of EcoRI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon EcoRI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 50 mM sodium chloride; 10 units of HindIII was further added, and digestion was effected at 37° C. for 4 hours. The reaction mixture was fractionated by agarose gel electrophoresis and about 1.5 μg of a DNA fragment (about 5.6 kb) resulting from cleavage of pAGE107 with EcoRI and HindIII and containing the G418 resistance gene and Ap resistance gene was recovered.

Two μg of pSV2-dhfr [Subramani et al.: Mol. Cell. Biol., 1,854 (1981)] was added to 100 μl of 10 mM Tris-hydrochloride buffer (pH 7.5) containing 6 mM magnesium chloride and 100 mM sodium chloride, 10 units of BglII was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon BglII digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mm magnesium chloride and 100 mM sodium chloride, 10 units of HindIII was further added, and digestion was effected at 37° C. for 4 hours. The reaction mixture was fractionated by agarose gel electrophoresis and about 0.2 μg of a pSV2-dhfr DNA fragment (0.76 kb) resulting from cleavage with BglII and HindIII and containing the dehydrofolate reductase (dhfr) gene was recovered.

Figure 37:
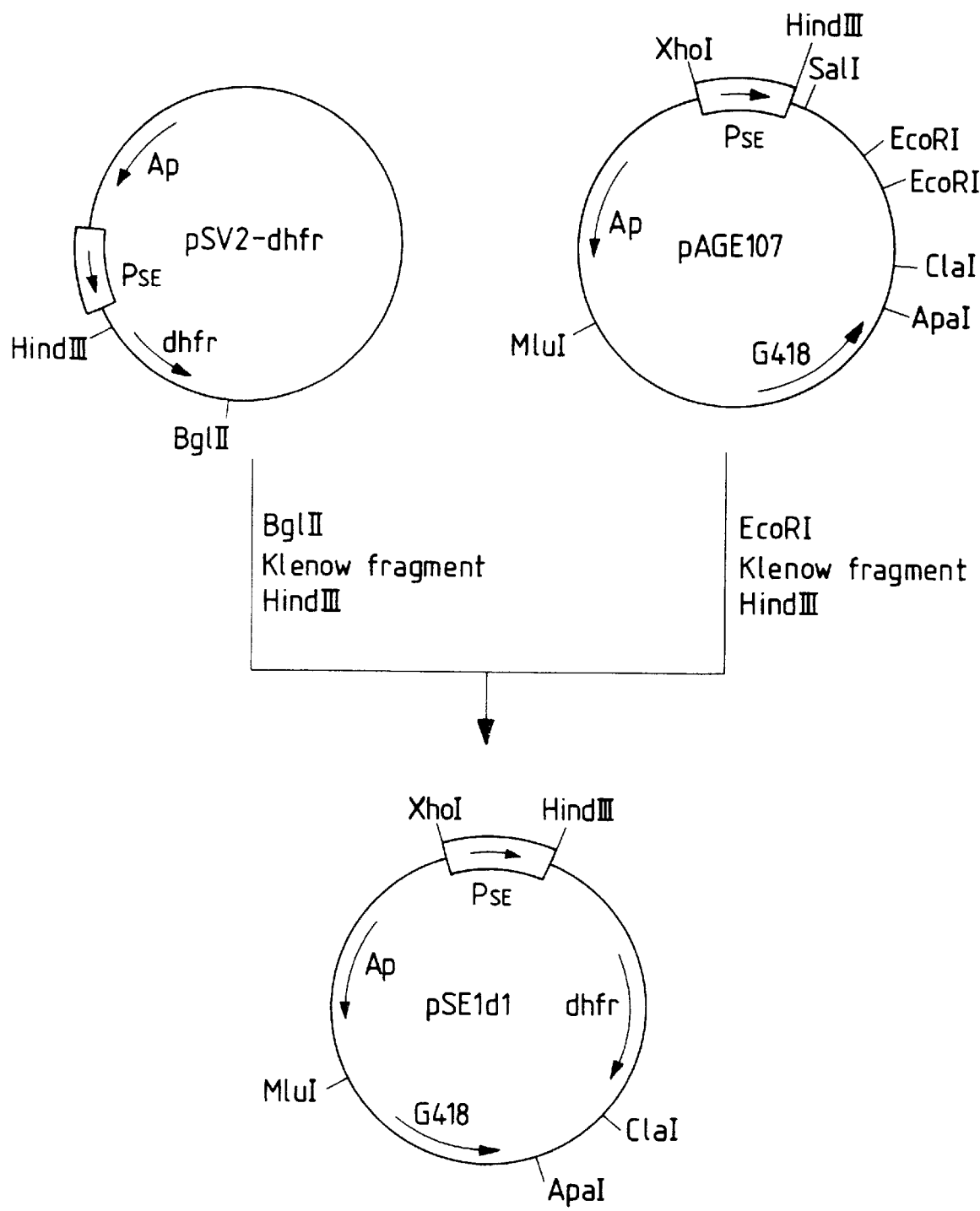
FIG. 37 shows a construction scheme for a plasmid, pSEd1.

Then, 0.1 μg of the HindIII-EcoRI fragment (about 5.6 kb) of pAGE107, as obtained above, and 0.1 μg of the BglII-HindIII fragment (about 0.76 kb) of pSV2-dhfr, as obtained above, were dissolved in a total of 20 μl of T4 ligase buffer; 350 units of T4 DNA ligase was added to the solution, and the mixture was incubated at 4° C. for 1 day. The thus-obtained recombinant plasmid DNA was used to transform *Escherichia coli* HB101 and the plasmid pSE1d1 shown in FIG. 37 was obtained.

(8) Construction of pSE1d2

A plasmid named pSE1d2 was constructed by deleting the HindIII cleavage site from pSE1d1, as follows.

Thus, 2 μg of pSE1d1 obtained in (7) was added to 100 μl of 10 mM Tris-hydrochloride buffer (pH 7.5) containing 6 mM magnesium chloride and 50 mM sodium chloride, 10 units of HindIII was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon HindIII digestion blunt-ended. The reaction mixture was subjected to phenol-chloroform extraction and then to ethanol precipitation, the precipitate was dissolved in 20 μl of T4 ligase buffer, 350 units of T4DNA ligase was. added to the solution, and the mixture was incubated at 4° C. for 1 day. The thus-obtained recombinant plasmid DNA was used to transform *Escherichia coli* HB101 and the plasmid pSE1d2 shown in FIG. 38 was obtained.

(9) Construction of pIg1SE1d2

A plasmid named pIg1SE1d2 was constructed by introducing the dhfr gene into pAGE503, as follows.

Two μg of pAGE503 obtained in (6) was added to 100 μl of 10 mM Tris-hydrochloride buffer (pH 7.5) containing 6 mM magnesium chloride and 50 mM sodium chloride, 10 units of ClaI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon ClaI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 50 mM sodium chloride; 10 units of XluI was further added, and digestion was effected at 37° C. for 4 hours. The reaction mixture was fractionated by agarose gel electrophoresis and about 1 μg of a DNA fragment (about 5.4 kb) resulting from cleavage of pAGE503 with ClaI and MluI and containing the KM50 immunoglobulin H chain promoter and enhancer was recovered.

Then, 2 μg of pSE1d2 obtained in (8) was added to 100μl of 10 mM Tris-hydrochloride-buffer (pH 7.5) containing 6 mM magnesium chloride and 100 mM sodium chloride, 10 units of XhoI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was conducted at 16° C. for 2 hours for rendering the 5' protruding ends formed upon XhoI digestion blunt-ended. The reaction mixture was subjected to phenol-chloroform extraction and then to ethanol precipitation, the precipitate was added to 30 μl of 10 mM Tris-hydrochloride buffer (pH 7.5) containing 6 mM magnesium chloride and 100 mM sodium chloride, 10 units of MluI was further added, and digestion was effected at 37° C. for 4 hours. The reaction mixture was fractionated by agarose gel electrophoresis and about 1 μg of a DNA fragment (about 3.8 kb) resulting from cleavage of pSE1d2 with XhoI and MluI and containing the dhfr gene was recovered.

Figure 39:
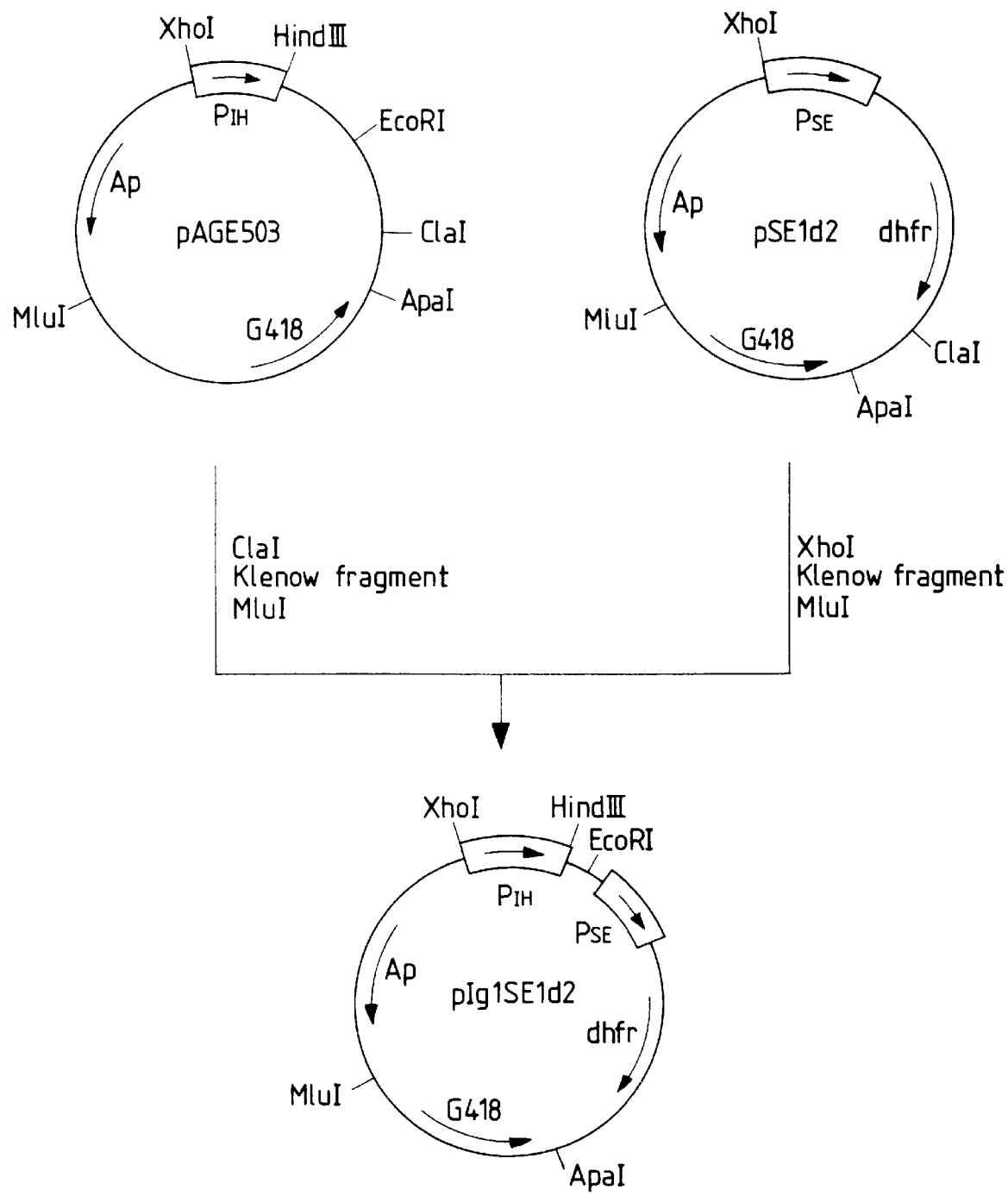
FIG. 39 shows a construction scheme for a plasmid, pIG1SE1d2.

Then, 1 μg of the ClaI-MluI fragment (about 5.4 kb) of pAGE503 as obtained above and 1 μg of the XhoI-MluI fragment (about 3.8 kb) of pSE1d2 as obtained above were dissolved in a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pIg1SE1d2 shown in FIG. 39 was obtained.

(10) Construction of pIg1SE1d3

A plasmid named pIg1SE1d3 was constructed by deleting the ApaI cleavage site from pIg1SE1d2, as follows.

Two μg of pIg1SE1d2 obtained in (9) was added to 100 μl of 10 mM Tris-hydrochloride buffer (pH 7.5) containing 6 mM magnesium chloride, 10 units of ApaI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was carried out at 16° C. for 2 hours for rendering the 3' protruding ends formed upon ApaI digestion blunt-ended. The reaction mixture was subjected to phenol-chloroform extraction and then to ethanol precipitation, the precipitate was dissolved in 20 μl of T4 ligase buffer, 350 units of T4 ligase was added to the solution, and ligation was effected at 4° C. for 24 hours. The thus-obtained recombinant plasmid DNA was used to transform *Escherichia coli* HB101 and the plasmid pIg1SE1d3 shown in FIG. 40 was obtained.

(11) Construction of pIg1SE1d4

For providing pIg1SE1d3 with a cloning site between the HindIII cleavage site and EcoRI cleavage site, a plasmid named pIg1SE1d4 was constructed containing the synthetic DNA defined by SEQ ID NO:17 as an insert, as follows.

Two μg of pIg1SE1d3 obtained in (10) was added to 30 μl of 10 mM Tris-hydrochloride buffer (pH 7.5) containing 6 mM magnesium chloride and 50 mM sodium chloride, 10 units each of HindIII and EcoRI were further added, and digestion was carried out at 37° C. for 4 hours. The reaction mixture was fractionated by agarose gel electrophoresis and about 1 μg of a DNA fragment (about 9.2 kb) resulting from cleavage of pIg1SE1d3 with HindIII and EcoRI and containing the KM50 cell immunoglobulin H chain promoter, enhancer, Ap resistance gene, G418 resistance gene and dhfr gene was recovered.

Figure 41:
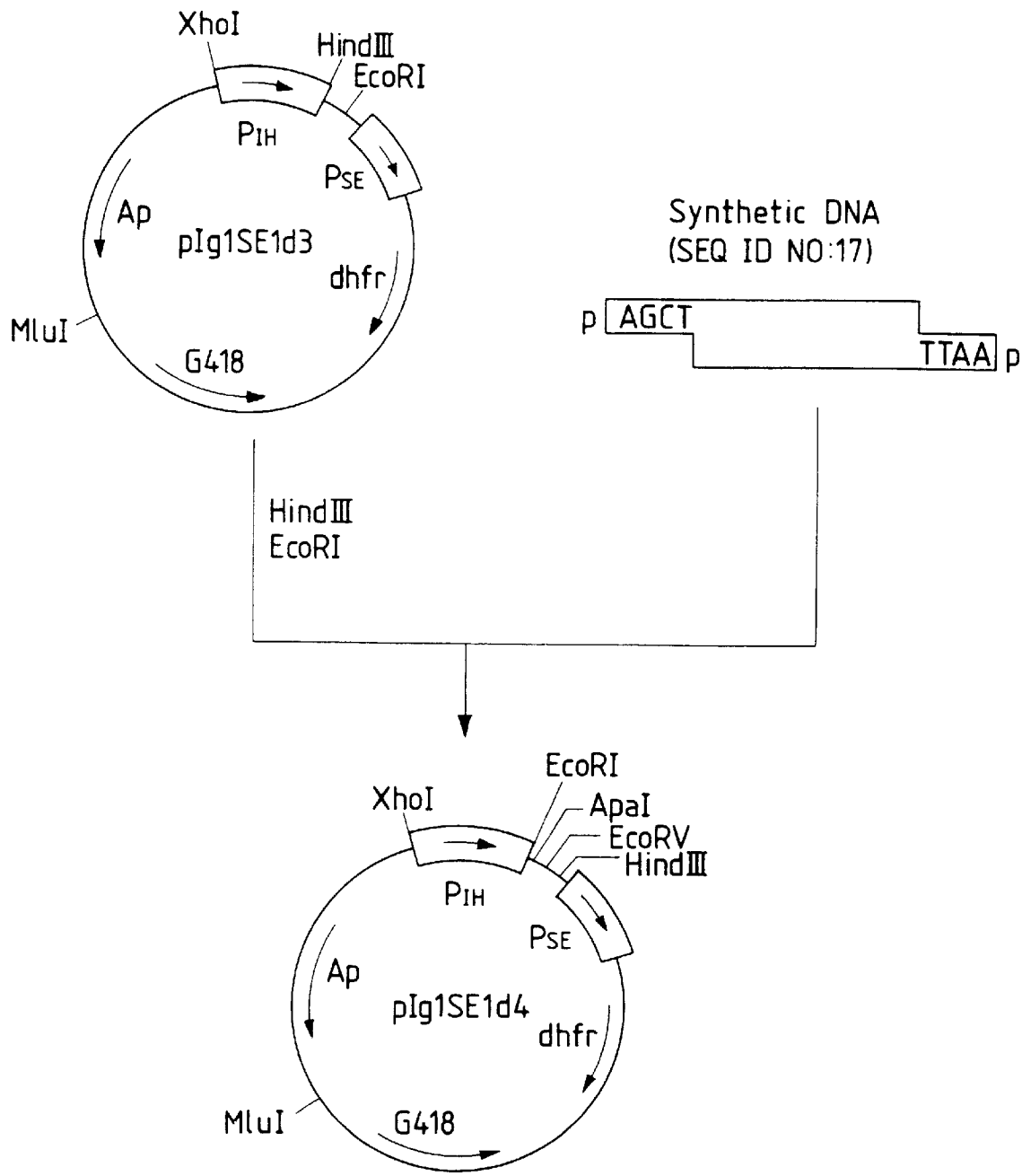
FIG. 41 shows a construction scheme for a plasmid, pIG1SE1d4.

Then, 0.1 μg of the HindIII-EcoRI fragment (about 9.2 kb) of pIg1SE1d3 as obtained above and 10 ng of the synthetic DNA (SEQ ID NO:17) were a total of 20 μl of T4 ligase buffer, 350 units of T4 DNA ligase was added to the solution, and the mixture was incubated at 4° C. for 1 day. The thus-obtained recombinant plasmid DNA was used to transform *Escherichia coli* HB101 and the plasmid pIg1SE1d4 shown in FIG. 41 was obtained.

3. Preparation of the Moloney mouse leukemia virus long terminal repeat (hereinafter abbreviated as "MoLTR")

It is known that MoLTR has promoter and enhancer activity [Kuwana et al.: Biochem. Biophys. Res. Commun., 149, 960 (1987)]. Therefore, for using MoLTR as a promoter and enhancer in vectors for chimeric human antibody expression, a plasmid, pPMOL3, containing MoLTR was constructed as follows.

Three μg of pPMOL1 described in JP-A-1-63394 was added to 30 μl of 10 mM Tris-hydrochloride buffer (pH 7.5) containing 7 mM magnesium chloride and 6 mM 2-mercaptoethanol, 10 units of ClaI was further added, and digestion was carried out at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived DNA polymerase I Klenow fragment was added, and the reaction was carried out at 16° C. for 2 hours for rendering the 5' protruding ends formed upon ClaI digestion blunt-ended. The reaction was terminated by extraction with phenol, the reaction mixture was subjected to chloroform extraction and then to ethanol precipitation, and 2 μg of a DNA fragment was recovered. This DNA fragment and 0.01 μg of a synthetic DNA linker XhoI (Takara Shuzo) were dissolved in 20 μl of T4 ligase buffer, 175 units of T4 DNA ligase was added, and the mixture was incubated at 4° C. for 1 day. The reaction mixture was used to transform *Escherichia coli* HB101 and the plasmid pPMOL2 shown in FIG. 42 was obtained. Then, 3 μg of pPMOL2 was added to 30 μl of 10 mM Tris-hydrochloride buffer (pH 7.5) containing 7 mM magnesium chloride, 10 mM sodium chloride and 6 mM 2-mercaptoethanol, 10 units of SmaI was further added, and digestion was conducted at 37° C. for 4 hours. The reaction mixture was subjected to phenol-chloroform extraction and then to ethanol precipitation, and 2 μg of a DNA fragment was recovered. This DNA fragment and 0.01 μg of a synthetic DNA linker (EcoRI; Takara Shuzo) were dissolved in 20 μl of T4 ligase buffer, 175 units of T4 DNA ligase was added, and the mixture was incubated at 4° C. for 1 day. The reaction mixture was used to transform *Escherichia coli* HB101 and the plasmid pPMOL3 shown in FIG. 43 was obtained.

4. Cloning of the human immunoglobulin IgG1 H chain constant region (Cγ1) cDNA and L chain constant region (Cκ) cDNA (1) Isolation of mRNA from the chimeric antibody producer cell line SP2-PC Chimera-1

Using mRNA extraction kit Fast Track (product number K1593-02) manufactured by Invitrogen, mRNA (6.2 μg) was isolated from 1×10⁸ cells of the chimeric antibody producer cell line SP2-PC Chimera-1 described in FEBS Letters, 244, 301–306 (1989) and capable of producing a chimeric antibody having anti-phosphorylcholine activity.

(2) Construction of an SP2-PC Chimera-1 cDNA library and cloning of the human immunoglobulin H chain constant region (Cγ1) cDNA and L chain constant region (Cκ) cDNA Starting with 2 μg of the mRNA obtained in (1) and using cDNA Synthesis Kit (product number 27-9260-01) manufactured by Pharmacia, EcoRI adapter joining was performed, followed by phosphorylation. The cDNA solution obtained was subjected to phenol-chloroform extraction and then to ethanol precipitation, and 4 μg of cDNA was recovered. This cDNA was dissolved in 20 μl of sterilized water and then fractionated by agarose gel electrophoresis, and about 0.3 μg each of two DNA fragments, about 1.8 kb and about 1.0 kb in size, were recovered.

Then, 5 μg of the vector pUC18 was added to 100 μl of 100 mM Tris-hydrochloride buffer (pH 7.5) containing 6 mM magnesium chloride and 100 mM sodium chloride, 50 units of EcoRI was further added, and digestion was carried out at 37° C. for 4 hours for cleaving the pUC18 DNA at the EcoRI site. The reaction mixture was subjected to phenol-chloroform extraction and then to ethanol precipitation, and about 3 μg of a DNA fragment resulting from cleavage of pUC18 at the EcoRI site thereof was recovered.

Then, 0.1 μg of the EcoRI fragment (about 2.7 kb) of pUC18 as obtained above and 0.1 μg each of the 1.8 kb and 1.0 kb cDNA fragments prepared from SP2-PC Chimera-1 cells were dissolved in a total of 20 μl of T4 ligase buffer; 350 units of T4 DNA ligase was added to the solution, and ligation was effected at 4° C. for 24 hours.

The thus-obtained recombinant plasmid DNA was used to transform *Escherichia coli* LE392. About 3,000 colonies obtained were fixed onto a nitrocellulose filter. From among the strains firmly bound at 65° C. to probes prepared by labeling the human immunoglobulin constant region chromosomal genes (IgG1 H chain constant region Cγ1 and L chain constant region Cκ) [Kameyama et al.: FEBS Letters, 244, 301 (1989)] with ³²P, a plasmid (pPCVHhCGI1) associable with Cγ1 and another (pPCVLhCK1) associable with Cκ were isolated.

(3) Introduction of an EcoRV site into the human Igκ chain constant region gene

An EcoRV site was introduced into the human Igκ chain constant region at a site near the 5' end thereof by site-directed mutagenesis using a kit (catalog number Q6210) manufactured by Promega. The plasmid pPCVLhCK1 (2 μg) was added to 30 μl of 10 mM Tris-hydrochloride buffer (pH 7.5) containing 6 mM magnesium chloride and 50 mM sodium chloride, 10 units of EcoRI and 10 units of KpnI were further added, and digestion was conducted at 37° C. for 4 hours. The reaction mixture was fractionated by agarose gel electrophoresis and about 0.2 μg of a DNA fragment (about 0.8 kb) resulting from cleavage of pPCV-LhCK1 with KpnI and EcoRI and containing the human immunoglobulin L chain constant region gene was recovered.

Then, 2 μg of pSELECT1 (a kit manufactured by Promega; catalog number Q6210) was added to 30 μl of 10 mM Tris-hydrochloride buffer (pH 7.5) containing 6 mM magnesium chloride and 50 mM sodium chloride, 10 units each of EcoRI and KpnI were further added, and digestion was carried out at 37° C. for 4 hours. The reaction mixture was fractionated by agarose gel electrophoresis and about 1 μg of a DNA fragment (about 5.7 kb) resulting from cleavage of pSELECT1 with EcoRI and KpnI was recovered.

Figure 44:
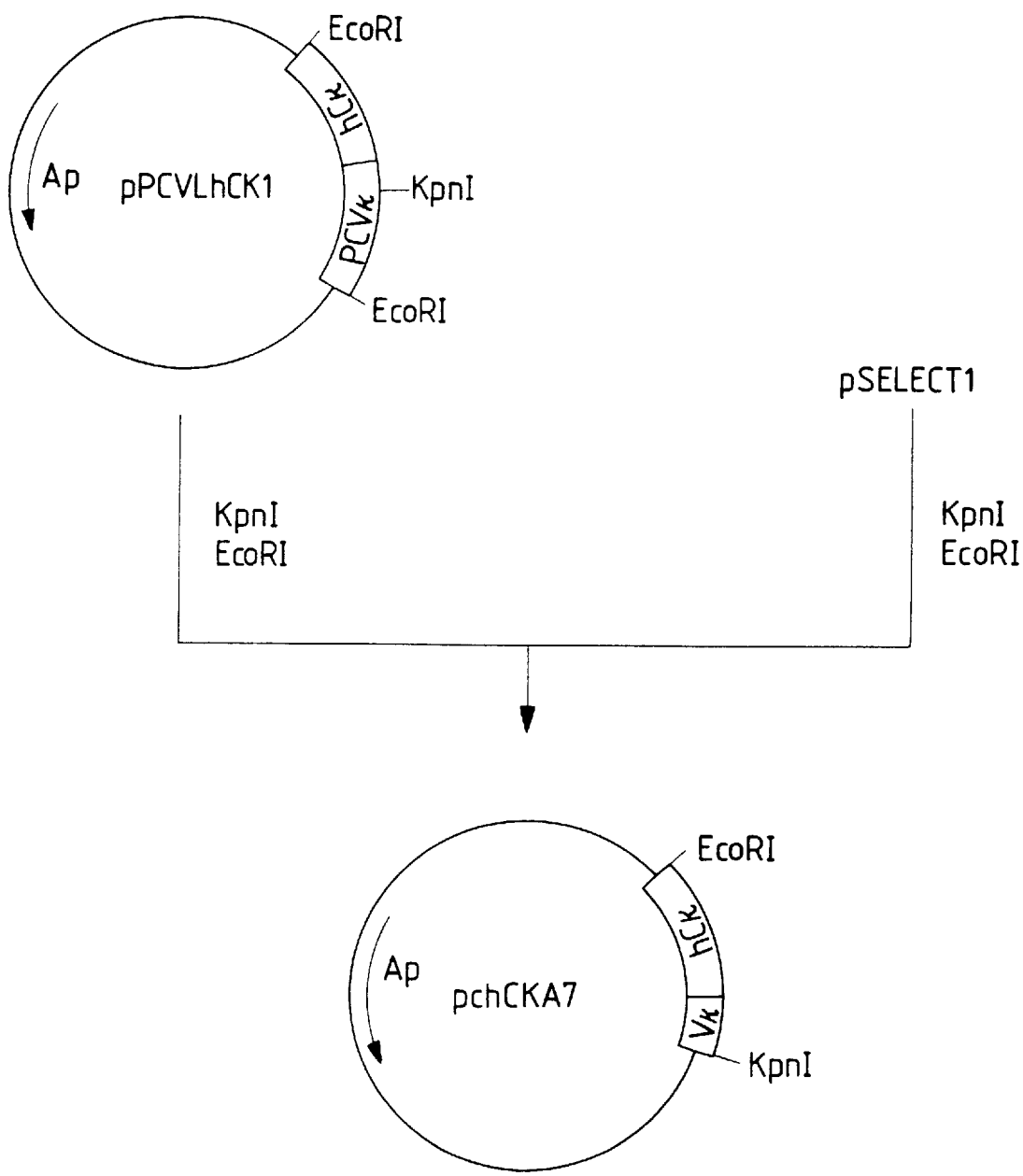
FIG. 44 shows a construction scheme for a plasmid, pchCKA7.

Then, 0.1 μg of the EcoRI-KpnI fragment (about 0.8 kb) of pPCVLhCK1 as obtained above and 0.1 μg of the EcoRI-KpnI fragment (about 5.7 kb) of pSELECT1 as obtained above were dissolved in a total of 20 μl of T4 ligase buffer; 350 units of T4 DNA ligase was added to the solution, and ligation was effected at 4° C. for 24 hours. The thus-obtained recombinant plasmid DNA was used to transform *Escherichia coli* JM109 and the plasmid pchCXA7 shown in FIG. 44 was obtained.

Then, using pchCKA7 and using the synthetic DNA defined by SEQ ID NO:18 as a mutagenic primer, the sequence covering the 12th base to 14 base from the N terminus of the human immunoglobulin L chain constant region, namely ACC, was converted to GAT and thus an EcoRV site was introduced into that site, to give a plasmid named pchCKB1 (FIG. 45).

Then, the EcoRV site of pchCKB1 was converted to a HindIII cleavage site in the following manner.

Thus, 2 μg of the plasmid pchCKB1 was added to 10 μl of 100 mM Tris-hydrochloride buffer (pH 7.5) containing 6 mM magnesium chloride and 100 mM sodium chloride, 10 units of EcoRI was further added, and digestion was effected at 37° C. for 4 hours. The reaction mixture was subjected to phenol-chloroform extraction and then to ethanol precipitation, the precipitate was dissolved in a total of 40 μl of DNA polymerase I buffer, 5 units of *Escherichia coli*-derived polymerase I Klenow fragment was added, and the reaction was carried out at 37° C. for 30 minutes for rendering the 5' protruding ends formed upon EcoRI digestion blunt-ended. The reaction mixture was subjected to phenol-chloroform extraction and then ethanol precipitation, the precipitate was dissolved, together with 0.1 μg of a HindIII linker (Takara Shuzo.), in 20 μl of T4 ligase buffer; 350 units of T4 ligase was added to the solution, and ligation was effected at 4° C. for 24 hours. The thus-obtained recombinant plasmid DNA was used to transform *Escherichia coli* HE101 and the plasmid pchCKC1 shown in FIG. 46 was obtained.

5. Construction of vectors for chimeric human antibody H chain expression (1) Construction of a vector to be used in constructing chimeric human antibody H chain expression vectors (vector for chimeric human antibody H chain expression)

The plasmid pIg1SE1d4 obtained in Paragraph 2 (11) (2 μg) was added to 30 μl of 10 mM Tris-hydrochloride buffer (pH 7.5) containing 6 mM magnesium chloride and 100 mM sodium chloride, 10 units each of EcoRV and ApaI were further added, and digestion was effected at 37° C. for 4 hours. The reaction mixture was fractionated by agarose gel electrophoresis and about 1.5 μg of a DNA fragment (about 9.2 kb) resulting from cleavage of pIg1SE1d4 with EcoRV and ApaI was recovered.

Then, 2 μg of pPCVHhCGI1 obtained in Paragraph 4 (2) was added to 30 μl of 10 mM Tris-hydrochloride buffer (pH 7.5) containing 6 mM magnesium chloride, 10 units of ApaI and 10 units of SmaI were further added, and digestion was conducted at 37° C. for 1 hour. The reaction mixture was fractionated by agarose gel electrophoresis and about 0.2 μg of a DNA fragment (about 1 kb) resulting from cleavage of pPCVHhCGI1 with ApaI and SmaI and containing the human immunoglobulin H chain constant region gene was recovered.

Figure 47:
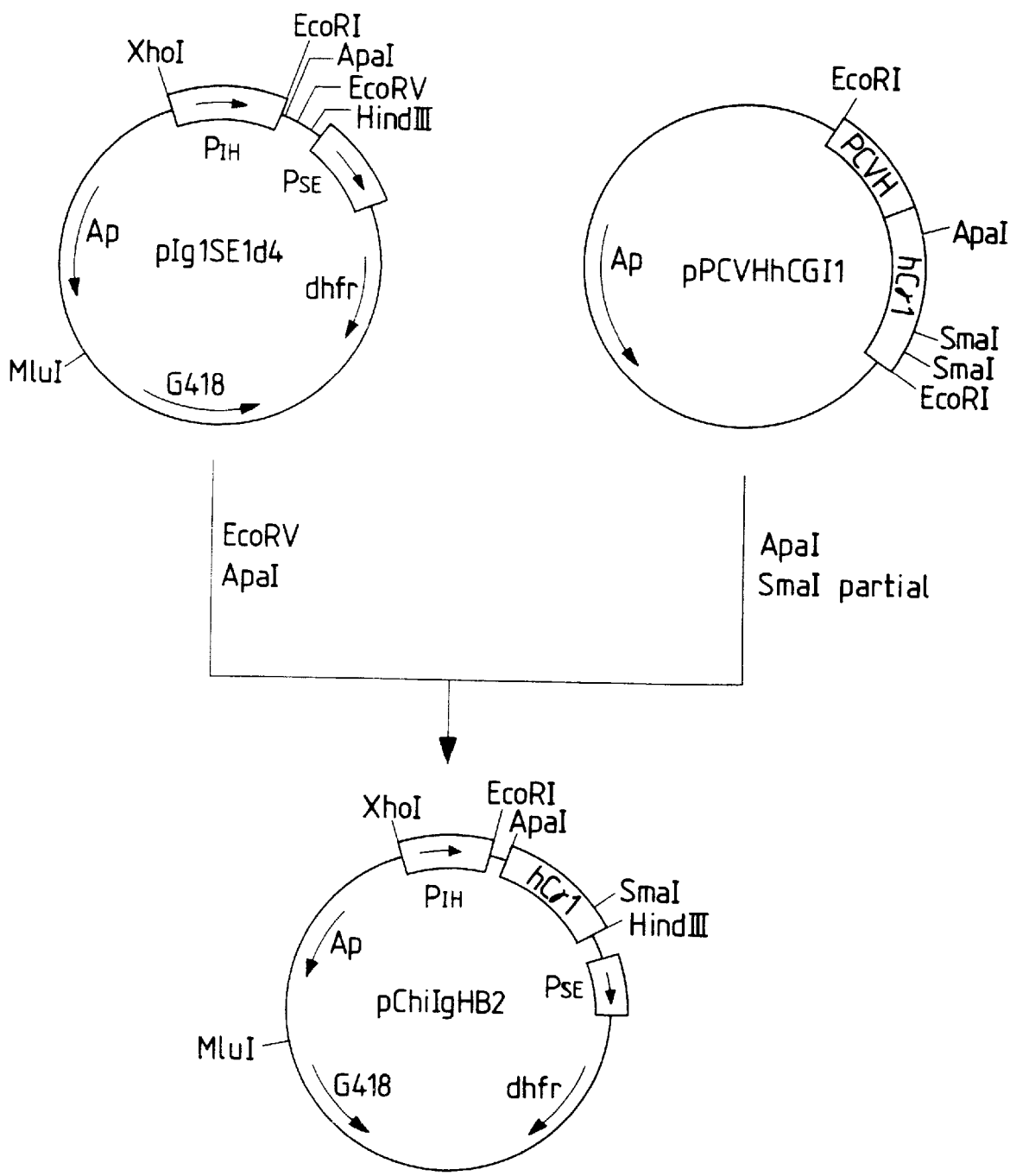
FIG. 47 shows a construction scheme for a plasmid, pChiIgHB2.

Then, 0.1 μg of the EcoRV-ApaI fragment (about 9.2 kb) of pIg1SE1d4 as obtained above and 0.1 μg of the ApaI-SmaI fragment (about 1 kb) of pPCVHhCGI1 as obtained above were dissolved in a total of 20 μl of T4 ligase buffer; 350 units of T4 DNA ligase was added to the solution, and ligation was conducted at 4° C. for 24 hours. The thus-obtained recombinant plasmid DNA was used to transform *Escherichia coli* HB101 and the vector pCHiIgHB2 for chimeric human antibody H chain expression as shown in FIG. 47 was obtained.

(2) Construction of a vector to be used in constructing chimeric human antibody L chain expression vectors (vector for chimeric human antibody L chain expression)

The plasmid pIg1SE1d4 obtained in Paragraph 2 (11) (2 μg) was added to 30 μl of 10 mM Tris-hydrochloride buffer (pH 7.5) containing 6 mM magnesium chloride and 100 mM sodium chloride, 10 units of EcoRV and 10 units of HindIII were further added, and digestion was effected at 37° C. for 4 hours. The reaction mixture was fractionated by agarose gel electrophoresis and about 1.5 μg of a DNA fragment (about 9.2 kb) resulting from cleavage of pIg1SE1d4 with EcoRV and HindIII was recovered.

Then, 2 μg of pckCKC1 obtained in Paragraph 4 (3) was added to 30 μl of 10 mM Tris-hydrochloride (pH 7.5) containing 6 mM magnesium chloride and 100 mM sodium chloride, 10 units of EcoRV and 10 units of HindIII were further added, and digestion was carried out at 37° C. for 1 hour. The reaction mixture was fractionated by agarose gel electrophoresis and about 0.2 μg of a DNA fragment (about 0.6 kb) resulting from cleavage of pPCVLhCK1 with EcoRV and HindIII and containing the human immunoglobulin L chain constant region gene was recovered.

Figure 48:
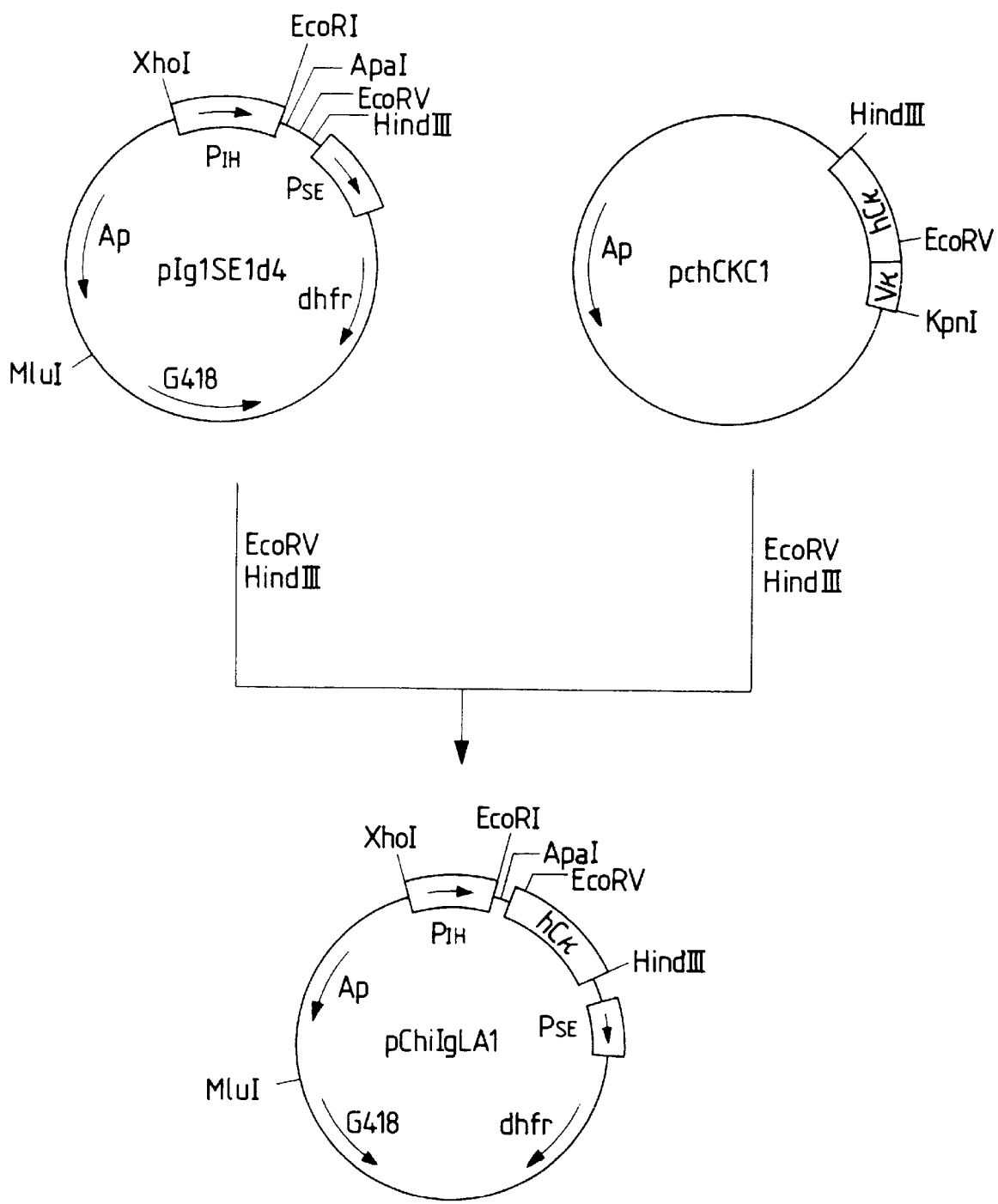
FIG. 48 shows a construction scheme for a plasmid, pChiIgLA1.

Then, 0.1 μg of the EcoRV-HindIII fragment (about 9.2 kb) of pIg1SE1d4 as obtained above and 0.1 μg of the EcoRV-HindIII fragment (about 0.6 kb) of pchCKC1 as obtained above were dissolved in a total of 20 μl of T4 ligase buffer, 350 units of T4 DNA ligase was added to the solution, and ligation was carried out at 4° C. for 24 hours. The thus-obtained recombinant plasmid DNA was used to transform *Escherichia coli* HB101 and the vector pChi-IgLA1 for chimeric human antibody L chain expression as shown in FIG. 48 was obtained.

REFERENCE EXAMPLE 2

Construction of a chimeric human antibody H chain expression vector, pChi641HA1

1. Isolation of mRNA from mouse anti-$GD_3$ monoclonal antibody KM-641-producing hybridoma cells Using mRNA extraction kit Fast Track (product number K1593-02) manufactured by Invitrogen, 34 μg of mRNA was isolated from $1 \times 10^8$ mouse anti-$GD_3$ monoclonal antibody KM-641-producing hybridoma cells obtainable as in Reference Example 1.

2. Construction of a KM-641 H chain cDNA library and a KM-641 L chain cDNA library.

Using 3 μg of the mRNA obtained in Paragraph 1 and using cDNA synthesis kit ZAP-cDNA Synthesis Kit (product number sc200400) manufactured by Stratagene, cDNA having an EcoRI adapter at the 5' terminus and cDNA having an XhoI adapter at the 3' terminus were synthesized. About 6 μg of each cDNA was dissolved in 10 μl of sterilized water and fractionated by agarose gel electrophoresis. In this way, about 0.1 μg of a cDNA fragment having a size of about 1.8 kb and corresponding to the H chain and a cDNA fragment having a size of about 1.0 kb and corresponding to the L chain were recovered. Then, 0.1 μg of the cDNA fragment of about 1.8 kb in size, 0.1 μg of the cDNA fragment of about 1.0 kb in size and 1 μg of Uni-ZAP XR (Stratagene; derived from the Lambda ZAPII vector by cleavage with EcoRI and XhoI, followed by treatment with calf intestine alkaline phosphatase), to be used as the vector, were dissolved in T4 ligase buffer; 175 units of T4 DNA ligase was added, and the mixture was incubated at 12° C. for 10 hours and further at room temperature for 2 hours. A 4-μl portion of the reaction mixture was packaged into the lambda phage by the conventional method [Maniatis et al. (ed.): Molecular Cloning, 1989, p. 2.95] using Giga Pak Gold (Stratagene), followed by transfection of *Escherichia coli* PLK-F with the packaging mixture by the conventional method [Maniatis et al. (ed.): Molecular Cloning, 1989, p. 2.95–107]. As an H chain cDNA library and as an L chain cDNA library, about 10,000 phage clones were respectively obtained. The phages were then fixed onto nitrocellulose filters by the conventional method [Maniatis et al. (ed.): Molecular Cloning, 1989, p. 2.112].

3. Cloning of the monoclonal antibody KM-641 H chain and L chain cDNAs

Figure 49:
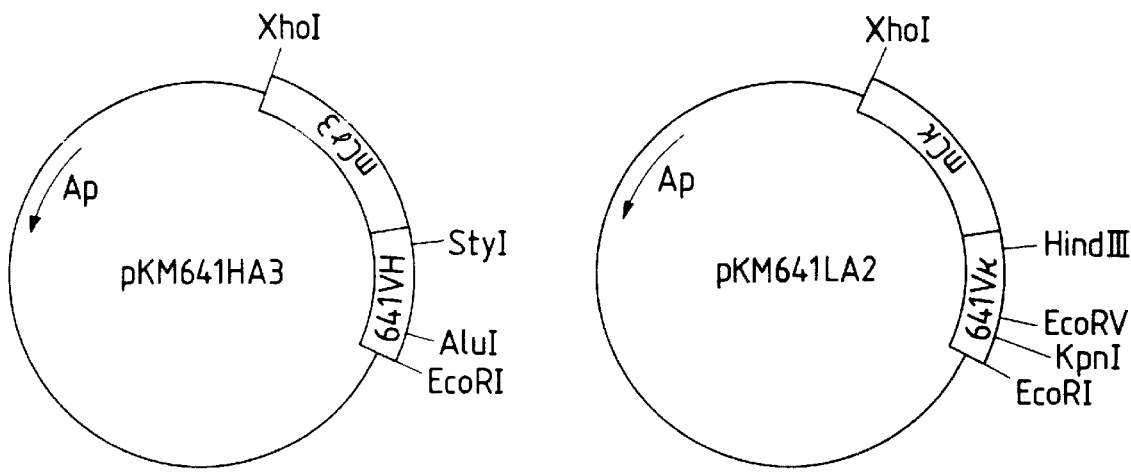
FIG. 49 shows a construction scheme for plasmids, pKM641HA3 and pKM641LA2.

Using probes prepared by labeling a mouse Cγ1 gene (mouse immunoglobulin constant region chromosomal gene)-containing EcoRI fragment (about 6.8 kb) [Roeder et al.: Proc. Natl. Acad. Sci. U.S.A., 78, 474 (1981)] and a mouse Cκ gene-containing HindIII-BamHI fragment (about 3 kb) [Sakano et al.: Nature, 280, 288 (1979)] with $^{32}$P, one phage clone strongly associable with the former probe at 65° C. and one phage clone strongly associable with the latter probe at 65° C. were isolated from the H chain cDNA library and L chain cDNA library constructed in Paragraph 2 in accordance with the conventional method [Maniatis et al. (ed.): Molecular Cloning, 1989, p. 2.108]. Then, by converting the phage clones to pBluescript plasmids using cDNA synthesis kit ZAP-cDNA Synthesis Kit (product number sc200400) manufactured by Stratagene, a KM-641 H chain cDNA-containing recombinant plasmid, pKM641HA3, and a KM-641 L chain cDNA-containing recombinant plasmid, pKM641LA2, were obtained. Cleavage of pKM641HA3 and pKM641LA2 with EcoRI and XhoI revealed that a cDNA fragment of about 1.6 kb and a cDNA fragment of about 0.9 kb had been inserted therein, respectively (FIG. 49).

4. Base sequences of the immunoglobulin variable regions in the KM-641 H chain cDNA (pKM641HA3) and KM-641 L chain cDNA (pKM641LA2)

The base sequences of the immunoglobulin regions in pKM641HA3 and pKM641LA2 obtained in Paragraph 3 were determined by the dideoxy method [Maniatis et al. (ed.): Molecular Cloning, 1989, p. 13.42] using Sequenase Version 2.0 DNA Sequencing Kit (United States Biochemical Corporation). The results obtained are shown in SEQ ID NO:19 and SEQ ID NO:20. In pKM641LA2, a methionine codon, presumably the initiation codon ATG, was found in the vicinity of the 5' terminus and the cDNA was a leader sequence-containing full-length one. In pKM641HA3, no methionine initiation codon was found and the leader sequence was partly lacking.

Figure 50:
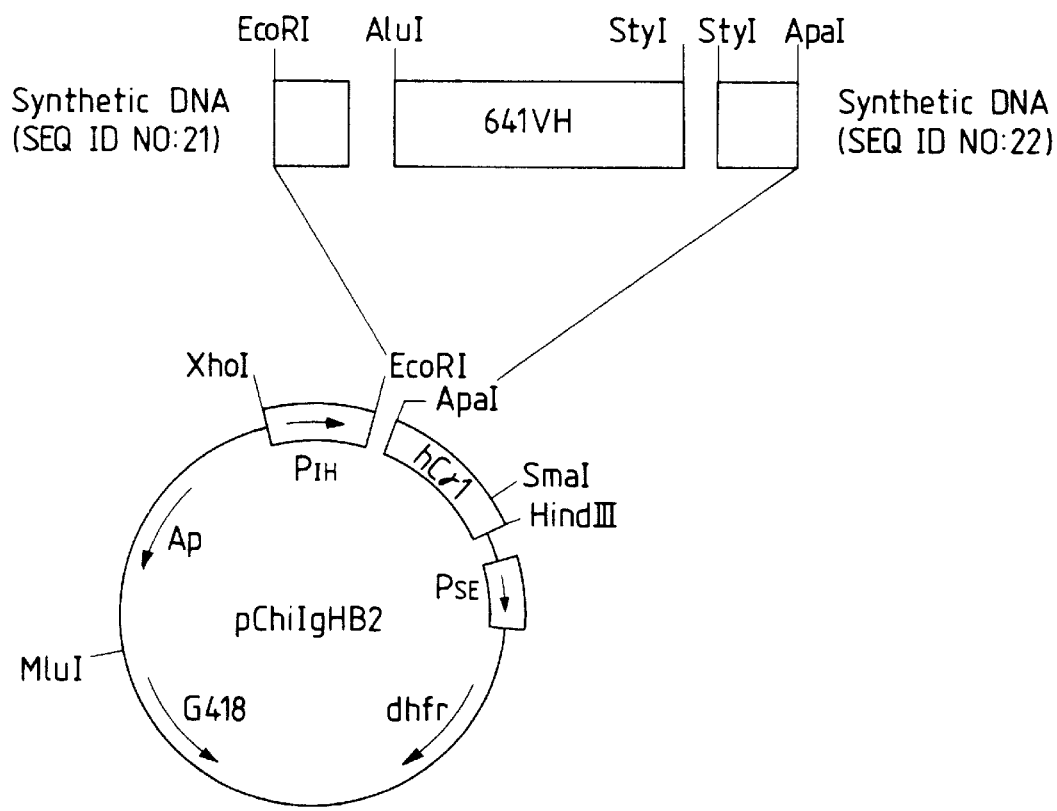
FIG. 50 shows a construction scheme for a plasmid, pChi641HA1.

5. Construction of a KM-641-derived chimeric human antibody H chain expression vector A chimeric human antibody H chain expression vector was constructed by joining the H chain variable region gene obtained by cleaving the plasmid pKM641HA3 at the AluI site near the 5' terminus of the variable region gene and at the StyI site near the 3' terminus of the variable region gene to the vector for chimeric human antibody H chain expression as obtained in Reference Example 1 using the synthetic DNAs defined by SEQ ID NO:21 and SEQ ID NO:22 (FIG. 50).

First, the DNA defined by SEQ ID NO:22 composed of the base sequence from the 3' terminus of the immunoglobulin H chain variable region in pKM641HA3 to the StyI cleavage site near said 3' terminus and the base sequence from the 5' terminus of the immunoglobulin H chain constant region in pAGE28 to the ApaI cleavage site near said 5' terminus and having a StyI cleavage site and an ApaI cleavage site on the respective termini (cf. FIG. 50) was synthesized using a DNA synthesizer. This synthetic DNA was then introduced into the plasmid pKM641HA3 in the following manner.

Figure 51:
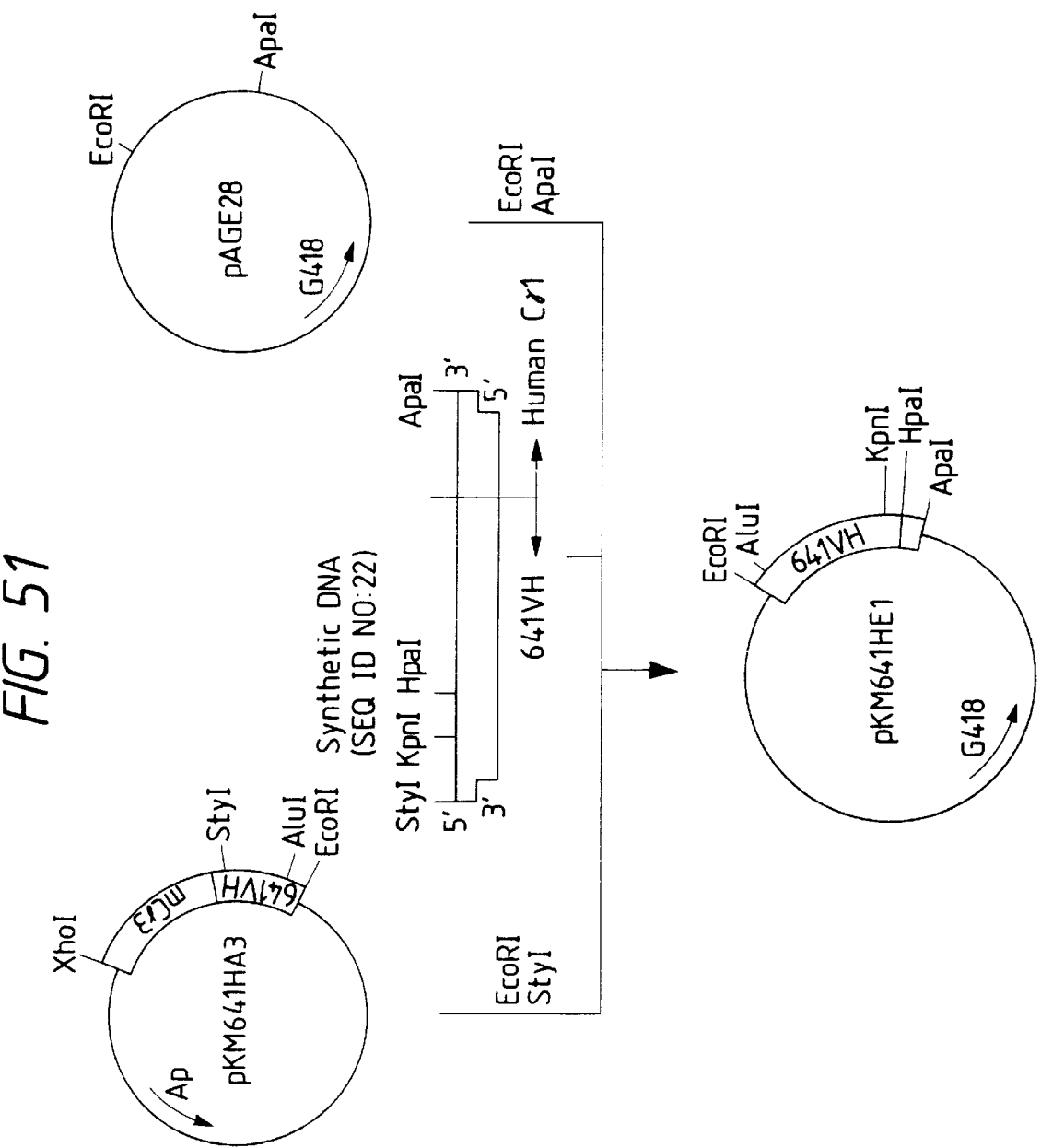
FIG. 51 shows a construction scheme for a plasmid, pKM641HE1.

Three µg of pKM641HA3 was added to 30 µl of 50 mM Tris-hydrochloride buffer (pH 7.5) containing 10 mM magnesium chloride, 50 mM sodium chloride and 1 mM DTT, 10 units of EcoRI and 10 units of StyI were further added, and digestion was effected at 37° C. for 4 hours. The reaction mixture was fractionated by agarose gel electrophoresis and about 0.3 µg of a 0.41 kb DNA fragment was recovered. Then, 3 µg of pAGE28 [Mizukami et al.: J. Biochem., 101, 1307–1310 (1987)] was added to 30 µl of 10 mM Tris-hydrochloride buffer (pH 7.5) containing 7 mM magnesium chloride and 6 mM 2-mercaptoethanol, 10 units of EcoRI and 10 units of ApaI were further added, and digestion was carried out at 37° C. for 4 hours. The reaction mixture was fractionated by agarose gel electrophoresis and about 2 µg of a 2.45 kb DNA fragment was recovered. Then, 0.1 µg of the EcoRI-StyI fragment (about 0.41 kb) of pKM641HA3, as obtained above, 0.1 µg of the EcoRI-ApaI fragment (about 2.45 kb) of pAGE28, as obtained above, and 0.3 µg of the synthetic DNA, defined by SEQ ID NO:22, were dissolved in a total of 20 µl of T4 ligase buffer; 350 units of T4 ligase was added to the solution, and ligation was conducted at 4° C. for 24 hours. The thus-obtained recombinant plasmid DNA was used to transform *Escherichia coli* HB101 and the plasmid pKM641HE1 shown in FIG. 51 was obtained.

Since pKM641HE1 had no leader sequence, the following measure was taken to supplement the deficit using the synthetic DNA defined by SEQ ID NO:21.

pKM641HE1 (3 µg) was added to 30 µl of 10 mM Tris-hydrochloride buffer (pH 7.5) containing 7 mM magnesium chloride and 6 mM 2-mercaptoethanol, 10 units of EcoRI and 10 units of ApaI were further added, and digestion was effected at 37° C. for 4 hours. The reaction mixture was fractionated by agarose gel electrophoresis and about 0.4 µg of a DNA fragment of about 0.42 kb in size was recovered. The EcoRI-ApaI fragment (about 0.42 kb; 0.4 µg) of pKM641HE1 was added to 30 µl of 10 mM Tris-hydrochloride buffer (pH 7.5) containing 7 mM magnesium chloride, 50 mM sodium chloride and 6 mM 2-mercaptoethanol, 10 units of AluI was further added, and digestion was effected at 37° C. for 4 hours. The reaction mixture was subjected to phenol-chloroform extraction and then to ethanol precipitation, and about 0.3 µg of a DNA fragment of about 0.4 kb in size was recovered.

Figure 52:
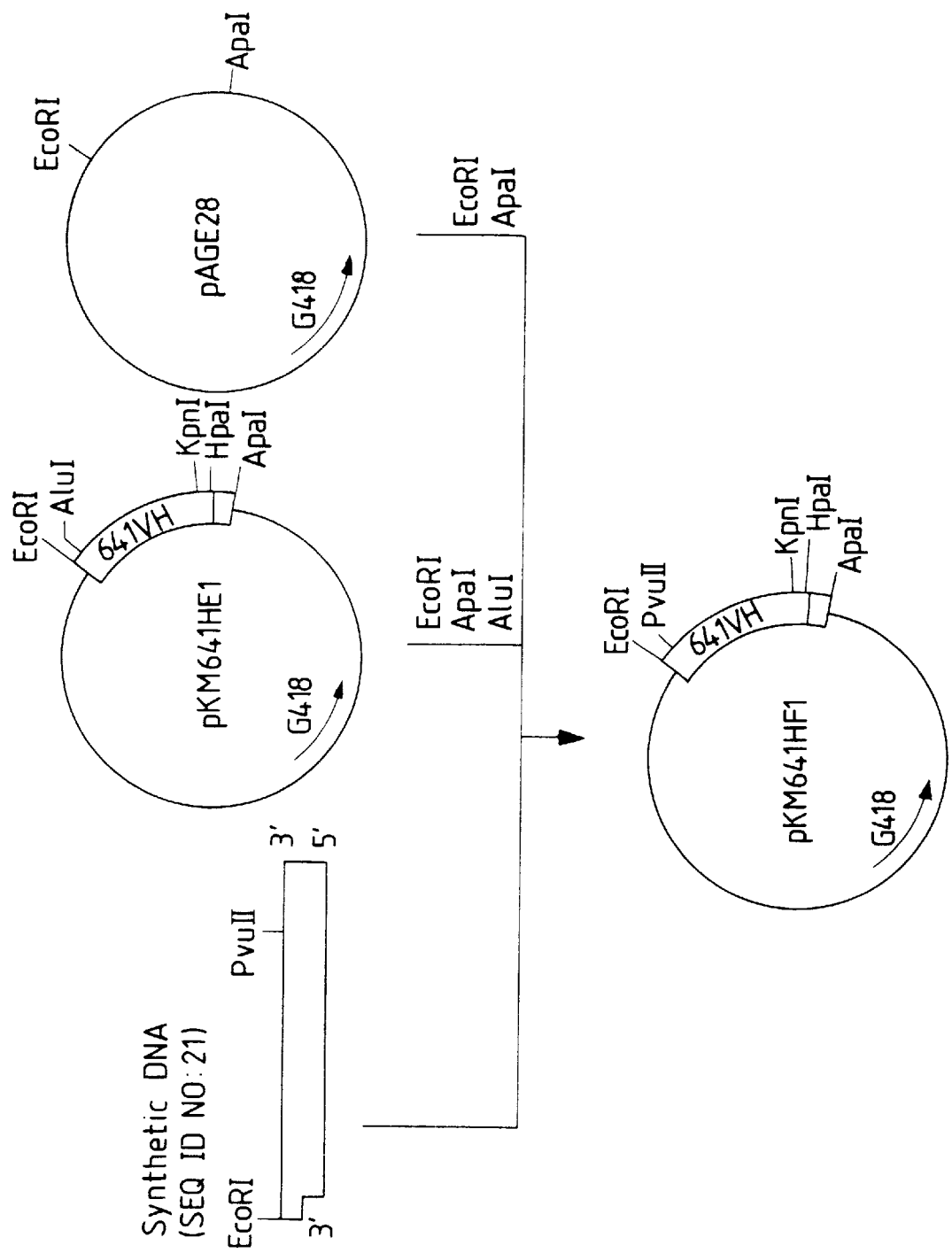
FIG. 52 shows a construction scheme for a plasmid, pKM641HF1.

Then, 0.1 µg of the AluI-ApaI fragmen (about 0.4 kb) of pKM641HE1 as obtained above, 0.1 µg of the EcoRI-ApaI fragment (about 2.45 kb) of pAGE28 as obtained above and 0.3 µg of the synthetic DNA defined by SEQ ID NO:21 were dissolved in a total of 20 µl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pKM641HF1 shown in FIG. 52 was obtained.

Figure 53:
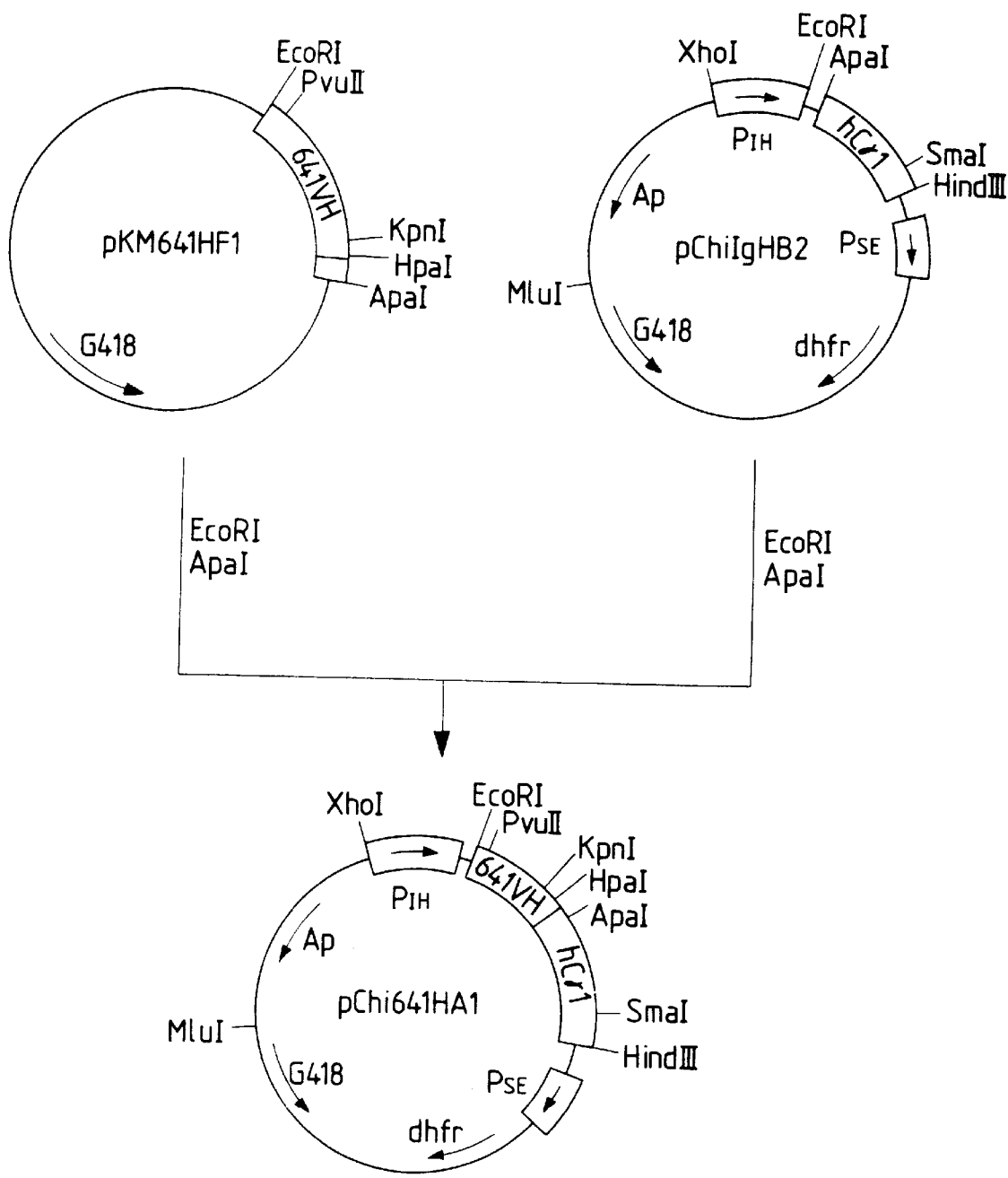
FIG. 53 shows a construction scheme for a plasmid, pChi641HA1.

Then, the immunoglobulin H chain variable region of pKM641HF1 was introduced into the vector pChiIgHB2 for chimeric human antibody H chain expression, as follows.

pKM641HF1 (3 µg) was added to 30 µl of 10 mM Tris-hydrochloride buffer (pH 7.5) containing 7 mM magnesium chloride and 6 mM 2-mercaptoethanol, 10 units of EcoRI and 10 units of ApaI were further added, and digestion was effected at 37° C. for 4 hours. The reaction mixture was fractionated by agarose gel electrophoresis and about 0.5 µg of a 0.44 kb DNA fragment was recovered. Then, 3 µg of pChiIgHB2 was added to 30 µl of 10 mM Tris-hydrochloride buffer (pH 7.5) containing 7 mM magnesium chloride and 6 mM 2-mercaptoethanol, 10 units of EcoRI and 10 units of ApaI were further added, and digestion was conducted at 37° C. for 4 hours. The reaction mixture was subjected to phenol-chloroform extraction and about 3 µg of DNA was recovered. Then, 0.1 µg of the EcoRI-ApaI fragment (about 0.44 kb) of pKM641HF1 as obtained above and 0.1 µg of the EcoRI-ApaI fragment (about 10.1 kb) of pChiIgHB2 as obtained above were dissolved in a total of 20 µl of T4 ligase buffer; 350 units of T4 ligase was added to the solution, and ligation was carried out at 4° C. for 24 hours. The thus-obtained recombinant plasmid DNA was used to transform *Escherichia coli* HB101 and the plasmid pChi641HA1 shown in FIG. 53 was obtained.

Figure 54:
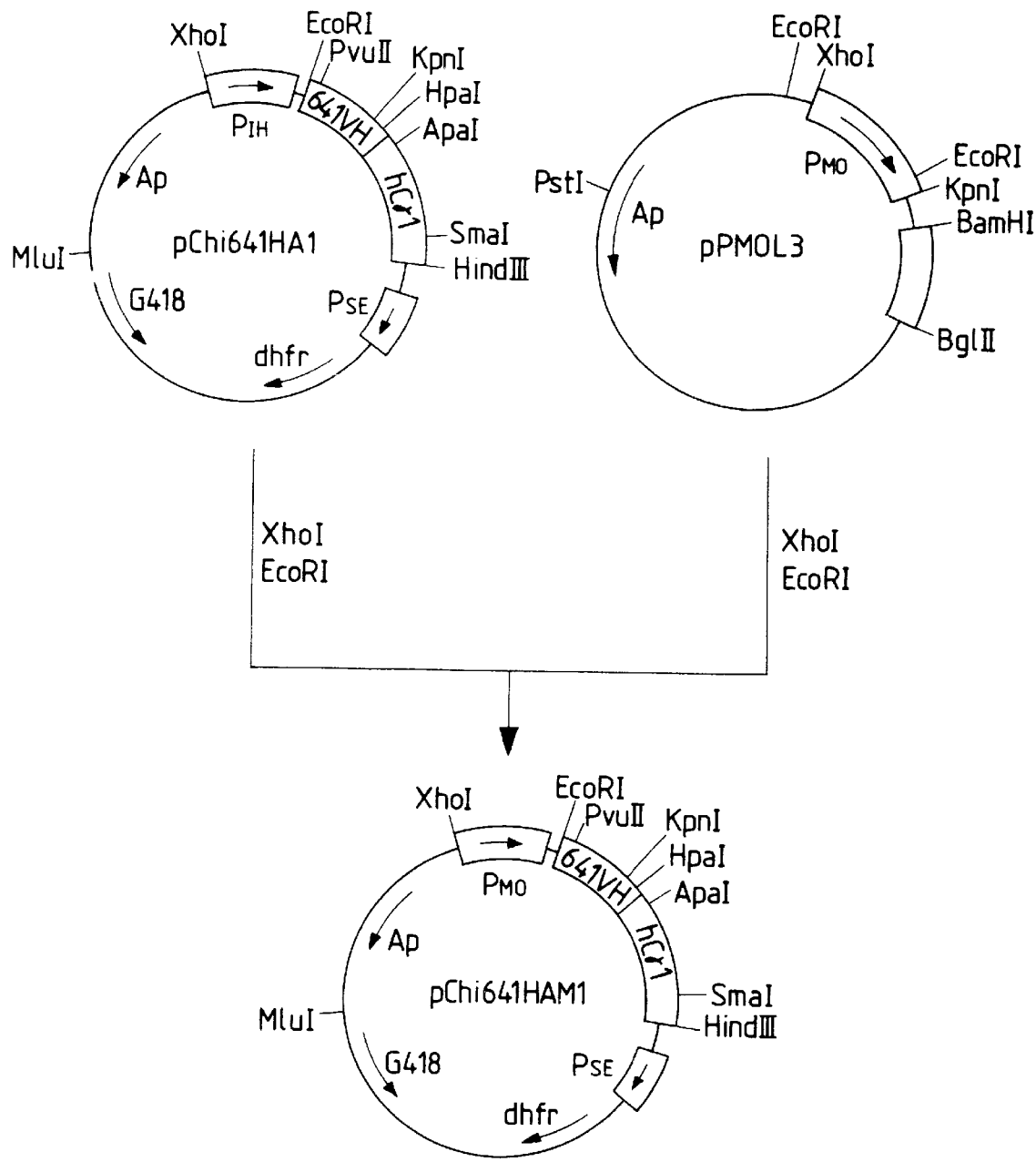
FIG. 54 shows a construction scheme for a plasmid, pChi641HAM1.

Then, the KM50-derived immunoglobulin H chain promoter and enhancer region of pChi641HA1 was replaced with MoLTR, as follows.

pChi641HA1 (3 µg) was added to 30 µl of 50 mM Tris-hydrochloride buffer (pH 7.5) containing 10 mM magnesium chloride, 50 mM sodium chloride and 1 mM DTT, 10 units of EcoRI and 10 units of XhoI were further added, and digestion was effected at 37° C. for 4 hours. The reaction mixture was fractionated by agarose gel electrophoresis and about 0.2 µg of a DNA fragment of about 8.8 kb in size was recovered. pPMOL3 (3 µg) obtained in Example 1, Paragraph 2 was added to 30 µl of 50 mM Tris-hydrochloride buffer (pH 7.5) containing 10 mM magnesium chloride, 50 mM sodium chloride and 1 mM DTT; 10 units of EcoRI and 10 units of XhoI were further added, and digestion was carried out at 37° C. for 4 hours. The reaction mixture was fractionated by agarose gel electrophoresis and about 0.3 µg of a MoLTR-containing DNA fragment (0.63 kg) was recovered. Then, 0.1 µg of the EcoRI-XhoI fragment of pChi641HA1 and 0.1 µg of the EcoRI-XhoI fragment of pPMOL3 were dissolved in 20 µl of T4 ligase buffer, 175 units of T4 DNA ligase war added, and the mixture was incubated at 4 ° C. for 1 day. The reaction mixture was used to transform *Escherichia coli* HB101 and the KM-641-derived chimeric human H chain expression vector pChi641HAM1 shown in FIG. 54 was obtained.

EXAMPLE 2

Production of human CDR-transplanted anti-GM$_2$ antibodies

1. Construction of DNAs each coding for human CDR-transplanted anti-GM$_2$ antibody H chain variable region and human CDR-transplanted anti-GM$_2$ antibody L chain variable region (1) Construction of DNA coding for human CDR-transplanted anti-GM$_2$ antibody H chain variable region A DNA coding for a human CDR-transplanted anti-GM$_2$ antibody H chain variable region, hKM796H, which contains amino acid sequences of SEQ ID NO:6, SEQ ID NO:7 and SEQ ID NO:8, was constructed in the following manner.

Figure 55:
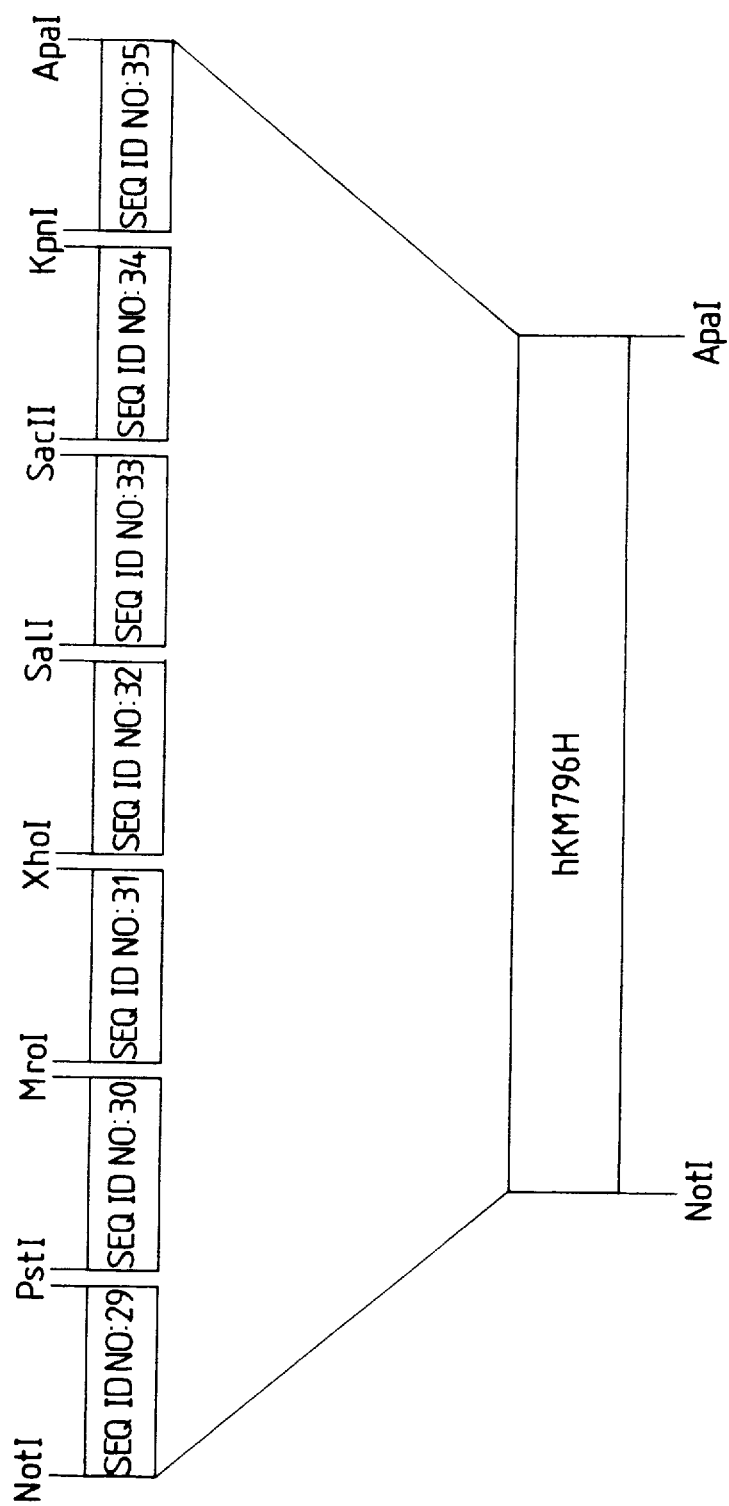
FIG. 55 shows a construction scheme for a DNA, hKM796H.

NEWM [BIO/TECHNOLOGY, 9, 266 (1991)] was used as human antibody H chain variable region-encoding DNA to which each CDR was to be transplanted. DNAs set forth in SEQ ID NO:23 through NO:29 corresponding to NEWM in which each CDR was replaced with amino acid sequences of SEQ ID NO:6, SEQ ID NO:7 and SEQ ID NO:8 were synthesized using an automatic DNA synthesizer (model 380A manufactured by Applied Biosystems Co., Ltd. ). The thus-obtained synthetic DNAs (50 picomoles each) were dissoloved in 20 μl of 50 mM Tris-hydrochloride buffer (pH 7.6) containing 10 mM magnesium chloride, 5 mM DTT, 0.1 EDTA and 0.5 mM ATP, 5 units of T4 polynucleotide kinase was added, and 5'-phosphorylation was carried out at 37° C. for 30 minutes. Ten picomoles each of the resulting phosphorylated synthetic DNAS, which had restriction enzyme sites on both ends, were ligated in the order of SEQ ID NO. (SEQ ID NO:23 throuth NO:29) using a DNA ligation kit (Takara Shuzo) in accordance with the manufacturer's instruction attached to the kit to obtain a DNA, hKM796H, shown in FIG. 55, The amino acid sequence corresponding to hKM796H is shown in SEQ ID NO:36.

(2) Construction of DNA coding for human CDR-transplanted anti-GM$_2$ antibody L chain variable region A DNA coding for a human CDR-transplanted anti -GM$_2$ antibody 1 chain variable region, hKM796L, which contains amino acid sequences of SEQ ID NO:9, SEQ ID NO:10 and SEQ ID NO:11, was constructed in the following manner.

Figure 56:
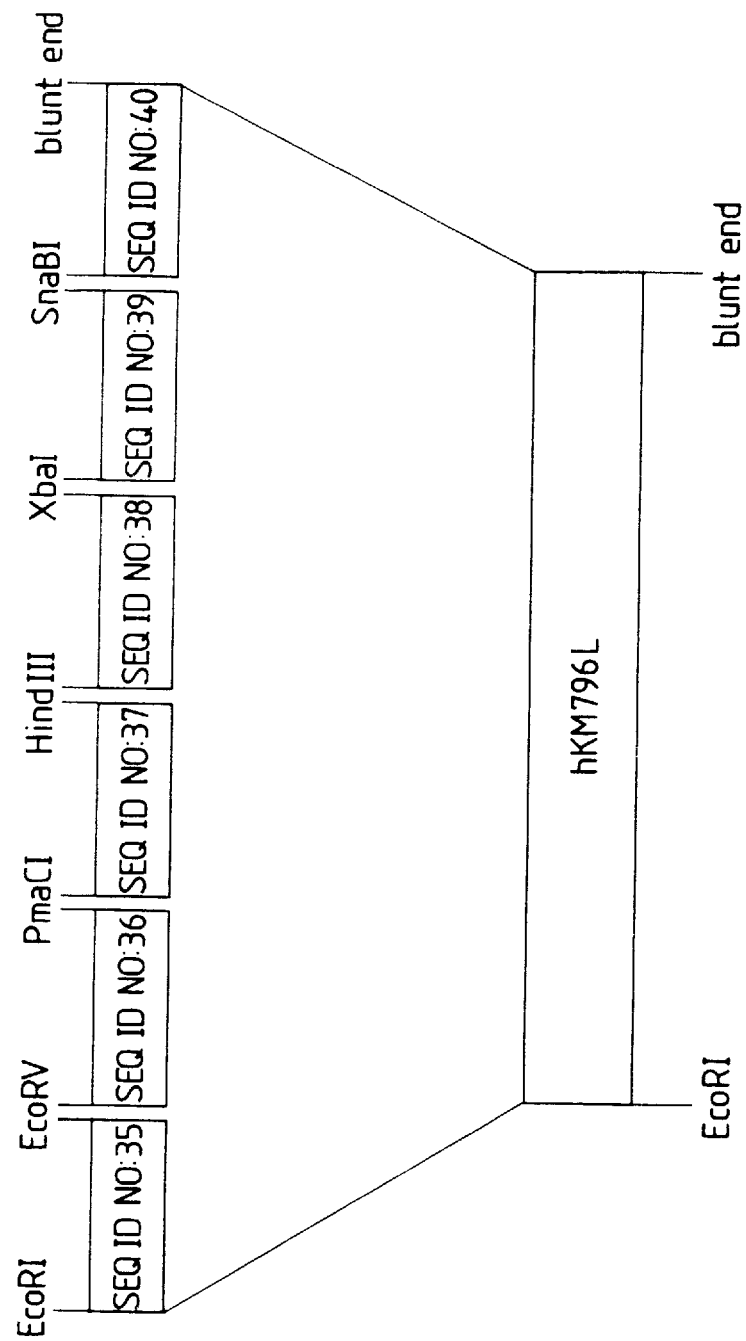
FIG. 56 shows a construction scheme for a DNA, hKM796L.

REI [BIO/TECHNOLOGY, 9, 266 (1991)] was used as human antibody L chain variable region-encoding DNA to which each CDR was to be transplanted. DNAs set forth in SEQ ID NO:30 through NO:35 corresponding to REI in which each CDR was replaced with amino acid sequences of SEQ ID NO:9, SEQ ID NO : 10 and SEQ ID NO:11 were synthesized using an automatic DNA synthesizer (model 380A manufactured by Applied Biosystems Co., Ltd.). The thus-obtained synthetic DNAs (50 picomoles each) were dissoloved in 20 μl of 50 mM Tris-hydrochloride buffer (pH 7.6) containing 10 mM magnesium chloride, 5 mM DTT, 0.1 EDTA and 0.5 mM ATP, 5 units of T4 polynucleotide kinase was added, and 5'-phosphorylation was carried out at 37° C. for 30 minutes. Ten picomoles each of the resulting phosphorylated Synthetic DNAs, which had restriction enzyme sites on both ends, were ligated in the order of SEQ ID NO. (SEQ ID NO:30 through NO:35) using a DNA ligation kit (Takara Shuzo) in accordance with the manufacturer's instruction attached to tho kit to obtain a DNA, hKM796L, shown in FIG. 56. The amino acid sequence corresponding to hKM796L is shown in SEQ ID: NO:37.

2. Construction of Human CDR-transplanted antibody H chain expression vector and human CDR-transplanted antibody L chain expression vector (1) Construction of human CDR-transplanted antibody H chain expression vector A NotI-ApaI fragment of the DNA coding for human CDR-transplanted antibody H chain variable region, obtained in Paragraph 1(1) of Example 2, was ligated to the plasmid pChi796HM1, obtained in Paragraph 7(3) of Example 1, in the following manner (FIG. 57).

Three μg of pChi796HM1, obtained in Paragraph 7(3) of Example 1, were dissolved in 30 μl of 10 mM Tris-hydrochloride buffer (pH 7.5) containing 10 mM magnesium chloride and 1 mM DTT, 10 units of ApaI were added thereto and the mixture was allowed to react at 37° C. for 1 hour. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. Ten units of NotI were added thereto to allow the mixture to react at 37° C. for 1 hour. The reaction mixture was fractionated by agarose gel electrophoresis to recover about 2 μg of a DNA fragment of about 9.0 kb. Then, about 0.1 μg of the thus-obtained ApaI-NotI fragment of pChi796HM1 was ligatod to 0.5 pmoles of the NotI-ApaI fragment of the DNA coding for human CDR-transplanted antibody H chain variable region, obtained in Paragraph 1(1) of Example 2, using a DNA ligation kit (Tekara Shuzo). The resulting recombinant plasmid DNA was used to transform *Escherichia coli* HB101 and the plasmid phKM796HM1 shown in FIG. 57 was obtained.

Figure 58:
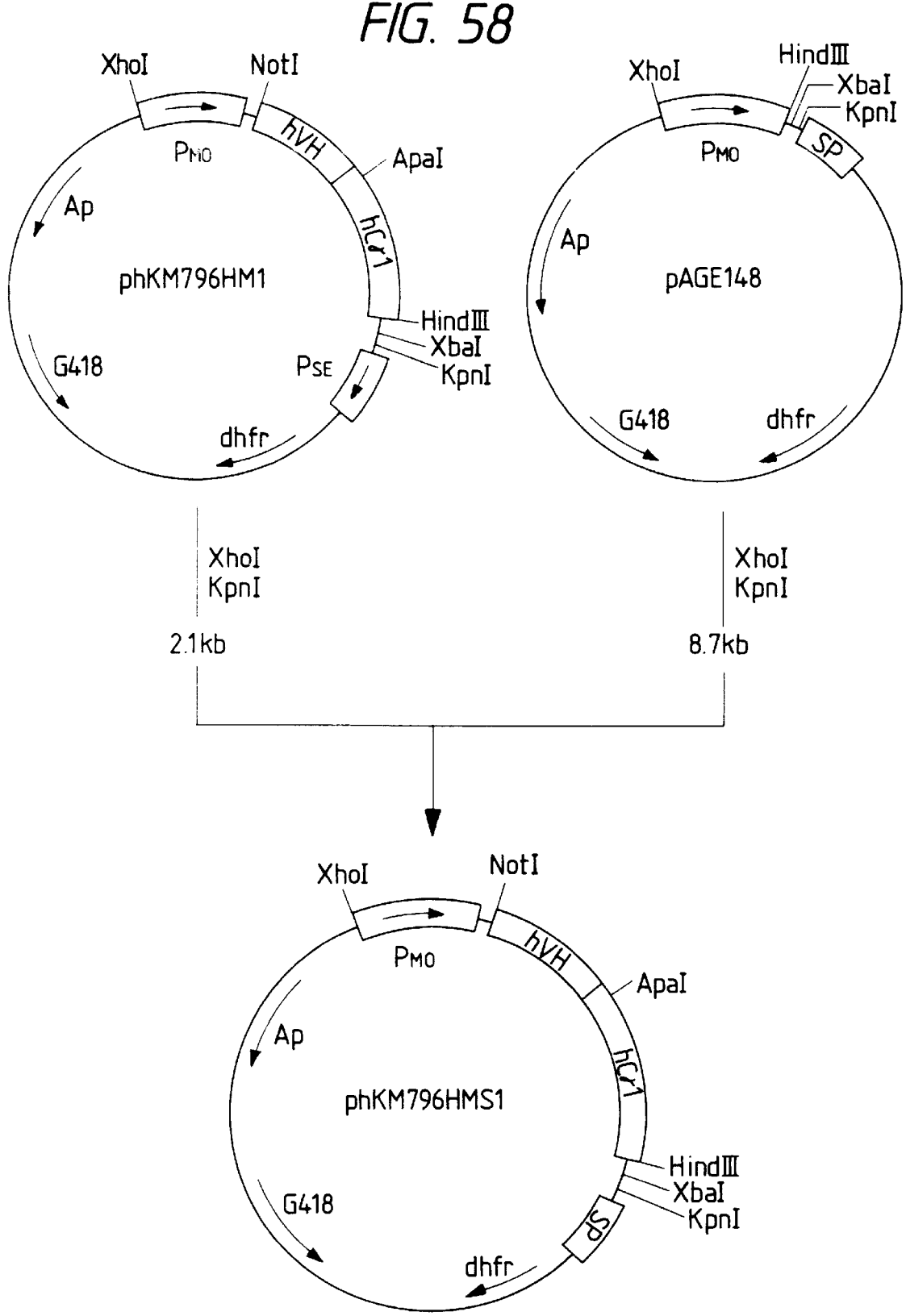
FIG. 58 shows a construction scheme for a plasmid, phKM796HMS1.

Then, a human CDR-transplanted antibody H chain expression vector was constructed by introducing β-globulin 3' splicing signal into the plasmid phKM796HM1 in the following manner (FIG. 58).

Three μg of phKM796HM1 were added to 30 μl of 10 mM Tris-hydrochloride buffer (pH 7.5) containing 10 nM magnesium chloride and 1 mM DTT, 1 unit of KpnI was added thereto. The mixture was allowed to react at 37° C. for 10 minutes to effect partial digestion. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. After adding 1 unit of XhoI, the mixture was allowed to react at 37° C. for 10 minutes to effect partial digestion. The reaction mixture was fractionated by agarose gel electrophoresis to recover about 0.2 μg of a DNA fragment of about 2.1 kb. Separately, 3 μg of pAGE148, obtained in Paragraph 7(2) of Example 1, were added to 30 μl of 10 mM Tris-hydrochloride buffer (pH 7.5) containing 10 mM magnesium chloride and 1 mM DTT. Ten units of KpnI were added thereto to allow the mixture to react at 37° C. for 1 hour. The reaction mixture was subjected to ethanol precipitation and the thus-obtained precipitate was dissloved in 30 μl of 50 mM Tris-hydrochloride buffer (pH 7.5) containing 10 mM magnesium chloride, 100 mM sodium chloride and 1 mM DTT. After adding 10 units of XhoI, the mixture was allowed to react at 37° C. for 1 hour and then fractionated by agarose gel electrophoresis to recover about 1 μg of a DNA fragment of about 8.7 kb. One tenth μg of the thus-obtained XhoI-KpnI fragment of phKM796HM1 was ligated to 0.1 μg of the XhoI-KpnI fragment of pAGE148 using a DNA ligation kit (Takara Shuzo). The thus-obtained recombinant plasmid DNA was used to transform *Escherichia coli* HB101 to obtain the plasmid phKM796HMS1 shown in FIG. 58.

(2) Construction of human CDR-transplanted antibody L chain expression vector

An EcoRI fragment having blunt ends of the DNA coding for human CDR-transplanted antibody L chain variable region, obtained in Paragraph 1 (2) of Example 2, was ligated to the chimeric human antibody L chain expression vector pChiIgLA1 in the following manner (FIG. 59).

Three μg of pChiIgLA1, obtained in Reference Example 1, were added to 30 μl of 50 mM Tris-hydrochloride buffer (pH 7.5) containing 10 mM magnesium chloride, 100 nM sodium chloride and 1 mM DTT, 10 units of EcoRI and 10 units of EcoRV were added thereto and the mixture was allowed to react at 37° C. for 1 hour. The reaction mixture was fractionated by agarose gel electrophoresis to recover about 1 μg of a DNA fragment of about 8.6 kb. Then, about 0.1 μg of the thus-obtained EcoRI-EcoRV fragment of pChiIgLA1 was ligated to 0.5 pmoles of the EcoRI fragment having blunt ends derived from the DNA coding for human CDR-transplanted antibody L chain variable region, obtained in Paragraph 1(2) of Example 2, using a DNA ligation kit (Takara Shuzo). The resulting recombinant plasmid DNA was used to transform Escherichia coli HB101 and the plasmid phKM796LI1 shown in FIG. 59 was obtained.

Figure 60:
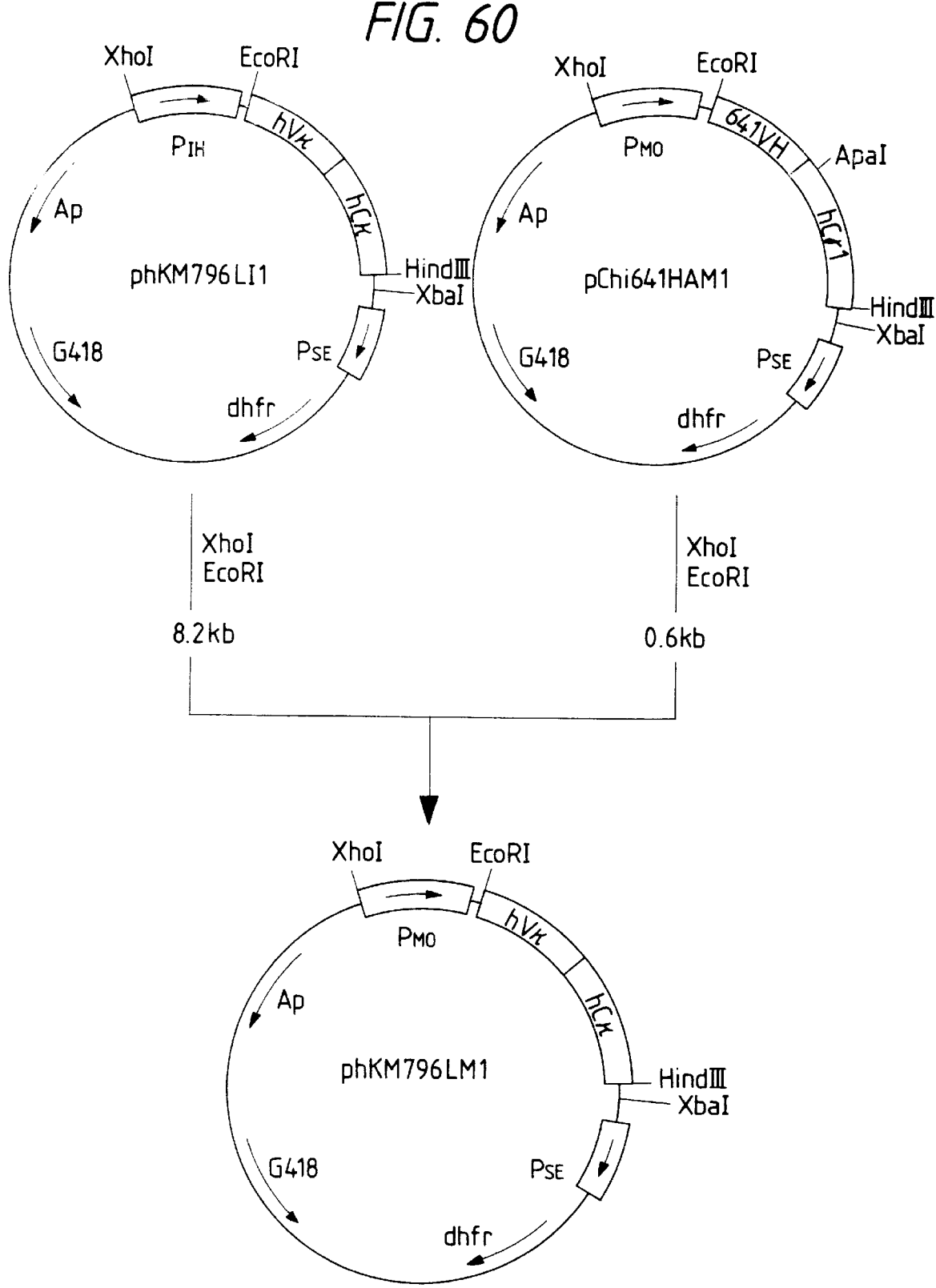
FIG. 60 shows a construction scheme for a plasmid, phKM796LM1.

Then, $P_{HO}$ was introduced into the plasmid phKM796LI1 in the following manner (FIG. 60).

Three μg of phKM796LI1 were added to 30 μl of 50 mM Tris-hydrochloride buffer (pH 7.5) containing 10 mM magnesium chloride, 100 mM sodium chloride and 1 mM DTT, 10 units of EcoRI and 10 units of XhoI were added thereto, and the mixture was allowed to react at 37° C. for 1 hour. The reaction mixture was fractionated by agarose gel electrophoresis to recover about 1 μg of a DNA fragment of about 8.2 kb. Separately, 3 μg of the chimeric human antibody H chain expression vector pChi641HAM1, obtained in Reference Example 2, were added to 30 μl of 50 mM Tris-hydrochloride buffer (pH 7.5) containing 10 mM magnesium chloride, 100 mM sodium chloride and 1 mM DTT. Ten units of EcoRI and 10 units of XhoI were added thereto to allow the mixture to react at 37° C. for 1 hour. The reaction mixture was fractionated by agarose gal electrophoresis to recover about 0.3 μg of a DNA fragment of about 6 kb. One tenth μg of the thus-obtained EcoRI-XhoI fragment of pChi641HAM1 was ligated to 0.1 μg of the EcoRI-XhoI fragment of phKM796LI1 using a DNA ligation kit (Takara Shuzo). The thus-obtained recombinant plasmid DNA was used to transform Escherichia coli HB101 to obtain the plasmid phKM796LM1 shown in FIG. 60.

Figure 61:
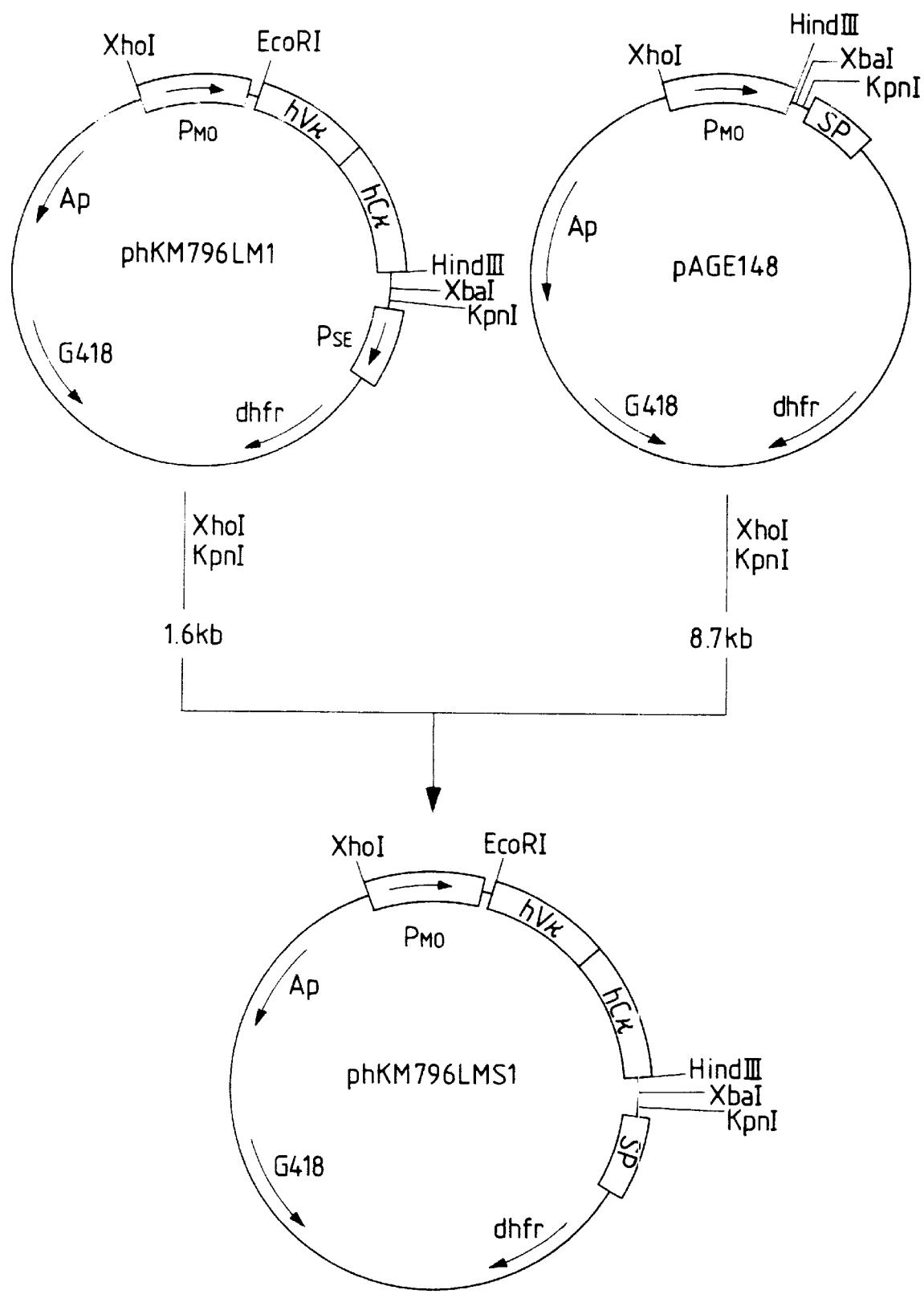
FIG. 61 shows a construction scheme for a plasmid, phKM796LMS1.

Then, a human CDR-transplanted antibody L chain expression vector was constructed by introducing β-globulin 3' splicing signal into the plasmid phKM796LM1 in the following manner (FIG. 61).

Three μg of phKM796LM1 were added to 30 μl of 10 mM Tris-hydrochloride buffer (pH 7.5) containing 10 mM magnesium chloride and 1 mM DTT, 10 units of KpnI were added thereto, and the mixture was allowed to react at 37° C. for 1 hour. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. After adding 10 units of XhoI, the mixture was allowed to react at 37° C. for 1 hour. The reaction mixture was fractionated by agarose gel electrophoresis to recover about 0.3 μg of a DNA fragment of about 1.6 kb. Separately, 3 μg of pAGE148, obtained in Paragraph 7 (2) of Example 1, were added to 30 μl of 10 mM Tris-hydrochloride buffer (pH 7.5) containing 10 mM magnesium chloride and 1 mM DTT. Ten units of KpnI were added thereto to allow the mixture to react at 37° C. for 1 hour. The reaction mixture was subjected to ethanol precipitation and the thus-obtained precipitate was dissolved in 30 μl of 50 mM Tris-hydrochloride buffer (pH 7,5) containing 10 mM magnesium chloride, 100 mM sodium chloride and 1 mM DTT. After adding 10 units of XhoI, the mixture was allowed to react at 37° C. for 1 hour and then fractionated by agarose gel electrophoresis to recover about 1 μg of a DNA fragment of about 8.7 kb. One tenth μg of the thus-obtained XhoI-KpnI fragment of phKM796LM1 was ligated to 0.1 μg of the XhoI-KpnI fragment of pAGE148 using a DNA ligation kit (Takara Shuzo). The thus-obtained recombinant plasmid DNA was used to transform Escherichia coli HB101 to obtain the plasmid phKM796LMS1 shown in FIG. 61.

Figure 62:
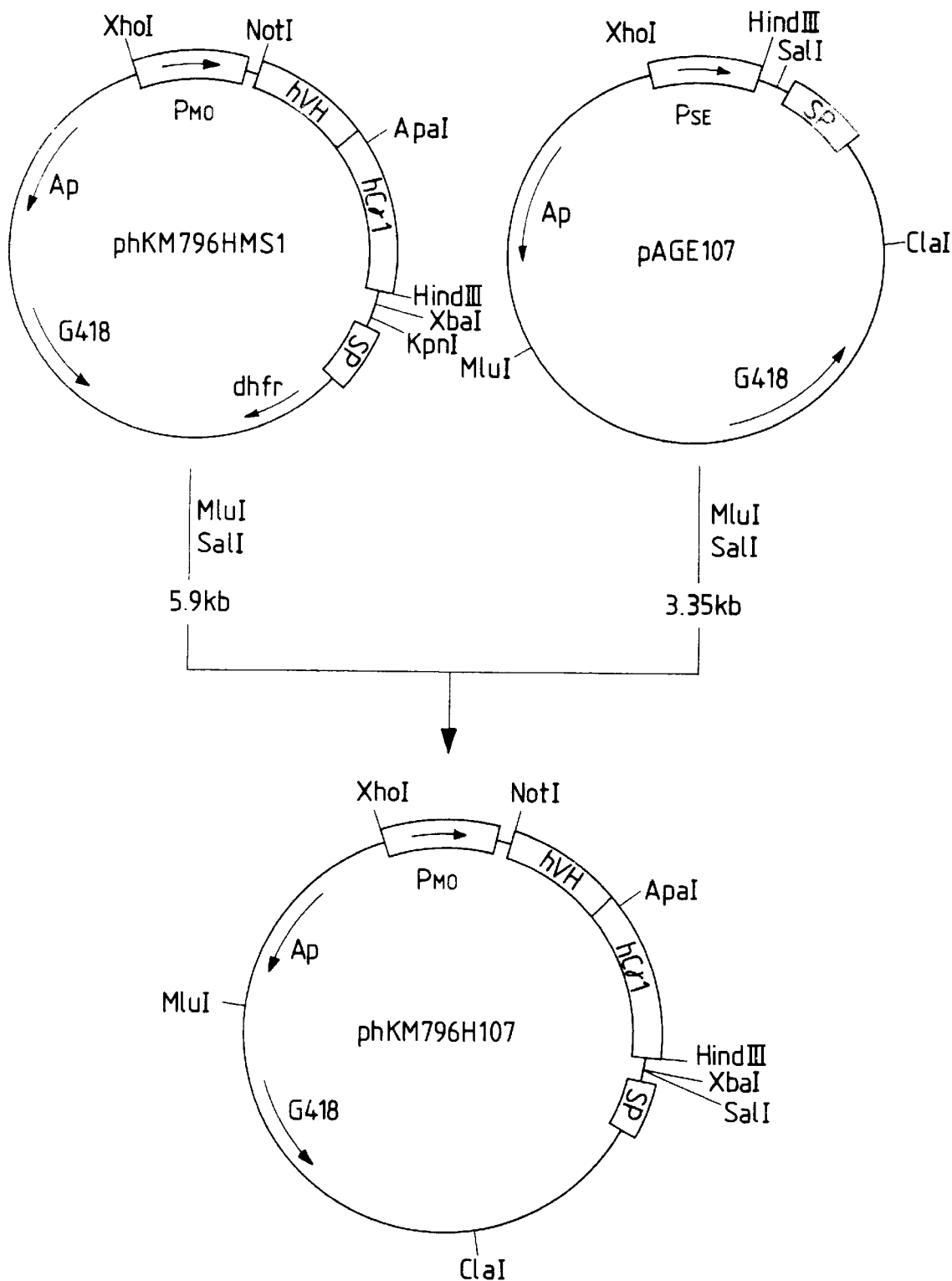
FIG. 62 shows a construction scheme for a plasmid, phKM796H107.
Figure 63:
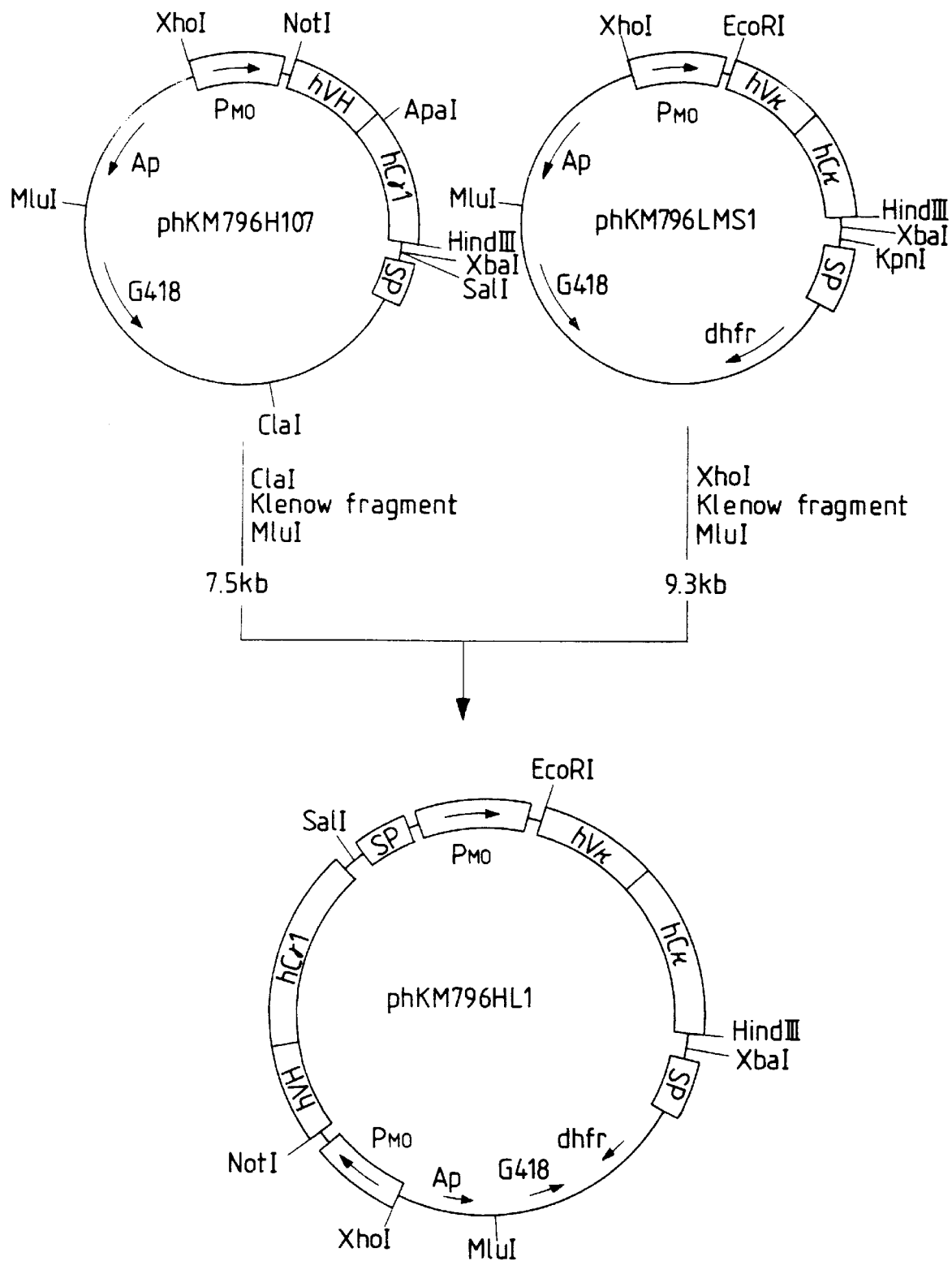
FIG. 63 shows a construction scheme for a plasmid, phKM796HL1.

3. Construction of human CDR-transplanted antibody H chain and L chain tandem expression vector A tandem expression vector containing both of cDNA coding for human CDR-transplanted antibody H chain and cDNA coding for human CDR-transplanted antibody L chain was constructed in the following manner (FIG. 62 and FIG. 63).

Three μg of phKM796HMS1, obtained in Paragraph 2(1) of Example 2, were dissolved in 30 μl of 50 mM Tris-hydrochloride buffer (pH 7.5) containing 10 mM magnesium chloride, 100 mM sodium chloride and 1 mM DTT, 1 unit of SalI was added thereto and the mixture was allowed to react at 37° C. for 10 minutes to effect partial digestion. The resulting mixture was subjected to ethanol precipitation and the thus-obtained precipitate was dissolved in 30 μl of 50 mM Tris-hydrochloride buffer (pH 7.5) containing 10 mM magnesium chloride, 100 mM sodium chloride and 1 mM DTT. Ten units of MluI was added thereto to allow the mixture to react at 37° C. for 1 hour. The reaction mixture was fractionated by agarose gel electrophoresis to recover about 0.2 μg of a DNA fragment of about 5.9 kb. Then, about 2 μg of pAGE107 as described in EP-A-0 405 285 was added to 30 μl of 50 mM Tris-hydrochloride buffer (pH 7.5) containing 10 mM magnesium chloride, 100 mM sodium chloride and 1 mM DTT, 10 units of MluI and 10 units of SalI were added thereto, and the mixture was allowed to react at 37° C. for 1 hour. The reaction mixture was fractionated by agarose gel electrophoresis to recover about 0.2 μg of a DNA fragment of about 3.35 kb. Then, 0.1 μg of the thus-obtained MluI-SalI fragment of phKM796HMS1 was ligated to 0.1 μg of the MluI-SalI fragment of pAGE107 using a DNA ligation kit (Takara Shuzo). The thus-obtained recombinant plasmid DNA was used to transform Escherichia coli HB101 to obtain the plasmid phKM796H107 shown in FIG. 62.

Then, 3 μg of phKM796H107 were added to 30 μl of 10 mM Tris-hydrochloride (pH 7.5) containing 10 mM magnesium chloride, 100 mM sodium chloride and 1 mM DTT, 10 units of ClaI was added thereto and the mixture was allowed to react at 37° C. for 1 hour. The reaction mixture was subjected to phenol-chloroform extraction and ethanol precipitation. The resulting precipitate was dissolved in 20 μl of DNA polymerase I buffer, 5 units of Escherichia coli-derived DNA polymerase I Klenow fragment were added, and the 5' cohesive ends produced by ClaI digestion were rendered blunt by incubation at 22° C. for 30 minutes. The reaction mixture was fractionated by agarose gel electrophoresis to recover about 0.2 μg of a DNA fragment of about 3.35 kb. The reaction mixture was also subjected to phenol-chloroform extraction and then to ethanol precipitation. The resulting precipitate was dissolved in 30 μl of 10 mM Tris-hydrochloride buffer (pH 7.5) containing 10 mM magnesium chloride, 100 mM sodium chloride and 1 mM DTT, 10 units of MluI were added thereto and the mixture was allowed to react at 37° C. for 1 hour. The reaction mixture was fractionated by agarose gel electrophoresis to recover about 0.3 μg of a DNA fragment of about 7.5 kb. Separately, 3 μg of phKM796LMS1 were added to 30 μl of 50 mM Tris-hydrochloride buffer (pH 7.5) containing 10 mM magnesium chloride, 100 mM sodium chloride and 1 mM DTT, 10 units of XhoI were added and the mixture was allowed to react at 37° C. for 1 hour. The reaction mixture was subjected to phenol-chloroform extraction and then to ethanol precipitation. The resulting precipitate was dissloved in 20 μl of DNA polymerase I buffer, 5 units of Escherichia coli-derived DNA polymerase I Klenow fragment were added, and the 5' cohesive ends produced by XhoI digestion were rendered blunt by incubation at 22° C. for 30 minutes. The reaction mixture was subjected to phenol-chloroform extraction followed by ethanol precipitation. The resulting precipitate was added to 30 μl of 10 mM Tris-hydrochloride buffer (pH 7.5) containing 10 mM magnesium chloride, 50 mM sodium chloride and 1 mM DTT, 10 units of MluI were added thereto, and the mixture was allowed to react at 37° C. for 1 hour. The reaction mixture was fractionated by agarose gel electrophoresis to recover about 0.3 μg of a DNA fragment of about 9.3 kb. Then, 0.1 μg of the thus-obtained MluI-ClaI fragment of phKM796H107 was ligated to 0.1 μg of the MluI-XhoI fragment of phKM796LMS1 using a DNA ligation kit (Takara Shuzo). The thus-obtained recombinant plasmid DNA was used to transform Escherichia coli HB101 to obtain the plasmid phKM796HL1 shown in FIG. 63.

4. Expression of human CDR-transplanted anti-GM$_2$ antibody in YB2/0 cells

The plasmids were introduced into YB2/0 cells by the electroporation method of Miyaji et al. [Cytotechnology 3, 133 (1990)].

After introduction of 4 μg of phKM796HL1 obtained in Paragraph 3 of Example 2 into 4×10$^6$ YB2/0 (ATCC CRL1581) cells, the cells were suspended in 40 ml of RPMI1640-FCS(10) [RPM1640 medium (Nissui Pharmaceutical) containing 10% of FCS, ¼ volume of 7.5% NaHCO$_3$, 3% of 200 mM L-glutamine solution (Gibco) and 0.5% of penicillin-streptomycin solution (Gibco; containing 5,000 units/ml penicillin and 5,000 μg/ml streptomycin)], and the suspension was distributed in 200-μl portions into wells of 96-well microliter plates. After 24 hours of incubation at 37° C. in a CO$_2$ incubator, G418 (Gibco) was added to a concentration of 5 mg/ml and then incubation was continued for 1 to 2 weeks. Transformant colonies appeared, the culture fluid was recovered from each well in which the cells had grown to confluence and an enzyme-linked immunosorbent assay (ELISA) described in Paragraph 11 of Example 1 was conducted for anti-GM$_2$ human CDR-transplanted antibody activity measurement.

The clone showing the highest activity in ELISA among the clones obtained gave a human CDR-transplanted anti-GM$_2$ antibody content of about 0.1 μg/ml of culture fluid.

Cells of the clone showing the above-mentioned human CDR-transplanted anti-GM$_2$ antibody activity were suspended in RPMI1640-FCS(10) medium containing 0.5 mg/ml G418 and 50 nM MTX to a concentration of 1 to 2×10$^5$ cells/ml, and the suspension was distributed in 2-ml portions into wells of 24-well plates. Incubation was performed at 37° C. in a CO$_2$ incubator for 1 to 2 weeks to induce 50 nM MTX-resistant clones. At the time of confluence, the human CDR-transplanted anti-GM$_2$ antibody activity in each culture fluid was determined by ELISA. The 50 nm MTX-resistant clone showing the highest activity among the clones obtained showed a human CDR-transplanted anti-GM$_2$ antibody content of about 1.0 μg/ml.

Cells of the above 50 nM MTX-resistant clone were suspended in RPMI1640-FCS(10) medium containing 0.5 mg/ml G418 and 200 nM MTX to a concentration of 1 to 2×10$^5$ cells/ml, and the suspension was distributed in 2-ml portions into wells of 24-well plates. Incubation was carried out at 37° C. in a CO$_2$ incubator for 1 to 2 weeks to induce 200 nM MTX-resistant clones. At the time of confluence, each culture fluid was assayed for human CDR-transplanted anti-GM$_2$ antibody activity by ELISA. The 200 nM MTX-resistant clone showing the highest activity among the clones obtained had a human CDR-transplanted anti-GM$_2$ antibody content of about 5.0 μg/ml.

As described in detail hereinabove, the present invention provides humanized antibodies reacting with the ganglioside GM$_2$.

While the invention has been described in detail and with reference to specific examples thereof, it will be apparent to one skilled in the art that various changes and modifications can be made therein without departing from the spirit and scope thereof.

What is claimed is:

1. A transformant that produces the antibody KM966, wherein said transformant is KM966 (FERM BP-3931).

2. A DNA sequence encoding a human chimeric antibody specific for the ganglioside $GM_2$, comprising a heavy chain variable region and a light chain variable region of a non human antibody and a heavy chain constant region and a light chain constant region of a human antibody wherein said chimeric human antibody is specific for the ganglioside $GM_2$ and wherein said heavy chain variable region has an amino acid sequence having amino acids 1–120 of SEQ ID NO:1 and said light chain variable region has an amino acid sequence having amino acids 1–107 of SEQ ID NO:2.

3. An isolated expression vector comprising the DNA sequence according to claim 2 operably linked to a promoter.

4. An isolated cell comprising the expression vector according to claim 3.

5. The cell according to claim 4 wherein said cell is an animal cell.

6. A method of making a humanized antibody specific for the ganglioside $GM_2$ comprising culturing the cell according to claim 4 under conditions such that said DNA sequence is expressed and said humanized antibody thereby produced.

* * * * *